United States Patent
Ness et al.

(10) Patent No.: US 10,258,988 B2
(45) Date of Patent: *Apr. 16, 2019

(54) DEVICE FOR GENERATING DROPLETS

(71) Applicant: Bio-Rad Laboratories, Inc., Hercules, CA (US)

(72) Inventors: Kevin D. Ness, Pleasanton, CA (US); Benjamin J. Hindson, Livermore, CA (US); Billy W. Colston, Jr., San Ramon, CA (US); Donald A. Masquelier, Tracy, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 236 days.

This patent is subject to a terminal disclaimer.

(21) Appl. No.: 15/365,883

(22) Filed: Nov. 30, 2016

(65) Prior Publication Data
US 2017/0144160 A1    May 25, 2017

Related U.S. Application Data

(63) Continuation of application No. 12/962,511, filed on Dec. 7, 2010, now Pat. No. 9,623,384, which is a
(Continued)

(51) Int. Cl.
*B01L 3/00* (2006.01)
*B01F 3/08* (2006.01)
(Continued)

(52) U.S. Cl.
CPC ...... *B01L 3/502784* (2013.01); *B01F 3/0807* (2013.01); *B01F 13/0062* (2013.01);
(Continued)

(58) Field of Classification Search
CPC .............. B01F 3/0807; B01F 13/0062; B01L 13/0241; B01L 13/502784; B01L 17/52;
(Continued)

(56) References Cited

U.S. PATENT DOCUMENTS

| 3,575,220 A | 4/1971 | Davis et al. |
|---|---|---|
| 4,051,025 A | 9/1977 | Ito |

(Continued)

FOREIGN PATENT DOCUMENTS

| CN | 2364458 Y | 2/2000 |
|---|---|---|
| DE | 102005037401 A1 | 2/2007 |

(Continued)

OTHER PUBLICATIONS

United States Patent and Trademark Office, Patent Trial and Appeal Board, "Decision Denying Institution of Inter Partes Review" related to IPR Case No. IPR2018-00300, dated Jun. 15, 2018, 19 pgs.

(Continued)

*Primary Examiner* — Michael L Hobbs
(74) *Attorney, Agent, or Firm* — Kolisch Hartwell, P.C.

(57) ABSTRACT

Devices and methods for generating droplets. An exemplary device comprises a substantially planar base portion including a bottom surface having a plurality of microfluidic channels formed therein as recessed regions of the bottom surface. The device also comprises a plurality of protrusions projecting from a top surface of the base portion and each formed integrally with the base portion. The device further comprises a sample well, a carrier well, and a droplet well. Each well has an upper portion created by one of the protrusions. A cover layer is attached to the bottom surface of the base portion and seals a bottom side of each microfluidic channel.

26 Claims, 65 Drawing Sheets

Related U.S. Application Data continuation of application No. 12/586,626, filed on Sep. 23, 2009, now Pat. No. 9,156,010.

(60) Provisional application No. 61/194,043, filed on Sep. 23, 2008, provisional application No. 61/206,975, filed on Feb. 5, 2009, provisional application No. 61/271,538, filed on Jul. 21, 2009, provisional application No. 61/275,731, filed on Sep. 1, 2009, provisional application No. 61/277,200, filed on Sep. 21, 2009, provisional application No. 61/277,203, filed on Sep. 21, 2009, provisional application No. 61/277,204, filed on Sep. 21, 2009, provisional application No. 61/277,216, filed on Sep. 21, 2009, provisional application No. 61/277,249, filed on Sep. 21, 2009, provisional application No. 61/277,270, filed on Sep. 22, 2009.

(51) Int. Cl.
| | | |
|---|---|---|
| *B01F 13/00* | (2006.01) | |
| *B01L 3/02* | (2006.01) | |
| *B01L 7/00* | (2006.01) | |
| *G01N 21/3563* | (2014.01) | |
| *C12Q 1/686* | (2018.01) | |
| *G01N 21/64* | (2006.01) | |
| *B01F 15/00* | (2006.01) | |
| *B29C 45/00* | (2006.01) | |
| *G01N 21/49* | (2006.01) | |
| *B29L 31/00* | (2006.01) | |

(52) U.S. Cl.
CPC ...... *B01F 15/00922* (2013.01); *B01L 3/0241* (2013.01); *B01L 3/502715* (2013.01); *B01L 7/525* (2013.01); *B29C 45/006* (2013.01); *B29C 45/0053* (2013.01); *C12Q 1/686* (2013.01); *G01N 21/3563* (2013.01); *G01N 21/49* (2013.01); *G01N 21/6428* (2013.01); *G01N 21/6486* (2013.01); *B01F 2003/0834* (2013.01); *B01F 2003/0842* (2013.01); *B01F 2215/0037* (2013.01); *B01L 7/52* (2013.01); *B01L 2200/0673* (2013.01); *B01L 2200/0689* (2013.01); *B01L 2200/10* (2013.01); *B01L 2200/12* (2013.01); *B01L 2300/041* (2013.01); *B01L 2300/0654* (2013.01); *B01L 2300/0816* (2013.01); *B01L 2300/0819* (2013.01); *B01L 2300/0858* (2013.01); *B01L 2300/0867* (2013.01); *B01L 2300/1822* (2013.01); *B01L 2400/0403* (2013.01); *B01L 2400/0478* (2013.01); *B01L 2400/0487* (2013.01); *B01L 2400/0622* (2013.01); *B29C 2045/0079* (2013.01); *B29L 2031/752* (2013.01); *G01N 2021/6439* (2013.01); *Y02A 90/26* (2018.01)

(58) Field of Classification Search
CPC .......... B01L 17/525; B01L 2300/0816; B01L 2300/0819; B01L 2300/1822; B01L 2400/0478; B01L 2400/0487; B01L 2400/0622; B01L 2400/0689
See application file for complete search history.

(56) References Cited

U.S. PATENT DOCUMENTS

| | | |
|---|---|---|
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,123,798 A | 9/2000 | Gandhi et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,176,962 B1 | 1/2001 | Soane et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,915,679 B2 | 7/2005 | Chien et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,060,227 B2 | 6/2006 | Staats |

(56) References Cited

U.S. PATENT DOCUMENTS

| | | |
|---|---|---|
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 9,328,376 B2 | 5/2016 | Hiddessen et al. |
| 9,417,190 B2 | 8/2016 | Hindson et al. |
| 9,500,664 B2 | 11/2016 | Ness et al. |
| 9,623,384 B2 | 4/2017 | Hindson et al. |
| 2001/0046701 A1 | 11/2001 | Schulte et al. |
| 2002/0003001 A1 | 1/2002 | Weigl et al. |
| 2002/0021866 A1 | 2/2002 | Everett et al. |
| 2002/0022261 A1 | 2/2002 | Anderson et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0089561 A1 | 7/2002 | Weitzel et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0006140 A1 | 1/2003 | Vacca et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0037739 A1 | 2/2004 | McNeely et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0090168 A1 | 5/2004 | Kumar et al. |
| 2004/0109793 A1 | 6/2004 | McNeely et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2004/0228770 A1 | 11/2004 | Gandhi et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0266582 A1 | 12/2005 | Modlin et al. |
| 2005/0277125 A1 | 12/2005 | Benn et al. |
| 2005/0282206 A1 | 12/2005 | Michael Corbett et al. |
| 2006/0014187 A1 | 1/2006 | Li et al. |
| 2006/0024831 A1 | 2/2006 | Kao et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2006/0234298 A1 | 10/2006 | Chiu et al. |
| 2007/0003442 A1 | 1/2007 | Link et al. |
| 2007/0010974 A1 | 1/2007 | Nicoli et al. |
| 2007/0039866 A1 | 2/2007 | Schroeder et al. |
| 2007/0048756 A1 | 3/2007 | Mei et al. |
| 2007/0054199 A1 | 3/2007 | Wakabayashi |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0253868 A1 | 11/2007 | Beebe et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0056948 A1 | 3/2008 | Dale et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166720 A1 | 7/2008 | Hsieh et al. |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0223721 A1 | 9/2008 | Cohen et al. |
| 2008/0241841 A1 | 10/2008 | Murakawa et al. |
| 2008/0257438 A1 | 10/2008 | Wang et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |

(56) References Cited

U.S. PATENT DOCUMENTS

| | | |
|---|---|---|
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0047713 A1 | 2/2009 | Handique |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0269248 A1 | 10/2009 | Falb et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0015606 A1 | 1/2010 | Davies et al. |
| 2010/0018584 A1 | 1/2010 | Bransky et al. |
| 2010/0020565 A1 | 1/2010 | Seward |
| 2010/0022414 A1 | 1/2010 | Link et al. |
| 2010/0022680 A1 | 1/2010 | Karnik et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0184928 A1 | 7/2010 | Kumacheva |
| 2010/0217736 A1 | 8/2010 | Sarel |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0003755 A1 | 1/2012 | Chapin et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |
| 2017/0065979 A1 | 3/2017 | Ness et al. |
| 2017/0144116 A1 | 5/2017 | Ness et al. |
| 2017/0144161 A1 | 5/2017 | Hindson et al. |

FOREIGN PATENT DOCUMENTS

| | | |
|---|---|---|
| EP | 1 522 582 A2 | 4/2005 |
| EP | 1677094 A2 | 7/2006 |
| EP | 1 522 582 B1 | 4/2007 |
| GB | 1 503 163 | 3/1978 |
| GB | 2 097 692 | 11/1982 |
| JP | 0295433 | 4/1990 |
| JP | 08035971 A | 2/1996 |
| JP | 2002505439 A | 2/2002 |
| JP | 2006180810 A | 7/2006 |
| JP | 2007175002 A | 7/2007 |
| JP | 2009536313 A | 10/2009 |
| JP | 2009538123 A | 11/2009 |
| JP | 2010506136 A | 2/2010 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 9944740 A1 | 9/1999 |
| WO | 0078455 A1 | 12/2000 |
| WO | 01/07159 | 2/2001 |
| WO | 01/12327 | 2/2001 |
| WO | 02/23163 | 3/2002 |
| WO | 02/060584 | 8/2002 |
| WO | 02063288 A1 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03052428 A1 | 6/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2006128098 A2 | 11/2006 |
| WO | 2007081385 A2 | 7/2007 |
| WO | 2007/091228 | 8/2007 |
| WO | 2007/091230 | 8/2007 |
| WO | 2007/092473 | 8/2007 |
| WO | 2007121489 A2 | 10/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008063227 A2 | 5/2008 |
| WO | 2008/070074 | 6/2008 |
| WO | 2008/070862 | 6/2008 |
| WO | 2008/109176 | 9/2008 |
| WO | 2008/109878 | 9/2008 |

(56) References Cited

FOREIGN PATENT DOCUMENTS

| WO | 2008/112177 | 9/2008 |
|---|---|---|
| WO | 2008109176 A3 | 9/2008 |
| WO | 2009/002920 | 12/2008 |
| WO | 2008148200 A1 | 12/2008 |
| WO | 2009/015863 | 2/2009 |
| WO | 2009/049889 | 4/2009 |
| WO | 2009/085246 | 7/2009 |
| WO | 2009152520 A2 | 12/2009 |
| WO | 2010/001419 | 1/2010 |
| WO | 2010/018465 | 2/2010 |
| WO | 2010036352 A1 | 4/2010 |
| WO | 2011/034621 | 3/2011 |
| WO | 2011/079176 | 6/2011 |

OTHER PUBLICATIONS

United States Patent and Trademark Office, Patent Trial and Appeal Board, "Decision Denying Institution of Inter Partes Review" related to IPR Case No. IPR2018-00301, dated Jun. 15, 2018, 21 pgs.

United States Patent and Trademark Office, Patent Trial and Appeal Board, "Decision Denying Institution of Inter Partes Review" related to IPR Case No. IPR2018-00302, dated Jun. 15, 2018, 23 pgs.

United States Patent and Trademark Office, Patent Trial and Appeal Board, "Decision Denying Institution of Inter Partes Review" related to IPR Case No. IPR2018-00489, dated Jun. 28, 2018, 23 pgs.

United States Patent and Trademark Office, Patent Trial and Appeal Board, "Decision Denying Institution of Inter Partes Review" related to IPR Case No. IPR2018-00490, dated Jun. 28, 2018, 25 pgs.

United States Patent and Trademark Office, Patent Trial and Appeal Board, "Decision Denying Institution of Inter Partes Review" related to IPR Case No. IPR2018-00432, dated Jun. 29, 2018, 20 pgs.

United States Patent and Trademark Office, Patent Trial and Appeal Board, "Decision Denying Institution of Inter Partes Review" related to IPR Case No. IPR2018-00433, dated Jun. 29, 2018, 23 pgs.

United States Patent and Trademark Office, Patent Trial and Appeal Board, "Decision Denying Institution of Inter Partes Review" related to IPR Case No. IPR2018-00434, dated Jun. 29, 2018, 22 pgs.

3M Specialty Materials, "3M Fluorinert Electronic Liquid FC-3283," product information guide, issued Aug. 2001.

A. Chittofrati et al., "Perfluoropolyether microemulsions," Progress in Colloid & Polymer Science 79, pp. 218-225, (1989).

A. Scherer, California Institute of Technology, "Polymerase Chain Reactors" PowerPoint presentation, 24 pgs., date unknown.

A. V. Yazdi et al., "Highly Carbon Dioxide Soluble Surfactants, Dispersants and Chelating Agents," Fluid Phase Equilibria, vol. 117, pp. 297-303, (1996).

Adam R. Abate et al., "Functionalized glass coating for PDMS microfluidic devices," Lab on a Chip Technology: Fabrication and Microfluidics, 11 pgs., (2009).

Amelia L. Markey et al., "High-throughput droplet PCR," Methods, vol. 50, pp. 277-281, Feb. 2, 2010.

Andrew D. Griffiths et al., "Miniaturising the laboratory in emulsion droplets," Trends in Biotechnology, vol. 24, No. 9, pp. 395-402, Jul. 14, 2006.

Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

Anna Musyanovych et al., "Miniemulsion Droplets as Single Molecule Nanoreactors for Polymerase Chain Reaction," Biomacromolecules, vol. 6, No. 4, pp. 1824-1828, (2005).

Anthony J. O'Lenick, Jr., "Silicone Emulsions and Surfactants—A Review," Silicone Spectator, Silitech LLC, May 2009 (original published May 2000).

Anthony J. O'Lenick, Jr., "Silicone Emulsions and Surfactants," Journal of Surfactants and Detergents, vol. 3, No. 3, Jul. 2000.

Anthony P. Shuber et al., "A Simplified Procedure for Developing Multiplex PCRs," Genome Research, published by Cold Spring Harbor Laboratory Press, pp. 488-493, (1995).

Ariel A. Avilion et al., "Human Telomerase RNA and Telomerase Activity in Immortal Cell Lines and Tumor Tissues," Cancer Research 56, pp. 645-650, Feb. 1, 1996.

Avishay Bransky et al., "A microfluidic droplet generator based on a piezoelectric actuator," Lab on a Chip, vol. 9, pp. 516-520, Nov. 20, 2008.

Bernhard G. Zimmermann et al., "Digital PCR: a powerful new tool for noninvasive prenatal diagnosis?," Prenatal Diagnosis, vol. 28 pp. 1087-1093, Nov. 10, 2008.

Bert Vogelstein et al., "Digital PCR," Proc. Natl. Acad. Sci. USA, vol. 96, pp. 9236-9241, Aug. 1999.

Burcu Kekevi et al., Synthesis and Characterization of Silicone-Based Surfactants as Anti-Foaming Agents, J. Surfact Deterg (2012), vol. 15, pp. 73-81, published online Jul. 7, 2011.

C. Holtze et al., "Biocompatible surfactants for water-in-fluorocarbon emulsions," Lab on a Chip, vol. 8, pp. 1632-1639, Sep. 2, 2008.

Charles N. Baroud et al., "Thermocapillary valve for droplet production and sorting," Physical Review E 75, 046302, pp. 046302-1-046302-5, Apr. 5, 2007.

Chia-Hung Chen et al., "Janus Particles Templated from Double Emulsion Droplets Generated Using Microfluidics," Langmuir, vol. 29, No. 8, pp. 4320-4323, Mar. 18, 2009.

Chloroform (Phenomenex), Solvent Miscibility Table, Internet Archive WayBackMachine, 3 pgs., Feb. 1, 2008.

Christopher B. Price, "Regular Review Point of Care Testing," BMJ, vol. 322, May 26, 2001.

Chunming Ding et al., "Direct molecular haplotyping of long-range genomic DNA with M1-PCR," PNAS, vol. 100, No. 13, pp. 7449-7453, Jun. 24, 2003.

Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).

Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.

Darren R. Link et al., "Electric Control of Droplets in Microfluidic Devices," Angewandte Chemie Int. Ed., vol. 45, pp. 2556-2560, (2006).

David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.

David Emerson et al., "Microfluidic Modelling Activities at C3M," Centre for Microfluidics & Microsystems Modelling, Daresbury Laboratory, pp. 1-26, May 15, 2006.

Dayong Jin et al., "Practical Time-Gated Luminescence Flow Cytometry. II: Experimental Evaluation Using UV LED Excitation," Cytometry Part A • 71A, pp. 797-808, Aug. 24, 2007.

Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).

Devin Dressman et al., "Transforming single DNA molecules into fluorescent magnetic particles for detection and enumeration of genetic variations," PNAS, vol. 100, No. 15, Jul. 22, 2003.

Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.

(56) References Cited

OTHER PUBLICATIONS

E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.
Edith J. Singley et al., "Phase behavior and emulsion formation of novel fluoroether amphiphiles in carbon dioxide," Fluid Phase Equilibria 128, pp. 199-219, (1997).
Eschenback Optik GMBH, Optics for Concentrated Photovoltaics (CPV), 1 pg., date unknown.
Frank Diehl et al., "Digital quantification of mutant DNA in cancer patients," Current Opinion in Oncology, vol. 19, pp. 36-42, (2007).
Frank McCaughan et al., "Single-molecule genomics," Journal of Pathology, vol. 220, pp. 297-306, Nov. 19, 2009.
Goldschmidt GMBH, "Abil® EM 90 Emulsifier for the formulation of cosmetic W/O creams and lotions," degussa. creating essentials brochure, pp. 1-7, May 2003.
Groff M. Schroeder et al., "Introduction to Flow Cytometry" version 5.1, 182 pgs. (2004).
Gudrun Pohl et al., "Principle and applications of digital PCR" review, www.future-drugs.com, Expert Rev. Mol. Diagn. 4(1), pp. 41-47, (2004).
Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Hidenori Nagai et al., "Development of a Microchamber Array for Picoliter PCR," Analytical Chemistry, vol. 73, No. 5, pp. 1043-1047, Mar. 1, 2001.
Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).
Ivonne Schneegaß et al., "Miniaturized flow-through PCR with different template types in a silicon chip thermocycler," Lab on a Chip, vol. 1, pp. 42-49, (2001).
J. Smid-Korbar et al., "Efficiency and usability of silicone surfactants in emulsions," International Journal of Cosmetic Science 12, pp. 135-139, (1990), presented at the 15$^{th}$ IFSCC International Congress, Sep. 26-29, 1988, London.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
James G. Wetmur, et al., "Linking Emulsion PCR Haplotype Analysis," PCR Protocols, Methods in Molecular Biology, vol. 687, pp. 165-175, (2011).
Jay Shendure et al., "Next-generation DNA sequencing," Nature Biotechnology, vol. 26, No. 10, pp. 1135-1145, Oct. 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Jian Qin et al., "Studying copy number variations using a nanofluidic platform," Nucleic Acids Research, vol. 36, No. 18, pp. 1-8, Aug. 18, 2008.
Jian-Bing Fan et al., "Highly parallel genomic assays," Nature Reviews/Genetics, vol. 7, pp. 632-644, Aug. 2006.
Jiaqi Huang et al., "Rapid Screening of Complex DNA Samples by Single-Molecule Amplification and Sequencing," PLoS ONE, vol. 6, Issue 5, pp. 1-4, May 2011.
John H. Leamon et al., "Overview: methods and applications for droplet compartmentalization of biology," Nature Methods, vol. 3, No. 7, pp. 541-543, Jul. 2006.
Jonas Jarvius et al., "Digital quantification using amplified single-molecule detection," Nature Methods, vol. 3, No. 9, pp. 15 pgs, Sep. 2006.
Kan Liu et al., "Droplet-based synthetic method using microflow focusing and droplet fusion," Microfluid Nanfluid, vol. 3, pp. 239-243, (2007), published online Sep. 22, 2006.

Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
Kristofer J. Thurecht et al., "Investigation of spontaneous microemulsion formation in supercritical carbon dioxide using high-pressure NMR," Journal of Supercritical Fluids, vol. 38, pp. 111-118, (2006).
Kristofer J. Thurecht et al., "Kinetics of Enzymatic Ring-Opening Polymerization of ε-Caprolactone in Supercritical Carbon Dioxide," Macromolecules, vol. 39, pp. 7967-7972, (2006).
L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Labsmith, "CapTite™ Microfluidic Interconnects" webpage, downloaded Jul. 11, 2012.
Labsmith, "Microfluid Components" webpage, downloaded Jul. 11, 2012.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Lung-Hsin Hung et al., "Rapid microfabrication of solvent-resistant biocompatible microfluidic devices," Lab on a Chip, vol. 8, pp. 983-987, Apr. 8, 2008.
M. Gasperlin et al., "The structure elucidation of semisolid w/o emulsion systems containing silicone surfactant," International Journal of Pharmaceutics 107, pp. 51-56, (1994).
Machiko Hori et al., "Uniform amplification of multiple DNAs by emulsion PCR," Biochemical and Biophysical Research Communications, vol. 352, pp. 323-328, (2007).
Marcel Margulies et al., "Genome sequencing in microfabricated high-density picolitre reactors," Nature, vol. 437, 51 pgs., Sep. 15, 2005.
Margaret Macris Kiss et al., "High-Throughput Quantitative Polymerase Chain Reaction in Picoliter Droplets," Analytical Chemistry, 8 pgs., downloaded Nov. 17, 2008.
Mats Gullberg et al., "Cytokine detection by antibody-based proximity ligation," PNAS, vol. 101, No. 22, pp. 8420-8424, Jun. 1, 2004.
Max Chabert et al., "Droplet fusion by alternating current (AC) field electrocoalescence in microchannels," Electrophoresis, vol. 26, pp. 3706-3715, (2005).
Mieczyslaw A. Piatyszek et al., "Detection of telomerase activity in human cells and tumors by a telomeric repeat amplification protocol (TRAP)," Methods in Cell Science 17, pp. 1-15, (1995).
Mohamed Abdelgawad et al., "All-terrain droplet actuation," Lab on a Chip, vol. 8, pp. 672-677, Apr. 2, 2008.
N. Garti et al., "Water Solubilization in Nonionic Microemulsions Stabilized by Grafted Siliconic Emulsifiers," Journal of Colloid and Interface Science vol. 233, pp. 286-294, (2001).
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
N. Reginald Beer et al., "On-Chip, Real-Time, Single-Coy Polymerase Chain Reaction in Picoliter Droplets," Analytical Chemistry, vol. 79, No. 22, pp. 8471-8475, Nov. 15, 2007.
Nathan A. Tanner et al., "Simultaneous multiple target detection in real-time loop-mediated isothermal amplification," BioTechniques, vol. 53, pp. 8-19, Aug. 2012.
Nathan Blow, "PCR's next frontier," Nature Methods, vol. 4, No. 10, pp. 869-875, Oct. 2007.

(56) References Cited

OTHER PUBLICATIONS

Neil Reginald Beer et al., "Monodisperse droplet generation and rapid trapping for single molecule detection and reaction kinetics measurement," Lab on a Chip, vol. 9, pp. 841-844, Dec. 5, 2008.
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Nicole L. Solimini et al., "Recurrent Hemizygous Deletions in Cancers May Optimize Proliferative Potential," Science, vol. 337, pp. 104-109, Jul. 6, 2012.
Nicole Pamme, "continuous flow separations in microfluidic devices," Lab on a Chip, vol. 7, pp. 1644-1659, Nov. 2, 2007.
Olga Kalinina et al., "Nanoliter scale PCR with TaqMan Detection," Nucleic Acids Research, vol. 25, No. 10 pp. 1999-2004, (1997).
Palani Kumaresan et al., "High-Throughput Single Copy DNA Amplification and Cell Analysis in Engineered Nanoliter Droplets," Analytical Chemistry, 17 pgs., Apr. 15, 2008.
Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.
Paul Vulto et al., "Phaseguides: a paradigm shift in microfluidic priming and emptying," Lab on a Chip, vol. 11, No. 9, pp. 1561-1700, May 7, 2011.
Peter Fielden et al., "Micro-Droplet Technology for High Throughout Systems and Methods," 1 pg., Mar. 8, 2006.
Piotr Garstecki et al., "Formation of droplets and bubbles in a microfluidic T-junction—scaling and mechanism of break-up," Lab on a Chip, vol. 6, pp. 437-446, (2006).
Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Polydimethylsiloxane, 5 pgs., published in FNP 52 (1992).
Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).
Qinyu Ge et al., "Emulsion PCR-based method to detect Y chromosome microdeletions," Analytical Biochemistry, vol. 367, pp. 173-178, May 10, 2007.
Qun Zhong et al., "Multiplex digital PCR: breaking the one target per color barrier of quantitative PCR," Lab on a Chip, vol. 11, pp. 2167-2174, (2011).
R. G. Rutledge et al., "Mathematics of quantitative kinetic PCR and the application of standard curves," Nucleic Acids Research, vol. 31, No. 16, pp. 1-6, (2003).
R. G. Rutledge, "Sigmoidal curve-fitting redefines quantitative real-time PCR with the prospective of developing automated high-throughput applications," Nucleic Acids Research. vol. 32, No. 22, pp. 1-8, (2004).
Randla M. Hill, "Silicone surfactants—new developments," Current Opinion in Colloid & Interface Science 7, pp. 255-261, (2002).
Rhutesh K. Shah et al., "Polymers fit for function Making emulsions drop by drop," Materials Today, vol. 11, No. 4, pp. 18-27, Apr. 2008.
Richard M. Cawthon, "Telomere length measurement by a novel monochrome multiplex quantitative PCR method," Nucleic Acids Research, vol. 37, No. 3, pp. 1-7, (2009).
Richard M. Cawthon, "Telomere measurement by quantitative PCR," Nucleic Acids Research, vol. 30, No. 10, pp. 1-6, (2002).
Richard Williams et al., "Amplification of complex gene libraries by emulsion PCR," Nature Methods, vol. 3, No. 7, pp. 545-550, Jul. 2006.
Russell Higuchi et al., "Kinetic PCR Analysis: Real-time Monitoring of DNA Amplification Reactions," Bio/Technology vol. II, pp. 1026-1030, Sep. 11, 1993.
S. Mohr et al., "Numerical and experimental study of a droplet-based PCR chip," Microfluid Nanofluid, vol. 3, pp. 611-621, (2007).
Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.
Shelley L. Anna et al., "Formation of dispersions using "flow focusing" in microchannels," Applied Physics Letters, vol. 82, No. 3, Jan. 20, 2003.
Shia-Yen Teh et al., "Droplet microfluidics," Lab on a Chip, vol. 8, pp. 198-220, Jan. 11, 2008.
Shinji Katsura et al., "Indirect micromanipulation of single molecules in water-in-oil emulsion," Electrophoresis, vol. 22, pp. 289-293, (2001).
Shuming Nie et al., "Optical Detection of Single Molecules," Annu. Rev. Biophys. BiomoL Struct. vol. 26, pp. 567-596, (1997).
Sigma-Aldrich, "Synthesis of Mesoporous Materials," Material Matters, 3.1, 17, (2008).
Sigrun M. Gustafsdottir et al., "In vitro analysis of DNA-protein interactions by proximity ligation," PNAS, vol. 104, No. 9, pp. 3067-3072, Feb. 27, 2007.
Simant Dube et al., "Mathematical Analysis of Copy Number Variation in a DNA Sample Using Digital PCR on a Nanofluidic Device," PLoS ONE, vol. 3, Issue 8, pp. 1-9, Aug. 6, 2008.
Somanath Bhat et al., "Effect of sustained elevated temperature prior to amplification on template copy number estimation using digital polymerase chain reaction," Analyst, vol. 136, pp. 724-732, (2011).
Somil C. Mehta et a., "Mechanism of Stabilization of Silicone Oil-Water Emulsions Using Hybrid Siloxane Polymers," Langmuir, vol. 24, No. 9, pp. 4558-4563, Mar. 26, 2008.
Stéphane Swillens et al., "Instant evaluation of the absolute initial number of cDNA copies from a single real-time PCR curve," Nucleic Acids Research, vol. 32, No. 6, pp. 1-6, (2004).
Steven A. Snow, "Synthesis and Characterization of Zwitterionic Silicone Sulfobetaine Surfactants," Langmuir, vol. 6, No. 2, American Chemical Society, pp. 385-391, (1990).
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).
Tatjana Schütze et al., "A streamlined protocol for emulsion polymerase chain reaction and subsequent purification," Analytical Biochemistry, vol. 410, pp. 155-157, Nov. 25, 2010.
Thinxxs Microtechnology AG, "Emerald Biosystems: Protein Crystallization," 1 pg., downloaded Mar. 8, 2011.
Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
Toshko Zhelev et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).
Ulf Landegren et al., "Padlock and proximity probes for in situ and array-based analyses: tools for the post-genomic era," Comp. Funct. Genom, vol. 4, pp. 525-530, (2003).
Vivienne N. Luk et al., "Pluronic Additives: A Solution to Sticky Problems in Digital Microfluidics," Langmuir, vol. 24, No. 12, pp. 6382-6289, May 16, 2008.
Y. M. Dennis Lo et al., "Digital PCR for the molecular detection of fetal chromosomal aneuploidy," PNAS, vol. 104, No. 32, pp. 13116-13121, Aug. 7, 2007.
Y. Sela et al., "Newly designed polysiloxane-graft-poly (oxyethylene) copolymeric surfactants: preparation, surface activity and emulsification properties," Colloid & Polymer Science 272, pp. 684-691, (1994).
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.

(56) References Cited

OTHER PUBLICATIONS

Yoon Sung Nam et al., "Nanosized Emulsions Stabilized by Semi-solid Polymer Interphase," Langmuir, ACS Publications, Jul. 23, 2010.
Young, Lee W., Authorized officer, International Searching Authority, International Search Report, PCT Application Serial No. PCT/US2009/05317; dated Nov. 20, 2009.
Young, Lee W., Authorized officer, International Searching Authority, Written Opinion of the International Searching Authority, PCT Application Serial No. PCT/US2009/05317; dated Nov. 20, 2009.
Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Zhen Guo et al., "Enhanced discrimination of single nucleotide polymorphisms by artificial mismatch hybridization," Nature Biotechnology vol. 15, pp. 331-335, Apr. 1997.
Bécamel, Philippe, Authorized Officer, The International Bureau of WIPO, "International Preliminary Report on Patentability" in connection with related International App. No. PCT/US2011/030101, dated Sep. 25, 2012, 7 pgs.
Becker, Holger et al., "Polymer microfabrication technologies for microfluidic systems", Analytical and Bioanalytical Chemistry, vol. 390, Nov. 8, 2007, pp. 89-111.
Bernoulli Pressure Lowering, http:\hyperphysics, pp. 1-4, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 4 pgs.
Brody, James P. et al., "Biotechnology at Low Reynolds Numbers", Biophysical Journal. vol. 71, Dec. 1996, pp. 3430-3441.
Chien, Ring-Ling et al., "Multiport flow-control system for lab-on-a-chip microfluidic devices", Fresenius Journal of Analytical Chemistry, vol. 371, Jul. 27, 2001, pp. 106-111.
Complainant' Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00300 Petition filed Dec. 14, 2017, 4 pgs.
Complainant' Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00301 Petition filed Dec. 14, 2017, 4 pgs.
Complainant' Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00302 Petition filed Dec. 14, 2017, 4 pgs.
Complainant' Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00432 Petition filed Jan. 9, 2018, 4 pgs.
Complainant' Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00433 Petition filed Jan. 9, 2018, 4 pgs.
Complainant' Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00434 Petition filed Jan. 9, 2018, 4 pgs.
Complainant' Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00489 Petition filed Jan. 15, 2018, 4 pgs.
Complainant' Ground Rule 4 Notice of Patent Priority Dates, Dates of Conception, and Dates of Reduction to Practice, in the matter of Certain Microfluidic Devices, United States International Trade Commission Investigation No. 337-TA-1068, filed Nov. 17, 2017, included as Exhibit in IPR2018-00490 Petition filed Jan. 15, 2018, 4 pgs.
De Mello, Andrew J. et al., "Chip technology for micro-separation", BioMethods, vol. 10, (1999), pp. 129-177.
Duffy, David C. et al., Rapid Prototyping of Microfluidic Systems in Poly(dimethylsiloxane), Analytical Chemistry, vol. 70, No. 23, Dec. 1, 1998, pp. 4974-4984.
Falb, Peter W. et al., U.S. Appl. No. 61/047,377, filed Apr. 23, 2008, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 75 pgs.
Galambos, Paul et al., "Precision Alignment Packaging for Microsystems with Multiple Fluid Connections", Proceedings of 2001 ASME: International Mechanical Engineering Conference and Exposition, Nov. 11-16, 2001 New York, NY, 8 pgs.
Giffo-Schmitt, Beate, Authorized Officer, The International Bureau of WIPO, "International Preliminary Report on Patentability" in connection with related International Application No. PCT/US2009/005317, dated Mar. 29, 2011, 8 pgs.
IPR2018-00300 Petition for Inter Partes Review filed by 10X Genomics, Inc. on Dec. 14, 2017 before the Patent Trial and Appeal Board, including Declaration of Dr. Khushroo Gandhi (Exhibit 1003); Curriculum Vitae of Dr. Khushroo Gandhi (Exhibit 1045) and Declaration of Ruth G. Davila (Exhibit 1049), 235 pgs.
IPR2018-00301 Petition for Inter Partes Review filed by 10X Genomics, Inc. on Dec. 14, 2017 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1044), 246 pgs.
IPR2018-00302 Petition for Inter Partes Review filed by 10X Genomics, Inc. on Dec. 14, 2017 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1044), 223 pgs.
IPR2018-00432 Petition for Inter Partes Review filed by 10X Genomics, Inc. on Jan. 9, 2018 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1049), 241 pgs.
IPR2018-00433 Petition for Inter Partes Review filed by 10X Genomics, Inc. on Jan. 9, 2018 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1044), 246 pgs.
IPR2018-00434 Petition for Inter Partes Review filed by 10X Genomics, Inc. on Jan. 9, 2018 before the Patent Trial and Appeal Board, including Declaration of Dr. Khushroo Gandhi (Exhibit 1003); Curriculum Vitae of Dr. Khushroo Gandhi (Exhibit 1039) and Declaration of Ruth G. Davila (Exhibit 1044), 225 pgs.
IPR2018-00489 Petition for Inter Partes Review filed by 10X Genomics, Inc. on Jan. 15, 2018 before the Patent Trial and Appeal Board, including Declaration of Dr. Khushroo Gandhi (Exhibit 1003); Curriculum Vitae of Dr. Khushroo Gandhi (Exhibit 1045) and Declaration of Ruth G. Davila (Exhibit 1049), 240 pgs.
IPR2018-00490 Petition for Inter Partes Review filed by 10X Genomics, Inc. on Jan. 15, 2018 before the Patent Trial and Appeal Board, including Declaration of Dr. Khushroo Gandhi (Exhibit 1003); Curriculum Vitae of Dr. Khushroo Gandhi (Exhibit 1044), 243 pgs.
Kawai, A. et al., "Mass-Production System of Nearly Monodisperse Diameter Gel Particles Using Droplets Formation in a Microchannel", Micro Total Analysis Systems, vol. 1, 2002, pp. 368-370.

(56) References Cited

OTHER PUBLICATIONS

Kumacheva, Eugenia, U.S. Appl. No. 60/924,921, filed Jun. 5, 2007, included as an exhibit in IPR2018-00300, IPR2018-00301 and IPR2018-00302 Petitions filed Dec. 14, 2017 and IPR2018-00432, IPR2018-00433 and IPR2018-00434 Petitions filed Jan. 9, 2018, 46 pgs.

Li, Paul C. H. et al., "Microfluidic Lab-on-a-Chip", (Book Chapter) Ewing's Analytical Instrumentation Handbook Third Edition, (2005), pp. 581-679.

Mair, Dieudonne A. et al., "Injection molded microfluidic chips featuring integrated interconnects", Lab on a Chip, vol. 6, Jul. 31, 2006, pp. 1346-1354.

Merriam-Webster Dictionary definition of "Gasket", included as an exhibit in IPR2018-00300 Petition filed Dec. 14, 2017, 1 page.

Nisisako, Takasi et al., "Microfluidic large-scale integration on a chip for mass production of monodisperse droplets and particles", Lab on a Chip, vol. 8, (2008), pp. 287-293.

Whitesides, George M. et al., "Flexible Methods for Microfluidics", Physics Today, Jun. 2001, pp. 42-48.

www.smithbearing.com, Fractional, Letter & Number Drill Sizes, included as an exhibit in IPR2018-00301 Petition filed Dec. 14, 2017 and IPR2018-00433 Petition filed Jan. 9, 2018, 1 page.

Young, Lee W, Authorized Officer, International Searching Authority, Commissioner of Patents, "International Search Report" in connection with related International App. No. PCT/US2011/030101, dated Jun. 1, 2011, 2 pgs.

Young, Lee W., Authorized Officer, International Searching Authority, Commissioner of Patents, "International Search Report" in connection with related International App. No. PCT/US2011/030101, dated Jun. 1, 2011, 9 pgs.

Edgar, J. Scott et al., "Capillary Electrophoresis Separation in the Presence of an Immiscible Boundary for Droplet Analysis", Analytical Chemistry, vol. 78, No. 19, Oct. 1, 2006, pp. 6948-6954.

European Patent Office, "Extended European Search Report" in connection with related European Patent Application No. 09816582.2, dated Feb. 27, 2018, 12 pgs.

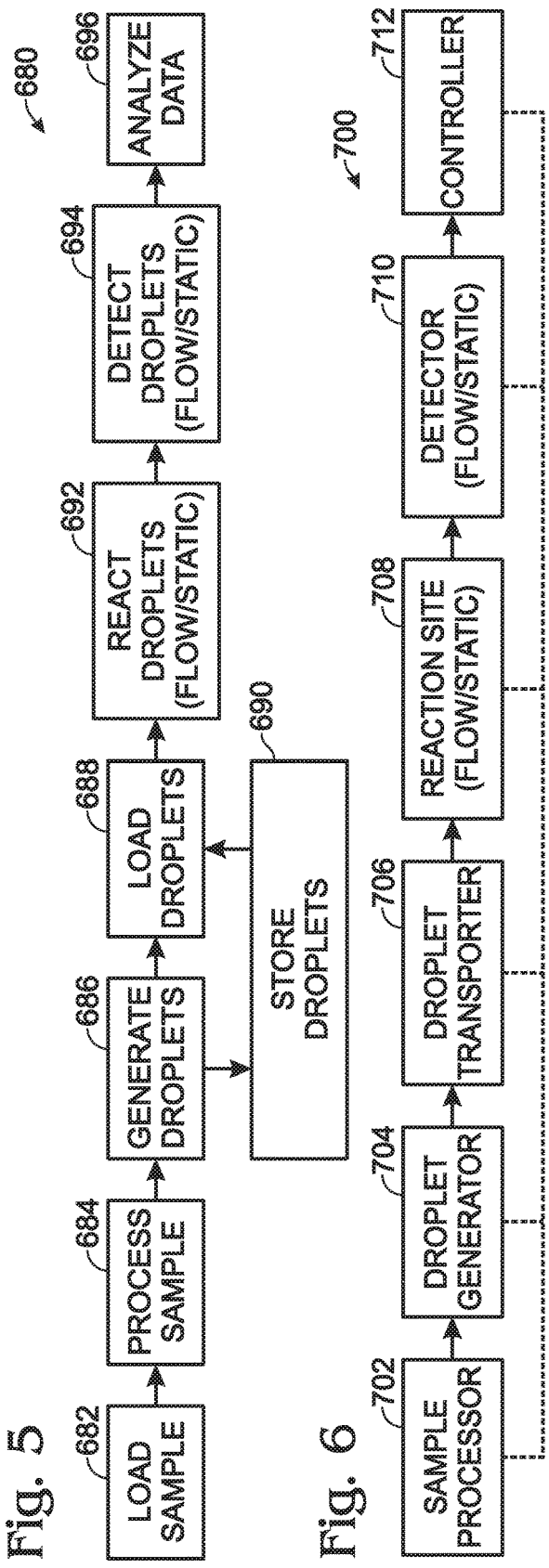

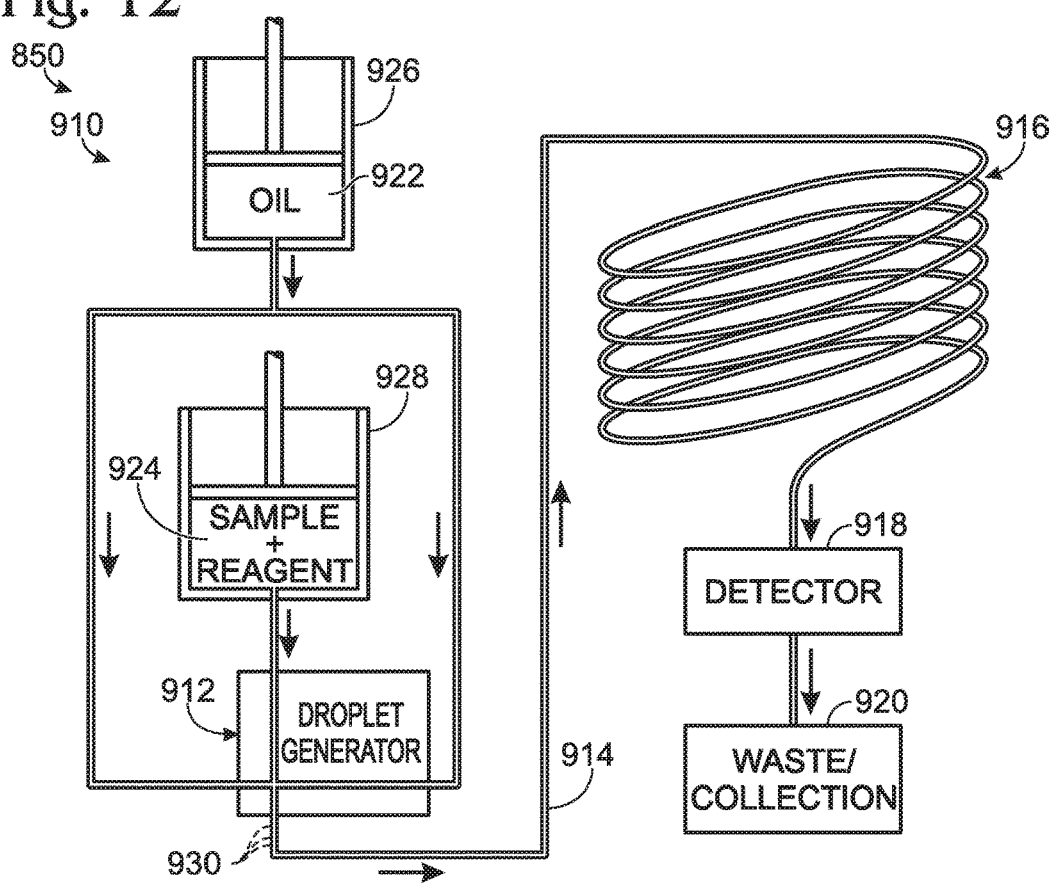
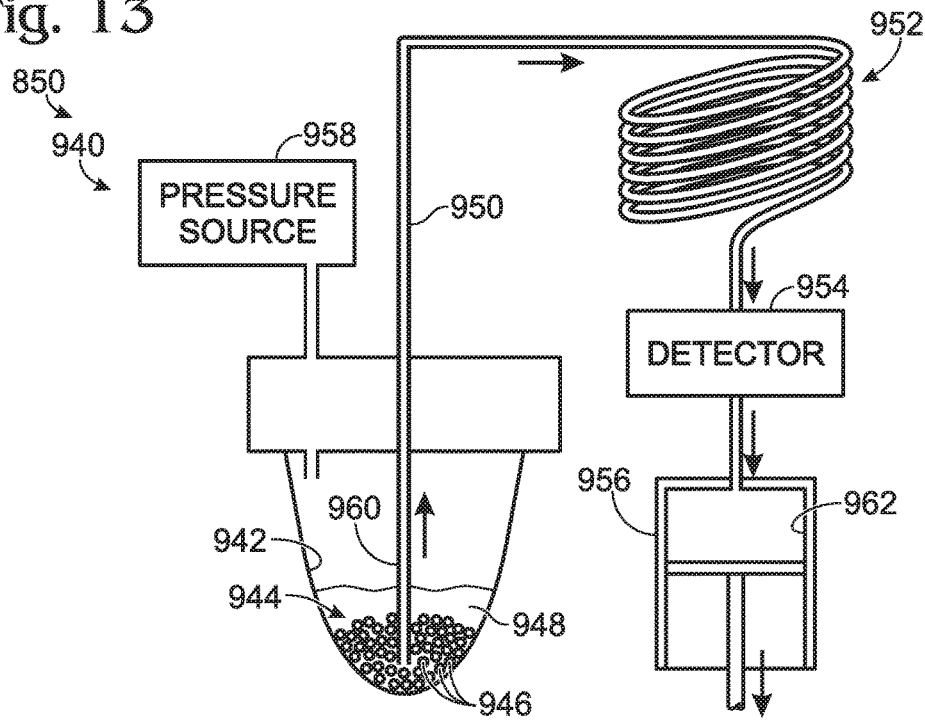

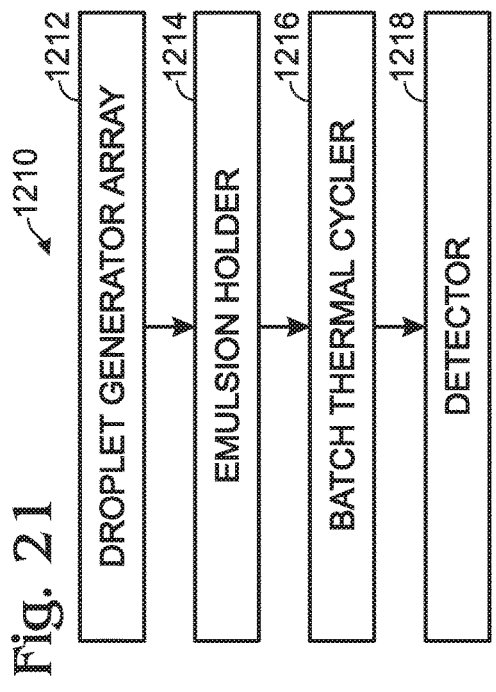
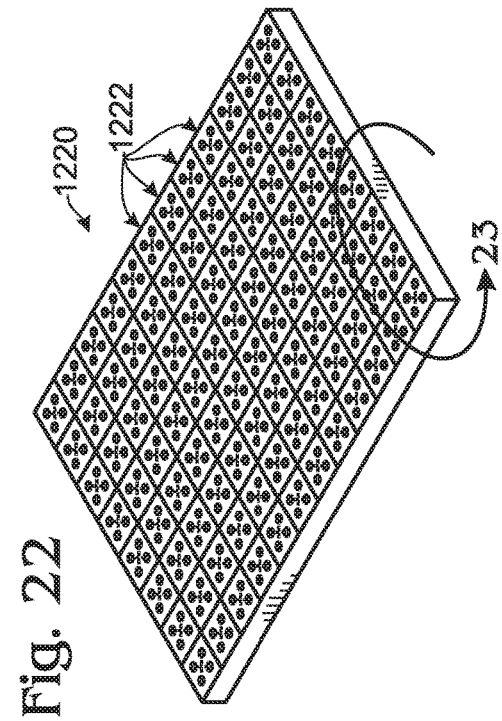
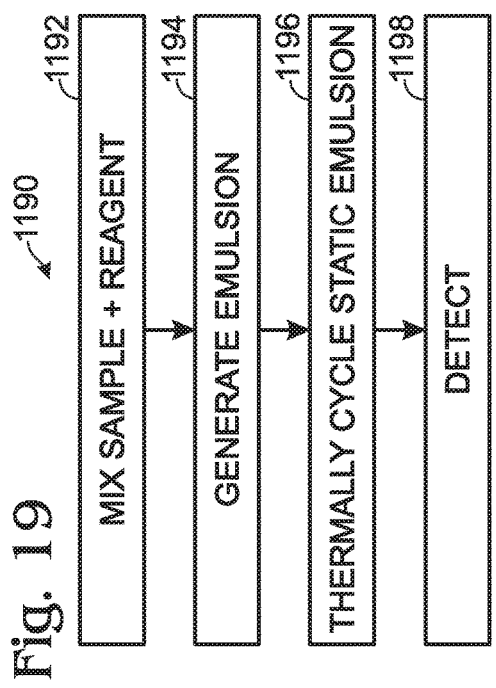
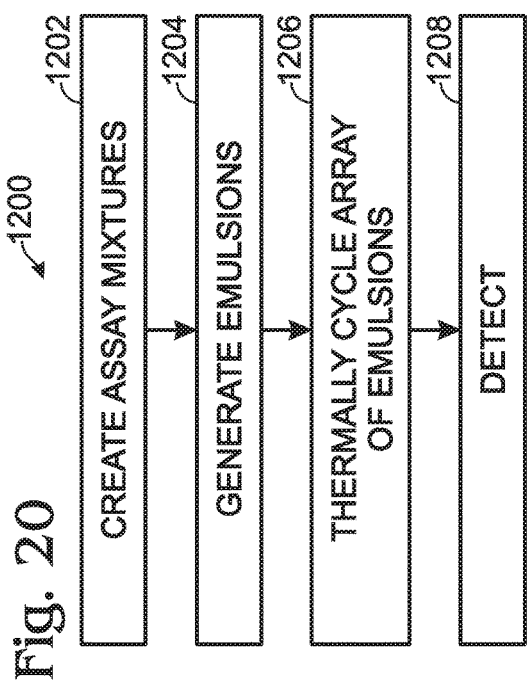

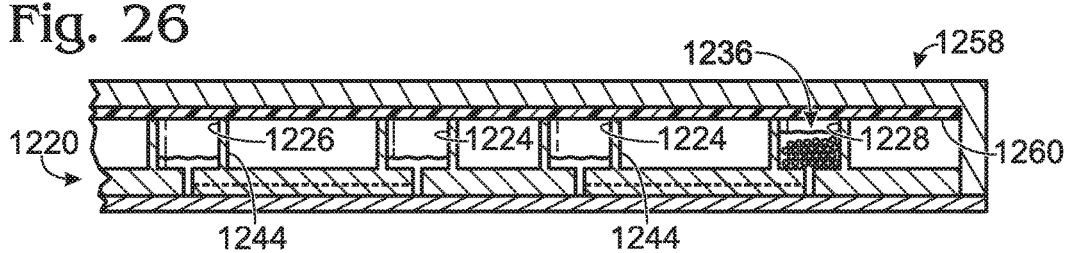
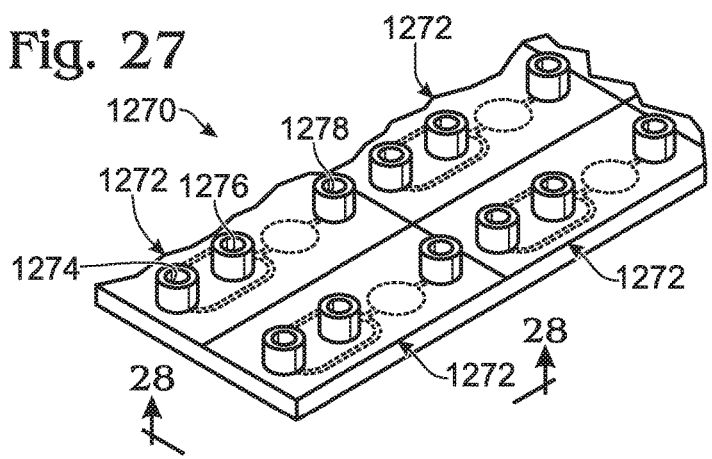
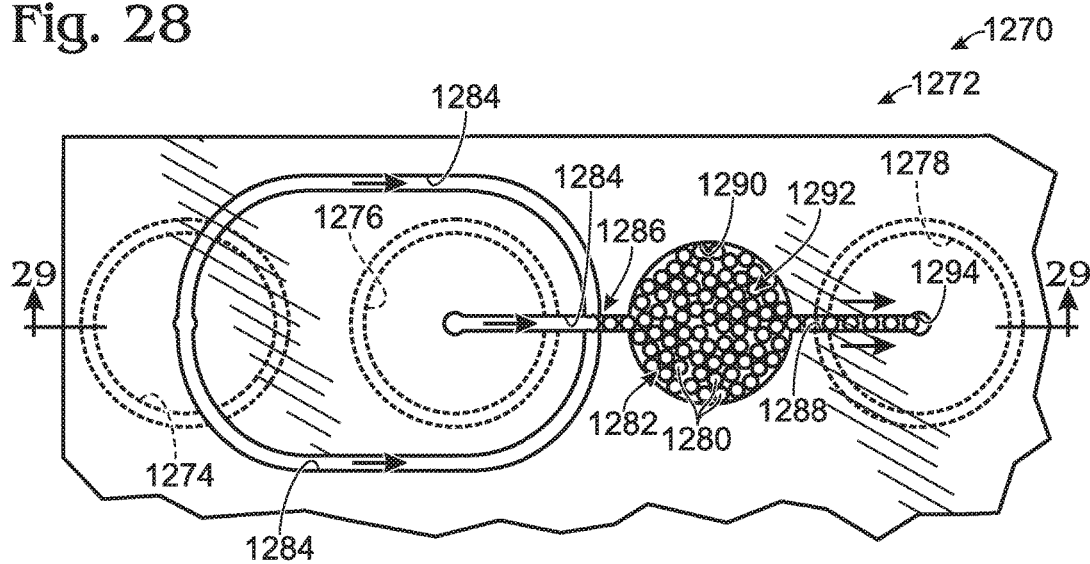

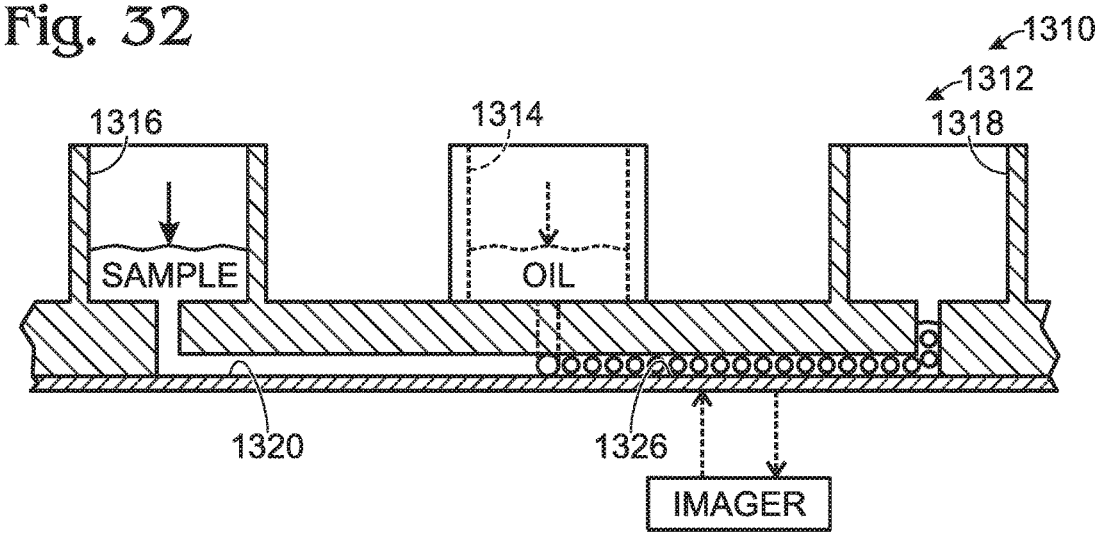
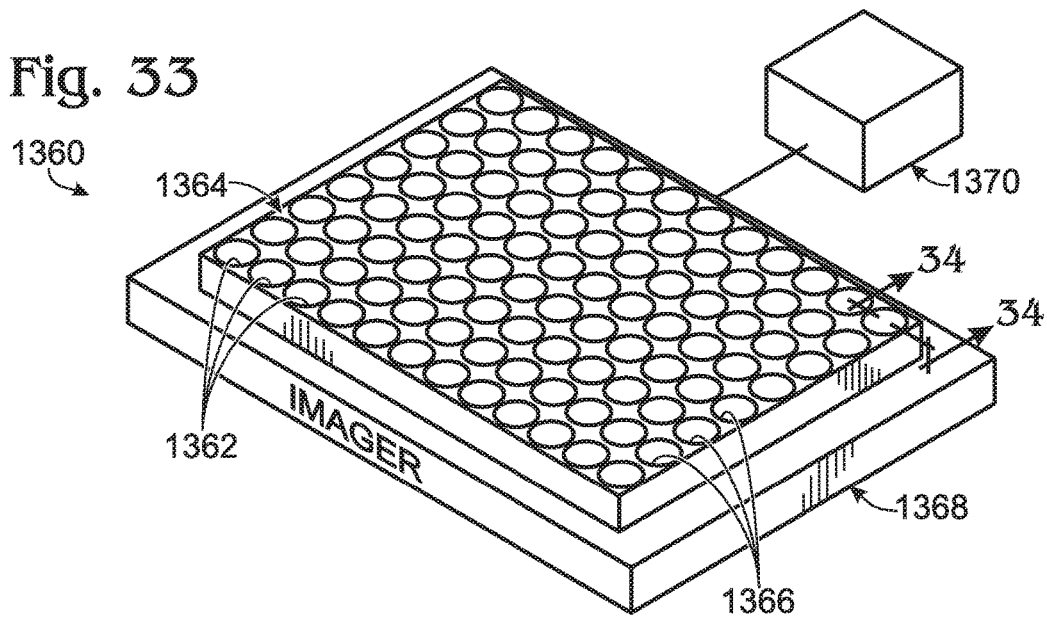
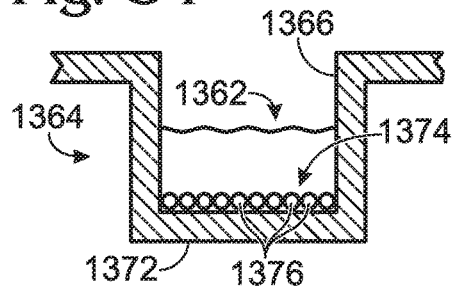

TO OTHER
REAGENT PUMPS

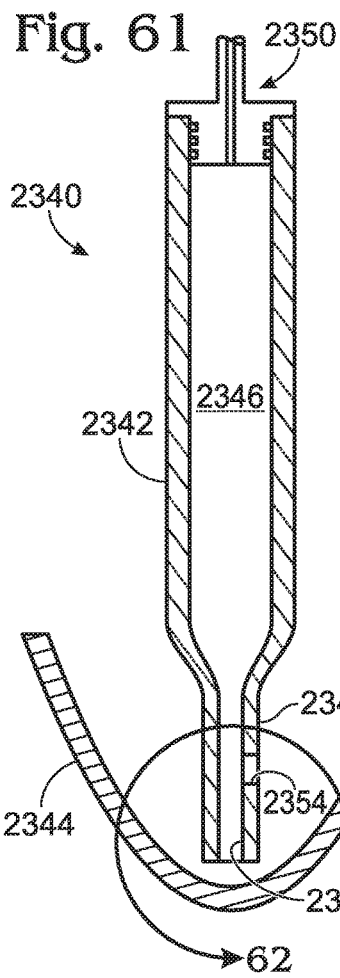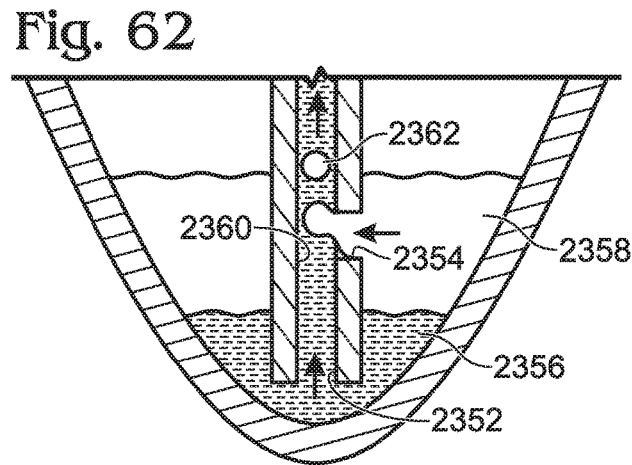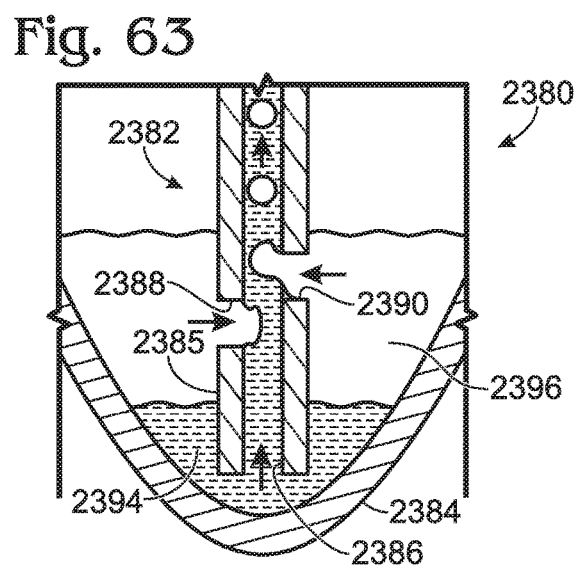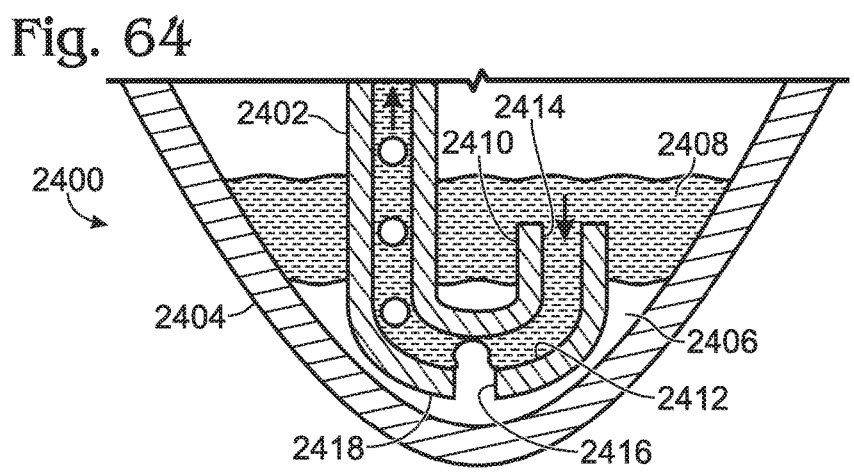

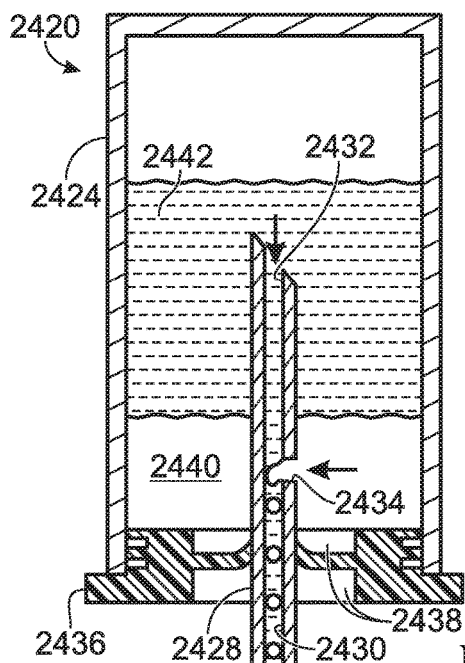
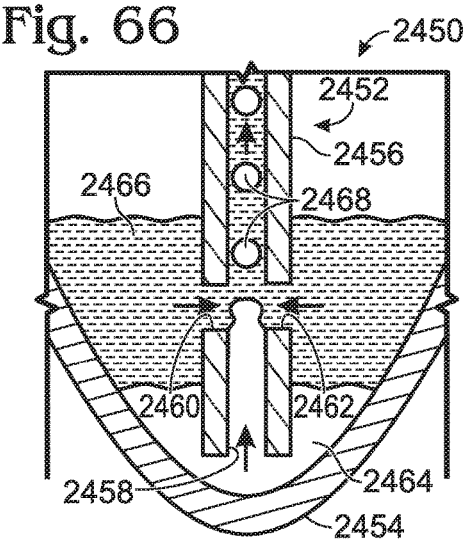
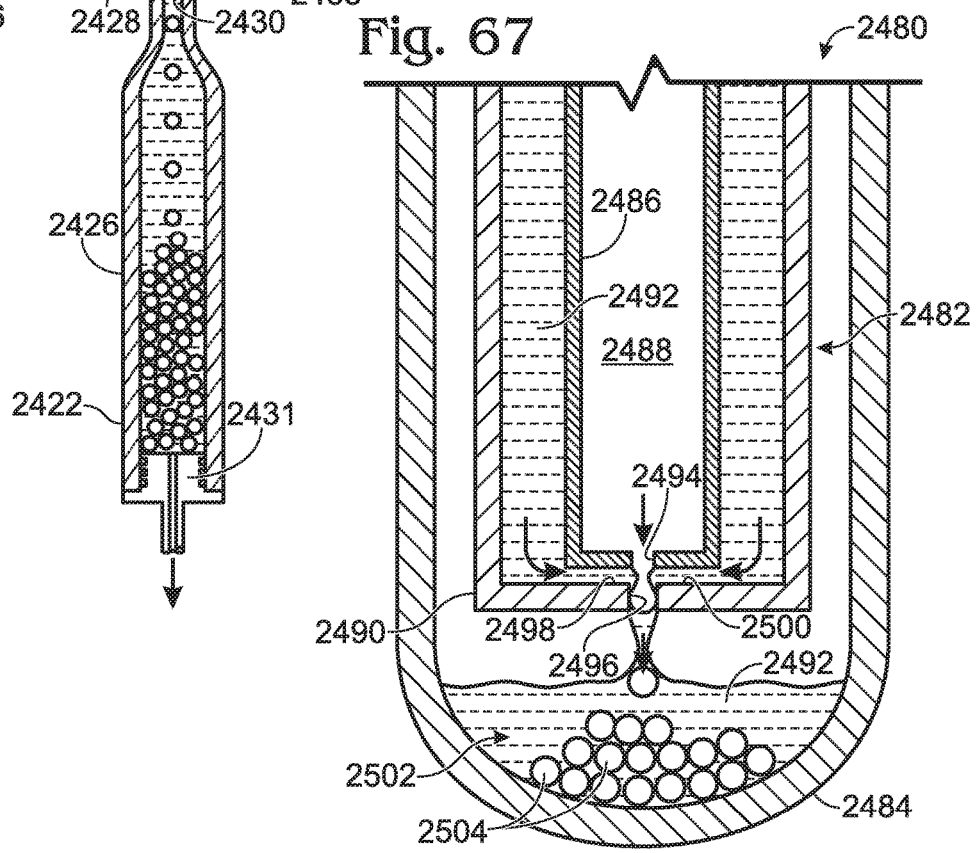

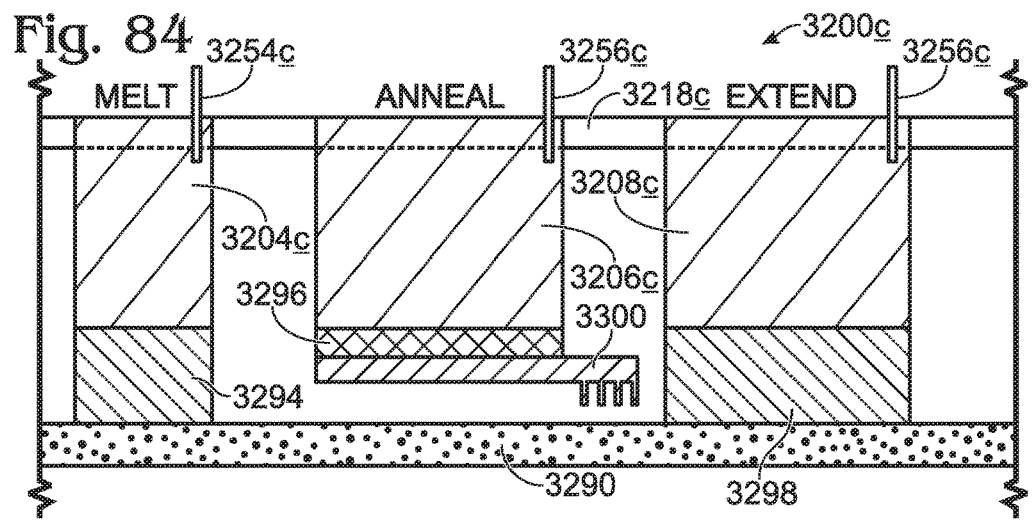
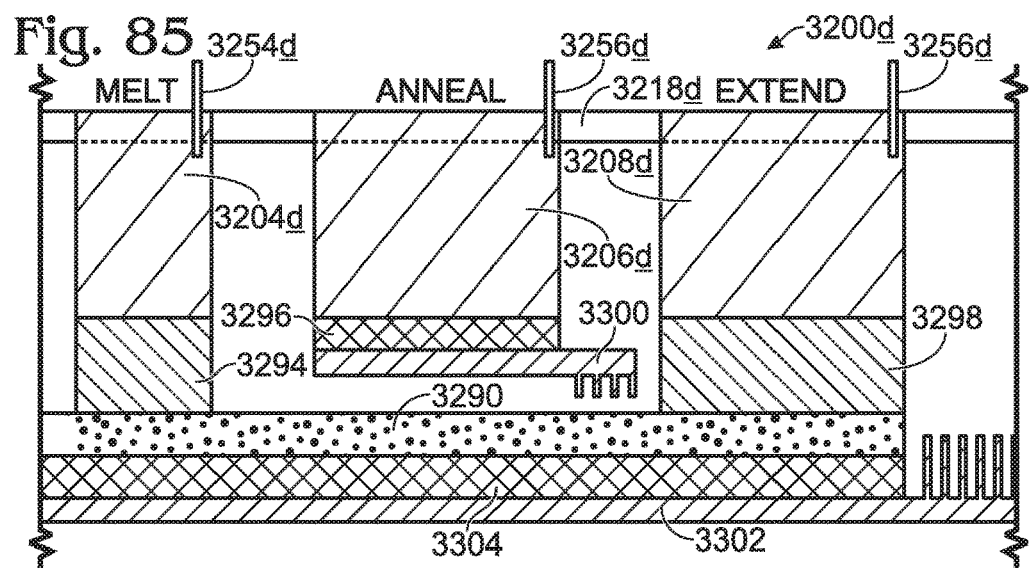
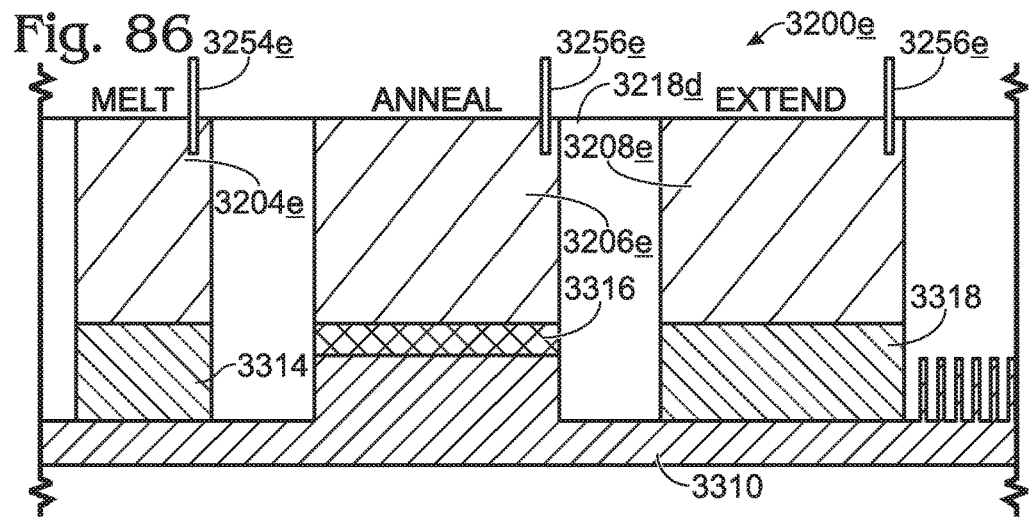

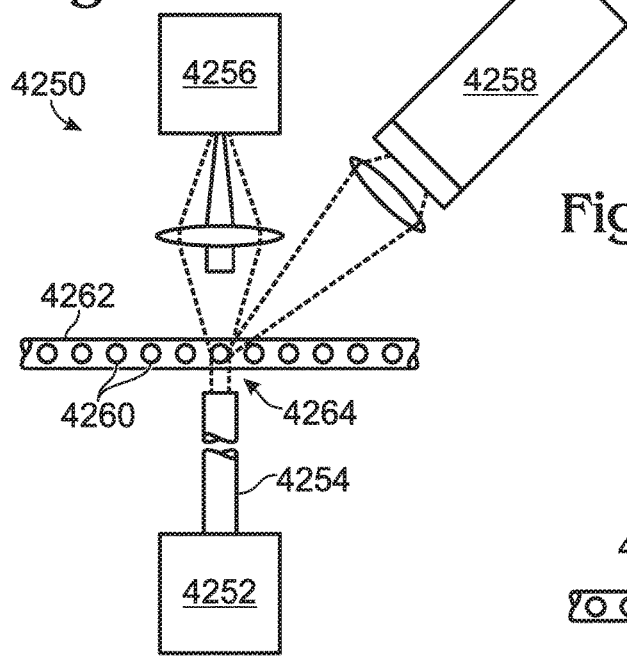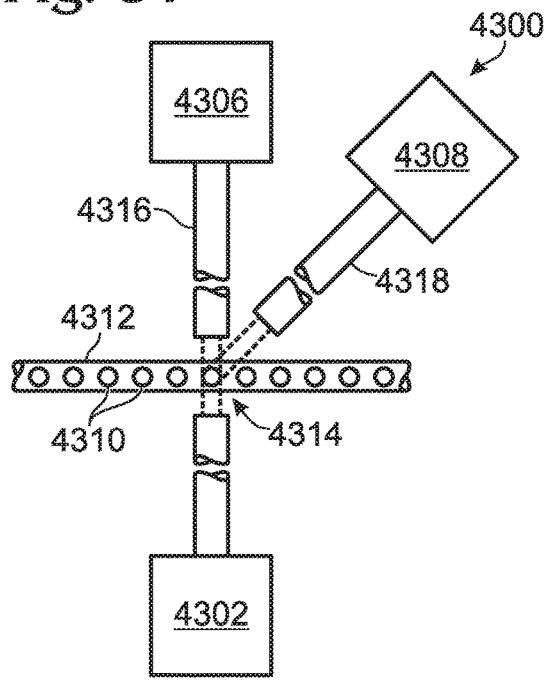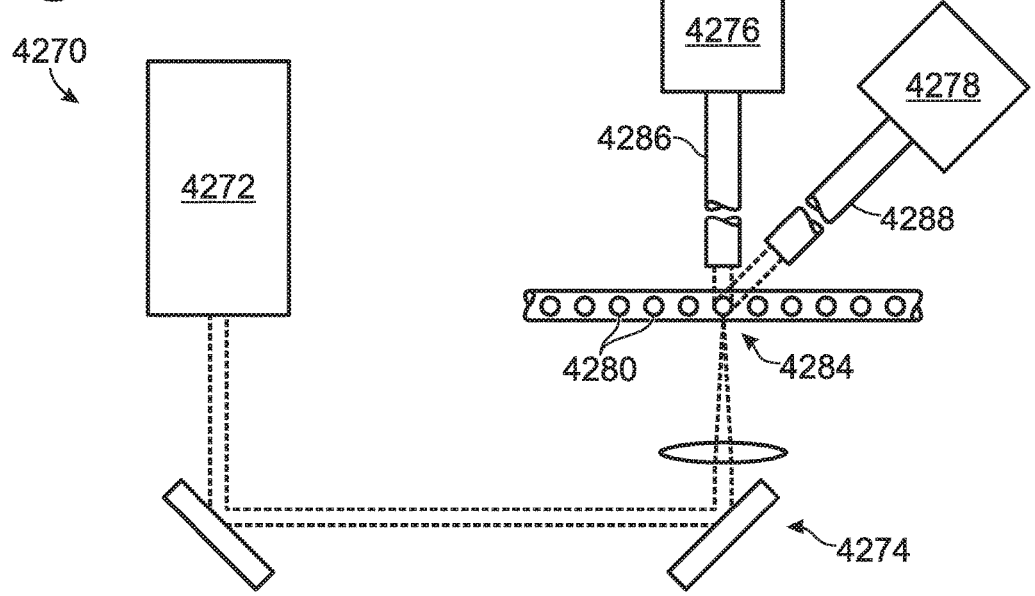

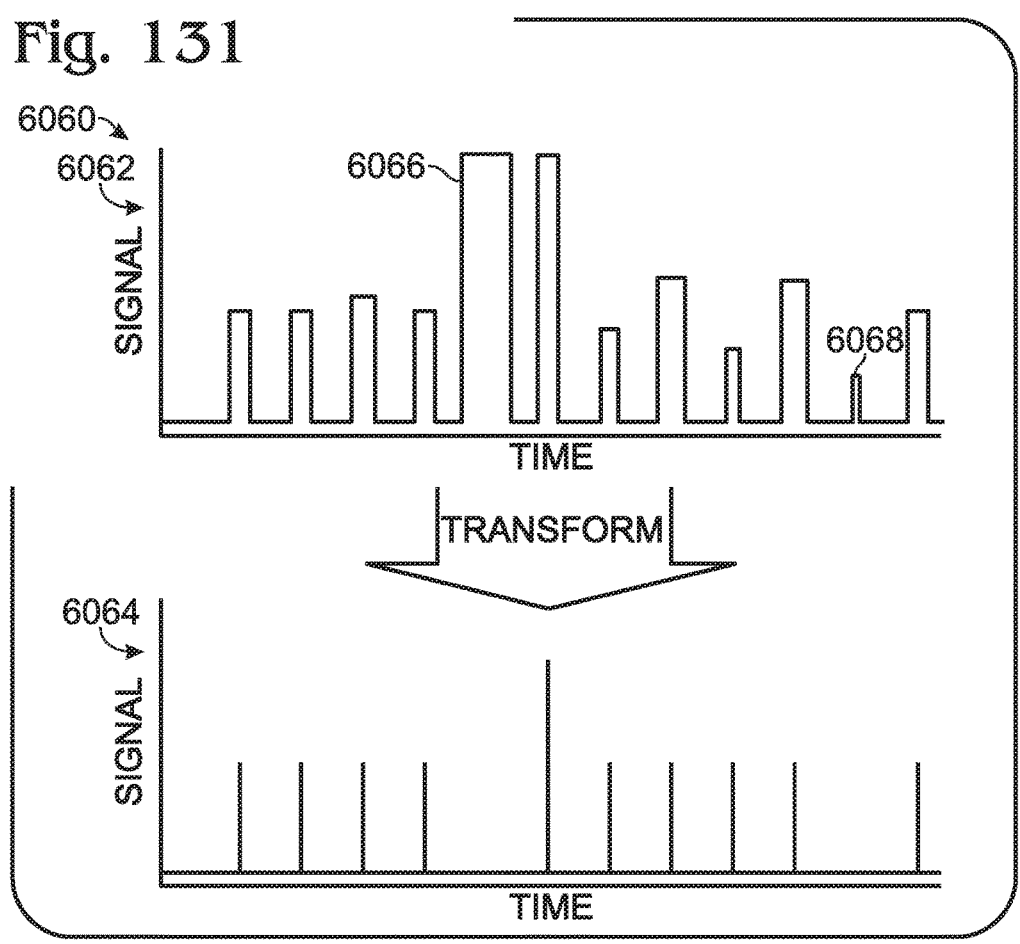

DEVICE FOR GENERATING DROPLETS

CROSS-REFERENCES TO PRIORITY APPLICATIONS

This application is a continuation of U.S. patent application Ser. No. 12/962,511, filed Dec. 7, 2010, now U.S. Pat. No. 9,623,384, which in turn is a continuation of U.S. patent application Ser. No. 12/586,626, filed Sep. 23, 2009, now U.S. Pat. No. 9,156,010, which in turn is based upon and claims the benefit under 35 U.S.C. § 119(e) of the following U.S. provisional patent applications: Ser. No. 61/194,043, filed Sep. 23, 2008; Ser. No. 61/206,975, filed Feb. 5, 2009; Ser. No. 61/271,538, filed Jul. 21, 2009; Ser. No. 61/275,731, filed Sep. 1, 2009; Ser. No. 61/277,200, filed Sep. 21, 2009; Ser. No. 61/277,203, filed Sep. 21, 2009; Ser. No. 61/277,204, filed Sep. 21, 2009; Ser. No. 61/277,216, filed Sep. 21, 2009; Ser. No. 61/277,249, filed Sep. 21, 2009; and Ser. No. 61/277,270, filed Sep. 22, 2009. These priority applications are incorporated herein by reference in their entireties for all purposes.

CROSS-REFERENCES TO OTHER MATERIALS

This application incorporates by reference in their entireties for all purposes the following materials: U.S. Pat. No. 7,041,481, issued May 9, 2006; and Joseph R. Lakowicz, PRINCIPLES OF FLUORESCENCE SPECTROSCOPY ($2^{nd}$ Ed. 1999).

INTRODUCTION

Assays are procedures for determining the presence, quantity, activity, and/or other properties or characteristics of components in a sample. In many cases, the samples to be assayed are complex, the components of interest within the samples—a nucleic acid, an enzyme, a virus, a bacterium, etc.—are only minor constituents of the samples, and the results of the assays are required quickly and/or for many samples. Unfortunately, current assay systems, such as polymerase chain reaction (PCR) assays for nucleic acids such as deoxyribonucleic acid (DNA), may be slow, sensitive to sample complexity, and/or prone to reporting false positives, among other disadvantages. Thus, there is a need for improved assay systems.

SUMMARY

The present disclosure provides devices and methods for generating droplets. An exemplary device comprises a substantially planar base portion including a bottom surface having a plurality of microfluidic channels formed therein as recessed regions of the bottom surface. The device also comprises a plurality of protrusions projecting from a top surface of the base portion and each formed integrally with the base portion. The device further comprises a sample well, a carrier well, and a droplet well. Each well has an upper portion created by one of the protrusions. A cover layer is attached to the bottom surface of the base portion and seals a bottom side of each microfluidic channel.

BRIEF DESCRIPTION OF THE DRAWINGS

FIG. 5 is a flowchart listing exemplary steps that may be performed in a method of sample analysis using droplet-based assays, in accordance with aspects of the present disclosure.

FIG. 6 is a schematic view of selected portions of an exemplary system for performing droplet-based assays, in accordance with aspects of the present disclosure.

FIG. 7 is a schematic view of an exemplary system with flow-based amplification, and with droplet generation and droplet loading that are decoupled from each other, in accordance with aspects of the present disclosure.

FIG. 12 is a schematic view of an example of the system of FIG. 10 in which droplet generation and droplet transport to a reaction site are coupled by continuous flow such that droplets are not stored, in accordance with aspects of the present disclosure.

FIG. 13 is a schematic view of an example of the system of FIG. 10 in which droplet generation and droplet transport to a reaction site are decoupled, such that droplets can be stored for an adjustable, selectable period of time after their generation and then loaded into the reaction site for droplet processing, in accordance with aspects of the present disclosure.

FIG. 19 is a flowchart listing exemplary steps that may be performed in a method of sample analysis using droplets subjected to conditions for amplification while disposed in a static fluid, in accordance with aspects of present disclosure.

FIG. 20 is a flowchart listing exemplary steps that may be performed in a method of sample analysis using parallel (batch) amplification of an array of emulsions, in accordance with aspects of the present disclosure.

FIG. 21 is a schematic view of selected portions of an exemplary system for performing the method of FIG. 20, in accordance with aspects of the present disclosure.

FIG. 22 is a view of an exemplary device equipped with an array of droplet generators, in accordance with aspects of the present disclosure.

FIG. 26 is a sectional view of the device of FIG. 22 taken as in FIG. 25, but with the pressure manifold replaced by an exemplary sealing member that seals wells of the device to permit thermal cycling, in accordance with aspects of present disclosure.

FIG. 27 is a fragmentary view of another exemplary device incorporating an array of droplet generators, in accordance with aspects of present disclosure.

FIG. 28 is a bottom view of a droplet generator of the device of FIG. 27, taken after droplet generation.

FIG. 32 is a sectional view of the droplet generator of FIG. 31, taken generally along line 32-32 of FIG. 31 and illustrating how droplets may be imaged from below the device.

FIG. 33 is a view of an exemplary imaging system for batch detection of an array of emulsions held by a plate, in accordance with aspects of the present disclosure.

FIG. 34 is a sectional view of the plate of FIG. 33, taken through a well of the plate, generally along line 34-34 of FIG. 33.

FIG. 61 is a cross-sectional side elevational view of a droplet generation system including a droplet generator and a fluid reservoir, in accordance with aspects of the present disclosure.

FIG. 62 is a magnified cross-sectional side elevational view of a distal portion of the droplet generation system of FIG. 61.

FIG. 63 is a cross-sectional side elevational view of a distal portion of another droplet generation system, in accordance with aspects of the present disclosure.

FIG. 64 is a cross-sectional side elevational view of a distal portion of yet another droplet generation system, in accordance with aspects of the present disclosure.

FIG. 65 is a cross-sectional side elevational view of still another droplet generation system, in accordance with aspects of the present disclosure.

FIG. 66 is a cross-sectional side elevational view of still another droplet generation system, in accordance with aspects of the present disclosure.

FIG. 67 is a cross-sectional side elevational view of still another droplet generation system, in accordance with aspects of the present disclosure.

FIGS. 82-89 are schematic sectional views of alternative embodiments of a thermocycler, in accordance with aspects of the present disclosure.

FIG. 95 is a schematic depiction of an optical detection system in which stimulating radiation is transferred toward sample-containing droplets through an optical fiber, in accordance with aspects of the present disclosure.

FIG. 96 is a schematic depiction of an optical detection system in which scattered and fluorescence radiation are transferred away from sample-containing droplets through optical fibers, in accordance with aspects of the present disclosure.

FIG. 97 is a schematic depiction of an optical detection system in which stimulating radiation is transferred toward sample-containing droplets through an optical fiber and in which scattered and fluorescence radiation are transferred away from the droplets through optical fibers, in accordance with aspects of the present disclosure.

FIG. 128 is a pair of graphs illustrating exemplary absorption and emission spectra of fluorescent dyes that may be suitable for use in the system of FIG. 114, in accordance with aspects of the present disclosure.

FIG. 129 is a schematic diagram illustrating exemplary use of the fluorescent dyes of FIG. 128 in an exemplary embodiment of the system of FIG. 114, in accordance with aspects of the present disclosure.

FIG. 130 is a flowchart of an exemplary approach to correcting for system variation within a test by processing a set of droplet test signals to a more uniform signal intensity, in accordance with aspects of the present disclosure.

FIG. 131 is a flowchart of an exemplary approach for transforming droplet signals based on the width of respective signal peaks providing the droplet signals, in accordance with aspects of the present disclosure.

DETAILED DESCRIPTION

The present disclosure provides systems, including apparatus and methods, for performing assays. These systems may involve, among others, (A) preparing a sample, such as a clinical or environmental sample, for analysis, (B) separating components of the samples by partitioning them into droplets or other partitions, each containing only about one component (such as a single copy of a nucleic acid target (DNA or RNA) or other analyte of interest), (C) amplifying or otherwise reacting the components within the droplets, (D) detecting the amplified or reacted components, or characteristics thereof, and/or (E) analyzing the resulting data. In this way, complex samples may be converted into a plurality of simpler, more easily analyzed samples, with concomitant reductions in background and assay times.

Figure 1:
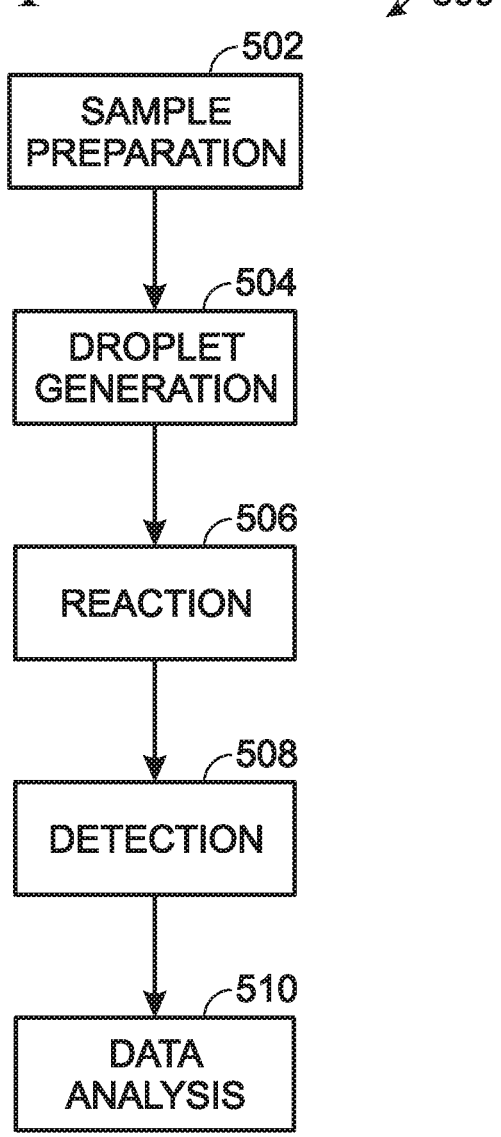
FIG. 1 is a flowchart listing exemplary steps that may be performed in a method of sample analysis using droplet-based assays, in accordance with aspects of the present disclosure.

FIG. 1 shows an exemplary system 500 for performing such a droplet-, or partition-, based assay. In brief, the system may include sample preparation 502, droplet generation 504, reaction (e.g., amplification) 506, detection 508, and data analysis 510. The system may be utilized to perform a digital PCR (polymerase chain reaction) analysis. More specifically, sample preparation 502 may involve collecting a sample, such as a clinical or environmental sample, treating the sample to release associated nucleic acids, and forming a reaction mixture involving the nucleic acids (e.g., for amplification of a target nucleic acid). Droplet generation 504 may involve encapsulating the nucleic acids in droplets, for example, with about one copy of each target nucleic acid per droplet, where the droplets are suspended in an immiscible carrier fluid, such as oil, to form an emulsion. Reaction 506 may involve subjecting the droplets to a suitable reaction, such as thermal cycling to induce PCR amplification, so that target nucleic acids, if any, within the droplets are amplified to form additional copies. Detection 508 may involve detecting some signal(s) from the droplets indicative of whether or not there was amplification. Finally, data analysis 510 may involve estimating a concentration of the target nucleic acid in the sample based on the percentage of droplets in which amplification occurred.

These and other aspects of the system are described below, in the following sections: (I) definitions, (II) system overview/architecture, (III) sample preparation/cartridge, (IV) droplet generator, (V) continuous flow thermocycler, (VI) detection, (VII) quantification/analysis, (VIII) controls and calibrations, (IX) clinical applications, and (X) multiplexed assays.

I. DEFINITIONS

Technical terms used in this disclosure have the meanings that are commonly recognized by those skilled in the art. However, the following terms may have additional meanings, as described below.

Emulsion—a composition comprising liquid droplets disposed in an immiscible carrier fluid, which also is liquid. The carrier fluid, also termed a background fluid, forms a continuous phase, which may be termed a carrier phase, a carrier, and/or a background phase. The droplets (e.g., aqueous droplets) are formed by at least one droplet fluid, also termed a foreground fluid, which is a liquid and which forms a droplet phase (which may be termed a dispersed phase or discontinuous phase). The droplet phase is immiscible with the continuous phase, which means that the droplet phase (i.e., the droplets) and the continuous phase (i.e., the carrier fluid) do not mix to attain homogeneity. The droplets are isolated from one another by the continuous phase and encapsulated (i.e., enclosed/surrounded) by the continuous phase.

The droplets of an emulsion may have any uniform or non-uniform distribution in the continuous phase. If non-uniform, the concentration of the droplets may vary to provide one or more regions of higher droplet density and one or more regions of lower droplet density in the continuous phase. For example, droplets may sink or float in the continuous phase, may be clustered in one or more packets along a channel, may be focused toward the center or perimeter of a flow stream, or the like.

Any of the emulsions disclosed herein may be monodisperse, that is, composed of droplets of at least generally uniform size, or may be polydisperse, that is, composed of droplets of various sizes. If monodisperse, the droplets of the emulsion may, for example, vary in volume by a standard deviation that is less than about plus or minus 100%, 50%, 20%, 10%, 5%, 2%, or 1% of the average droplet volume. Droplets generated from an orifice may be monodisperse or polydisperse.

An emulsion may have any suitable composition. The emulsion may be characterized by the predominant liquid compound or type of liquid compound in each phase. The predominant liquid compounds in the emulsion may be water and oil. "Oil" is any liquid compound or mixture of liquid compounds that is immiscible with water and that has a high content of carbon. In some examples, oil also may have a high content of hydrogen, fluorine, silicon, oxygen, or any combination thereof, among others. For example, any of the emulsions disclosed herein may be a water-in-oil (W/O) emulsion (i.e., aqueous droplets in a continuous oil phase). The oil may, for example, be or include at least one silicone oil, mineral oil, fluorocarbon oil, vegetable oil, or a combination thereof, among others. Any other suitable components may be present in any of the emulsion phases, such as at least one surfactant, reagent, sample (i.e., partitions thereof), other additive, label, particles, or any combination thereof.

Standard emulsions become unstable when heated (e.g., to temperatures above 60° C.) when they are in a packed state (e.g., each droplet is near a neighboring droplet), because heat generally lowers interfacial tensions, which can lead to droplet coalescence. Thus, standard packed emulsions do not maintain their integrity during high-temperature reactions, such as PCR, unless emulsion droplets are kept out of contact with one another or additives (e.g., other oil bases, surfactants, etc.) are used to modify the stability conditions (e.g., interfacial tension, viscosity, steric hindrance, etc.). For example, the droplets may be arranged in single file and spaced from one another along a channel to permit thermal cycling in order to perform PCR. However, following this approach using a standard emulsion does not permit a high density of droplets, thereby substantially limiting throughput in droplet-based assays.

Any emulsion disclosed herein may be a heat-stable emulsion. A heat-stable emulsion is any emulsion that resists coalescence when heated to at least 50° C. A heat-stable emulsion may be a PCR-stable emulsion, which is an emulsion that resists coalescence throughout the thermal cycling of PCR (e.g., to permit performance of digital PCR). Accordingly, a PCR-stable emulsion may be resistant to coalescence when heated to at least 80° C. or 90° C., among others. Due to heat stability, a PCR-stable emulsion, in contrast to a standard emulsion, enables PCR assays to be performed in droplets that remain substantially monodisperse throughout thermal cycling. Accordingly, digital PCR assays with PCR-stable emulsions may be substantially more quantitative than with standard emulsions. An emulsion may be formulated as PCR stable by, for example, proper selection of carrier fluid and surfactants, among others. An exemplary oil formulation to generate PCR-stable emulsions for flow-through assays is as follows: (1) Dow Corning 5225C Formulation Aid (10% active ingredient in decamethylcyclopentasiloxane)—20% w/w, 2% w/w final concentration active ingredient, (2) Dow Corning 749 Fluid (50% active ingredient in decamethylcyclopentasiloxane)—5% w/w, 2.5% w/w active ingredient, and (3) Poly(dimethylsiloxane) Dow Corning 200® fluid, viscosity 5.0 cSt (25° C.)—75% w/w. An exemplary oil formulation to generate PCR-stable emulsions for batch assays is as follows: (1) Dow Corning 5225C Formulation Aid (10% active ingredient in decamethylcyclopentasiloxane)—20% w/w, 2% w/w final concentration active ingredient, (2) Dow Corning 749 Fluid (50% active ingredient in decamethylcyclopentasiloxane)—60% w/w, 30% w/w active ingredient, and (3) Poly(dimethylsiloxane) Dow Corning 200® fluid, viscosity 5.0 cSt (25° C.)—20% w/w.

Partition—a separated portion of a bulk volume. The partition may be a sample partition generated from a sample, such as a prepared sample, that forms the bulk volume. Partitions generated from a bulk volume may be substantially uniform in size or may have distinct sizes (e.g., sets of partitions of two or more discrete, uniform sizes). Exemplary partitions are droplets. Partitions may also vary continuously in size with a predetermined size distribution or with a random size distribution.

Droplet—a small volume of liquid, typically with a spherical shape, encapsulated by an immiscible fluid, such as a continuous phase of an emulsion. The volume of a droplet, and/or the average volume of droplets in an emulsion, may, for example, be less than about one microliter (i.e., a "microdroplet") (or between about one microliter and one nanoliter or between about one microliter and one picoliter), less than about one nanoliter (or between about one nanoliter and one picoliter), or less than about one picoliter (or between about one picoliter and one femtoliter), among others. A droplet (or droplets of an emulsion) may have a diameter (or an average diameter) of less than about 1000, 100, or 10 micrometers, or of about 1000 to 10 micrometers, among others. A droplet may be spherical or nonspherical. A droplet may be a simple droplet or a compound droplet, that is, a droplet in which at least one droplet encapsulates at least one other droplet.

Surfactant—a surface-active agent capable of reducing the surface tension of a liquid in which it is dissolved, and/or the interfacial tension with another phase. A surfactant, which also or alternatively may be described as a detergent and/or a wetting agent, incorporates both a hydrophilic portion and a hydrophobic portion, which collectively confer a dual hydrophilic-lipophilic character on the surfactant. A surfactant may be characterized according to a Hydrophile-Lipophile Balance (HLB) value, which is a measure of the surfactant's hydrophilicity compared to its lipophilicity. HLB values range from 0-60 and define the relative affinity of a surfactant for water and oil. Nonionic surfactants generally have HLB values ranging from 0-20 and ionic surfactants may have HLB values of up to 60. Hydrophilic surfactants have HLB values greater than about 10 and a greater affinity for water than oil. Lipophilic surfactants have HLB values less than about 10 and a greater affinity for oil than water. The emulsions disclosed herein and/or any phase thereof, may include at least one hydrophilic surfactant, at least one lipophilic surfactant, or a combination thereof. Alternatively, or in addition, the emulsions disclosed herein and/or any phase thereof, may include at least one nonionic (and/or ionic) detergent. Furthermore, an emulsion disclosed herein and/or any phase thereof may include a surfactant comprising polyethyleneglycol, polypropyleneglycol, or Tween 20, among others.

Packet—a set of droplets or other isolated partitions disposed in the same continuous volume or volume region of a continuous phase. A packet thus may, for example, constitute all of the droplets of an emulsion or may constitute a segregated fraction of such droplets at a position along a channel. Typically, a packet refers to a collection of droplets that when analyzed in partial or total give a statistically relevant sampling to quantitatively make a prediction regarding a property of the entire starting sample from which the initial packet of droplets was made. The packet of droplets also indicates a spatial proximity between the first and the last droplets of the packet in a channel.

As an analogy with information technology, each droplet serves as a "bit" of information that may contain sequence specific information from a target analyte within a starting sample. A packet of droplets is then the sum of all these "bits" of information that together provide statistically relevant information on the analyte of interest from the starting sample. As with a binary computer, a packet of droplets is analogous to the contiguous sequence of bits that comprises the smallest unit of binary data on which meaningful computations can be applied. A packet of droplets can be encoded temporally and/or spatially relative to other packets that are also disposed in a continuous phase (such as in a flow stream), and/or with the addition of other encoded information (optical, magnetic, etc.) that uniquely identifies the packet relative to other packets.

Test—a procedure(s) and/or reaction(s) used to characterize a sample, and any signal(s), value(s), data, and/or result(s) obtained from the procedure(s) and/or reaction(s). A test also may be described as an assay. Exemplary droplet-based assays are biochemical assays using aqueous assay mixtures. More particularly, the droplet-based assays may be enzyme assays and/or binding assays, among others. The enzyme assays may, for example, determine whether individual droplets contain a copy of a substrate molecule (e.g., a nucleic acid target) for an enzyme and/or a copy of an enzyme molecule. Based on these assay results, a concentration and/or copy number of the substrate and/or the enzyme in a sample may be estimated.

Reaction—a chemical reaction, a binding interaction, a phenotypic change, or a combination thereof, which generally provides a detectable signal (e.g., a fluorescence signal) indicating occurrence and/or an extent of occurrence of the reaction. An exemplary reaction is an enzyme reaction that involves an enzyme-catalyzed conversion of a substrate to a product.

Any suitable enzyme reactions may be performed in the droplet-based assays disclosed herein. For example, the reactions may be catalyzed by a kinase, nuclease, nucleotide cyclase, nucleotide ligase, nucleotide phosphodiesterase, polymerase (DNA or RNA), prenyl transferase, pyrophosphatase, reporter enzyme (e.g., alkaline phosphatase, beta-galactosidase, chloramphenicol acetyl transferse, glucuronidase, horse radish peroxidase, luciferase, etc.), reverse transcriptase, topoisomerase, etc.

Sample—a compound, composition, and/or mixture of interest, from any suitable source(s). A sample is the general subject of interest for a test that analyzes an aspect of the sample, such as an aspect related to at least one analyte that may be present in the sample. Samples may be analyzed in their natural state, as collected, and/or in an altered state, for example, following storage, preservation, extraction, lysis, dilution, concentration, purification, filtration, mixing with one or more reagents, pre-amplification (e.g., to achieve target enrichment by performing limited cycles (e.g., <15) of PCR on sample prior to PCR), removal of amplicon (e.g., treatment with uracil-d-glycosylase (UDG) prior to PCR to eliminate any carry-over contamination by a previously generated amplicon (i.e., the amplicon is digestible with UDG because it is generated with dUTP instead of dTTP)), partitioning, or any combination thereof, among others. Clinical samples may include nasopharyngeal wash, blood, plasma, cell-free plasma, buffy coat, saliva, urine, stool, sputum, mucous, wound swab, tissue biopsy, milk, a fluid aspirate, a swab (e.g., a nasopharyngeal swab), and/or tissue, among others. Environmental samples may include water, soil, aerosol, and/or air, among others. Research samples may include cultured cells, primary cells, bacteria, spores, viruses, small organisms, any of the clinical samples listed above, or the like. Additional samples may include foodstuffs, weapons components, biodefense samples to be tested for bio-threat agents, suspected contaminants, and so on.

Samples may be collected for diagnostic purposes (e.g., the quantitative measurement of a clinical analyte such as an infectious agent) or for monitoring purposes (e.g., to determine that an environmental analyte of interest such as a bio-threat agent has exceeded a predetermined threshold).

Analyte—a component(s) or potential component(s) of a sample that is analyzed in a test. An analyte is a specific subject of interest in a test where the sample is the general subject of interest. An analyte may, for example, be a nucleic acid, protein, peptide, enzyme, cell, bacteria, spore, virus, organelle, macromolecular assembly, drug candidate, lipid, carbohydrate, metabolite, or any combination thereof, among others. An analyte may be tested for its presence, activity, and/or other characteristic in a sample and/or in partitions thereof. The presence of an analyte may relate to an absolute or relative number, concentration, binary assessment (e.g., present or absent), or the like, of the analyte in a sample or in one or more partitions thereof. In some examples, a sample may be partitioned such that a copy of the analyte is not present in all of the partitions, such as being present in the partitions at an average concentration of about 0.0001 to 10,000, 0.001 to 1000, 0.01 to 100, 0.1 to 10, or one copy per partition.

Reagent—a compound, set of compounds, and/or composition that is combined with a sample in order to perform a particular test(s) on the sample. A reagent may be a target-specific reagent, which is any reagent composition that confers specificity for detection of a particular target(s) or analyte(s) in a test. A reagent optionally may include a chemical reactant and/or a binding partner for the test. A reagent may, for example, include at least one nucleic acid, protein (e.g., an enzyme), cell, virus, organelle, macromolecular assembly, potential drug, lipid, carbohydrate, inorganic substance, or any combination thereof, and may be an aqueous composition, among others. In exemplary embodiments, the reagent may be an amplification reagent, which may include at least one primer or at least one pair of primers for amplification of a nucleic acid target, at least one probe and/or dye to enable detection of amplification, a polymerase, nucleotides (dNTPs and/or NTPs), divalent magnesium ions, potassium chloride, buffer, or any combination thereof, among others.

Nucleic acid—a compound comprising a chain of nucleotide monomers. A nucleic acid may be single-stranded or double-stranded (i.e., base-paired with another nucleic acid), among others. The chain of a nucleic acid may be composed of any suitable number of monomers, such as at least about ten or one-hundred, among others. Generally, the length of a nucleic acid chain corresponds to its source, with synthetic nucleic acids (e.g., primers and probes) typically being shorter, and biologically/enzymatically generated nucleic acids (e.g., nucleic acid analytes) typically being longer.

A nucleic acid may have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone. Exemplary artificial nucleic acids include glycol nucleic acids (GNA), peptide nucleic acids (PNA), locked nucleic acid (LNA), threose nucleic acids (TNA), and the like.

The sequence of a nucleic acid is defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil) and guanine pairs with cytosine. A nucleic acid that can bind to another nucleic acid in an antiparallel fashion by forming a consecutive string of such base pairs with the other nucleic acid is termed "complementary."

Replication—a process forming a copy (i.e., a direct copy and/or a complementary copy) of a nucleic acid or a segment thereof. Replication generally involves an enzyme, such as a polymerase and/or a ligase, among others. The nucleic acid and/or segment replicated is a template (and/or a target) for replication.

Amplification—a reaction in which replication occurs repeatedly over time to form multiple copies of at least one segment of a template molecule. Amplification may generate an exponential or linear increase in the number of copies as amplification proceeds. Typical amplifications produce a greater than 1,000-fold increase in copy number and/or signal. Exemplary amplification reactions for the droplet-based assays disclosed herein may include the polymerase chain reaction (PCR) or ligase chain reaction, each of which is driven by thermal cycling. The droplet-based assays also or alternatively may use other amplification reactions, which may be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like. Amplification may utilize a linear or circular template.

Amplification may be performed with any suitable reagents. Amplification may be performed, or tested for its occurrence, in an amplification mixture, which is any composition capable of generating multiple copies of a nucleic acid target molecule, if present, in the composition. An amplification mixture may include any combination of at least one primer or primer pair, at least one probe, at least one replication enzyme (e.g., at least one polymerase, such as at least one DNA and/or RNA polymerase), and deoxynucleotide (and/or nucleotide) triphosphates (dNTPs and/or NTPs), among others. Further aspects of assay mixtures and detection strategies that enable multiplexed amplification and detection of two or more target species in the same droplet are described elsewhere herein, such as in Section X, among others.

PCR—nucleic acid amplification that relies on alternating cycles of heating and cooling (i.e., thermal cycling) to achieve successive rounds of replication. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. PCR generally produces an exponential increase in the amount of a product amplicon over successive cycles.

Any suitable PCR methodology or combination of methodologies may be utilized in the droplet-based assays disclosed herein, such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, or universal fast walking PCR, among others.

Digital PCR—PCR performed on portions of a sample to determine the presence/absence, concentration, and/or copy number of a nucleic acid target in the sample, based on how many of the sample portions support amplification of the target. Digital PCR may (or may not) be performed as endpoint PCR. Digital PCR may (or may not) be performed as real-time PCR for each of the partitions.

PCR theoretically results in an exponential amplification of a nucleic acid sequence (analyte) from a sample. By measuring the number of amplification cycles required to achieve a threshold level of amplification (as in real-time PCR), one can theoretically calculate the starting concentration of nucleic acid. In practice, however, there are many factors that make the PCR process non-exponential, such as varying amplification efficiencies, low copy numbers of starting nucleic acid, and competition with background contaminant nucleic acid. Digital PCR is generally insensitive to these factors, since it does not rely on the assumption that the PCR process is exponential. In digital PCR, individual nucleic acid molecules are separated from the initial sample into partitions, then amplified to detectable levels. Each partition then provides digital information on the presence or absence of each individual nucleic acid molecule within each partition. When enough partitions are measured using this technique, the digital information can be consolidated to make a statistically relevant measure of starting concentration for the nucleic acid target (analyte) in the sample.

The concept of digital PCR may be extended to other types of analytes, besides nucleic acids. In particular, a signal amplification reaction may be utilized to permit detection of a single copy of a molecule of the analyte in individual droplets, to permit data analysis of droplet signals for other analytes in the manner described in Section VII (e.g., using an algorithm based on Poisson statistics). Exemplary signal amplification reactions that permit detection of single copies of other types of analytes in droplets include enzyme reactions.

Qualitative PCR—a PCR-based analysis that determines whether or not a target is present in a sample, generally without any substantial quantification of target presence. In exemplary embodiments, digital PCR that is qualitative may be performed by determining whether a packet of droplets contains at least a predefined percentage of positive droplets (a positive sample) or not (a negative sample).

Quantitative PCR—a PCR-based analysis that determines a concentration and/or copy number of a target in a sample.

RT-PCR (reverse transcription-PCR)—PCR utilizing a complementary DNA template produced by reverse transcription of RNA. RT-PCR permits analysis of an RNA sample by (1) forming complementary DNA copies of RNA, such as with a reverse transcriptase enzyme, and (2) PCR amplification using the complementary DNA as a template. In some embodiments, the same enzyme, such as Tth polymerase, may be used for reverse transcription and PCR.

Real-time PCR—a PCR-based analysis in which amplicon formation is measured during the reaction, such as after completion of one or more thermal cycles prior to the final thermal cycle of the reaction. Real-time PCR generally provides quantification of a target based on the kinetics of target amplification.

Endpoint PCR—a PCR-based analysis in which amplicon formation is measured after the completion of thermal cycling.

Amplicon—a product of an amplification reaction. An amplicon may be single-stranded or double-stranded, or a combination thereof. An amplicon corresponds to any suitable segment or the entire length of a nucleic acid target.

Primer—a nucleic acid capable of, and/or used for, priming replication of a nucleic acid template. Thus, a primer is a shorter nucleic acid that is complementary to a longer template. During replication, the primer is extended, based on the template sequence, to produce a longer nucleic acid that is a complementary copy of the template. A primer may be DNA, RNA, an analog thereof (i.e., an artificial nucleic acid), or any combination thereof. A primer may have any suitable length, such as at least about 10, 15, 20, or 30 nucleotides. Exemplary primers are synthesized chemically. Primers may be supplied as at least one pair of primers for amplification of at least one nucleic acid target. A pair of primers may be a sense primer and an antisense primer that collectively define the opposing ends (and thus the length) of a resulting amplicon.

Probe—a nucleic acid connected to at least one label, such as at least one dye. A probe may be a sequence-specific binding partner for a nucleic acid target and/or amplicon. The probe may be designed to enable detection of target amplification based on fluorescence resonance energy transfer (FRET). An exemplary probe for the nucleic acid assays disclosed herein includes one or more nucleic acids connected to a pair of dyes that collectively exhibit fluorescence resonance energy transfer (FRET) when proximate one another. The pair of dyes may provide first and second emitters, or an emitter and a quencher, among others. Fluorescence emission from the pair of dyes changes when the dyes are separated from one another, such as by cleavage of the probe during primer extension (e.g., a 5' nuclease assay, such as with a TAQMAN probe), or when the probe hybridizes to an amplicon (e.g., a molecular beacon probe). The nucleic acid portion of the probe may have any suitable structure or origin, for example, the portion may be a locked nucleic acid, a member of a universal probe library, or the like. In other cases, a probe and one of the primers of a primer pair may be combined in the same molecule (e.g., AMPLIFLUOR primers or SCORPION primers). As an example, the primer-probe molecule may include a primer sequence at its 3' end and a molecular beacon-style probe at its 5' end. With this arrangement, related primer-probe molecules labeled with different dyes can be used in a multiplexed assay with the same reverse primer to quantify target sequences differing by a single nucleotide (single nucleotide polymorphisms (SNPs)). Another exemplary probe for droplet-based nucleic acid assays is a Plexor primer.

Label—an identifying and/or distinguishing marker or identifier connected to or incorporated into any entity, such as a compound, biological particle (e.g., a cell, bacteria, spore, virus, or organelle), or droplet. A label may, for example, be a dye that renders an entity optically detectable and/or optically distinguishable. Exemplary dyes used for labeling are fluorescent dyes (fluorophores) and fluorescence quenchers.

Reporter—a compound or set of compounds that reports a condition, such as the extent of a reaction. Exemplary reporters comprise at least one dye, such as a fluorescent dye or an energy transfer pair, and/or at least one oligonucleotide. Exemplary reporters for nucleic acid amplification assays may include a probe and/or an intercalating dye (e.g., SYBR Green, ethidium bromide, etc.).

Code—a mechanism for differentiating distinct members of a set. Exemplary codes to differentiate different types of droplets may include different droplet sizes, dyes, combinations of dyes, amounts of one or more dyes, enclosed code particles, or any combination thereof, among others. A code may, for example, be used to distinguish different packets of droplets, or different types of droplets within a packet, among others.

Binding partner—a member of a pair of members that bind to one another. Each member may be a compound or biological particle (e.g., a cell, bacteria, spore, virus, organelle, or the like), among others. Binding partners may bind specifically to one another. Specific binding may be characterized by a dissociation constant of less than about $10^{-4}$, $10^{-6}$, $10^{-8}$, or $10^{-16}$ M. Exemplary specific binding partners include biotin and avidin/streptavidin, a sense nucleic acid and a complementary antisense nucleic acid (e.g., a probe and an amplicon), a primer and its target, an antibody and a corresponding antigen, a receptor and its ligand, and the like.

Channel—an elongate passage for fluid travel. A channel generally includes at least one inlet, where fluid enters the channel, and at least one outlet, where fluid exits the channel. The functions of the inlet and the outlet may be interchangeable, that is, fluid may flow through a channel in only one direction or in opposing directions, generally at different times. A channel may include walls that define and enclose the passage between the inlet and the outlet. A channel may, for example, be formed by a tube (e.g., a capillary tube), in or on a planar structure (e.g., a chip), or a combination thereof, among others. A channel may or may not branch. A channel may be linear or nonlinear. Exemplary nonlinear channels include a channel extending along a planar flow path (e.g., a serpentine channel) a nonplanar flow path (e.g., a helical channel to provide a helical flow path). Any of the channels disclosed herein may be a microfluidic channel, which is a channel having a characteristic transverse dimension (e.g., the channel's average diameter) of less than about one millimeter. Channels also may include one or more venting mechanisms to allow fluid to enter/exit without the need for an open outlet. Examples of venting mechanisms include but are not limited to hydrophobic vent openings or the use of porous materials to either make up a portion of the channel or to block an outlet if present.

Fluidics Network—an assembly for manipulating fluid, generally by transferring fluid between compartments of the assembly and/or by driving flow of fluid along and/or through one or more flow paths defined by the assembly. A fluidics network may include any suitable structure, such as one or more channels, chambers, reservoirs, valves, pumps, thermal control devices (e.g., heaters/coolers), sensors (e.g., for measuring temperature, pressure, flow, etc.), or any combination thereof, among others.

II. SYSTEM OVERVIEW/ARCHITECTURE

This Section describes the architecture of illustrative systems, including methods and apparatus, for droplet-based assays. The features and aspects of the systems disclosed in this Section may be combined with one another and/or with any suitable aspects and features of methods and apparatus shown and/or described elsewhere in the present disclosure. Additional pertinent disclosure may be found in the U.S. provisional patent applications listed above under Cross- References and incorporated herein by reference, particularly Ser. No. 61/277,270, filed Sep. 22, 2009.

Figure 2:
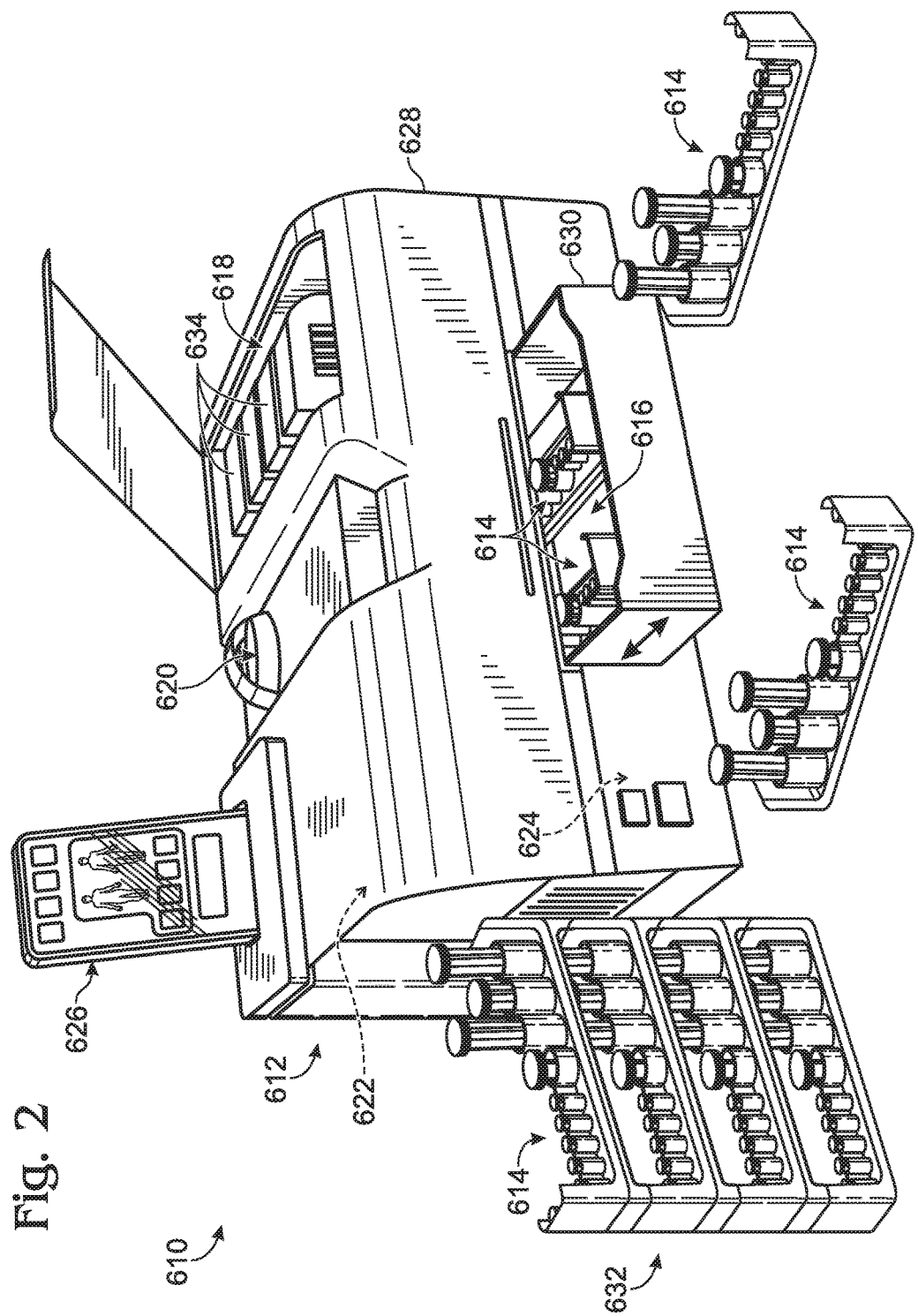
FIG. 2 is a perspective view of an exemplary embodiment of a system for performing droplet-based assays, with the system comprising an instrument and cartridges that connect to the instrument to provide sample preparation that is actuated and controlled by the instrument, in accordance with aspects of the present disclosure.
Figure 3:
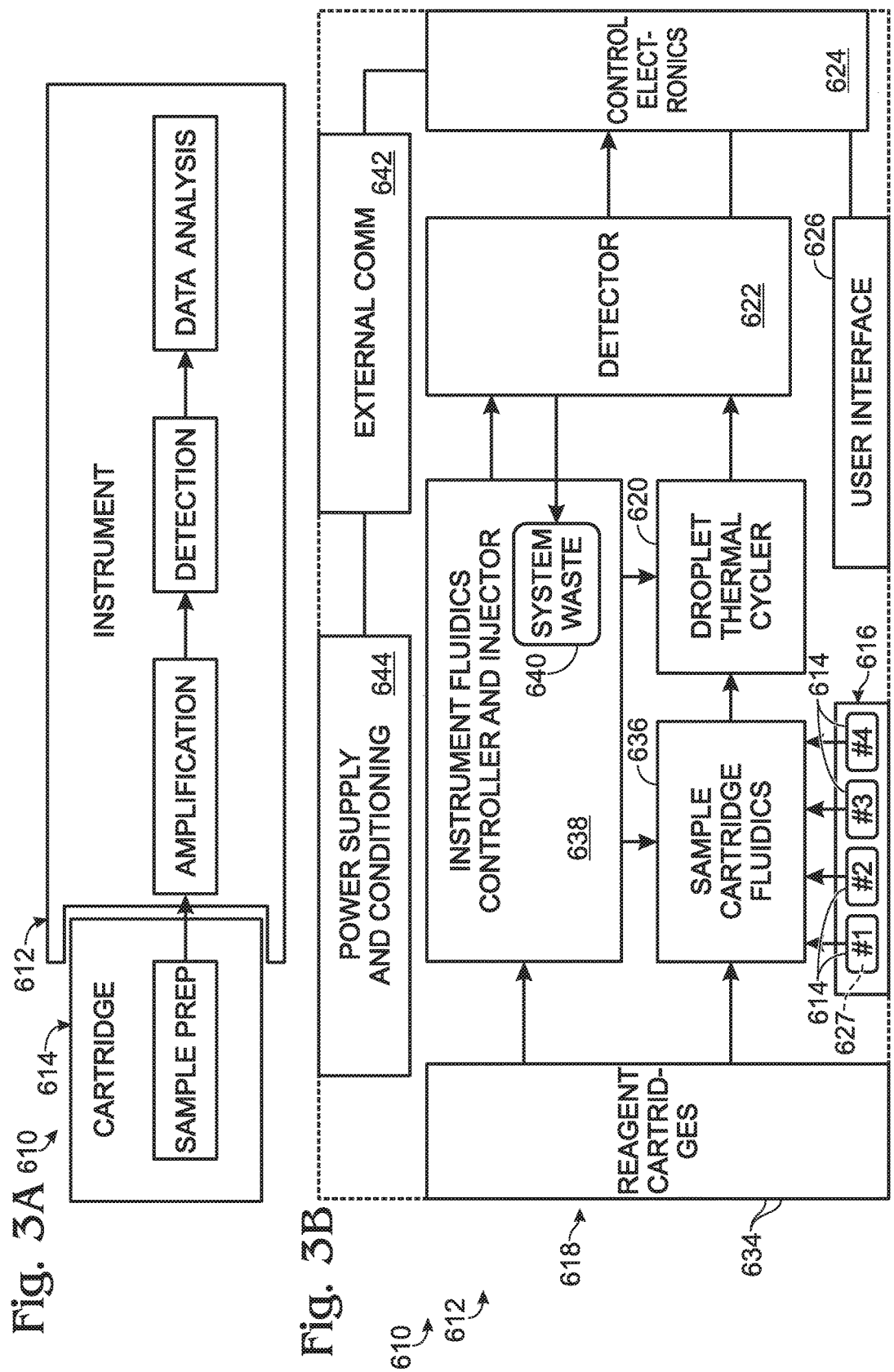
FIG. 3A is a schematic view of an exemplary sequence of processes performed by the system of FIG. 2.
FIG. 3B is a schematic view of the instrument of FIG. 2.

A. Exemplary Instrument-Cartridge System for Sample Preparation and Analysis FIGS. 2 and 3A show perspective and schematic views, respectively, of an exemplary system 600 for performing droplet-based assays. System 610 may comprise an instrument 612 and one or more sample cartridges 614 that connect to the instrument, to provide sample preparation that is actuated and controlled by the instrument. Sample preparation may include any combination of the processes disclosed in Section III or elsewhere in the present disclosure, such as extraction, purification, lysis, concentration, dilution, reagent mixing, and/or droplet generation, among others. Instrument 612 may perform amplification of nucleic acid in the droplets, detection of signals from the droplets, and data analysis, among others.

Instrument 612 may be equipped with a sample loading region 616, a reagent fluidics assembly 618, a thermal cycler 620, a detector 622, control electronics 624 (i.e., a controller), and a user interface 626, among others. The instrument also may include a housing 628, which may support, position, fix, enclose, protect, insulate, and/or permit/restrict access to each other instrument component.

Sample loading region 616 may permit placement of sample cartridges 614 into the instrument, generally after a sample has been introduced into a port of each cartridge. The sample loading region may have an open configuration for receiving sample cartridges and a closed configuration that restricts cartridge introduction and removal (e.g., during instrument actuation of loaded sample cartridges). For example, the sample loading region may include a tray 630 that is an extendible and retractable and that receives the sample cartridges and positions the cartridges for operational engagement with instrument 612. The tray may be pulled out manually for loading sample cartridges into the tray and pushed in manually for cartridge operation, or may be coupled to a drive mechanism that drives opening and closing of the sample loading region.

Sample cartridges 614 are depicted in various positions in FIG. 2. Some of the cartridges have been loaded into tray 630, which is extended, while other cartridges are disposed outside instrument 612 (e.g., stacked, indicated at 632), before or after their use with the instrument. The sample cartridges may be primed/loaded with one or more fluid reagents before the cartridges are connected to the instrument (e.g., during cartridge manufacture), and/or the sample cartridges may be primed with one or more fluid reagents supplied by the instrument. Further aspects of sample cartridges that may be suitable for use with instrument 612 are described elsewhere in the present disclosure, particularly in Section III.

FIG. 3B shows a schematic view of selected aspects of system 610. The arrows extending across junctions between system components generally show directions of fluid or data flow within the system. The line segments extending across the junctions indicate an electrical connection and/or signal communication.

Sample cartridges 614 may receive fluid for sample preparation from reagent fluidics assembly 618. Fluidics assembly 618 may include reagent cartridges or containers 634 (also see FIG. 2), which may be disposable and/or reusable (i.e., refillable). Fluidics assembly 618 also may include sample cartridge fluidics 636, which, in conjunction with a fluidics controller and injector 638, enable controlled fluid flow. For example, fluid may flow from the reagent cartridges to the sample cartridges, may flow within each sample cartridge, and/or may flow from each sample cartridge to thermal cycler 620 as droplets disposed in an immiscible carrier fluid.

Thermal cycler 620 may subject the droplets to thermal cycles that promote amplification, in preparation for detection of droplet signals by detector 622. Further aspects of thermal cyclers and detectors are described elsewhere herein, such as in Sections V and VI. After detection, the droplets and carrier fluid may flow to a waste receptacle 640.

Data from detector 622 may be communicated to control electronics 624. The control electronics may analyze the data (e.g., as described in Section VII), and communicate the data to user interface 626, among others. The control electronics also may receive input data, such as preferences, instructions, and/or commands, from the user interface. The control electronics may be in communication with and/or may be programmed to control any other aspects of system 600. For example, the control electronics may be in communication with cartridges 614. In some embodiments, each cartridge may be a "smart cartridge" that carries a memory device 627. The memory device may be readable by the controller, and, optionally, writable, too. The memory device may carry information about the cartridge, such as reagents pre-loaded to the cartridge, data about the loaded sample, aspects of sample processing performed by the cartridge, or any combination thereof, among others. The control electronics also may be connected to an external communication port 642, which also may provide data input/output. A power supply 644 (e.g., a line or battery power source) may provide power to the control electronics. The power may be conditioned by any suitable element(s) (e.g., a rectifier) between the power supply and the control electronics.

B. Exemplary Instrument for Analysis of Pre-Prepared Samples

Figure 4:
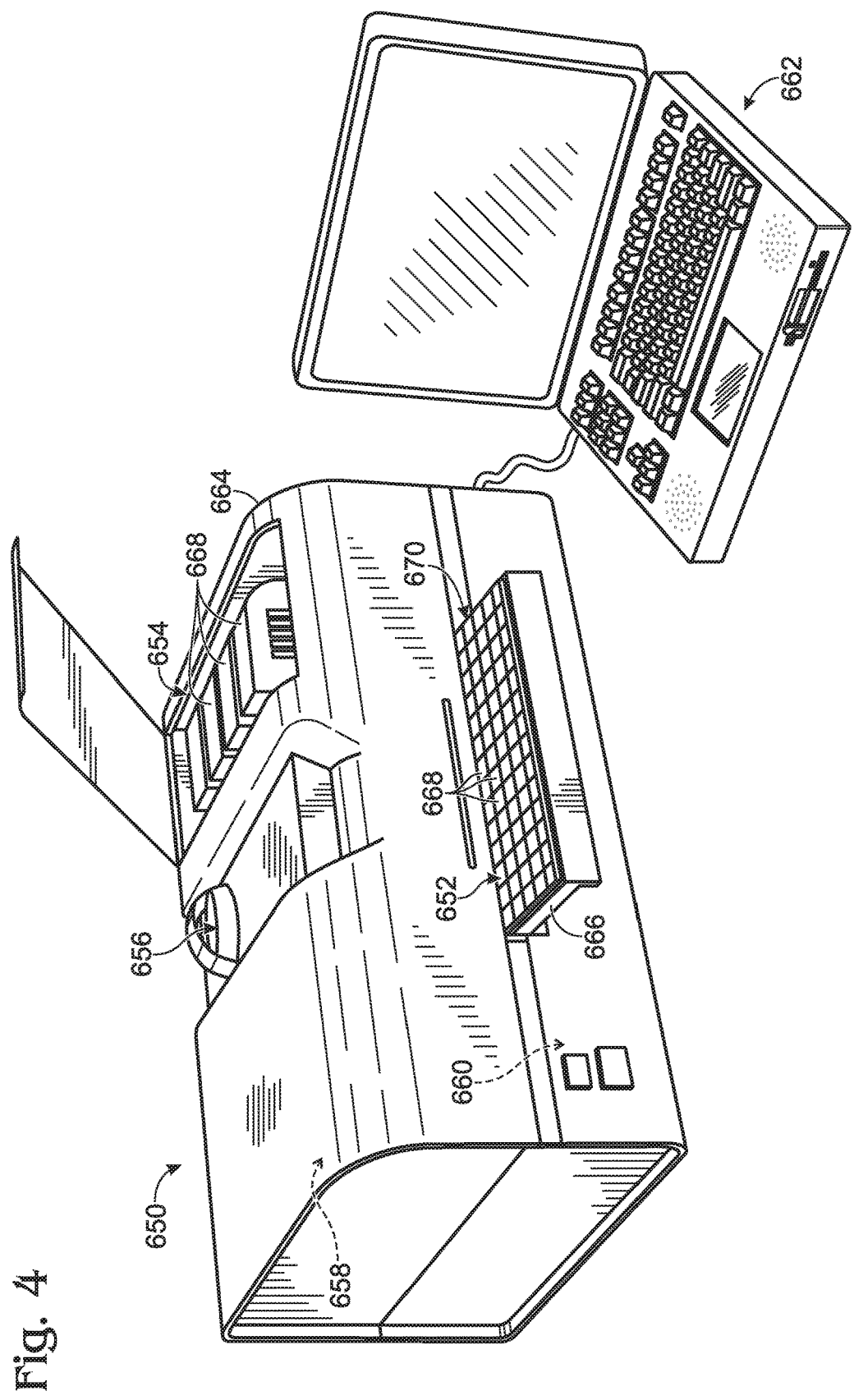
FIG. 4 is a perspective view of another exemplary embodiment of an instrument for performing droplet-based assays, with the instrument designed to utilize pre-prepared samples, in accordance with aspects of the present disclosure.

FIG. 4 shows another exemplary system constructed as an instrument 650 for performing droplet-based assays. Instrument 650 may be capable of performing droplet-based assays of nucleic acid amplification, generally as described above for system 610. However, instrument 650 may be designed to process and analyze samples that are supplied as pre-formed emulsions or prepared samples (e.g., purified nucleic acids that are not yet in emulsion form).

Instrument 650 may be equipped with a sample loading region 652, a reagent fluidics assembly 654, a thermal cycler 656, a detector 658, control electronics 660 (i.e., a controller), a user interface 662, and a housing 664, among others, which each may function generally as described above for system 610. However, sample loading region 652 and reagent fluidics assembly 654 may differ from the analogous structures in instrument 612. In particular, the sample preparation procedures performed in the sample cartridges of system 610 (see FIG. 2) are performed outside of instrument 650, before sample loading.

Sample loading region 652 may include a tray 666 and an array of compartments or reservoirs 668, such as wells. Reservoirs 668 may be provided by a plate 670, such as a microplate, which may be received and/or supported by the tray. Plate 670 may be removable, to permit placing samples into reservoirs 668 while the plate is spaced from the instrument. Alternatively, or in addition, samples may be placed into reservoirs 668 while the reservoirs are supported by the tray/instrument. In some examples, plate 670 may be a droplet generator plate (e.g., see below in this Section and Sections III and IV). If structured as a droplet generator plate, the plate may generate droplets before or after the plate is loaded into instrument 650.

Each reservoir may receive a pre-prepared sample. The pre-prepared sample may or may not be in emulsion form. If not in emulsion form, the sample may have been processed before loading into the reservoir (e.g., processed by extraction, purification, lysis, concentration, dilution, reagent mixing, or any combination thereof), to ready the sample for droplet generation. Alternatively, the sample may be a pre-formed emulsion of droplets in an immiscible carrier fluid. The emulsion may be formed prior to loading the sample into the reservoir by partitioning into droplets an assay mixture that includes a sample and at least one reagent. Each droplet thus may contain a partition of the sample. Droplet packets from the emulsions may be transported serially or in parallel from reservoirs 668 to at least one thermal cycler 656 of the instrument.

User interface 662 of instrument 650 may (or may not) be different in configuration from user interface 626 of system 610 (compare FIGS. 2 and 4). For example, user interface 662 may be spaced from the body of instrument 650 (e.g., disposed outside of and spaced from housing 664). User interface 662 may be in wired or wireless communication with control electronics 660 of the instrument.

C. Overview of Droplet-Based Assay Systems

FIG. 5 shows a flowchart 680 listing exemplary steps that may be performed in a method of sample analysis using droplet-based assays. The steps listed may be performed in any suitable combination and in any suitable order and may be combined with any other step(s) of the present disclosure.

At least one sample may be loaded, indicated at 682. The sample may be loaded by placing the sample into a port (e.g., a well, chamber, channel, etc.) defined by any of the system components disclosed herein. The sample may be loaded in any suitable form, such as unlysed or lysed, purified or crude, pre-mixed with reagent or not pre-mixed, diluted or concentrated, partitioned into droplets or non-partitioned, or the like. In some cases, a plurality of samples may be loaded into respective ports and/or into an array of reservoirs.

The sample may be processed, indicated at 684. Any suitable combination of sample processing steps may be performed after (and/or before) sample loading to prepare the sample for droplet generation. Exemplary processing steps are described in Section III.

Droplets may be generated from the sample, indicated at 686. For example, droplet generation may be performed after the sample has been modified by mixing it with one or more reagents to form a bulk assay mixture. Droplet generation may divide the bulk assay mixture into a plurality of partitioned assay mixtures (and thus sample partitions) that are isolated from one another in respective droplets by an intervening, immiscible carrier fluid. The droplets may be generated from a sample serially, such as from one orifice and/or one droplet generator (which may be termed an emulsion generator). Alternatively, the droplets may be generated in parallel from a sample, such as from two or more orifices and/or two or more droplet generators in fluid communication with (and/or supplied by) the same sample. As another example, droplets may be generated in parallel from a perforated plate defining an array of orifices. In some examples, the droplets may be generated in bulk, such as by agitation or sonication, among others. In some examples, a plurality of emulsions may be generated, either serially or in parallel, from a plurality of samples.

Droplets may be loaded (i.e., introduced) into a reaction site (also termed a reactor), indicated at 688. The droplets may be loaded by flow transport, which may be continuous or stopped one or more times. Thus, the droplets may (or may not) be stored, indicated at 690, at one or more discrete storage sites, after their generation and before loading into the reaction site. Alternatively, the droplets may be loaded into a reaction site without substantial flow, for example, with the droplets contained by a vessel that is moved to the reaction site. In other examples, the droplets may be generated at the reaction site (e.g., inside a thermal cycler). In any event, after droplet generation, droplets may be placed into a reaction site with the droplets disposed in a vial (or other vessel), a reaction channel (e.g., in tubing), an imaging chamber/flow cell with a high aspect ratio, or the like. Further aspects of droplet manipulation, such as selection for transport/loading, transport, storage, routing, pre-processing (e.g., heating), and concentration are described below in this Section.

A "reaction site" is a region where droplets are subjected to conditions to promote one or more reactions of interest, such as nucleic acid amplification. Accordingly, a reaction site may provide one or more temperature-controlled zones of fixed or varying temperature (and/or other physical conditions) suitable for a particular reaction(s) to be performed and/or promoted in the droplets. The reaction site may be a flow-through site, where the droplets are subjected to fixed or varying reaction conditions while flowing through at least one channel or may be a static site where the droplets are subjected to fixed or varying reaction conditions while the droplets are disposed in a stationary volume of fluid (i.e., not flowing). An exemplary reaction site, namely, a flow-based thermal cycler, is included in many of the exemplary systems of this Section and is described in more detail in Section V.

Droplets may be "reacted," indicated at 692. More specifically, the droplets may be subjected to one or more suitable reaction conditions in a reaction site, according to the type of assay mixture(s) contained by the droplets, such that components of the droplets, or the droplets themselves, undergo a desired reaction (or change of state). For example, the droplets may be subjected to thermal cycling (or may be processed isothermally) for amplification assays, such as any of the assays described in Section I, among others.

Reaction of droplets generally subjects the droplets to one or more conditions that promote at least one binding and/or chemical reaction of interest in the droplets. Reaction of droplets also generally subjects the droplets to each condition for a predefined period (or periods) of time, which may be fixed or variable, and may be repeated. The droplets may be subjected to two or more conditions serially or in parallel, and once or a plurality of times, for example, cyclically. Exemplary conditions include a temperature condition (i.e., to maintain droplet temperature, heat droplets, and/or or cool droplets), exposure to light, variations in pressure, or the like.

Droplets may be reacted by flow through a reaction site, in a "flow reaction." Droplets may be subjected to at least one condition that is uniform or that varies spatially along a flow path through the reaction site. For example, the temperature along the flow path may vary spatially, to heat and cool droplets as the droplets follow the flow path. In other words, the reaction site may include one, two, or more temperature-controlled zones of at least substantially fixed temperature that the droplets travel through. Further aspects of flow-through reaction sites with fixed temperature zones and thermal cycling are described elsewhere herein, such as in Section V, among others.

Droplets alternatively may be reacted while disposed in a static volume of fluid, that is, without substantial fluid flow, in a "static reaction." For example, the droplets may react while disposed in a well or a chamber, among others. In this case, the droplets may be subjected to a fixed condition during the reaction (e.g., a fixed temperature for an isothermal reaction), or to a variable condition that varies temporally (i.e., with respect to time) during the reaction (without the requirement for the droplets to move). For example, the droplets may be held in a temperature-controlled zone that changes in temperature over time, such as cyclically to perform PCR. In any event, static reactions may permit batch reaction of arrays of emulsions in parallel, such as in batch amplification of emulsions.

Droplets may be detected, indicated at 694. Detection may be performed serially while the droplets are flowing (i.e., flow-based or dynamic detection). Alternatively, detection may be performed with the droplets disposed in a static volume of fluid (i.e., static detection, such as with flow stopped (i.e., stopped-flow detection)). In some examples, static detection (or dynamic detection) may include imaging a set of substantially static (or flowing) droplets, which may be arranged generally linearly or in a plane, to obtain an image of the droplets. Further aspects of detection, including flow-based and stopped-flow detection are described elsewhere herein, such as in Section VI, among others.

Dynamic/static modes of reaction and detection may be combined in any suitable manner. For example, flow-based reaction of droplets may be combined with flow-based detection or stopped-flow detection (e.g., imaging) of the droplets. Alternatively, static reaction of droplets, such as batch amplification of emulsions, may be combined with flow-based detection or static detection (e.g., imaging) of the droplets.

Data detected from the droplets may be analyzed, indicated at 696. Data analysis may, for example, assign droplet signals as positive or negative for amplification of a nucleic acid target (or two or more targets in a multiplexed reaction), may determine a number and/or fraction of the droplets that are positive for amplification, may estimate a total presence (e.g., concentration and/or number of molecules) of the nucleic acid target in the sample, or the like. Further aspects of data analysis are described elsewhere herein, such as in Sections VII and VIII, among others.

FIG. 6 shows selected portions of an exemplary system 700 for performing droplet-based assays. Any one component or combination of the depicted system components may be omitted from the system, and any additional components disclosed elsewhere herein may be added to the system. The arrows indicate an exemplary sequence in which sample, droplets, and/or data may move between structural components of the system. However, each of the structural components may be used more than once with the same droplets, and/or may be utilized in a different sequence than shown here.

System 700 may include one or more of any or each of the following components: a sample processor 702 (also termed a sample processing station), a droplet generator 704, a droplet transporter 706, a reaction site (or reactor) 708 (also termed a reaction station (e.g., a heating station, which may heat or heat and cool)), a detector 710 (also termed a detection station), and a controller 712, among others. Any combination of the components may be connected to one another physically, fluidically, electrically, and/or signal transfer, among others.

The components may operate as follows, with reference to steps of method 680 (FIG. 5). Sample processor 702 may receive a sample to be analyzed, such as a sample that is loaded in step 682, and may process the sample in the manner described above for step 684. Droplet generator 704 may generate droplets as described for step 686. Droplet transporter 706 may load the droplets generated, as described for step 688, and thus may provide selectable transport/loading, transport, storage (step 690), routing, pre-processing (e.g., heating), and concentration, among others, of the generated droplets. Reaction site 708 may enable a flow reaction or a static reaction of the loaded droplets, and detector 710 may provide dynamic or static detection of droplets, as described for step 694. Controller 712 may analyze data received from detector 710, as described for step 696. Also, controller 712 may be in communication with and/or may be programmed to control any suitable combination of system components, as indicated by dashed lines extending from the controller to each other system component. Controller also may contain a computer-readable medium (e.g., a storage device, such as a hard drive, CD-ROM, DVD-ROM, floppy disk, flash memory device, etc.) including instructions for performing any of the methods disclosed herein.

D. Exemplary System with Flow-Based Amplification

FIG. 7 shows a schematic view of an exemplary system 720 with flow-based amplification and with droplet loading that is decoupled from droplet generation. Any one component or combination of the depicted system components may be omitted from the system, and any additional components disclosed elsewhere herein may be added to the system. The solid arrows indicate an exemplary sequence in which sample 722, reagent 724, and droplets 726 may move between structural components of the system. The vertical dashed arrows above and below various system components indicate optional addition (e.g., inflow) and/or removal (e.g., outflow) of an immiscible carrier fluid (e.g., oil) and/or waste with respect to these components.

System 720 may include a mixer 728 and a droplet generator 730. Mixer 728 may receive a sample 722 and at least one reagent 724 and combine them to form an assay mixture. The mixer may be an automated device, or mixing may be performed manually by a user, such as by bulk mixing, before loading the assay mixture into the droplet generator. Droplet generator 730 may receive the assay mixture from the mixer and generate an emulsion 732 of droplets 726 in an immiscible carrier fluid 734, such as oil that is introduced into the droplet generator, indicated at 736, at the same time as the assay mixture. Formation of droplets 726 may be driven by pressure and/or pumping, indicated at 738. In some examples, the droplet generator may function as the mixer by generating droplets from confluent streams of sample and reagent. Waste fluid also may exit the droplet generator, indicated at 740.

System 720 may have any suitable number of droplet generators. The droplet generators may be used to generate any suitable number of separate, distinct emulsions from one sample or a plurality of samples, and from one reagent or a plurality of reagents (e.g., reagents for different species of nucleic acid target). Exemplary mixers and droplet generators are described in Sections III and IV.

Emulsion 732 or a set of distinct emulsions may be stored in at least one storage site 742 or in a plurality of such sites before droplets of the emulsion(s) are reacted. As a result, droplet generation may be decoupled from reaction of the droplets. The storage site may, for example, be a well, a chamber, a tube, or an array thereof, such as formed by a plate (e.g., a microplate).

System also may include a serial arrangement of a droplet transport portion 744, (also termed a droplet transporter) and a thermal cycler 746. Transport portion 744 may include a droplet pick-up or intake region 748 that forms an inlet at which droplets 726 are transferred from storage site 742 into the transport portion. Transport portion 744 also may include a droplet loader 750 that sends droplets to thermal cycler 746. The transport portion also may include one or more storage sites 752 for storing droplets after they have been transferred into transport portion 744.

In some examples, the transport portion also may be capable of loading droplets more directly to the detector, without sending them first to the thermal cycler. In particular, system 720 may include a bypass channel 753 or bypass pathway that connects transport portion 744 to the detector without travel through the thermal cycler. The system may include one or more valves that can be operated to send droplets either to bypass channel 753 or to thermal cycler 746. The use of bypass channel 753 may, for example, permit more rapid calibration of system components, because calibration droplets can travel to the detector faster if thermal cycling is omitted. Section VIII describes further aspects of the use of a bypass channel and calibration droplets.

Carrier fluid and/or waste fluid optionally may be removed from storage site 742, droplet pick-up region 748, and/or droplet loader 750, indicated respectively at 754-758. Alternatively, or in addition, carrier fluid may be added to the droplet pick-up region, indicated at 759, and/or the droplet loader, indicated at 760, such as to facilitate driving droplets into thermal cycler 746 and/or to flush droplets from the pick-up region and/or droplet loader.

An emulsion including droplets 726 may flow through (a) thermal cycler 746, (b) at least one detection site (e.g., a detection channel/chamber) adjacent at least one detection window 762 that is operatively disposed with respect to detector 764, and (c) through an oil recovery region 766 and then to a waste receptacle. One or more valves 770 may be disposed generally between the thermal cycler and the detector, to provide control of emulsion flow downstream of the thermal cycler, with respect to the at least one detection channel/chamber. For example, valves 770 may be operated to stop flow of droplets adjacent to the detection window and/or to switch flow of the emulsion between two or more detection windows (e.g., see Section VI). Carrier fluid may be removed from the emulsion and/or introduced into the emulsion in or near thermal cycler 746 and/or detector 764, indicated respectively at 772, 774. Removal of carrier fluid may, for example, provide a more concentrated emulsion for detection. Introduction of carrier fluid may, for example, provide flow-focusing of droplets within a detection channel and/or with respect to the detection window (e.g., see Section VI). Alternatively, or in addition, droplets may be sent to a waste receptacle, indicated at 775, for collection from the thermal cycler, without traveling through a detection station.

Carrier fluid also may be removed from the flow stream by oil recovery region 766, indicated at 776. Removal may be effected by any suitable mechanism, such as pillars, at least one membrane, one or more oil-selective side channels, gravity separation, or the like.

E. Overview of Droplet Manipulation

Figure 8:
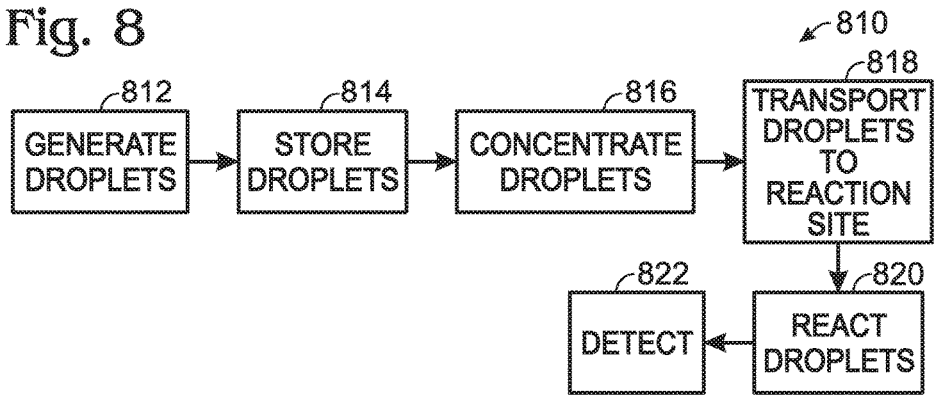
FIG. 8 is a flowchart listing exemplary steps that may be performed in a method of sample analysis using droplet-based assays in which droplets are transported from a droplet generator and/or a droplet storage site to a reaction site, in accordance with aspects of the present disclosure.
Figure 9:
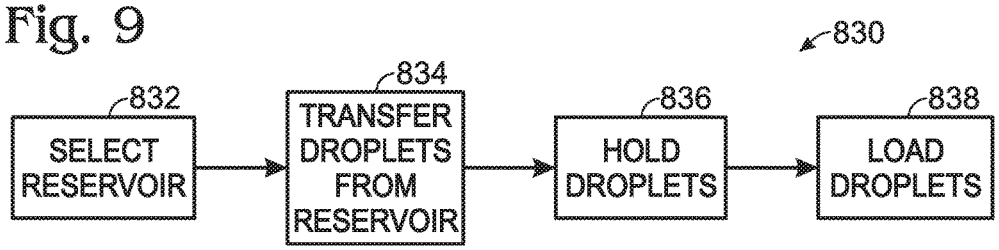
FIG. 9 is a flowchart listing exemplary steps that may be included in a droplet transport step in the method of FIG. 8, in accordance with aspects of the present disclosure.
Figure 10:
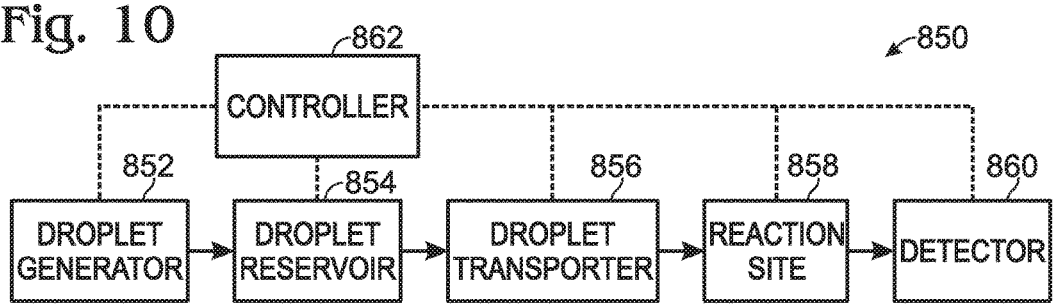
FIG. 10 is a schematic view of selected portions of an exemplary system for performing droplet-based assays in which droplets are transported from a droplet generator and/or droplet storage site to a reaction site, with horizontal arrows indicating droplet travel between structural components of the system, in accordance with aspects of the present disclosure.

FIGS. 8-10 provide an overview of droplet manipulation, including methods and apparatus, emphasizing droplet transport and exemplary types of droplet manipulation that may be performed in connection therewith (e.g., storage, concentration, selection, etc.).

FIG. 8 shows a flowchart 810 listing exemplary steps that may be performed in an exemplary method of sample analysis using droplet-based assays in which droplets are transported from a droplet generator and/or a droplet reservoir to a reaction site. The steps listed may be performed in any suitable combination and in any suitable order and may be combined with any other suitable step(s) of the present disclosure.

Droplets may be generated, indicated at 812. The droplets may be generated serially, in parallel, or in bulk. Further aspects of droplet generation are disclosed elsewhere herein, such as in Sections III and VI, among others.

The droplets, optionally, may be stored, indicated at 814. A set of droplets (e.g., an emulsion) may be stored in a droplet reservoir. In some examples, two or more distinct sets of droplets may be stored in two or more respective reservoirs, such as in an array of emulsions. In some examples, storage of the droplets may be omitted.

The droplets, optionally, may be concentrated, indicated at 816. Concentrating droplets (also termed concentrating an emulsion) results in an increase in the number of droplets per unit volume of emulsion and increases the volume fraction occupied by the droplets in an emulsion. Concentration of an emulsion may be conducted before, during, and/or after droplet storage.

One or more of the droplets (including one or more packets of droplets) may be transported to a reaction site, indicated at 818. Transport may be achieved by continuous flow, or by flow initiated selectably in one or more discrete stages, after droplet generation and/or initial droplet storage. The droplets may be reacted at the reaction site, indicated at 820.

Signals may be detected from droplets of the packet, indicated at 822. For example, one or more measurements may be performed on one or a plurality of the droplets during and/or after reaction of the droplets. Further aspects of droplet detection are disclosed elsewhere herein, such as in Section VI, among others.

FIG. 9 shows a flowchart 830 listing exemplary steps that may be included in a step of transporting droplets (i.e., step 818) in the method of FIG. 8.

A droplet reservoir (also termed an emulsion reservoir) may be selected, indicated at 832. The droplet reservoir may be selected from an array of droplet reservoirs holding distinct emulsions and/or distinct assay mixtures. Selection may be performed by a controller, by a user, or a combination thereof.

Droplets from the selected reservoir may be transferred to a droplet transporter, indicated at 834. The transferred droplets may be referred to as a packet. In some examples, a plurality of reservoirs may be selected and a plurality of droplet packets from respective selected reservoirs may be transferred serially (or in parallel) to the droplet transporter.

The packet(s) of droplets, optionally, may be held (i.e., stored) by the droplet transporter, indicated at 836. Droplets may be stored by the droplet transporter by stopping flow of the droplets, such as by isolating the droplets from a flow stream traveling to the reaction site. Accordingly, the droplets may be held in static (non-flowing) fluid (i.e., without substantial net flow of the continuous phase).

The packet of droplets, or at least a portion thereof, may be loaded into a reaction site (e.g., a thermal cycler), indicated at 838, which may be described as the droplets being sent or introduced into the reaction site. Packets of droplets may be loaded serially. Alternatively, packets of droplets may be loaded in parallel, such as loaded into distinct thermal cyclers or into separate flow paths through the same thermal cycler. In some examples, the step of holding droplets may be omitted, such that transfer of a packet of droplets from the reservoir and loading the packet into a reaction site occur by continuous flow.

FIG. 10 shows selected portions of an exemplary system 850 capable of performing the method of FIG. 8. The arrows indicate an exemplary sequence in which droplets may move between structural components of the system. However, each of the structural components may be optional, may be used more than once with the same packet of droplets, and/or may be utilized in a different sequence than shown here.

System 850 may incorporate at least one droplet generator 852, at least one droplet reservoir 854, at least one droplet transporter 856, at least one reaction site 858 (also termed a reaction region or droplet processing assembly), and at least one detector 860. All or any subset of these structural components may be connected to one another, with any suitable relative spatial relationships, to form an instrument or an instrument-cartridge assembly (e.g., see FIGS. 2-4). In some examples, one or more of the system components may be utilized remotely, such as a droplet generator that forms droplets (and/or a droplet reservoir that stores droplets) while the droplet generator is not connected to the transporter, reaction site, and/or detector. System 850 also may be equipped with at least one controller 862, which may be in communication with and/or may be programmed to control any suitable combination of system components, as indicated by dashed lines extending from the controller to each other system component.

Droplets formed by droplet generator 852 may be transported by droplet transporter 856, after droplet formation, to reaction site 858, to promote one or more reactions, and to detector 860, to provide detection of droplet signals. Before and/or during their transport, the droplets may be received by at least one droplet reservoir 854 or serially (or in parallel) by two or more droplet reservoirs, and then stored in the droplet reservoir(s) for an adjustable (and selectable) period of time. Droplet storage is an optional part of the system and thus the droplet reservoir may be omitted.

Any suitable droplet generator(s) 852 and detector(s) 860 may be incorporated into the system, such as any of the droplet generators and/or detectors disclosed herein (e.g., see Sections III, IV, and VI).

A "droplet reservoir," also termed a "storage site" or "emulsion reservoir," is any compartment where droplets can be stored, generally in a static volume of fluid, and then accessed at a selectable time. The droplet reservoir may be a well, a chamber, or the like. Exemplary droplet reservoirs may be provided as an array of isolated or isolatable storage sites, such as an array of wells or chambers, among others. The array of storage sites may be provided by a plate.

Droplet transporter 856 may be composed of one or more structures and/or one or more devices that provide selectable transport of droplets from at least one droplet generator and/or at least one droplet reservoir to a reaction site. Selectable transport may permit selection of the different droplet packets sent to a reaction site, the order in which the droplet packets are sent, the time at which each droplet packet is sent, etc. Different droplet packets may have different sample-reagent combinations, different droplets sizes, different sample and/or reagent dilutions, etc. In any event, the selection may be performed by a controller, a user, or a combination thereof. For example, the selection may be based on an order selected by a user and/or programmed into the controller, an arbitrary order selected by the controller, or a dynamic order determined in real time by the controller based on one or more assay results obtained by the system, or a combination thereof, among others.

F. Exemplary Droplet Transporter

Figure 11:
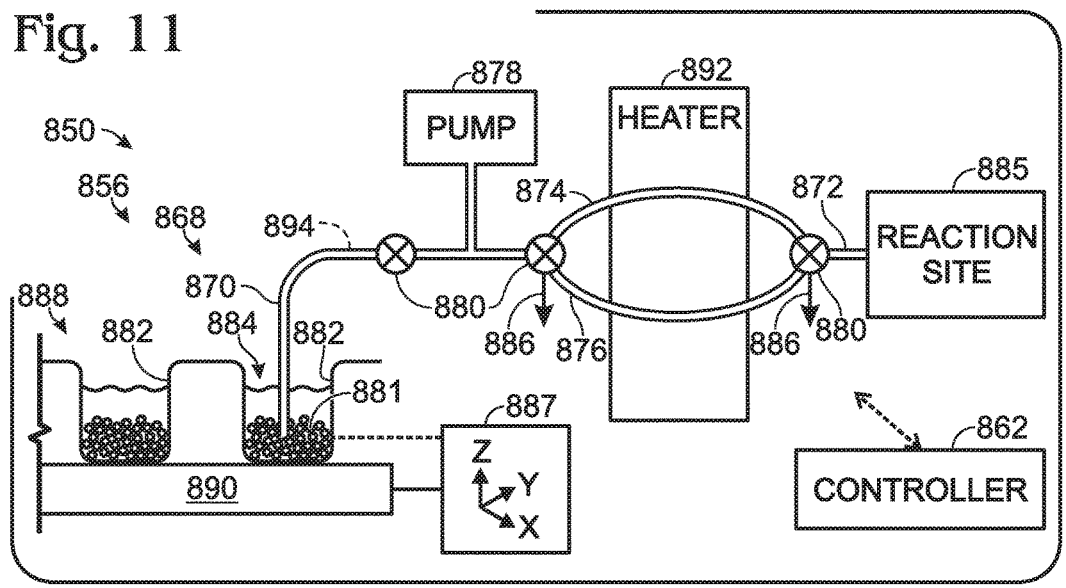
FIG. 11 is a schematic view of an exemplary droplet transporter connecting a droplet storage site to a reaction site, in accordance with aspects of the present disclosure.

FIG. 11 shows selected aspects of an example 868 of droplet transporter 856 (FIG. 10). Transporter 868 may incorporate any combination of at least one intake conduit 870, at least one outflow conduit 872, at least one storage site 874, 876, one or more pumps 878 and/or pressure sources/sinks, and/or one or more valves 880 (e.g., 2-way, 3-way, 4-way, and/or multi-position valves and/or injection loops), among others. The transporter also may include one or more unions, tees, crosses, debubblers, or any combination thereof, among others.

Intake conduit 870 may be configured to receive droplets 881 by picking up and/or taking in droplets from a droplet reservoir 882 (or continuously from a droplet generator). Thus, the intake conduit may abut and/or extend into the droplet reservoir, to provide contact with an emulsion 884 containing the droplets, such that fluid can flow from the emulsion into the intake conduit. The intake conduit may be described as a needle, a tip, a tube, or a combination thereof, among others, and may be sized in cross-section to receive droplets in single file or multiple file (side-by-side).

Outflow conduit 872 may be joined directly to the intake conduit or may be separated from the intake conduit by one or more valves 880, storage sites 874, 876, or the like. For example, in FIG. 11, the intake and outflow conduits are separated by three valves 880 and two storage sites (874, 876).

Each pump 878 (and/or positive/negative pressure source/sink) may drive fluid flow through the intake conduit and/or the outflow conduit, and/or to and/or from the holding site(s). The pump also may drive fluid through a reaction site 885, or a distinct pump may be used for this purpose. In some examples, droplet transporter 868 may include at least one pump (or pressure source/sink) to transfer droplets into the transporter and at least one other pump (or pressure sources/sink) to drive droplets out of the transporter for droplet loading into reaction site 885.

Each storage site 874, 876 may be connected to intake conduit 870 and outflow conduit 872, to permit fluid flow between these structures. For example, valves 880 may provide selectable and adjustable fluid communication between intake conduit 870, outflow conduit 872, and the storage sites. The valves also may permit fluid to be sent, indicated at 886, from either storage site 874, 876 to a waste port.

Droplet transporter 868 may include any other suitable elements. For example, the transporter further may be equipped with a drive assembly 887 that drives relative movement of intake conduit 870 with respect to droplet reservoir 882, in one, two, or three dimensions. For example, an array 888 of droplet reservoirs (e.g., a plate with wells) may be connected to and/or supported by a stage or other support member 890 that is driven in x-, y-, and z-directions, to permit selectable placement of the intake conduit into each of the reservoirs of the array/plate, in any order. In other examples, the droplet reservoirs may remain stationary while the intake conduit is driven into contact with the contents of selected reservoirs. Droplet transporter 868 also or alternatively may incorporate at least one heater 892, which may be positioned to apply heat to any suitable portion (or all) of the droplet transporter, such as droplet reservoirs 882, intake conduit 870, one or more storage sites 874, 876, outflow conduit 872, or any combination thereof, among others. Application of heat may pre-process the droplets, prior to loading the droplets into the reaction site, such as to promote an enzyme reaction (e.g., reverse transcription), to activate a reagent (e.g., an enzyme such as in a hot start prior to an amplification reaction; see Section V), or the like.

The droplet transporter (and/or any other portion of system 850) further may include at least one packing feature 894 to increase the concentration of droplets. The packing feature may increase the volume fraction of an emulsion occupied by droplets, which may, for example, be desirable to decrease the amount of energy spent on heating carrier fluid, to increase the rate at which droplets may be detected by a flow-based (serial) detector, and/or to increase the number of droplets that may be detected simultaneously by an imaging detector, among others. A suitable concentration of droplets (i.e., the "packing density") may be achieved during droplet generation or the packing density may be increased after droplet generation. An increase in packing density may be achieved by removing carrier fluid from an emulsion, while the emulsion is static (e.g., during storage) or flowing, and/or by selective intake of droplets from a stored emulsion, among others. Droplets may be concentrated locally in a stored emulsion by (1) centrifugation, (2) gravity coupled with a density difference between the droplets and the carrier fluid (i.e., the droplets float or sink in the carrier fluid), (3) electrokinetic concentration of droplets, (4) magnetic concentration of droplets, or the like. The packing density may be increased during flow by using one or more side vent lines of smaller diameter (or one or more membranes) that selectively permit lateral flow (and removal) of carrier fluid. Alternatively, or in addition, the packing density may be increased during fluid flow by utilizing droplet inertia.

G. Exemplary System with Coupled Droplet Generation and Transport

FIG. 12 shows a continuous flow example 910 of system 850 (see FIG. 10) in which droplet generation and droplet transport to a reaction site are coupled by continuous flow such that droplets are not stored. System 910 may comprise a serial arrangement of a droplet generator 912, a droplet transport region 914, a thermal cycler 916, a detector 918, and a waste/collection reservoir 920. Droplet generator 912 may be supplied by a carrier fluid, such as oil 922, and a non-partitioned assay mixture 924 of sample and reagent. The oil and the assay mixture each may be driven to droplet generator 912 by a respective pump or pressure source 926, 928. Here, the droplet generator is structured as a cross, but any other configuration may be suitable (e.g., see Sections III and IV). Droplets 930 formed by the droplet generator may flow continuously through droplet transport region 914 to thermal cycler 916, due to continuous fluid flow driven by pumps 926, 928. In other examples, one or more additional pumps or pressure sources/sinks may be used to drive flow through the thermal cycler.

H. Exemplary Systems with Decoupling of Droplet Generation and Transport

Figure 14:
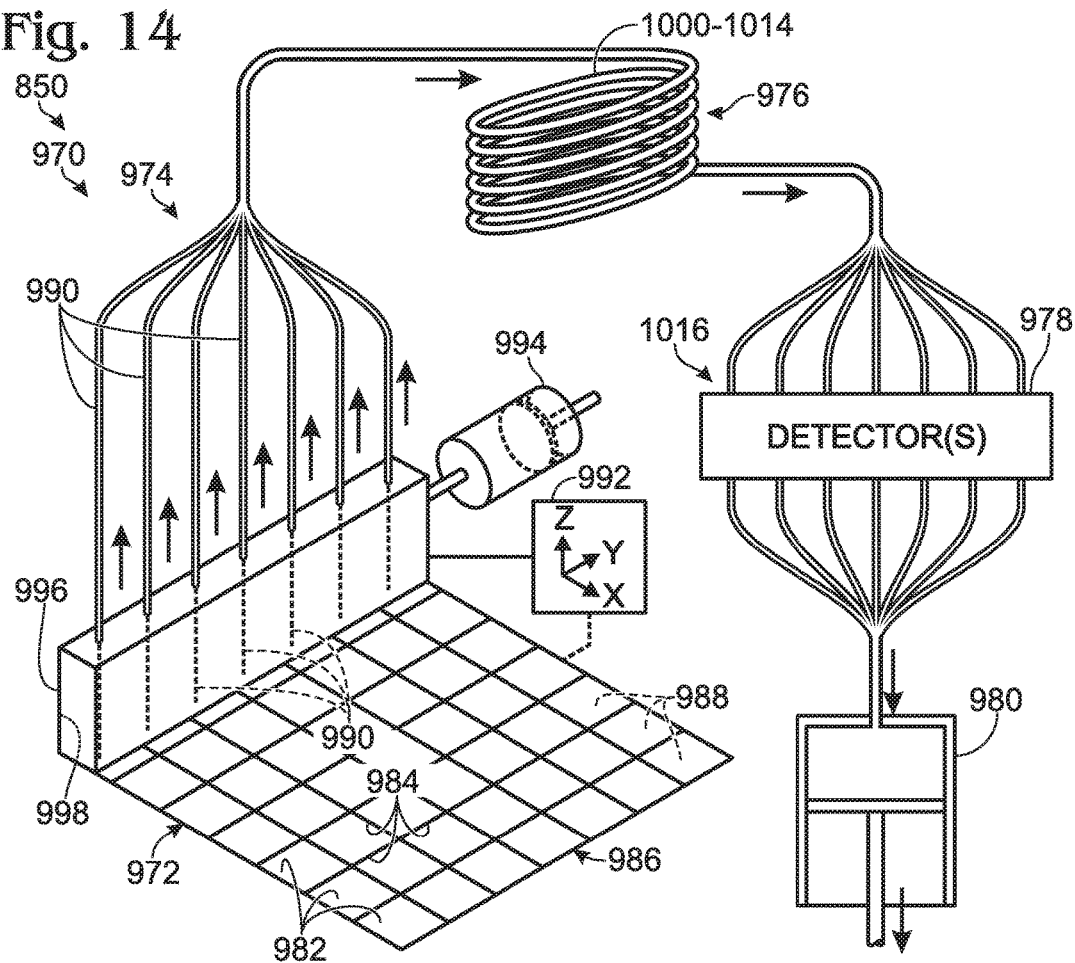
FIG. 14 is a schematic view of an example of a system generally related to the system of FIG. 13, with selected elements replicated such that the system is capable of transporting, reacting, and/or detecting a plurality of distinct droplet packets in parallel, in accordance with aspects of the present disclosure.

FIGS. 13 and 14 show exemplary systems with decoupling of droplet generation and transport.

FIG. 13 shows an example 940 of system 850 in which droplet generation and droplet transport to a reaction site are decoupled. System 940 may include a droplet reservoir 942 holding an emulsion 944 of preformed droplets 946 in a carrier fluid 948. Droplets 946 may be formed off-line from downstream portions of system 940. The droplets, when formed by at least one droplet generator, may flow continuously into droplet reservoir 942. Alternatively, the droplets may be transferred into the droplet reservoir with a fluid transfer device (e.g., a pipette or syringe) from another storage site at a selectable time after droplet generation. In any event, droplet reservoir 942 may be placed into connection with downstream components of system 940 after (or before) droplet formation, permitting droplets 946 to be stored for an adjustable, selectable period of time after (and, optionally, before) the droplet reservoir becomes connected to the downstream system components.

System 940 may incorporate a serial arrangement of a droplet transport region 950, a thermal cycler 952, a detector 954, and at least one pressure source/sink, such as a downstream pressure sink (e.g., syringe pump 956), an upstream pressure source 958, or both. Droplet transport region 950 may include an intake conduit 960 that extends into droplet reservoir 942 and into contact and fluid communication with emulsion 944. Droplets 946 may be drawn into the intake conduit as a result of a negative pressure exerted by a downstream vacuum source (or pressure sink) 956 (e.g., a syringe pump), and/or a positive pressure exerted on emulsion 944 by an upstream pressure source 960 (e.g., another pump), among others. As shown here, the droplets may be dispersed non-uniformly in the emulsion, for example, concentrated selectively toward the top or the bottom of the emulsion by gravity, centrifugation, magnetic attraction, electrokinetic motion, and/or the like, to permit removal of droplets at a higher packing density than the average packing density in the emulsion. Alternatively, or in addition, the carrier fluid may be removed selectively (e.g., removed and discarded) where the droplet packing density is lower than average. In any event, droplets 946 may be driven by continuous flow from the emulsion, through transport region 950 and thermal cycler 952, past detector 954, and into a reservoir 962 provided by syringe pump 956.

FIG. 14 shows an example 970 of system 850 that is generally related to system 940 of FIG. 13, with selected components replicated such that system 970 is capable of transporting, reacting, and/or detecting a plurality of droplet packets in parallel. System 970 may include a serial arrangement of an emulsion array 972, a droplet transporter 974, a thermal cycler 976, one or more detectors 978, and one or more pumps or pressure sources/sinks, such as a syringe pump 980.

Emulsion array 972 may include emulsions 982 held in an array of droplet reservoirs 984 formed by a plate 986. The emulsions may be formed separately from the plate and then transferred to the plate. Alternatively, the plate may be a droplet generator plate incorporating an array of droplet generators 988, which form the emulsions contained in droplet reservoirs 984. Further aspects of droplet generator plates are disclosed below in this Section and in Sections III and IV.

Droplet transporter 974 may include a line of intake conduits or needles 990 for intake of droplets in parallel from a row of droplet reservoirs 984 of plate 986. The tips of intake conduits 990 may be spaced to match the spacing of droplet reservoirs 984 in each row of the plate. Droplet transporter 974 also may include a drive assembly 992 that drives relative movement of plate 986 and intake conduits 990 in at least two dimensions or in three dimensions. In particular, operation of the drive assembly may place the intake conduits serially into fluid communication with each row of emulsions, in a predefined or selectable order. In other examples, the droplet transporter may include a three-dimensional array of intake conduits, which may be arranged in correspondence with the rows and columns of droplet reservoirs formed by plate 986, to permit parallel uptake of droplets from two or more rows of droplet reservoirs (e.g., all of the droplet reservoirs in parallel). With any arrangement of intake conduits, each intake conduit may be connected to a respective valve. Operation of the valve may determine whether an intake conduit is active or inactive for droplet intake. Alternatively, the intake conduits may be connected to the same multi-position valve, which may be operated to select only one of the intake conduits for droplet intake at a time, to provide serial intake of droplets from droplet reservoirs.

Droplet intake may be driven by one or more pumps. For example, a negative pressure applied by syringe pump 980 may draw droplets into intake conduits 990. Alternatively, or in addition, a positive pressure applied by a positive pressure source, such as a pump 994 of droplet transporter 974, may push droplets into the intake conduits, in a manner analogous to that described for system 940 of FIG. 13. In particular, pump 994 may be connected to droplet transporter 974 via a manifold 996. Each intake conduit may extend through the manifold in a sealed relationship with the manifold. The manifold may be movable into a sealed relationship with each row of droplet reservoirs, by operation of drive assembly 992, to form a sealed chamber 998 over each row serially. Accordingly, pump 994 may pressurize the chamber to urge droplets from the reservoirs of a row in parallel into the intake conduits.

Thermal cycler 976 may include a plurality of reaction channels provided by coiled tubes 1000-1014 each forming a separate, respective connection with a different intake conduit 990. The coiled tubes may follow a generally helical path interspersed with one another. For example, the tubes may be braided together and/or wrapped collectively. In any event, droplet transporter 974 may load packets of droplets into the coiled tubes in parallel, and the packets may be thermally cycled in parallel, while following separate flow paths. Droplets from each coiled tube also may be detected in parallel, indicated at 1016, by detector 978. In other examples, each intake conduit 990 may be connected to a respective, distinct thermal cycler, or intake conduits 990 may feed droplets into the same coiled tube or other reaction channel.

I. Exemplary Decoupled System Utilizing an Autosampler

Figure 15:
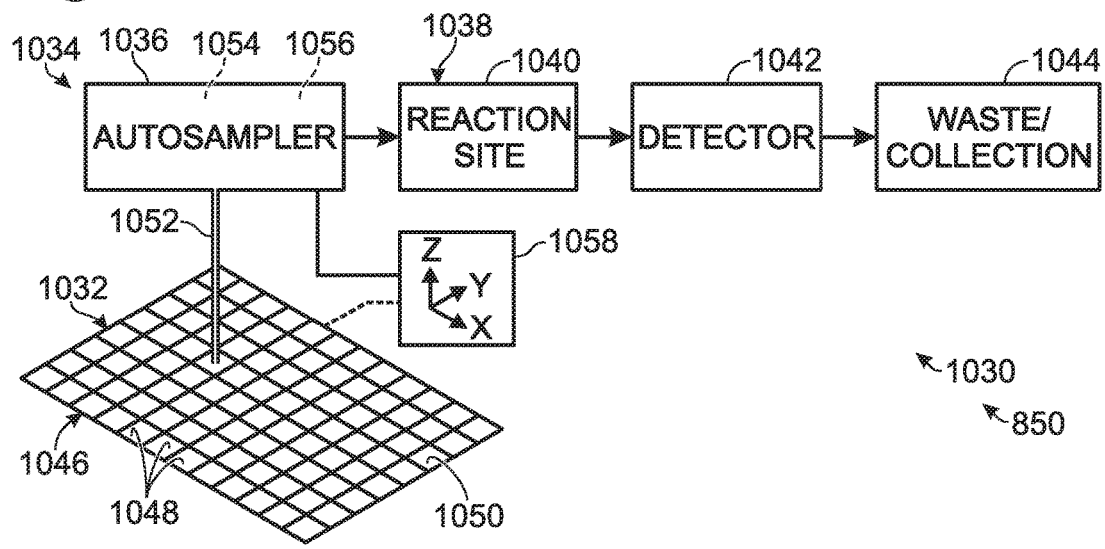
FIG. 15 is a schematic view of another example of the system of FIG. 10 in which droplet generation and droplet transport to a reaction site are decoupled, with the system utilizing an autosampler to transport selected droplet packets from an emulsion array to a reaction site, in accordance with aspects of present disclosure.
Figure 16:
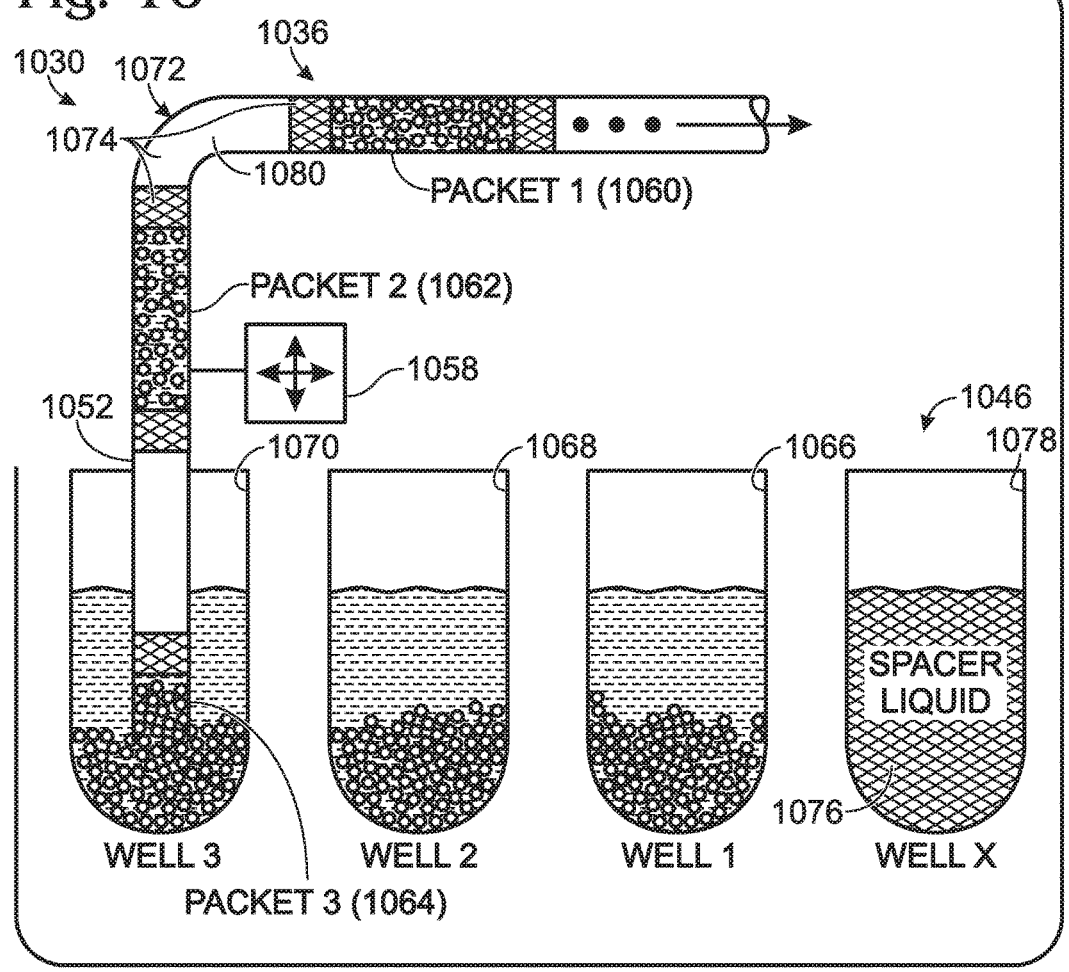
FIG. 16 is a fragmentary view of selected portions of the system of FIG. 15, with the autosampler picking up droplet packets serially from the emulsion array and separated from one another by at least one spacer fluid, in accordance with aspects of present disclosure.

FIGS. 15 and 16 show an exemplary system combining decoupling of droplet generation and transport with autosampling.

FIG. 15 shows another example 1030 of system 850 of FIG. 10 in which droplet generation and droplet transport to a reaction site are decoupled. System 1030 may incorporate a serial arrangement of a reservoir array 1032, a droplet transporter 1034 comprising an autosampler 1036, a reaction site 1038 (e.g., a thermal cycler 1040), a detector 1042, and a waste/collection reservoir 1044. Droplets may travel from array 1032 to reaction site 1038 through the action of autosampler 1036, may be detected by detector 1042 during/after reaction, and then may be collected after detection by reservoir 1044.

Reservoir array 1032 may be structured as a plate 1046 providing an array of droplet reservoirs, such as wells 1048, each containing droplets 1050. Accordingly, plate 1046 may be structured as a droplet generator plate having any combination of the features described elsewhere herein. Alternatively, plate 1046 may hold droplets that were generated separately from the plate and then transferred to the wells of the plate.

Autosampler 1036 generally includes any device or assembly of devices that provides serial intake of fluid into a conduit (e.g., an intake conduit) from an array of reservoirs. The autosampler generally is capable of picking up droplets from any reservoir or sequence of reservoirs of the array and may be controllable to intake a variable volume of fluid from each reservoir. The autosampler may include a needle 1052 that serves as an intake conduit, one or more pumps or pressure sources/sinks 1054, one or more valves 1056, or any combination thereof, among others. The autosampler may include a drive assembly 1058 that controllably drives motion of needle 1052 in three dimensions, such as along three orthogonal axes. For example, the drive assembly may permit the needle to be positioned in an x-y plane over any selected reservoir 1048, and then to be moved along a z-axis, to move the needle into contact with fluid in the selected reservoir, for droplet intake, and then out of contact with the fluid, for movement to another reservoir (or for intake of air). In other examples, the drive assembly may drive movement of the array of reservoirs while the needle remains stationary. In other examples, there may be a z-axis drive assembly to drive z-axis motion of the needle, and an x-y axis drive assembly to drive x-y motion of the array of reservoirs, or vice versa.

FIG. 16 shows selected portions of system 1030 of FIG. 15, with needle 1052 of autosampler 1036 picking up droplet packets 1060-1064 from a corresponding respective series of wells 1066-1070 of plate 1046. Adjacent droplet packets may be separated from one another in autosampler 1036 by any suitable spacer region 1072. The spacer region may contain one or more segments 1074 of one or more spacer fluids. For example, a spacer liquid 1076 may be disposed in a well 1078 of the array or in another accessible reservoir. Needle 1052 may move to well 1078, to take in spacer liquid 1076, after each droplet packet is picked up. Alternatively, or in addition, needle 1052 may take in a volume of a spacer gas, such as air 1080, between packets, while the needle is out of contact with liquid. The use of a spacer gas is optional. The spacer fluid may contain the same immiscible carrier fluid as the droplet packets or a different immiscible carrier fluid. In some embodiments, the spacer fluid may be labeled, such as with a dye, to make it distinguishable from the carrier fluid of a droplet packet and/or to mark a boundary (i.e., a leading or trailing end) of a droplet packet. Alternatively, or in addition, the spacer fluid and/or spacer region may be distinguishable from a droplet packet by a decrease in concentration (i.e., an at least substantial absence) of droplets between droplet packets.

J. Exemplary Systems with Multi-Stage Decoupling

Figure 17:
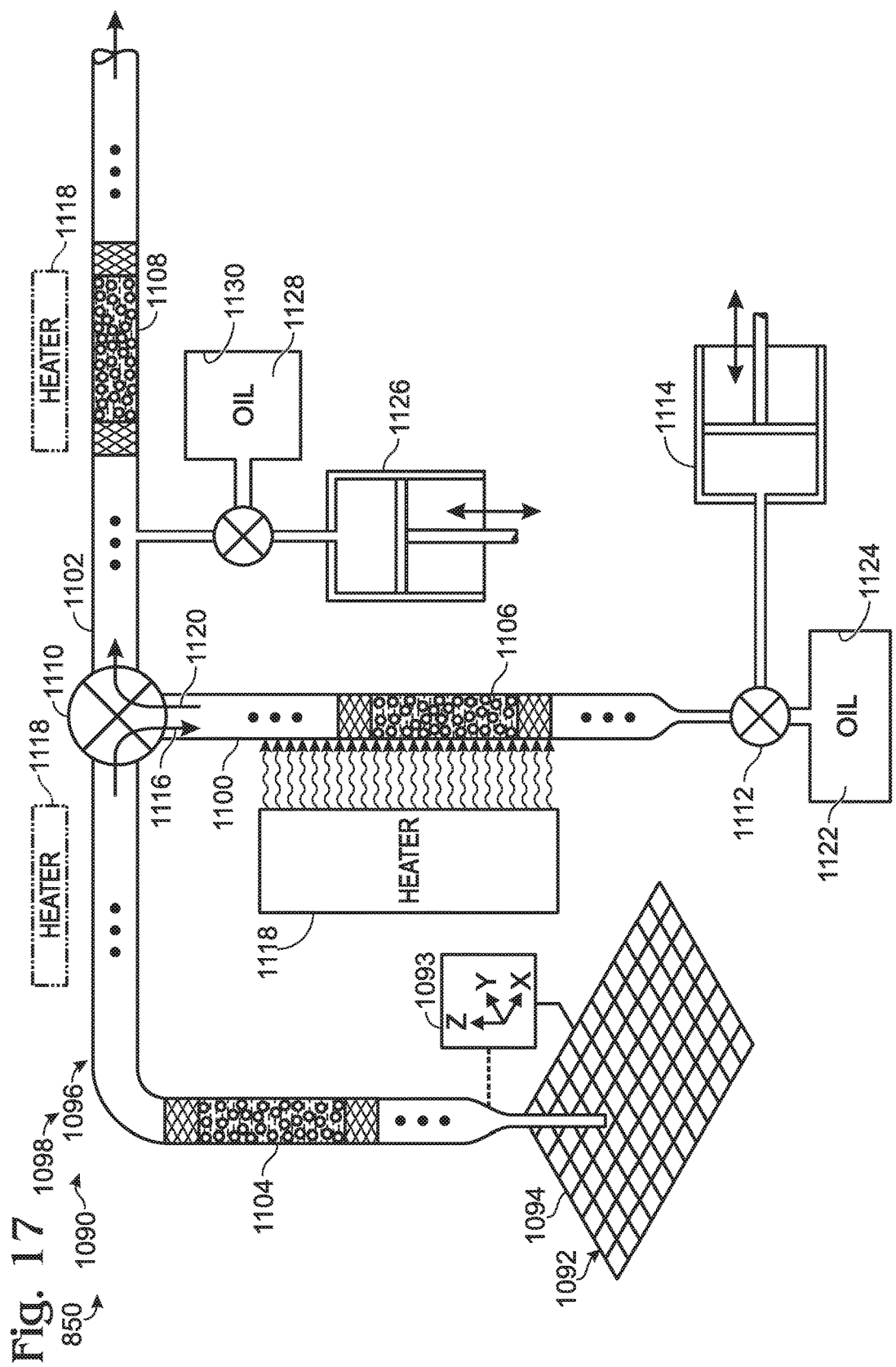
FIG. 17 is a schematic, fragmentary view of an example of the system of FIG. 10 that enables multi-stage decoupling of droplet generation and droplet loading into a reaction site, with the system providing storage of a packet of droplets (a) as part of an array of emulsions and then (b) in an intermediate storage site prior to introducing the packet into a reaction site, in accordance with aspects of the present disclosure.
Figure 18:
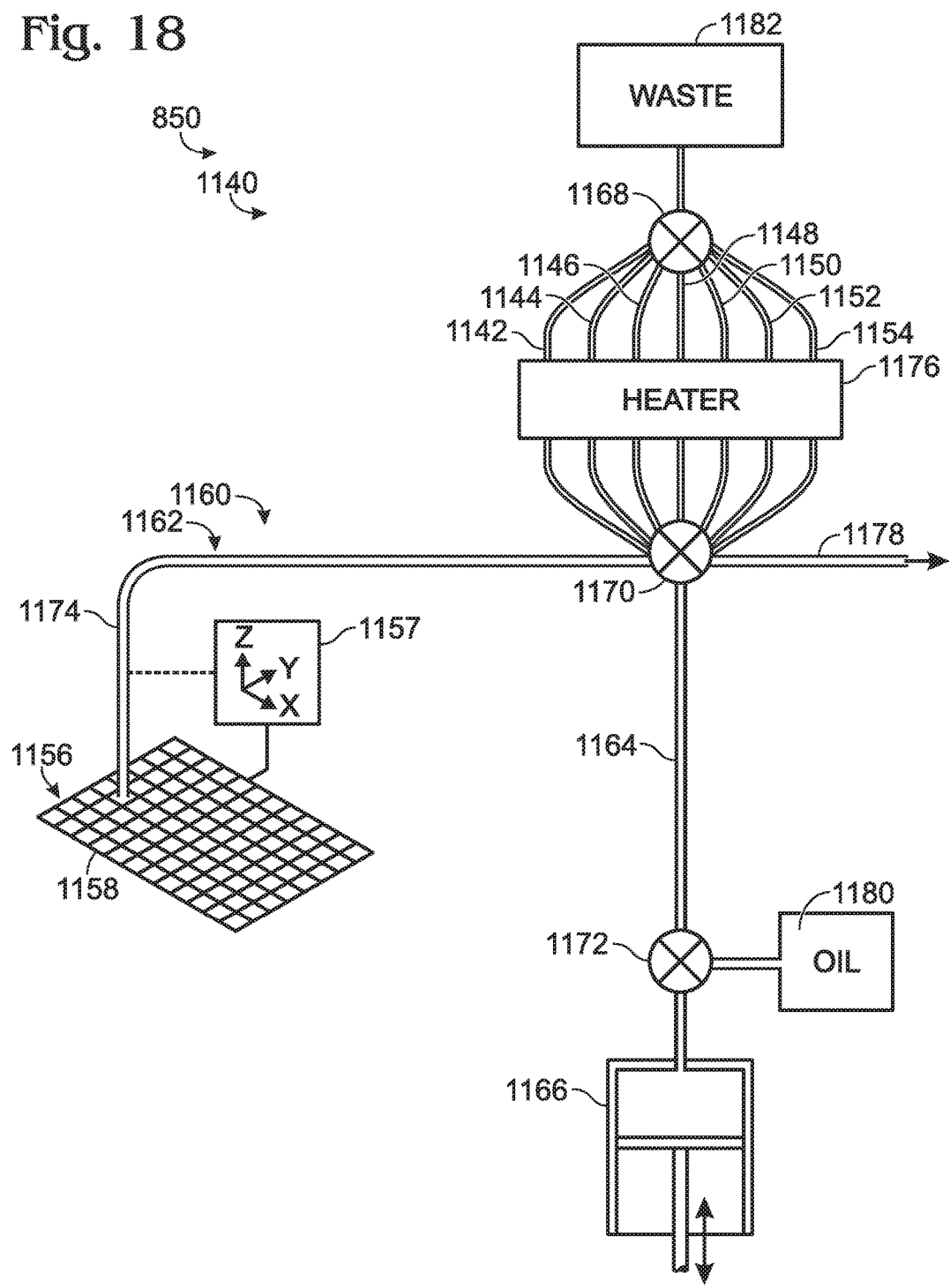
FIG. 18 is a schematic, fragmentary view of another example of the system of FIG. 10 that enables multi-stage decoupling of droplet generation and droplet loading into a reaction site, with the system related to that of FIG. 17 but including a plurality of isolated, intermediate storage sites that can be accessed in an arbitrary order, in accordance with aspects of present disclosure.

FIGS. 17 and 18 show exemplary systems combining multi-stage decoupling of droplet generation from droplet loading into a reaction site, and also show transport with autosampling.

FIG. 17 shows an example 1090 of system 850 of FIG. 10 that enables multi-stage decoupling of droplet generation and droplet loading into a reaction site. More particularly, system 1090 provides storage of a packet of droplets first within an array of emulsions and then in a distinct storage site, after intake and prior to loading the packet into a downstream reaction site. System 1090 may comprise an emulsion array 1092 coupled to a drive assembly 1093. The emulsion array may be held by a plate 1094 (e.g., a microplate or droplet generator plate). System 1090 also may comprise a droplet transporter 1096 that provides selectable intake, holding, heating, and loading.

Droplet transporter 1096 may incorporate an autosampler 1098, at least one storage site 1100, and an outflow region 1102. Autosampler 1098 may transfer droplet packets 1104-1108 into transporter 1096 from selected wells of plate 1094, generally as described with respect to FIGS. 15 and 16.

One or more valves 1110, 1112, in cooperation with one or more pumps 1114, may be operated to determine the flow path and residency time of each packet. For example, valve 1110 may be operated to permit the droplet packets to flow continuously to a downstream reaction site after each packet is transferred into transporter 1096. Alternatively, or in addition, valve 1110 may be operated to transfer a droplet packet (or multiple packets, see FIG. 16) along an inflow path, indicated by an arrow at 1116, to storage site 1100 (e.g., a holding channel or holding chamber). Pump 1114 may be utilized to drive fluid movement into the storage site.

Droplet packet 1106 may occupy storage site 1100 for any suitable period of time. In some examples, packet 1106 may be heated by a heater 1118 while the packet is disposed in the storage site. Alternatively, or in addition, packet 1106 may be heated upstream of holding site 1100, such as while the packet is contained by plate 1094, during flow to the holding site, and/or while disposed in outflow region 1102, among others. In any event, droplet packet 1106 may be permitted to leave the holding site by operation of valve 1110, to open an outflow path, indicated at 1120, to outflow region 1102. Also, pump 1114 may drive flow of droplet packet 1106 with the aid of a carrier fluid 1122 obtained from a connected reservoir 1124. The carrier fluid also may function to flush droplets from the holding site, to permit re-use of the site with a different packet of droplets without substantial cross-contamination. In any event, pump 1114 may drive packet 1106 through outflow region 1102, and then another pump 1126 may drive the packet to a downstream reaction site with the aid of a carrier fluid 1128 obtained from a connected reservoir 1130. The use of downstream pump 1126 permits valve 1110 to be re-positioned, to close outflow path 1120 and open inflow path 1116, such that pump 1114 can drive another packet (e.g., packet 1104) into holding site 1100.

FIG. 18 shows another example 1140 of system 850 (see FIG. 10) that enables multi-stage decoupling of droplet generation and droplet loading into a reaction site. System 1140 is related generally to system 1090 of FIG. 17 but includes a plurality of isolatable storage sites 1142-1154 that can be accessed in a selectable sequence, to provide loading of droplet packets from the storage sites into a reaction site according to the sequence. System 1140 may comprise a serial arrangement of an emulsion array 1156 coupled to a drive assembly 1157. The emulsion array may be held by a plate 1158 (e.g., a droplet generator plate). System 1140 also may comprise a droplet transporter 1160. The transporter may enable selectable intake of droplet packets from plate 1158, holding of each packet for an adjustable period of time, and selectable loading of the packets into a reaction site.

Transporter 1160 may be equipped with an autosampler 1162, a temporary holding station 1164, at least one pump 1166, and one or more valves 1168-1172, among others. Pump 1166 may drive intake of droplets into an intake conduit 1174 of autosampler 1162. The droplets may represent one packet or a plurality of spaced packets. In any event, pump 1166 may drive flow of the packet into holding station 1164. Multi-position valve 1170 then may be operated to open a flow path from holding station 1164 to one of storage sites 1142-1154, and pump 1166 may drive the packet from the station to the storage site. This process may be repeated one or more times to place other packets into other storage sites 1142-1154. A heater 1176 may apply heat to droplet packets disposed in the storage sites.

Droplet packets in the storage sites may be loaded serially into a downstream reaction site in a selectable order. In particularly, valve 1170 may be positioned to open a flow path between a selected storage site and station 1164. Pump 1166 then may drive a droplet packet(s) from the selected storage site into station 1164. Valve 1170 next may be re-positioned to open a flow path from station 1164 to an outflow conduit 1178. Then, pump 1166 may drive the droplet packet from station 1164 to outflow conduit 1178, with the aid of a carrier fluid 1180 traveling behind the packet. Pump 1166 may drive the packet from outflow conduit 1178 to a downstream reaction site, or another pump may be utilized (e.g., see FIG. 17). In some examples, the droplet packet(s) in a storage site may be driven to a waste reservoir 1182, instead of being transferred to station 1164.

K. Overview of Amplification in Static Fluid

FIGS. 19-21 relate to exemplary systems for sample analysis using droplet-based assays in which amplification is performed with stationary emulsions and/or by batch amplification of an array of emulsions.

FIG. 19 shows a flowchart 1190 listing exemplary steps that may be performed in a method of sample analysis using droplets subjected to conditions for amplification while disposed in a static fluid. The steps listed may be performed in any suitable order and in any suitable combination and may be combined with any other steps disclosed elsewhere herein.

A sample and at least one reagent may be mixed to create an assay mixture for amplification, indicated at 1192. The sample and reagent may be combined manually or automatically. In some embodiments, one or more samples and one or more reagents may be mixed to create a plurality of distinct and separate assay mixtures.

At least one emulsion may be generated from at least one assay mixture, indicated at 1194. The emulsion may be generated by serial, parallel, or bulk droplet generation (e.g., see Sections III and IV). If more than one emulsion is generated, the emulsions may be generated in parallel or serially with respect to one another.

The at least one emulsion may be thermally cycled while the emulsion remains stationary, indicated at 1196. In particular, the emulsion may be disposed in a container that restricts directional flow of the emulsion as it is thermally cycled.

Signals may be detected from droplets of the emulsion, indicated at 1198. The signals may be detected while the emulsion is flowing or not flowing (e.g., see Section VI), and may involve serial droplet detection or imaging, among others.

FIG. 20 shows a flowchart 1200 listing exemplary steps that may be performed in a method of sample analysis using parallel amplification of an array of emulsions. The steps listed may be performed in any suitable order and in any suitable combination and may be combined with any other steps disclosed elsewhere herein.

A plurality of assay mixtures may be created, indicated at 1202. Each assay mixture may be an amplification mixture capable of amplifying at least one species (or two or more species) of nucleic acid target, if present, in the amplification mixture. The assay mixtures may contain respective distinct samples, distinct reagents (e.g., to amplify different species of nucleic acid target), or any combination thereof. In some embodiments, the assay mixtures may be created or disposed in an array, such as a planar array formed by a plate.

Emulsions may be generated from the respective assay mixtures, indicated at 1204. The emulsions may be generated serially or in parallel with respect to one another, and droplets of each emulsion may be generated serially, in parallel, or in bulk.

The emulsions may be thermally cycled in an array, indicated at 1206. The array may be a linear array, a planar (two-dimensional) array, or a three-dimensional array.

Droplets signals may be detected from one or more droplets of each emulsion, indicated at 1208. Detection may be performed while the emulsions remain disposed in the array and in a device holding the emulsions in the array (e.g., a plate). Alternatively, detection may be performed after removal of droplets from the array. More particularly, detection may be performed after transfer of the droplets from a container/vessel (e.g., a plate, well, or a vial) that holds the droplets. For example, the droplets may be transferred out of the container/vessel to a detection site (e.g., a detection channel, chamber, recess) adjacent a detection window. Transfer may be achieved with any suitable manual or automated fluid transfer device. Furthermore, detection may be flow-based detection (e.g., serial droplet detection) or static/stopped-flow detection (e.g., imaging), among others.

FIG. 21 shows a schematic view of selected portions of an exemplary system 1210 for performing the method of FIG. 20. Any one component or combination of the depicted system components may be omitted from the system, and any additional structural components disclosed elsewhere herein may be added to the system. The arrows indicate an exemplary sequence in which sample and emulsions may move between structural components of the system. However, the structural components may be utilized in a different sequence than shown here.

System 1210 may include a droplet generator array 1212, an emulsion holder 1214, a batch thermal cycler 1216, and a detector 1218. Droplet generator array 1212 may include a set of droplet generators connected to one another in a linear, planar, or three-dimensional array. Alternatively, system 1210 may employ a plurality of droplet generators that are not held in an array. In any event, a plurality of emulsions may be generated by the droplet generators and disposed in at least one emulsion holder (e.g., a plurality of vials, or a plate with an array of wells or chambers, among others). The emulsions may flow continuously from their respective droplet generators to the emulsion holder(s), which may be connected to the droplet generators. Alternatively, the emulsions may be transferred to the holder(s), such as with a manual or automated fluid transfer device, at a selectable time. In any event, the emulsion holder(s) and the emulsions held therein may be thermally cycled by batch thermal cycler 1216 with the emulsions held in an array. Each site of the array may be defined by the emulsion holder, by a receiver structure of the thermal cycler, or both, among others. After thermal cycling, detector 1218 may be used to perform flow-based or static/stopped-flow detection of droplets. In some examples, the detector may image droplets of the emulsions while the emulsions are still disposed in the emulsion holder, and optionally, while the emulsion holder is operatively coupled to the thermal cycler.

L. Exemplary Droplet Generator Arrays for a Batch Amplification System

FIGS. 22-32 relate to exemplary devices for generating an array of emulsions, which may (or may not) be reacted in parallel, such as batch-amplified.

Figure 23:
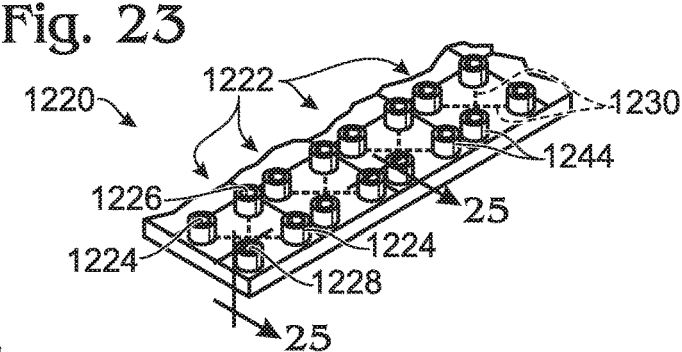
FIG. 23 is a fragmentary view of the device of FIG. 22, taken generally at the region indicated at "23" in FIG. 22, and illustrating a subset of the droplet generators.

FIGS. 22 and 23 show an exemplary device 1220 equipped with an array of droplet generators. Device 1220 may be structured as a plate incorporating an array of droplet generators 1222. Each droplet generator may have any suitable droplet generator structure, such as any of the structures described in Sections III and IV. Each droplet generator may include a plurality of reservoirs, such as wells 1224, 1226, 1228 that can be accessed (e.g., fluid loaded and/or removed) from above the plate. The reservoirs may be termed ports and may be connected fluidly by channels 1230 formed near the bottom of the reservoirs. An intersection of the channels may form a site or intersection 1232 of droplet generation where droplets are formed by any suitable mechanism, such as flow-focusing.

Figure 24:
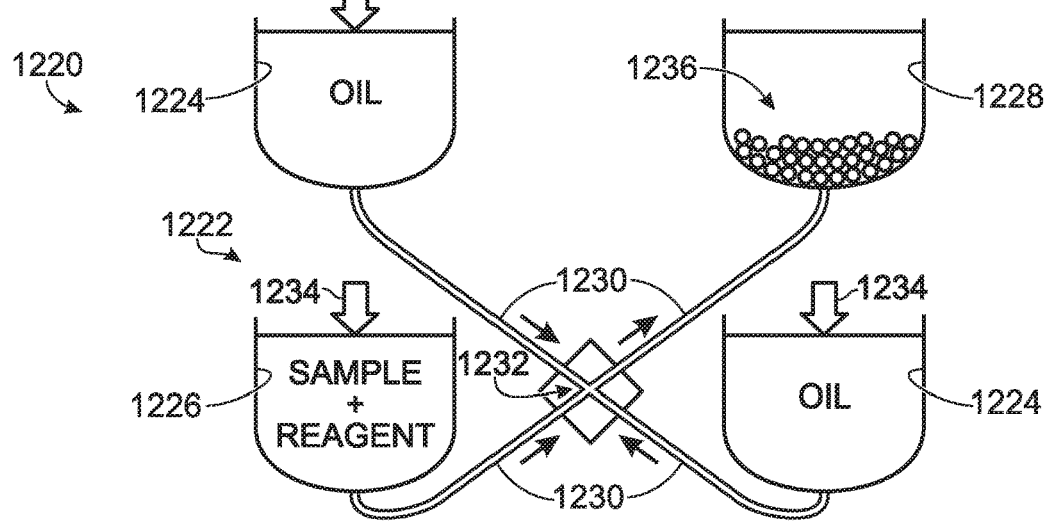
FIG. 24 is a schematic view of one of the droplet generators of FIG. 23, illustrating how droplets are generated and driven to a droplet reservoir by application of pressure.

FIG. 24 shows a schematic view of one of droplet generators 1222, which has a four-port configuration. To form droplets from the generator, one or more oil wells 1224 may be loaded with a carrier fluid (e.g., oil). Also, a sample well 1226 may be loaded with a sample (e.g., an assay mixture, such as a PCR mixture including sample and reagent to perform a reaction, such as amplification)). Pressure may be applied, indicated by vertical arrows at 1234, to oil wells 1224 and sample well 1226, to drive fluid flow, droplet generation, and flow of the resulting droplets as an emulsion 1236 to emulsion well 1228. Fluid flow is indicated by arrows extending parallel to channels 1230. In other examples, each droplet generator may include only one oil well and one sample well, to provide a three-port configuration (see below) or one or more oil reservoirs may be shared by droplet generators of the plate.

Figure 25:
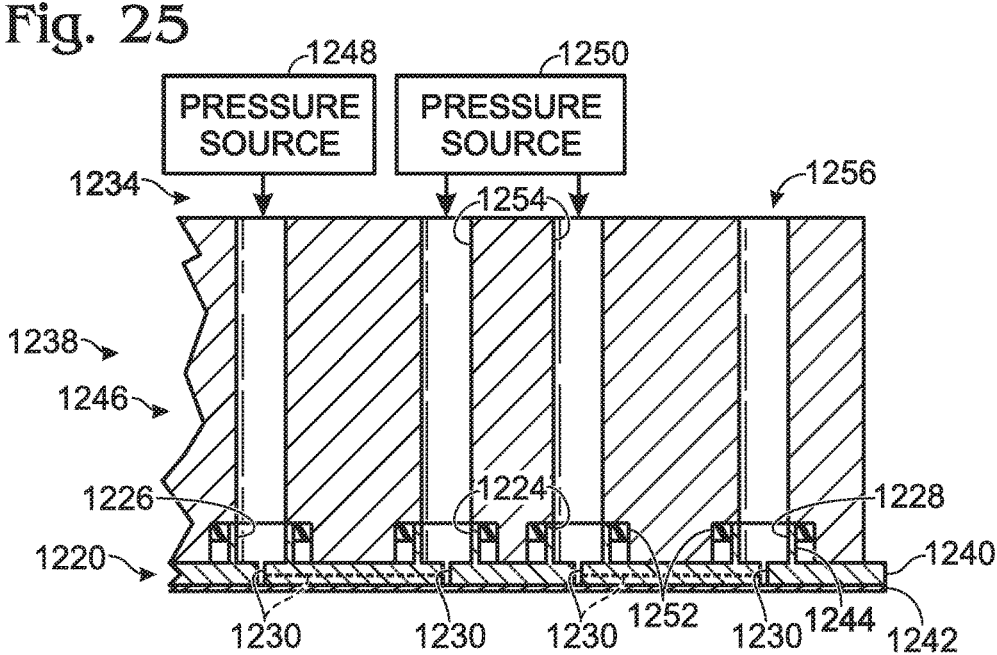
FIG. 25 is a sectional view of the device of FIG. 22, taken generally along line 25-25 of FIG. 23, and with the device assembled with an exemplary pressure manifold for applying pressure to the droplet generators to drive droplet generation, in accordance with aspects of present disclosure.

FIG. 25 shows a sectional view of plate 1220 assembled with an exemplary pressure manifold 1238 for applying pressure to droplet generators 1222 (see FIGS. 22-24), to drive droplet generation (and emulsion formation). In this view, the wells are shown without fluid to simplify the presentation. Also, the four wells visible in this view do not all belong to the same droplet generator, but for simplification, these wells are described as if they do.

Plate 1220 may include an upper member 1240 and a lower member 1242. Upper member 1240 may define wells 1224-1228, which may, for example, be created by ridges 1244 (e.g., annular ridges; also see FIG. 23) that project upward from a base portion of the upper member and that form laterally enclosing side walls of each well. The upper member also may define the top walls and side walls of channels 1230. These channels may provide communication for fluid movement from wells 1224, 1226 and to well 1228 of the droplet generator and may be formed in the bottom surface of the upper member (such as in the cross pattern depicted in FIG. 23). Lower member 1242, which may be termed a cover layer, may be disposed below upper member 1240 and attached to the upper member 1240 via the bottom surface of the upper member. The lower member may overlap at least a portion of the upper member's bottom surface, from below, to cover and seal openings, such as channels 1230, formed in the bottom surface of upper member 1240. Lower member 1242 thus may form a bottom wall of channels 1230, such that the channels are enclosed and fluid cannot escape from the bottom of the plate via the wells or the channels. In some embodiments, upper member 1240 may be formed of a polymer, such as by injection molding.

Pressure manifold 1238 may include a manifold body or routing member 1246 that is connected or connectable to one or more pressure sources 1248, 1250. Manifold body 1246 may mate with plate 1220 from above to form a seal with wells 1224-1228 of the droplet generators via sealing elements or gaskets 1252, such as elastomeric O-rings. The manifold body also may define channels 1254 that communicate with wells 1224-1228.

Any suitable combination of channels 1254 of the manifold body may be connected or connectable to one or more pressure sources, to permit parallel or serial droplet generation from all or a subset of the droplet generators. Accordingly, the pressure manifold may permit pressurization of only one of the droplet generators at a time, or parallel pressurization of two or more of the droplet generators, to drive parallel emulsion formation from two or more droplet generators of the plate in a batch process. For example, oil wells 1224 of a subset or all of the droplet generators may be pressurized with pressure source 1250, and sample wells 1226 may be pressurized with another pressure source 1248, to permit the pressures exerted on fluid in the oil wells and the sample wells to be adjusted independently. Thus, in some examples, the manifold may permit one pressure to be applied to the oil wells in parallel, and another pressure to be applied independently to the sample wells in parallel. Alternatively, the same pressure source may exert pressure on the oil wells and the sample wells. The manifold further may permit emulsion wells 1228 to be independently pressurized with respect to the other wells (e.g., to form a pressure sink to draw fluid into the emulsion wells), may permit the emulsion wells to be vented during emulsion generation, indicated at 1256, to form a pressure drop with respect to the pressurized oil and sample wells, or a combination thereof.

FIG. 26 shows plate 1220 with the pressure manifold replaced by an exemplary cover or sealing member 1258 after emulsion formation. (An emulsion is present in emulsion well 1228, and the oil and assay mixture fluids are substantially depleted from wells 1224 and 1226.) Cover 1258 may seal wells 1224-1228 to, for example, prevent fluid loss by evaporation. The cover may include a resilient member 1260 that engages ridges 1244 to cover and seal each well. In some examples, the resilient member may be complementary to at least a portion of the wells, such as to form caps and/or plugs for individual wells. In some examples, cover 1258 may cover and seal only emulsion wells 1228. In some examples, a plurality of covers may be used. In any event, after assembling plate 1220 with cover 1258, the plate may be subjected to thermal cycling to induce amplification in emulsion wells of the plate. For example, the plate and its cover may be disposed in a thermally cycled chamber. Alternatively, each emulsion may be transferred from plate 1220 to another container, such as a sealable tube (e.g., for use with a Cepheid SmartCycler) or a sealable well/chamber of a plate (e.g., a 96-well PCR plate), for thermal cycling. In other examples, sealing the emulsion in a container to reduce evaporation may not be required if the carrier fluid is capable of forming a sufficient liquid barrier to evaporation for the droplets.

Droplet signals from the emulsions may be detected during/after thermal cycling, either with or without transfer of the emulsions from emulsion wells 1228 to a detection site. In some examples, plate 1220 may permit imaging from beneath the plate. In some embodiments, emulsion wells 1228 may be sealed with a cover layer of optical quality (e.g., transparent), such as a tape or thin sheet, among others. The plate then may be inverted, and droplets imaged through the cover layer. In this case, the carrier fluid and assay mixture compositions may be selected such that the droplets sink in the emulsion, to form a monolayer on the cover layer. In some examples, the detector may be equipped with confocal optics to enable collection of image data from droplets that are not disposed in a monolayer.

Plate 1220 may have any suitable number of droplet generators 1222 (see FIGS. 22-24), disposed in any suitable number of rows and columns. In some embodiments, the droplet generators and/or wells thereof may correspond in spacing, number, and/or row/column arrangement to wells of a standard microplate. For example, the center-to-center distance, number, and/or arrangement of droplet generators (and/or wells) may correspond to a microplate with 6, 24, 96, 384, 1536, etc. wells, among others. Thus, the plate may have 6, 24, 96, 384, or 1536 droplet generators and/or wells (total wells or of a given type (e.g., emulsion wells), which may be spaced by about 18, 9, 4.5, 2.25, or 1.125 millimeters, among others. With an arrangement of ports corresponding to a standard microplate, instruments designed for parallel fluid transfer to/from standard microplates may be utilized with plate 1220.

FIG. 27 shows another exemplary device 1270 incorporating an array of droplet generators 1272. Device 1270 may be structured as a plate and may have any of the features described above for plate 1220 (see FIGS. 22-26).

Each droplet generator 1272 may include a plurality of ports, which may be structured as wells 1274-1278. In particular, droplet generator 1272 may have a three-port configuration of an oil well 1274 to receive a carrier fluid, a sample well 1276 to receive a sample (e.g., a prepared sample that is an assay mixture, such as an amplification mixture), and an emulsion well 1278 to receive an overflow portion of an emulsion generated by the droplet generator.

FIG. 28 shows a bottom view of droplet generator 1272, taken after generation of droplets 1280 to form an emulsion 1282. The droplet generator may include a network of channels 1284 that carry fluid from oil well 1274 and sample well 1276 to a site or intersection 1286 of droplet generation. A pair of channels 1284 may extend from oil well 1274 to site 1286 and another channel 1284 may extend from sample well to site 1286, to form a cross structure at which droplets are formed by flow focusing of fluid from the sample well by carrier fluid disposed on opposing sides of fluid stream from the sample well.

Droplets 1280 may flow from droplet generation site 1286 to emulsion well 1278 via an outlet channel 1288. The outlet channel may widen as it extends from site 1286 to form a chamber 1290. The chamber may have a high aspect ratio, with a height/thickness that generally corresponds to the diameter of the droplets, to promote formation of a monolayer 1292 of droplets in the chamber. Droplets also may flow past chamber 1290 to emulsion well 1278. However, emulsion well 1278 may function predominantly as an overflow site to collect excess emulsion. In other embodiments, emulsion well 1278 may be omitted. In any event, chamber 1290 may be connected to a vent 1294, which may be disposed generally downstream of the chamber, to permit escape of air as an emulsion flows into the chamber.

Figure 29:
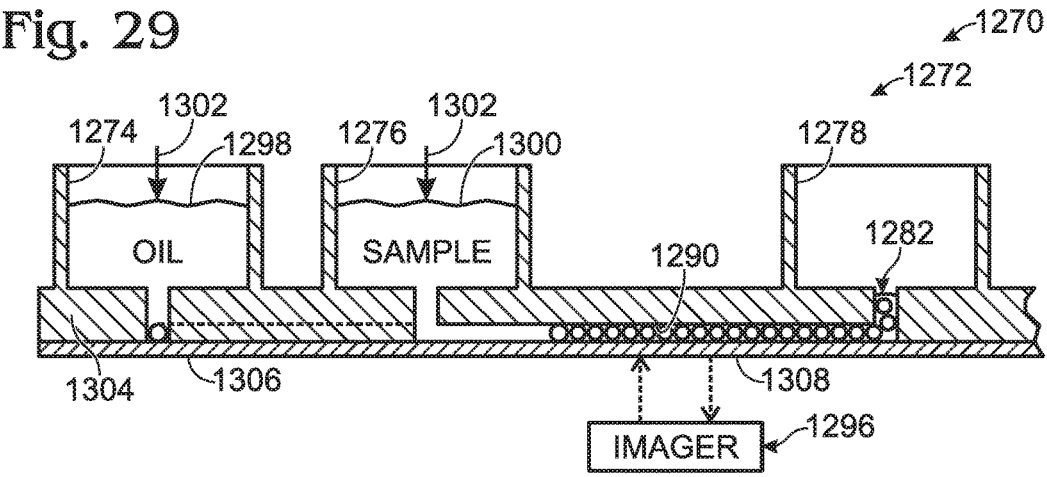
FIG. 29 is a sectional view of the droplet generator of FIG. 28, taken generally along line 29-29 of FIG. 28 and illustrating how droplets may be imaged from below the device.

FIG. 29 shows a sectional view of droplet generator 1272 and illustrates how droplets may be generated and then imaged with an imager 1296 from below plate 1270. To generate droplets, oil well 1274 may be loaded with a carrier fluid 1298 and sample well 1276 with a sample (e.g., an assay mixture 1300). Pressure may be applied to the oil well and the sample well, indicated by pressure arrows at 1302, to drive droplet generation. For example, pressure may be applied using a pressure manifold, as described above for FIG. 25. In other examples, fluid flow and droplet generation may be driven by application of a vacuum to emulsion well 1278, or by spinning plate 1270 in a centrifuge to apply a centripetal force perpendicular to a plane defined by the plate, among others. In some examples, plate 1270 may be designed with an oil reservoir that supplies carrier fluid to two or more droplet generators 1272. In particular, channels may extend from the oil reservoir to two or more sites 1286 of droplet generation. In other examples, pistons received in the wells may be used to drive droplet generation (e.g., see Section III).

The droplets may be reacted in chamber 1290. For example, plate 1270 may be placed in a heating station, such as a thermal cycler, to induce amplification of one or more nucleic acid targets in the droplets. Before heating the plate, wells 1274-1278 may be sealed from above with at least one sealing member, as described above for FIG. 26, to reduce evaporation. Alternatively, the plate may be heated without sealing the wells because fluid in the chamber may be resistant to evaporation.

Plate 1270 may be designed to permit imaging droplets in the chamber. For example, the plate may include an upper member 1304 attached to a lower member 1306, as described above for plate 1220 (see FIGS. 25 and 26), with at least one of the members forming a viewing window or optical window 1308 through which the droplets may be imaged. Accordingly, the upper member and/or the lower member may be transparent, to permit imaging from above and/or below the plate. Plate 1270 may provide the capability to image droplets in place, without unsealing any ports after reaction of the droplets (e.g., opening ports by removing a plate cover). Plate 1270 may reduce the risk of release of amplicon formed in the plate during reaction, which could contaminate other subsequent reactions, because the amplicon can be held in the same substantially enclosed compartment (e.g., chamber 1290) during reaction and imaging. In some examples, the imaging device may be configured to collected image data from droplets as they are being reacted, for example, while they are being thermally cycled.

Chamber 1290 may have any suitable area. For example, the chamber may have a substantially larger footprint than a port, such as occupying at least about 2, 5, or 10 times the area of the port.

Figure 30:
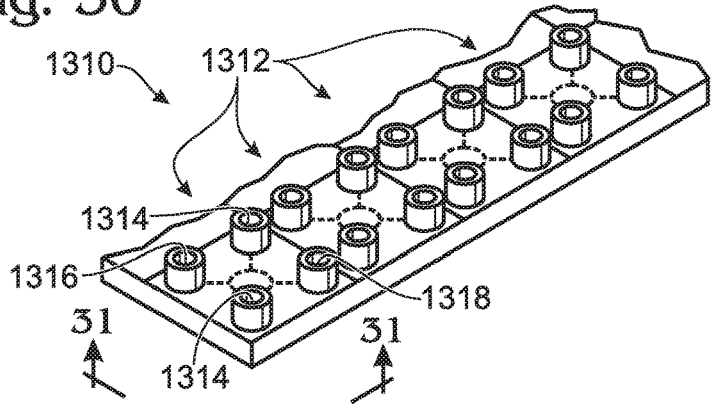
FIG. 30 is a fragmentary view of yet another exemplary device incorporating an array of droplet generators, in accordance with aspects of present disclosure.

FIG. 30 shows yet another exemplary device 1310 incorporating an array of droplet generators 1312. Device 1310 may be structured as a plate, and each droplet generator 1312 may be structured and may operate generally as described above for droplet generators 1222 (see FIGS. 22-26). In particular, each droplet generator may include a pair of oil wells 1314, a sample well 1316, and an emulsion well 1318.

Figure 31:
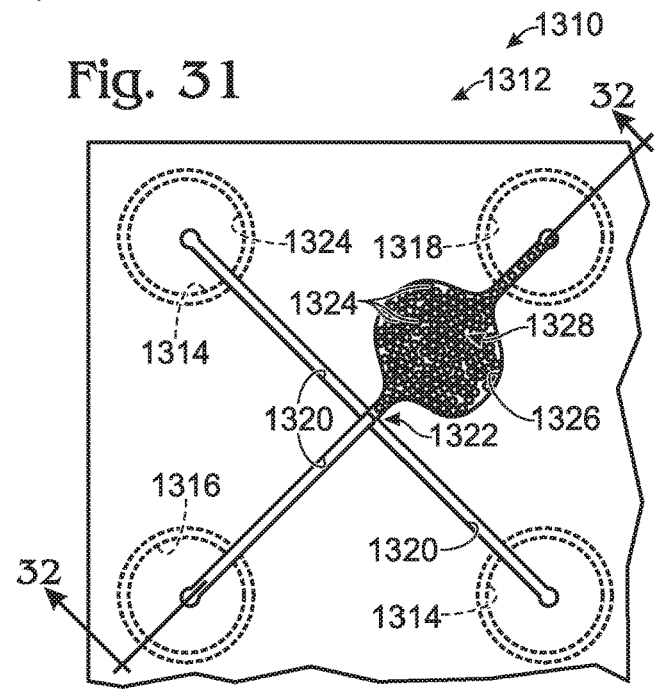
FIG. 31 is a bottom view of a droplet generator of the device of FIG. 30, taken after droplet generation.

FIG. 31 shows a bottom view of a droplet generator 1312 of plate 1310 after droplet generation. The droplet generator may include a network of channels 1320 that permit flow of a carrier fluid and an assay mixture, respectively, from oil wells 1314 and sample well 1316 to a site 1322 of droplet generation. Droplets 1324 formed may flow into a chamber 1326 to form a substantial monolayer 1328 of droplets, as described above for chamber 1290 (see FIGS. 27-29).

FIG. 32 shows a sectional view of droplet generator 1312 and illustrates how droplets may be generated and then imaged from below (and/or above) the device. In particular, plate 1310 may form a viewing window above and/or below chamber 1326.

M. Exemplary Detection for a Batch Amplification System

FIGS. 33-40 show exemplary modes of detection for a batch amplification system.

FIG. 33 shows an exemplary imaging system 1360 for batch detection of an array of emulsions 1362 that are held by a plate 1364 in an array of wells 1366. The emulsions may be reacted (e.g., amplified by thermal cycling) in plate 1364 or may be transferred to the plate with a fluid transfer device after reaction, among others. Plate 1364 may be disposable (e.g., formed of plastic) or re-usable (e.g., formed of quartz), depending on the application.

Imaging system 1360 may include an imaging device or imager 1368 connected to a controller 1370, such as a computer. Any suitable aspects of imaging system 1360 may be used in other imaging systems of the present disclosure. Also, imaging system 1360 may incorporate any other feature(s) disclosed for other imaging systems of the present disclosure. Imager 1368 may (or may not) be a fluorescence imager. The imager may collect images of droplets disposed in wells 1366, for example, using a CCD camera or a line-scan CCD, among others. For a larger field of view, plate 1364 and/or the camera may be placed on, and/or may be otherwise connected to, a translation stage to drive motion in x-, y-, and, optionally, z-directions. In some examples, imager 1368 may, for example, include a laser/PMT device, as is used for detection of microarrays. Further aspects of imaging devices and methods that may be suitable are described in Section VI.

FIG. 34 shows a fragmentary view of plate 1364, with well 1366 holding an emulsion 1362 to be imaged. The well may include a bottom wall 1372, which may be flat, transparent, substantially non-fluorescent, or any combination thereof, to make the well suitable for imaging from below plate 1364. Well 1366 may have an inner surface that is hydrophobic, which may prevent aqueous droplets from wetting the well surface.

Well 1366 may contain a substantial monolayer 1374 of droplets 1376. The monolayer may be disposed adjacent bottom wall 1372. Monolayer 1374 may be obtained by selecting a suitable diameter of the well, number of droplets in the well, and size of each droplet. Also, monolayer formation may be promoted by selecting a carrier fluid composition that is less dense than the fluid phase of the droplets, such that the droplets sink to the bottom of the well. Monolayer formation also may be promoted by spinning plate 1364 in a centrifuge.

Figure 35:
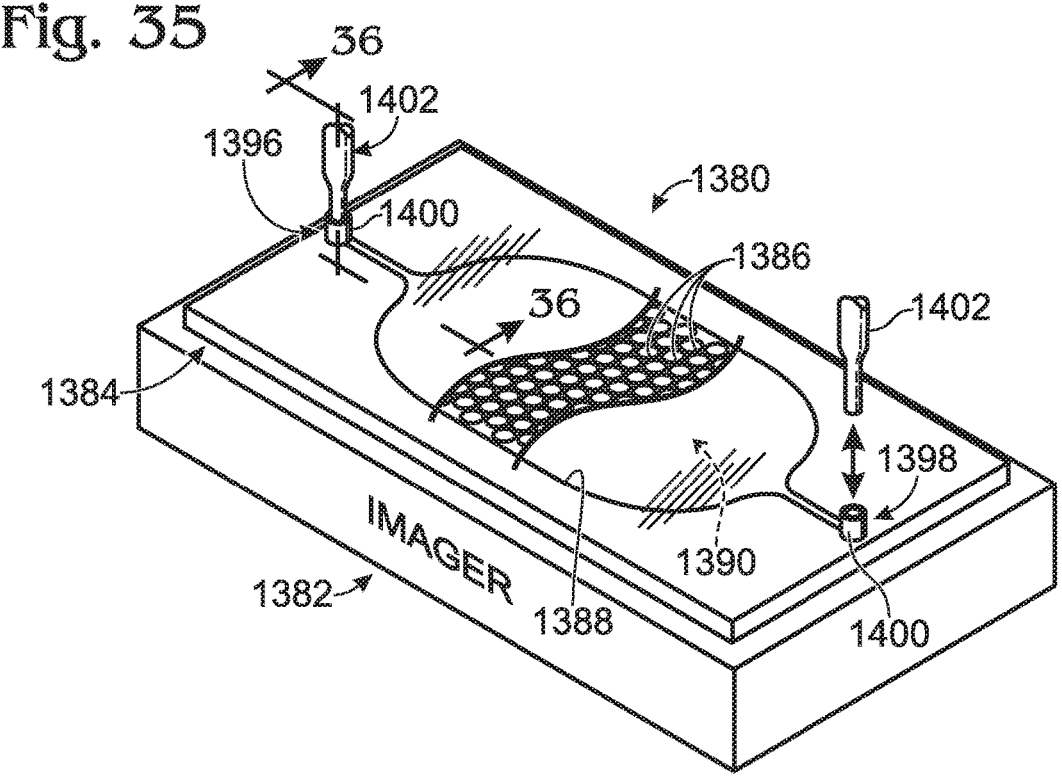
FIG. 35 is a view of an exemplary imaging system for detecting images of emulsions held by slides, in accordance with aspects of the present disclosure.
Figure 36:
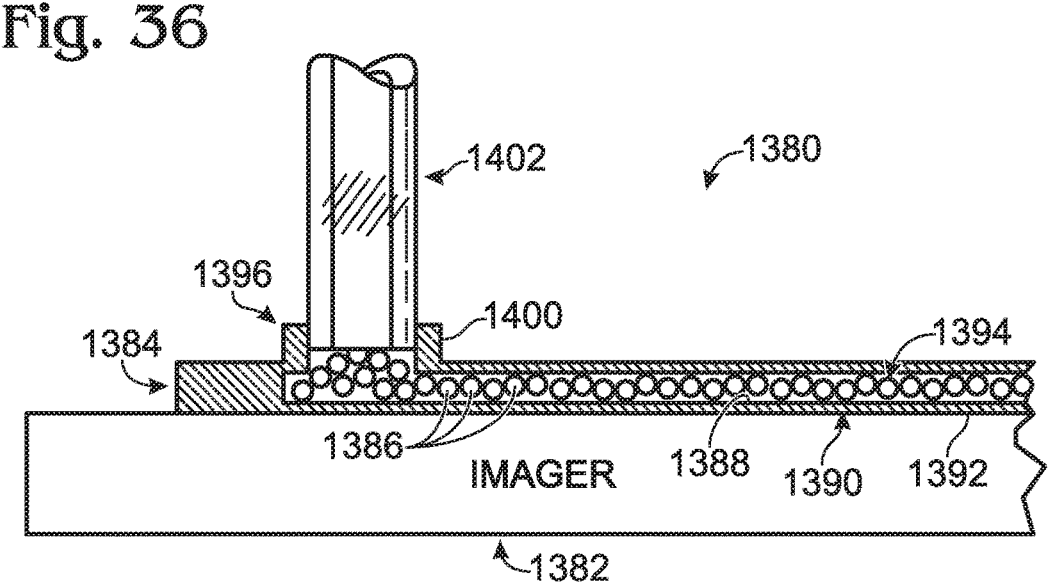
FIG. 36 is a sectional view through a slide of the imaging system of FIG. 35, taken generally along line 36-36 of FIG. 35.

FIGS. 35 and 36 show an exemplary imaging system 1380 for detecting images of droplets held in one or more detection chambers, to provide parallel detection of droplets. System 1380 may include an imager 1382 and at least one imaging slide 1384 operatively disposed with respect to the imager, to permit image collection of droplets 1386 held by the slide.

Slide 1384 may define an imaging chamber 1388 and a viewing window 1390 adjacent the imaging chamber. The imaging chamber may have a high aspect ratio, with a length and width that are many times the height/thickness of the chamber. Accordingly, imaging chamber 1388 may be sized to form a monolayer of droplets 1386 adjacent viewing window 1390, which may be formed by a bottom wall 1392 of the slide (see FIG. 36). In some examples, the height of chamber 1388 may correspond to the diameter of the droplets, such as being about the same as the droplet diameter or no more than about twice the droplet diameter, among others. The droplets may be loaded into the imaging slide (as part of an emulsion 1394) after a reaction, such as amplification (e.g., thermal cycling), has been performed in the droplets. Alternatively, the emulsion may be loaded into chamber 1388 before reaction, the slide optionally sealed, and then the emulsion reacted (e.g., thermally cycled) and imaged in the same slide.

Imaging chamber 1388 may be connected to a pair of ports 1396, 1398, which may permit an emulsion to be introduced into and removed from the chamber (see FIG. 35). One or both of the ports may include a fitting 1400 that enables sealed engagement with a flow-based fluid transfer device 1402. The fluid transfer device, via either port, may introduce fluid (e.g., an emulsion or wash fluid) into the chamber and may remove and/or flush fluid from the chamber (e.g., to permit the slide to be re-used and/or the emulsion to be collected). Slide 1384 may be imaged in any suitable orientation, such as horizontally, as shown in FIGS. 35 and 36, vertically, or the like. Loading droplets into the imaging slide may be performed with any suitable fluid transfer device (e.g., a pipette, syringe, autosampler, etc.), which may be controlled (e.g., positioned and actuated for fluid inflow and outflow) manually or with a controller (e.g., a computer).

In other embodiments, droplet imaging may be performed with a slide that lacks a chamber. For example, a cover slip may be utilized with the slide to form a monolayer of droplets between the slide and the cover slip. In this case, the slide may, for example, be a standard microscope slide, a slide with a shallow well formed in one of its faces, a slide with projections that space the cover slip from a planar surface of the slide, or the like.

Imaging system 1380 may be configured to image two or more slides 1384 serially or in parallel. Accordingly, imager 1382 may have an imaging area sufficient to encompass the viewing windows of two or more slides at the same time. Alternatively, or in addition, imager 1382 may be operatively coupled to a slide exchanger that can position a set of slides serially in an imaging area of the imager, by adding each slide to the imaging area for imaging, and then removing the slide from the imaging area after imaging.

Figure 37:
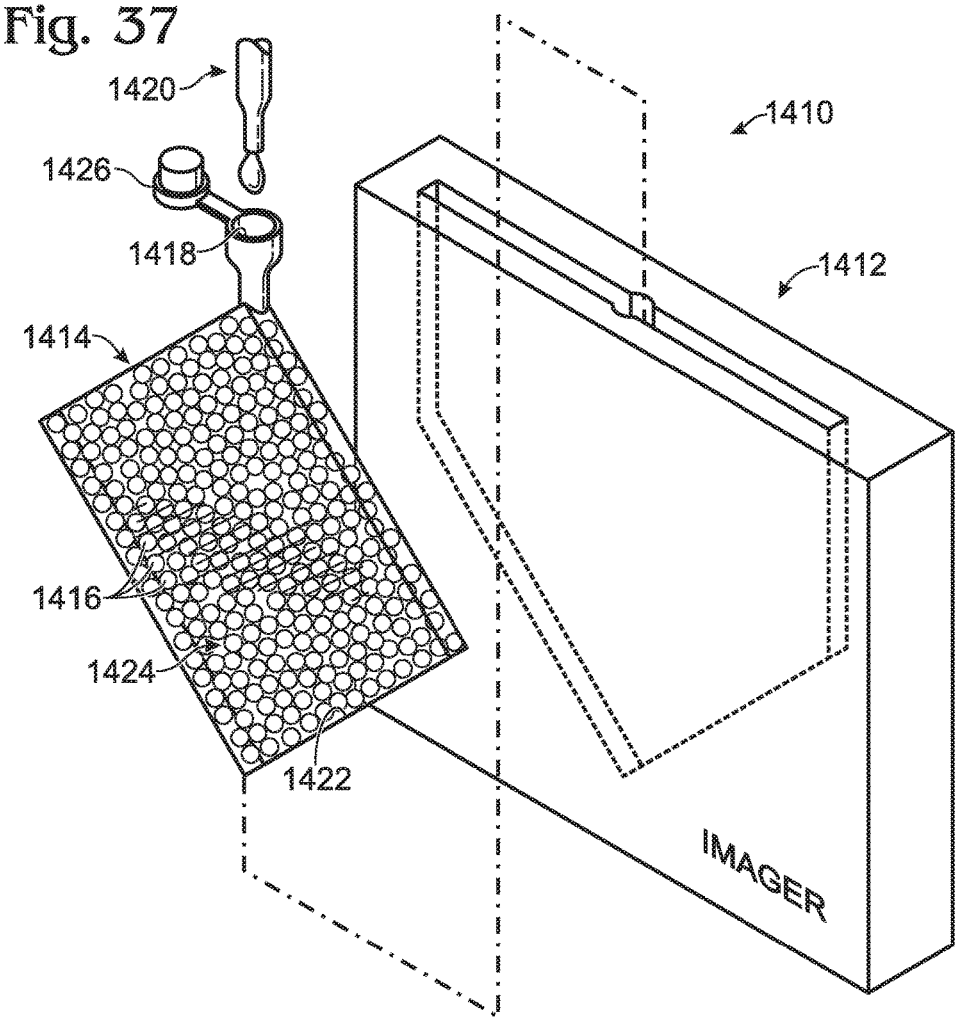
FIG. 37 is an exploded view of an exemplary imaging system that includes a vial being loaded with droplets before detection to image the droplets, in accordance with aspects of present disclosure.

FIG. 37 shows an exploded view of an exemplary imaging system 1410 including an imager 1412 and a vial 1414 that holds droplets 1416 to be imaged by the imager. Vial 1414 may define an inlet region or mouth 1418 to receive the droplets from a fluid transfer device 1420, and an imaging chamber 1422 to hold the droplets while they are imaged. Air may be vented through the inlet region as an emulsion is loaded into the chamber or the vial may define a separate vent for this purpose. Chamber 1422 may (or may not) have a high aspect ratio to promote formation of a monolayer of droplets. Also, the vial may include at least one viewing window 1424, which may be formed by one or more walls of the vial, through which light may be transmitted. The vial may be disposable (e.g., formed of a polymer) or re-usable (e.g., formed of quartz). The vial may be spun in a centrifuge after loading and before imaging. Spinning may, for example, concentrate droplets in chamber 1422 and/or remove air bubbles from the detection chamber. Vial 1414 also may include a cap 1426 to seal the vial. Droplets may be reacted (e.g., amplified by thermal cycling) in the vial after loading and before imaging, or may be loaded after reaction. In other embodiments, the vial may have any other suitable shape that defines a chamber, such as a chamber including a planar surface, and forms a viewing window, such as a viewing window adjacent the planar surface.

Figure 38:
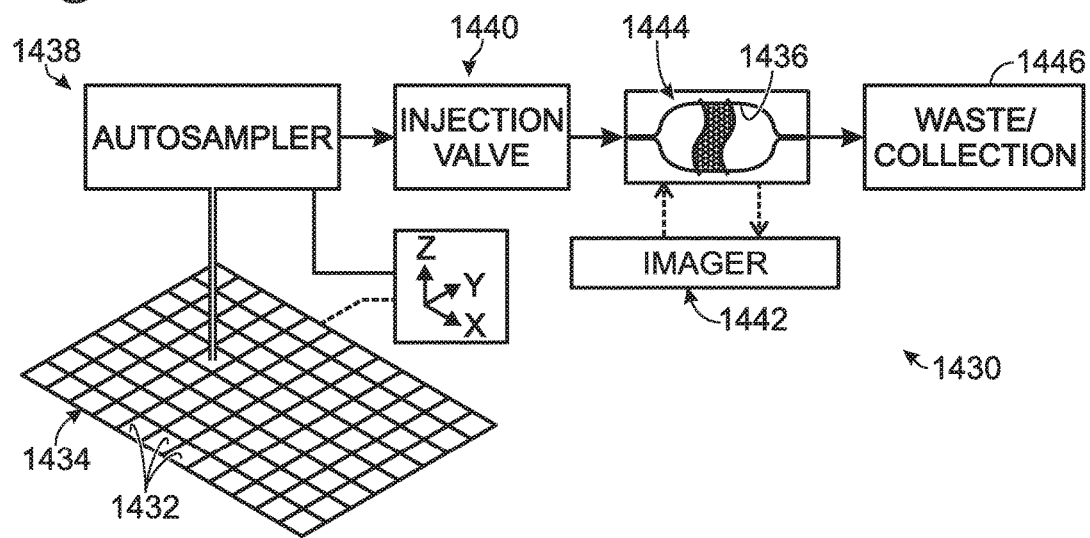
FIG. 38 is a schematic view of an exemplary system for imaging amplified emulsions by transport of droplets of the emulsions to a detection chamber by flow from a plate holding the emulsions, in accordance with aspects of the present disclosure.

FIG. 38 shows a schematic view of an exemplary system 1430 for stopped-flow imaging of reacted emulsions 1432 transported from an array. Emulsions 1432 may be held in an array by a plate 1434 and may be reacted in the array or may be transferred to the array after reaction. The emulsions (or at least a portion thereof) may be transported serially to at least one imaging chamber 1436 using an autosampler 1438 connected to an injection valve 1440. Exemplary imaging chambers that may be suitable are shown in FIGS. 35 and 36 of this Section and in Section VI. The injection valve may be used to control filling, holding, emptying, and, optionally, flushing the imaging chamber. An imager 1442 may be operatively disposed with respect to a viewing window 1444 adjacent the imaging chamber, to provide image collection of droplets disposed in the imaging chamber. After each emulsion is imaged, the emulsion may be removed from the imaging chamber by flow to a waste/collection reservoir 1446. Further aspects of autosamplers are described above in relation to FIGS. 15-18.

Figure 39:
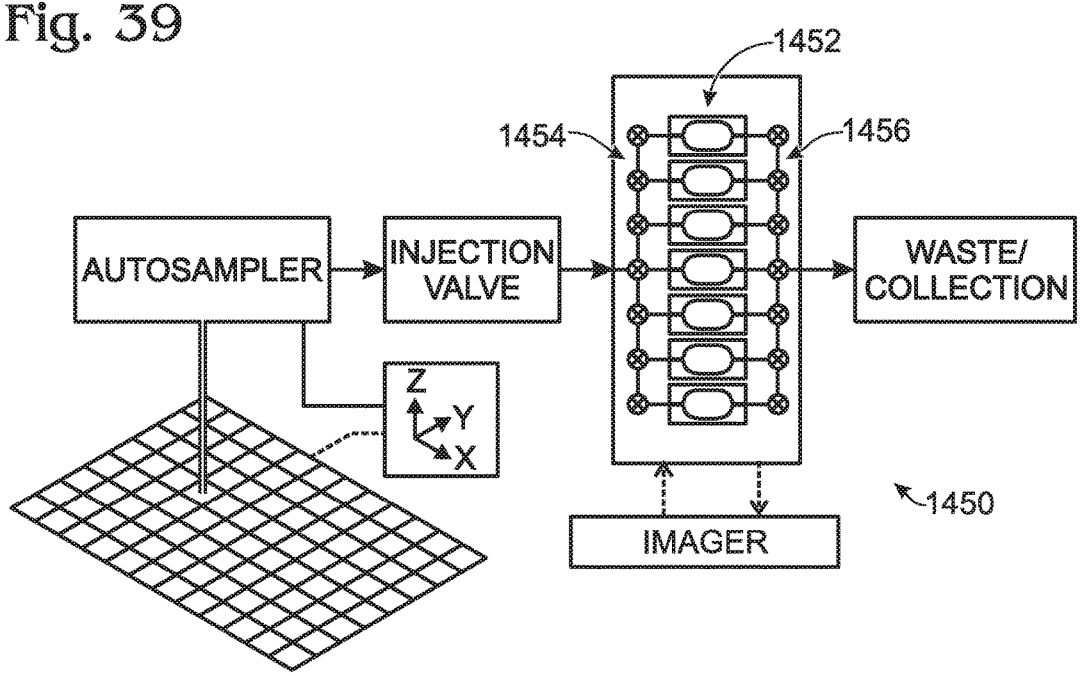
FIG. 39 is a schematic view of an exemplary system for imaging amplified emulsions transported to a plurality of detection chambers by flow from a plate holding the emulsions, in accordance with aspects of the present disclosure.

FIG. 39 shows a schematic view of another exemplary system 1450 for stopped-flow imaging of reacted emulsions transported from an array. System 1450 is related to system 1430 of FIG. 38 but includes a plurality of imaging chambers 1452. One or more inlet valves 1454 and/or outlet valves 1456 may be operated to determine an order in which the imaging chambers are filled with emulsions, isolated from fluid flow for imaging, emptied, and/or flushed, among others.

Figure 40:
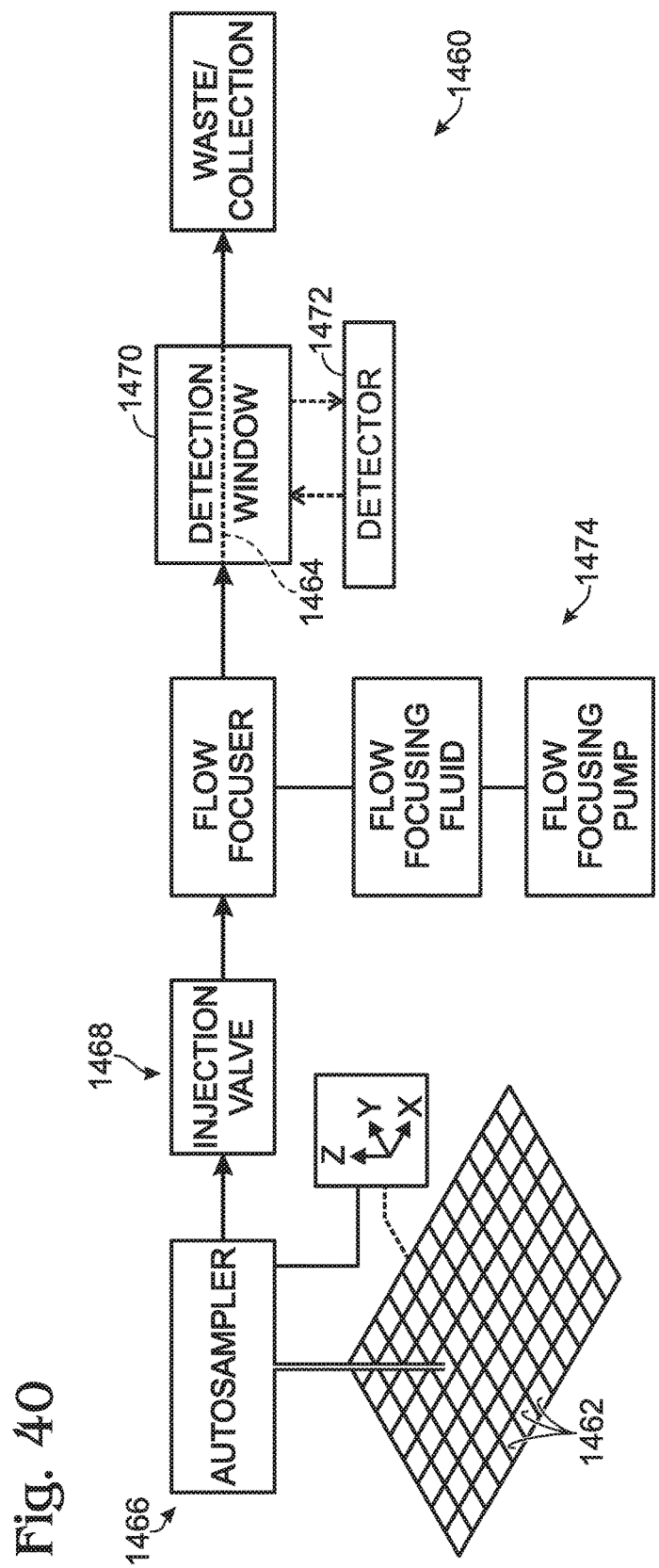
FIG. 40 is a schematic view of an exemplary system for transport of droplets from an array of emulsions to a detection channel, in accordance aspects of the present disclosure.

FIG. 40 shows a schematic view of an exemplary system 1460 for transport of reacted emulsions 1462 from an array to a detection channel 1464, for serial droplet detection. System may include an autosampler 1466 and an injection valve 1468 that serially load emulsions 1462 into detection channel 1464, for flow past a viewing window 1470 that is operatively disposed with respect to a detector 1470. A flow-focusing assembly 1472 may focus droplets in the flow stream before they reach detection channel 1464. Further aspects of flow-focusing upstream of a detection channel are described in Section VI.

N. Additional Embodiments

This example describes additional aspects of system architecture, in accordance with aspects of the present disclosure, presented without limitation as a series of numbered sentences.

(i). Flow System

1. A system for analyzing a sample, comprising (A) a droplet generator configured to generate droplets containing portions of a sample to be analyzed, the droplets being disposed in an immiscible fluid forming a sample emulsion, (B) a heating and cooling station having a fluid inlet and a fluid outlet, (C) a detection station downstream from the heating and cooling station, (D) a channel forming a single-pass continuous fluid route from the fluid inlet to the fluid outlet of the heating and cooling station, (E) a pump for moving the sample emulsion through the channel, (F) a controller programmed to operate fluid transport through the channel, and (G) an analyzer configured to process data collected at the detection station.

2. The system of paragraph 1, wherein the detection system is situated to detect presence of target in the sample emulsion after passing through the heating and cooling system.

3. The system of paragraph 1 further comprising a droplet reservoir, a first fluid conduit connecting the droplet generator to the reservoir, and a second fluid conduit connecting the reservoir to the fluid inlet of the heating and cooling station.

4. The system of paragraph 1, wherein the droplet generator is adapted for single-use detachable connection to the heating and cooling station without exposing the heating and cooling station to contamination from sample contained in the sample emulsion.

5. The system of paragraph 1, wherein the droplet generator is configured to generate the sample emulsion external to the heating and cooling station.

6. The system of paragraph 1, wherein the heating and cooling station includes multiple heating zones along the fluid route configured for performing a polymerase chain reaction on a nucleic acid target contained in a droplet.

7. The system of paragraph 1, wherein the heating and cooling station includes at least one thermoelectric cooler.

8. The system of paragraph 1, wherein the controller is programmed to adjust the droplet generator to alter droplet size based on data received from the detection station.

9. The system of paragraph 1, wherein the controller is programmed to alter sample concentration prior to droplet generation based on data received from the detection station.

10. The system of paragraph 1, wherein the controller is programmed to alter a sample preparation procedure prior to droplet generation in the droplet generator based on data received from the detection station.

11. The system of paragraph 1, wherein the analyzer is programmed to determine a concentration of a target molecule in the sample based at least partially on the frequency of droplets containing the target out of a population of droplets containing sample portions.

12. The system of paragraph 1, wherein the droplet generator includes a sample reservoir, an oil source, an oil/sample intersection, and an emulsion outlet, the emulsion outlet having a distal end portion adapted for detachable sealed engagement with a receiving port on the heating and cooling station.

13. The system of paragraph 1, wherein the droplet generator is contained in a cartridge having at least one piston for driving emulsification.

14. The system of paragraph 1, wherein the droplet generator is contained in a cartridge having at least one piston for pumping sample emulsion through the channel network.

15. The system of paragraph 1, wherein the channel includes a helical capillary tube portion passing through the heating and cooling station.

16. The system of paragraph 15, wherein the capillary tube portion has a diameter approximately equal to the diameter of droplets generated by the droplet generator.

17. The system of paragraph 1, wherein the capillary tube portion includes a hot-start segment passing through a hot-start zone prior to a denaturation zone in the heating and cooling station.

18. The system of paragraph 1, wherein the heating and cooling station includes thermoelectric coolers configured for controlling temperatures in heating and cooling zones by transferring heat between a thermal core and the heating and cooling zones.

19. The system of paragraph 15, wherein the helical capillary tube portion defines a helical path that decreases in length over successive cycles.

20. The system of paragraph 1, wherein the heating and cooling station includes (a) a core defining a central longitudinal axis, (b) a plurality of segments attached to the core and defining a plurality of temperature regions; and (c) a plurality of heating elements configured to maintain each temperature region approximately at a desired temperature, a portion of the channel configured to transport a sample emulsion cyclically through the temperature regions.

21. The system of paragraph 20, wherein the plurality of segments includes a plurality of inner segments defining the plurality of temperature regions and a plurality of outer segments attached to the inner segments, and wherein the portion of the channel is disposed between the inner and outer segments.

22. The system of paragraph 21, wherein the portion of channel includes fluidic tubing that wraps around the inner segments.

23. The system of paragraph 21, wherein the fluidic tubing is disposed in grooves of the inner segments that wrap substantially helically around the inner segments.

24. The system of paragraph 1, wherein the droplet generator is contained in a disposable cartridge.

25. The system of paragraph 24, wherein the cartridge includes a cell lysing region, a separating region, a reagent mixing region, and a droplet generation region for extracting nucleic acid from a sample and formation of droplets into a heat stable sample emulsion.

26. The system of paragraph 1, wherein the channel has open ends for permitting continuous flow of a sample emulsion.

27. The system of paragraph 1, wherein the droplet generator is capable of generating a heat stable sample emulsion.

(ii). Droplet Generator Plate

1. A device for generating an array of emulsions, comprising a plate including one or more oil reservoirs and forming an array of emulsion generator units, each unit including a sample port, a droplet collection site, and a channel intersection that receives a sample from the sample port and a carrier fluid from at least one oil reservoir and generates an emulsion of sample droplets in the carrier fluid that flows to the droplet collection site.

2. The device of paragraph 1, wherein the sample port is a well that permits sample loading from above the plate.

3. The device of paragraph 1, wherein each emulsion generator unit includes at least one oil reservoir.

4. The device of paragraph 3, wherein the at least one oil reservoir is a well that permits loading of the carrier fluid from above the plate.

5. The device of paragraph 1, wherein the sample ports collectively form a port array, and wherein the port array is arranged in correspondence with wells of a standard microplate.

6. The device of paragraph 5, wherein the plate has 96 sample ports.

7. The device of paragraph 1, wherein the channel intersection includes a pair of oil inlets, and wherein the pair of oil inlets connect to one or more oil reservoirs.

8. The device of paragraph 7, wherein channel intersection includes a sample inlet that receives sample from the sample port, and wherein the pair of oil inlets flank the sample inlet on opposing sides of the sample inlet.

9. The device of paragraph 1, wherein the droplet collection site includes a well.

10. The device of paragraph 1, wherein the droplet collection site defines a cavity bounded by walls of the plate disposed above and below the cavity.

11. The device of paragraph 10, wherein the cavity has a height that corresponds in size to the droplets such that a substantial monolayer of the droplets is formed in the cavity when the emulsion flows into the cavity.

12. The device of paragraph 10, wherein the cavity has a width and a thickness, and wherein the width is at least about ten times the thickness.

13. The device of paragraph 10, wherein an outlet channel extends from the channel intersection to the droplet collection site, wherein the plate defines a plane, and wherein the cavity and the outlet channel each have a width measured parallel to the plane, and wherein the width of the cavity is substantially greater than the width of the outlet channel.

14. The device of paragraph 10, wherein the cavity is a chamber, and wherein the chamber is connected to a vent that permits escape of gas from the chamber as the emulsion flows into the chamber.

15. The device of paragraph 1, wherein the droplet collection site defines a cavity and includes a window formed by a transparent wall of the plate adjacent to the cavity, and wherein the window permits optical detection, through the transparent wall, of droplets in the cavity.

16. The device of paragraph 15, wherein the window is formed below the cavity.

17. The device of paragraph 1, wherein the plate includes an upper member attached to a lower member, wherein the upper member defines the sample port, wherein an upper region of the channel intersection is formed in a bottom surface of the upper member, and wherein the lower member is attached to the bottom surface to form a bottom wall of the channel intersection.

18. The device of paragraph 1, further comprising a cover that assembles with the plate to seal the sample ports.

19. The device of paragraph 1, wherein the emulsion generator units are arranged in rows and columns with two or more units per row and per column.

(iii). Batch Array Method

1. A method of sample analysis, comprising (A) forming an array of emulsions, each emulsion including partitions of a respective sample disposed in droplets; (B) applying heat to the emulsions while they are disposed in the array, to induce nucleic acid amplification in droplets of the emulsions; (C) detecting signals from droplets of each emulsion; and (D) estimating a presence, if any, of a nucleic acid target in each respective sample based on the signals detected.

2. The method of paragraph 1, wherein the step of forming includes a step of generating the emulsions with a plate that includes an array of emulsion generator units.

3. The method of paragraph 2, wherein the plate includes a plurality of reservoirs to hold the respective samples, and wherein the step of generating includes a step of applying pressure to the plurality of reservoirs after placing the respective samples into the reservoirs.

4. The method of paragraph 2, wherein the step of generating includes a step of spinning the plate in a centrifuge.

5. The method of paragraph 2, wherein the step of forming includes a step of removing each emulsion from the plate and disposing such emulsion at a position within the array.

6. The method of paragraph 2, wherein the plate defines an array of sample ports that open upwardly, and wherein the step of generating includes a step of disposing each respective sample in a sample port.

7. The method of paragraph 2, wherein the step of applying heat is performed with the emulsions held in the array by the plate.

8. The method of paragraph 1, wherein the step of applying heat is performed with the emulsion disposed in a cavity, wherein the cavity has a width and a thickness, and wherein the width is many times the thickness.

9. The method of paragraph 8, wherein the width is at least about ten times the thickness.

10. The method of paragraph 1, wherein the step of applying heat includes a step of heating the emulsions to a temperature sufficient to melt nucleic acid duplexes in the droplets.

11. The method of paragraph 1, wherein the step of applying heat includes a step of thermally cycling the array of emulsions to induce amplification by PCR.

12. The method of paragraph 1, wherein the step of detecting signals includes a step of imaging droplets of each emulsion.

13. The method of paragraph 12, wherein the step of imaging droplets is performed while the emulsions are still disposed in the array.

14. The method of paragraph 13, wherein the step of forming includes (a) a step of generating droplets of each emulsion with a plate and (b) a step of collecting the emulsions in an array of chambers defined by the plate, wherein the step of applying heat is performed while the emulsions are disposed in the array of chambers, and wherein the step of imaging is performed through a transparent window formed by a wall of the plate adjacent to each chamber.

15. The method of paragraph 11, wherein the step of thermally cycling is performed without sealing the plate from above after disposing the emulsions in the array of chambers.

16. The method of paragraph 1, further comprising a step of transferring at least a portion of each emulsion out of the array and to a detection station after the step of applying heat.

17. The method of paragraph 16, wherein the step of transferring is performed serially with the emulsions.

18. The method of paragraph 16, wherein the step of transferring is performed with an autosampler.

19. The method of paragraph 16, wherein the step of detecting signals includes a step of detecting droplet signals serially as droplets flow past a detection window.

20. The method of paragraph 16, wherein the step of detecting includes a step of imaging droplets.

21. The method of paragraph 1, wherein the step of estimating a presence provides a qualitative determination of whether the nucleic acid target is present or absent in the respective sample.

22. The method of paragraph 1, wherein the step of estimating a presence includes a step of estimating a concentration and/or a copy number of the nucleic acid target in the respective sample.

23 The method of paragraph 22, wherein the step of estimating a presence includes a step of assigning a starting copy number of two or more molecules of a nucleic acid target to at least one of the droplets based on one or more detected signals.

24. The method of paragraph 1, wherein the step of estimating includes a step of utilizing an algorithm based on Poisson statistics.

25. The method of paragraph 1, wherein the step of applying heat induces nucleic acid amplification of respective different species of nucleic acid target in at least two of the emulsions.

26. The method of paragraph 1, wherein the step of applying heat induces nucleic acid amplification of two or more distinct species of nucleic acid target in at least one of the emulsions, and wherein the step of estimating includes a step of estimating a presence for each of the distinct species of nucleic acid target.

(iv). Single Emulsion—Batch Amplification

1. A method of sample analysis, comprising (A) forming an emulsion including droplets disposed in a carrier fluid, each droplet containing a partition of a sample prepared as a reaction mixture for amplification of a nucleic acid target; (B) disposing at least a portion of the emulsion in a chamber that is many times wider than an average diameter of the droplets; (C) applying heat to the at least a portion of the emulsion disposed in the chamber to induce nucleic acid amplification in droplets; (D) detecting signals from droplets of the emulsion; and (E) estimating a presence, if any, of the nucleic acid target in the sample based on the signals detected.

2. The method of paragraph 1, wherein the emulsion flows continuously into the chamber from a site of droplet generation.

3. The method of paragraph 1, wherein the step of applying heat includes a step of thermal cycling the at least a portion of the emulsion to induce PCR amplification of the nucleic acid target.

4. The method of paragraph 1, wherein the chamber is at least about ten times wider than the average diameter of the droplets.

5. The method of paragraph 1, wherein the step of detecting signals includes a step of collecting an image of a plurality of the droplets.

6. The method of paragraph 1, wherein the step of detecting signals includes a step of detecting signals serially from the droplets as such droplets are traveling through a detection station.

7. The method of paragraph 1, wherein the droplets form a substantial monolayer in the chamber.

8. The method of paragraph 7, wherein the average separation between adjacent pairs of droplets in the chamber is less than an average diameter of the droplets.

(v). System for Batch Amplification

1. A system for sample analysis, comprising (A) a droplet generator that forms an emulsion including droplets that each contain a partition of a sample prepared as a reaction mixture for amplification of a nucleic acid target; (B) an emulsion holder defining a cavity to contain at least a portion of the emulsion, the cavity being many times wider than an average diameter of the droplets; (C) a heating station to apply heat to the at least a portion of the emulsion disposed in the cavity to induce nucleic acid amplification in droplets; (D) a detection station to detect signals from droplets of the emulsion; and (E) a controller in communication with the detection station and programmed to estimate a presence, if any, of the nucleic acid target in the sample based on the signals detected.

2. The system of paragraph 1, further comprising a plate including the droplet generator and a plurality of other droplet generators.

3. The system of paragraph 1, wherein the emulsion holder is connected to the droplet generator such that generated droplets flow continuously into the cavity.

4. The system of paragraph 1, wherein the detection station includes at least one detection chamber and at least one imaging device to collect images of droplets disposed in the detection chamber.

5. The system of paragraph 1, further comprising a fluid transfer device to transfer droplets from the cavity to the detection station.

6. The system of paragraph 1, wherein the fluid transfer device is a manually controlled pipette.

7. The system of paragraph 1, wherein the fluid transfer device is an autosampler.

8. The system of paragraph 1, wherein the cavity has a thickness that corresponds to the average diameter of the droplets such that the droplets form a substantial monolayer in the cavity.

9. The system of paragraph 1, wherein the cavity is a chamber.

10. The system of paragraph 1, wherein the cavity is at least ten times wider than the average diameter of the droplets.

(vi). High Throughput System

1. A system for droplet-based sample analysis, comprising (A) a sample input station to hold a plurality of emulsions each including partitions of a respective sample disposed in droplets; (B) a heating station to apply heat to droplets to induce amplification of a nucleic acid target, if present, in individual droplets; (C) a detection station to detect signals from droplets that have been heated by the heating station; (D) a fluidics network connecting the sample input station, the heating station, and the detection station, to provide fluid flow from the sample input station to the heating station and the detection station; and (E) a controller programmed to control an order in which packets of droplets from the emulsions are transferred from the sample input station to the heating station, and to estimate a presence of a nucleic acid target in samples corresponding to the packets based on signals from the detection station.

2. The system of paragraph 1, wherein the fluidics network includes a holding station to store packets of droplets upstream from the heating station.

3. The system of paragraph 2, wherein the controller is programmed to control a sequence in which packets are transferred into the holding station from the sample input station and also to control a sequence in which such packets are loaded into the heating station from the holding station.

4. The system of paragraph 3, wherein at least a portion of at least one of the sequences is selected by the controller based on signals detected by the detection station.

5. The system of paragraph 2, wherein the holding station includes a plurality of discrete storage sites, and wherein the controller is programmed to control loading of packets into the storage sites and unloading of the packets from the storage sites.

6. The system of paragraph 5, wherein holding station is designed to permit loading the storage sites with packets in an arbitrary order and unloading the packets from the storage sites in an arbitrary order.

7. The system of paragraph 2, wherein the holding station includes at least one heater configured to apply heat to packets disposed in the holding station.

8. The system of paragraph 1, wherein the controller is programmed to control formation of a spacer segment of fluid in the fluidics network between adjacent packets of droplets as the adjacent packets are introduced into the fluidics network from the sample input station.

9. The system of paragraph 1, wherein the fluidics network includes an autosampler that picks up packets of droplets from the sample input region and loads such packets into the heating station.

10. The system of paragraph 1, wherein the controller is programmed to receive inputs from a user selecting a sequence and to control transfer of packets to the heating station according to the sequence.

11. The system of paragraph 1, wherein the detection station detects signals from droplets disposed in a flow stream.

11. The system of paragraph 1, wherein the detection station collects images of droplets.

12. The system of paragraph 1, wherein the detection station detects fluorescence signals from droplets.

(vii). Batch System I

1. A system for sample analysis, comprising (A) at least one droplet generator that forms a plurality of emulsions including droplets that each contain a sample partition prepared as a reaction mixture for amplification of a nucleic acid target; (B) a plate defining an array of cavities to hold the emulsions; (C) a heating and cooling device to heat the emulsions disposed in the cavities to induce nucleic acid amplification in droplets; (D) a detection assembly to detect signals from intact droplets of the emulsions; and (E) a controller in communication with the detection assembly and programmed to estimate a presence, if any, of the nucleic acid target in a sample based on signals detected from the intact droplets.

2. The system of paragraph 1, wherein the droplet generator is integrated with the plate.

3. The system of paragraph 2, wherein each cavity is supplied by a separate droplet generator.

4. The system of paragraph 2, wherein each cavity is supplied by the same droplet generator.

5. The system of paragraph 1, wherein the droplet generator is not part of the plate.

6. The system of paragraph 1, wherein the droplet generator includes at least one oil reservoir, a sample reservoir, and a fluid path from each reservoir to at least one cavity.

7. The system of paragraph 1, further comprising a pressure source that drives droplet generation.

8. The system of paragraph 1, wherein the detection assembly is configured to detect signals from droplets while disposed in the cavities.

9. The system of paragraph 1, further comprising a fluid transfer device configured to transfer droplets from the cavities to a detection site of the detection assembly.

10. The system of paragraph 9, wherein the detection site is separate from the plate.

11. The system of paragraph 9, wherein the detection assembly is configured to detect droplets serially.

12. The system of paragraph 9, wherein the detection assembly is configured to image batches of droplets.

13. The system of paragraph 12, wherein the detection assembly is configured to image droplet batches serially, each droplet batch corresponding to a different emulsion.

14. The system of paragraph 1, wherein the detection assembly includes confocal optics.

15. The system of paragraph 1, wherein each cavity is bounded above and below by walls of the plate.

16. The system of paragraph 1, wherein each cavity is bounded by a transparent wall of the plate that permits detection of droplets in such cavity through the transparent wall.

17. The system of paragraph 1, wherein the droplet generator includes a sample reservoir that opens upwardly to permit sample loading from above the plate.

18. The system of paragraph 1, wherein the cavity is a well, further comprising a sealing member to seal the well.

19. The system of paragraph 1, wherein the droplet generator includes one or more orifices from which the droplets are generated serially.

20. The system of paragraph 1, wherein the droplet generator is configured to form droplets that are monodisperse.

21. The system of paragraph 1, wherein the controller is configured to estimate the presence of the nucleic acid target based on a percentage of droplets that are determined to be positive for amplification of the nucleic acid target.

(viii). Batch System II

1. A system for sample analysis, comprising (A) a droplet generator including an oil reservoir, a sample reservoir, a cavity, and a channel intersection that receives a sample from the sample reservoir and a carrier fluid from the oil reservoir and generates droplets that flow to the cavity as an emulsion; and (B) a heating device to heat the droplet generator to induce nucleic acid amplification in droplets of the emulsion in the cavity.

2. The system of paragraph 1, further comprising a plate that includes the droplet generator and a plurality of other droplet generators.

3. The system of paragraph 1, further comprising a pressure source that drives droplet generation.

4. The system of paragraph 3, wherein the pressure source includes a manifold that forms a sealed relation with the droplet generator.

5. The system of paragraph 1, further comprising a detection assembly to detect signals from droplets of the emulsion.

6. The system of paragraph 5, wherein the detection assembly is configured to detect signals from droplets while the droplets are disposed in the cavity.

7. The system of paragraph 5, wherein the detection assembly is configured to detect signals from the droplets while the droplet generator is thermally coupled to the heating device.

8. The system of paragraph 5, wherein the detection assembly is configured to image a batch of droplets.

9. The system of paragraph 8, wherein the detection assembly includes confocal optics.

10. The system of paragraph 5, further comprising a controller in communication with the detection assembly and programmed to estimate a presence, if any, of a nucleic acid target in the sample based on the signals detected.

11. The system of paragraph 1, wherein the heating device includes a temperature-controlled chamber that receives the droplet generator.

12. The system of paragraph 1, wherein the heating device is a heating and cooling device that thermally cycles the droplet generator to induce PCR amplification in the droplets of the emulsion in the cavity.

13. The system of paragraph 1, wherein the cavity is bounded above and below by walls of the droplet generator.

14. The system of paragraph 1, wherein the cavity is bounded by a transparent wall of the droplet generator that permits detection of droplets in the cavity through the transparent wall.

15. The system of paragraph 1, wherein the cavity is a well, further comprising a sealing member to seal the well.

(ix). Miscellaneous 1

1. A method of sample analysis, comprising (A) generating a plurality of droplets from a sample, each droplet containing a mixture to test occurrence of a reaction; (B) storing a packet of the droplets for a selectable time period; (C) introducing at least a portion of the packet into a channel after the step of storing; (D) subjecting the portion of the packet to one more conditions that promote occurrence of the reaction by moving the at least a portion of the packet along the channel; and (E) performing, after the step of subjecting and on each of a plurality of droplets of the at least a portion of the packet, at least one measurement related to occurrence of the reaction.

2. The method of paragraph 1, wherein the step of generating includes a step of generating the plurality of droplets by fluid flow from at least one orifice.

3. The method of paragraph 1, wherein the step of generating includes a step of generating droplets with each droplet capable of amplification of a nucleic acid target, if present, in the droplet, wherein the step of subjecting includes a step of subjecting the at least a portion of the packet to conditions that promote amplification of the nucleic acid target in droplets of the at least a portion of the packet, and wherein the step of performing includes a step of performing the at least one measurement to permit determination of whether amplification of the nucleic acid target occurred in individual droplets.

4. The method of paragraph 1, wherein the step of storing includes a step of storing the packet of droplets in a compartment that is in fluid isolation from the channel, and wherein the step of introducing includes a step of placing the compartment and the channel in fluid communication with one another.

5. The method of paragraph 1, wherein the packet of droplets is disposed in a volume of carrier fluid, wherein the step of storing includes a step of stopping flow of the volume of carrier fluid, and wherein the step of introducing includes a step of starting flow of at least a portion of the volume of carrier fluid.

6. The method of paragraph 1, wherein the step of subjecting includes a step of thermally cycling the at least a portion of the packet.

7. The method of paragraph 1, further comprising (1) a step of determining a number of droplets in which amplification of a nucleic acid target occurred based on data obtained from the step of performing, and (2) a step of estimating a total presence of the nucleic acid target in the sample based on the number of droplets.

8. The method of paragraph 1, wherein the steps of storing, introducing, subjecting, and performing are performed with a plurality of different packets, and wherein the packets are introduced serially into the channel.

9. The method of paragraph 8, further a step of selecting a relative order in which at least two of the different packets are introduced into the channel.

10. The method of paragraph 9, wherein the step of selecting is based on a result obtained based on the step of performing with droplets of another packet.

11. A method of sample analysis for a nucleic acid target, comprising (A) generating a plurality of droplets from a sample, each droplet being capable of amplification of a nucleic acid target, if present, in the droplet; (B) storing a packet of the droplets for a selectable time period; (C) introducing at least a portion of the stored packet into a channel; (D) moving the portion of the packet along the channel such that the portion is subjected to conditions that promote amplification of the nucleic acid target in droplets of the portion; and (E) performing at least one measurement related to amplification of the nucleic acid target on each of a plurality of droplets after the step of moving.

12. A method of sample analysis, comprising (A) providing a channel, an array of samples, an array of reagents, and predefined flow paths connecting all of the samples and reagents to the channel, to permit selection of any combination of sample and reagent from the arrays; (B) selecting a combination of a sample from the array of samples and a reagent from the array of reagents; (C) generating droplets each including the combination and containing an assay mixture to be tested for occurrence of a reaction involving the sample and the reagent selected; (D) introducing a plurality of the droplets into the channel; (E) subjecting the plurality of droplets to one or more conditions that promote occurrence of the reaction while moving the plurality of droplets along the channel; and (F) performing at least one measurement related to occurrence of the reaction on one or more of the plurality of droplets after the step of subjecting.

14. The method of paragraph 12, wherein the combination is a first combination, further comprising a step of selecting a second combination of sample and reagent from the arrays, wherein the steps of generating, introducing, subjecting, and performing are repeated with the second combination.

15. The method of paragraph 14, wherein the second combination is selected based on a result obtained using data from the step of performing at least measurement on the first combination.

16. The method of paragraph 14, further comprising a step of changing the array of samples to add or subtract at least one sample, the array of reagents to add or subtract at least one reagent, or both, and wherein the step of selecting a second combination selects a combination after the step of changing.

17. The method of paragraph 16, wherein the step of changing is performed while the step of subjecting is performed with the first combination.

18. The method of paragraph 14, wherein the step of selecting a second combination of sample and reagent is performed based on a user command received after the step of selecting a first combination.

19. The method of paragraph 18, wherein the user command is received during the step of subjecting with the first combination.

20. The method of paragraph 19, wherein the step of introducing for the first combination is performed until a predefined condition is satisfied if the user command is not received, and wherein the step of introducing is interrupted by the user command before the predefined condition is satisfied.

21. The method of paragraph 20, wherein the predefined condition is a predefined number of droplets introduced, a predefined time interval during which droplets are introduced, or both.

22. The method of paragraph 14, wherein the array of reagents includes different pairs of primers for amplification of different nucleic acid targets.

23. A method of sample analysis, comprising (A) providing a channel, an array of samples, an array of reagents, and predefined flow paths connecting all of the samples and reagents to the channel; (B) selecting first and second combinations of sample and reagent from the arrays; (C) generating a first packet of droplets each including the first combination and a second packet of droplets each including the second combination; (D) introducing a plurality of droplets of the first packet and of the second packet serially into the channel; (E) subjecting the plurality of droplets of each packet to one or more conditions that promote occurrence of a reaction involving the first combination or the second combination while moving each plurality of droplets along the channel; and (F) performing at least one measurement related to occurrence of the reaction on one or more of the plurality of droplets after the step of subjecting.

24. An apparatus for sample analysis, comprising (A) an adjustable number of ports to receive samples; (B) an adjustable number of sites to hold reagents; (C) a channel that extends through one or more temperature-controlled zones and that connects to the ports and the sites by predefined flow paths; (D) a droplet generator that generates droplets of a selected combination of a sample and a reagent for introduction into the channel; (E) a detector positioned to provide one or more measurements on droplets of the selected combination after the droplets have been disposed in at least one temperature-controlled zone; and (F) a controller that controls combination of samples with reagents.

(x). Miscellaneous 2

1. A system for generating microdroplets comprising (A) a sample-containing apparatus comprising a sample containing chamber and a first microfluidic channel having an inlet end and an outlet end, wherein the inlet end of the first microfluidic channel is connected to the sample containing chamber; and (B) a microdroplet generator apparatus comprising the outlet end of the first microfluidic channel, a second microfluidic channel having an inlet end, and a spacer region that is filled with an immiscible fluid, wherein the outlet end of the first microfluidic channel forms one wall of the microdroplet generator apparatus, the inlet end of the second microfluidic channel forms another wall of the microdroplet generator region, and the spacer region separates the first microfluidic channel outlet end from the second microfluidic channel inlet end such that the first microfluidic channel outlet end only contacts the immiscible fluid.

2. The system of paragraph 1, wherein the sample containing apparatus is removable.

3. The system of paragraph 1, wherein the immiscible fluid is an oil.

4. A method of nucleic acid amplification comprising (A) diluting or concentrating a sample comprising a plurality of nucleic acid targets and components for performing nucleic acid amplification; (B) producing microdroplets within an immiscible fluid in a capillary tube, wherein a plurality of microdroplets containing a single nucleic acid template from the plurality of nucleic acid targets is formed, and wherein the tube has a first open end for fluid inlet and a second open end for fluid outlet to permit a continuous flow; and (C) amplifying the single nucleic acid template in the microdroplets by heating and cooling such that a plurality of single nucleic acid templates within the microdroplets are amplified.

5. The method of paragraph 4, wherein the microdroplets comprise at least 2 different size microdroplets.

6. The method of paragraph 4, wherein a first microdroplet size is between 20 and 100 microns, and a second microdroplet size is between 100 and 250 microns.

7. A method of nucleic acid amplification of a sample, comprising (A) providing a biological sample; (B) producing microdroplets within an immiscible fluid in a capillary tube, wherein the microdroplets comprise nucleic acids and components for performing nucleic acid amplification and wherein the tube has a first open end for fluid inlet and a second open end for fluid outlet to permit a continuous flow and the tube is in contact with at least two solid heating blocks, wherein the heating blocks are maintained at different temperatures and the temperature of at least one heating block is controlled by a thermoelectric controller; (C) moving the microdroplets through the tube; and (D) thermally cycling the microdroplets in the tube to amplify the nucleic acids.

8. A sequence detection system able to detect a single nucleic acid mutation using the method of (A) producing microdroplets within an immiscible fluid in a capillary tube, wherein a plurality of microdroplets containing a single nucleic acid template from the plurality of nucleic acid targets is formed; (B) amplifying the single nucleic acid template in the microdroplets by heating and cooling such that a plurality of single nucleic acid templates within the microdroplets are amplified; and (C) detecting the presence or absence of a nucleic acid mutation through the method of enzymatic nucleic acid amplification or ligation; wherein detection of a single nucleic acid mutation has >10% better signal discrimination compared to real-time PCR.

9. A sequence detection system able to accurately detect the absolute concentration of a target nucleic acid using the method of (A) producing microdroplets within an immiscible fluid in a capillary tube, wherein a plurality of microdroplets containing a single nucleic acid template from the plurality of nucleic acid targets is formed; (B) amplifying the single nucleic acid template in the microdroplets by heating and cooling such that a plurality of single nucleic acid templates within the microdroplets are amplified; and (C) detecting the presence or absence of a target nucleic acid through the method of fluorescently detecting a signal generated by an enzymatic nucleic acid amplification or ligation reaction within the intact droplet; wherein detection of the absolute concentration of the target nucleic acid has >10% better quantitative resolution compared to real-time PCR or quantitative PCR, and/or an adjustable quantitative resolution based on the total number of droplets and target nucleic acid molecules processed.

10. A sequence detection system able to accurately detect the concentration of a target nucleic acid using the method of (A) producing microdroplets within an immiscible fluid in a capillary tube, wherein a plurality of microdroplets containing a single nucleic acid template from the plurality of nucleic acid targets is formed; (B) amplifying the single nucleic acid template in the microdroplets by heating and cooling such that a plurality of single nucleic acid templates within the microdroplets are amplified; and (C) detecting the presence or absence of a target nucleic acid through the method of fluorescently detecting a signal generated by an enzymatic nucleic acid amplification or ligation reaction within the intact droplet; wherein detection of small changes (<40%) in the absolute concentration of a target nucleic acid within a sample or between samples.

11. A sequence detection system able to detect a gene copy number variation using the method of (A) producing microdroplets within an immiscible fluid, wherein a plurality of microdroplets containing a single nucleic acid template from the plurality of nucleic acid targets is formed; (B) amplifying the single nucleic acid template in the microdroplets by heating and cooling such that a plurality of single nucleic acid templates within the microdroplets are amplified; and (C) detecting the number of gene insertions or deletions in a genome through the method of counting the number of PCR amplicons of the target gene relative to the number of PCR amplicons of a reference gene having a known number of gene copies per genome; wherein detection of a target gene copy number per genome has better signal discrimination compared to relative quantification (delta cycle threshold or delta delta cycle threshold) by real time PCR in its ability to discriminate single copy differences where the number or copies of the target gene is greater than 2 but less than 20.

12. A sequence detection system able to detect a low abundant single nucleotide mutation using the method of (A) producing microdroplets within an immiscible fluid, wherein a plurality of microdroplets containing a single nucleic acid template from the plurality of nucleic acid targets is formed; (B) producing microdroplets within an immiscible fluid, wherein a plurality of microdroplets containing a single nucleic acid template from the plurality of nucleic acid targets is formed wherein in partitioning the sample reduces the ratio of target nucleic acid to competing background nucleic acids; (C) amplifying the single nucleic acid template in the microdroplets by heating and cooling such that a plurality of single nucleic acid templates within the microdroplets are amplified; and (D) detecting a single nucleotide mutation in a genetic sequence; wherein detection of a single nucleotide mutation has at least ten times better signal discrimination compared by real time PCR in its ability to detect a mutant genome possessing a single point mutation where the relative concentration of mutant genetic sequence is less than or equal to 0.1° A of the wild type genome.

(xi). Miscellaneous 3

1. A method of performing asynchronous sequential high-throughput PCR, comprising (A) providing one or more biological samples; (B) dividing each of the one or more samples into one or more droplets using one or more droplet generators; (C) isolating and storing the one or more droplets from each of the one or more samples, thereby forming a droplet packet from each of the samples; and (D) sequentially selecting at least a portion of each of the packets and causing the portion to a flow through a thermal cycling device.

2. The method of paragraph 1, wherein the method further includes at least one of (A) random access, (B) result-driven, on-demand triage/diagnostics, (C) asynchronous loading, (D) stat mode, (E) a flexible number of samples, (F) a flexible number of reagents, and (G) digital PCR.

3. An apparatus, comprising (A) an injection molded portion comprising at least a channel for transporting a biological sample and a second channel for receiving a droplet carrier fluid, partitioning the sample into one or more sample droplets, and directing the droplets to an outlet, and (B) an instrument portion comprising an inlet for receiving the droplets from the outlet a thermal cycler, and a detector; wherein together the injection molded and the instrument portions perform one or more nucleic acid assays.

4. The apparatus of paragraph 3, further comprising at least one of a droplet generator, a bead blender, a low-cost disposable, and a reservoir or holding coil at the outlet.

III. SAMPLE PREPARATION/CARTRIDGE

This Section describes exemplary systems for sample preparation, including cartridges for sample lysis and droplet generation.

It may be desirable to separate an enzymatic amplification system such as a PCR-based DNA amplification system into disposable and nondisposable components, for example, by creating a disposable cartridge or other disposable vessel that would prepare and present samples to a nondisposable PCR instrument or other reader. Such a separation could facilitate rapid and low-cost DNA testing and analysis. The disposable cartridge may be designed as a single-use cartridge, to avoid the possibility of cross contamination between samples. Although the terms "cartridge" or "disposable cartridge" will be used to reference the disposable portion of the DNA amplification system, the disposable portion generally may take various forms, and need not be rectangular or symmetric in any particular manner or dimension.

A suitable disposable cartridge will be configured to receive a sample and to prepare (or at least partially prepare) the sample for amplification and analysis, prior to PCR thermocycling and amplification. The cartridge may include an interface configured to pass the prepared sample to a non-disposable portion of the system, which generally will be referred to as an "instrument," for subsequent PCR amplification and analysis steps. In some cases, the interface between the cartridge and the instrument also may be configured to transfer various fluids, such as oil and/or aqueous fluid, from the instrument to the cartridge, to "prime" or partially prime the cartridge for sample preparation. In other cases, the cartridge may be partially or entirely pre-primed with fluids, so that fluid transfer from the instrument is not necessary.

A disposable cartridge according to the present disclosure may be configured to generate droplets or packets of droplets, each containing a mixture of sample and reagent, which then may be transported from the disposable cartridge to the related instrument for rapid serial injection into a continuous flow thermal cycler. The cartridge or other disposable vessel then may be removed from the system and discarded. The cartridge may be configured to perform sample preparation steps relatively quickly, as measured by sample throughput from the cartridge to the PCR instrument. For example, a cartridge according to the present disclosure may be configured to perform sample preparation in a time of less than 5 minutes per sample, to achieve throughput of at least 10 samples per hour. The cartridge also may be constructed from and function in conjunction with non-hazardous materials, to minimize environmental impact.

Figure 41:
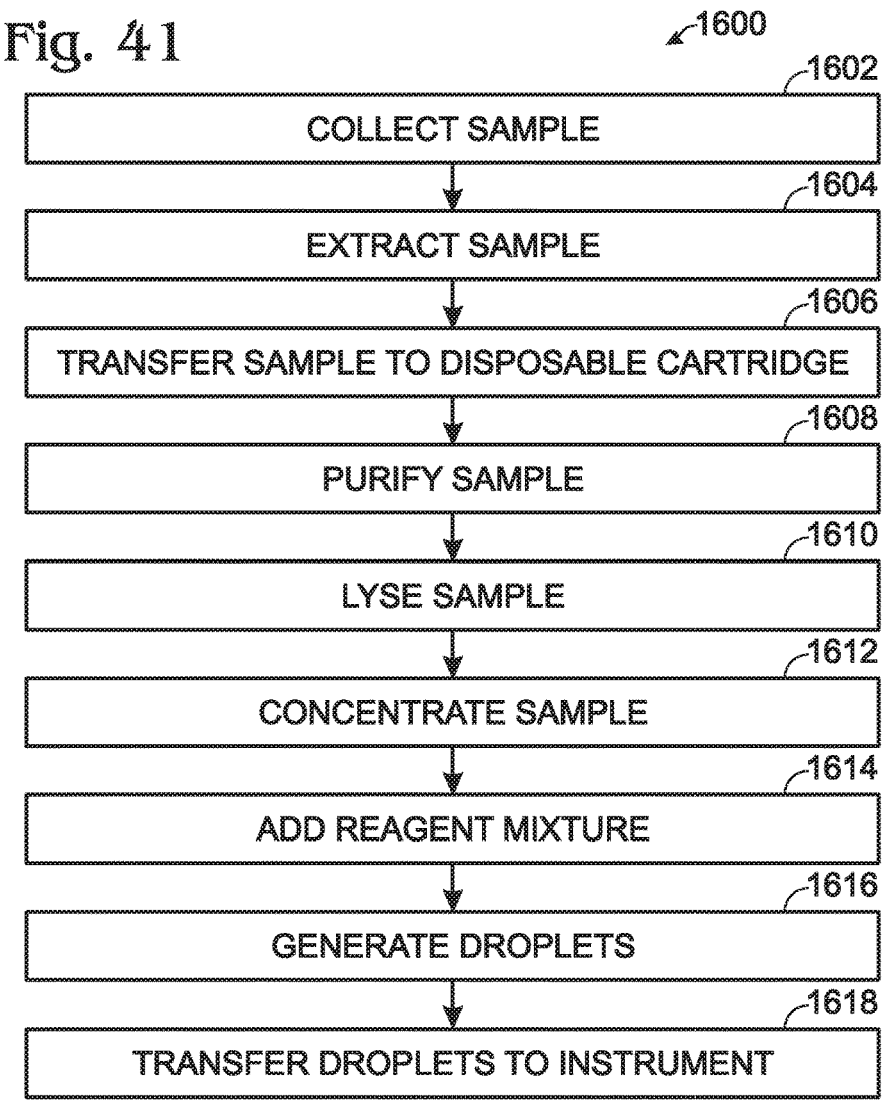
FIG. 41 is a flowchart depicting the steps of a DNA amplification method that may be performed within or in conjunction with a disposable cartridge of a DNA amplification system, in accordance with aspects of the present disclosure.

FIG. 41 is a flowchart depicting the steps of a DNA amplification method, generally indicated at 1600, that may be performed within or in conjunction with a disposable cartridge of a DNA amplification system according to the present disclosure. The major functions that the disposable cartridge is configured to perform are purification, lysis, reagent mixing, and sample isolation into droplets. However, more generally, any subset or combination of the steps depicted in FIG. 41 may be performed within the cartridge. Alternatively, one or more of the depicted steps, such as sample collection and extraction, may be performed prior to transferring target-containing material into the cartridge, while other steps are performed within the cartridge. Similarly, one or more of the depicted steps, such as droplet generation, may be performed after transferring target-containing material out of the cartridge. Furthermore, the steps depicted in FIG. 41 may be performed in various different orders, only some of which will be described below.

At step 1602 of method 1600, a sample is collected for subsequent analysis. This is typically done by a medical practitioner, a law enforcement agent, a scientist, or some other person with reason to collect a sample for nucleic acid analysis. The sample may, for example, be collected using a sample collector, such as a swab, a sample card, a specimen drawing needle, a pipette, a syringe, and/or by any other suitable method. Furthermore, pre-collected samples may be stored in wells such as a single well or an array of wells in a plate, may be dried and/or frozen, may be put into an aerosol form, or may take the form of a culture or tissue sample prepared on a slide. Such pre-collected samples then may be obtained and prepared for droplet-based processing in a disposable cartridge. The collected sample typically will include one or more cells, bacteria, viruses, or other material potentially or actually containing a target sequence of nucleotides suitable for PCR amplification.

At step 1604, the collected sample is extracted from the sample collector. This may be accomplished, for example, by transferring the sample from the sample collector using a pipette, a syringe, or the like, or by soaking and/or rinsing a sample collector in one or more suitable solutions, such as a digestive buffer solution, a lysis buffer solution, or an appropriate binder-containing solution, among others. Extraction may occur within a chamber of the disposable portion of the PCR system, in which case the sample will be transferred to the cartridge, as indicated at step 1606 of method 1600, prior to extraction. Alternatively, extraction may occur outside of the cartridge, and the resulting sample or sample-containing solution then may be transferred to the cartridge. In either case, the cartridge may be configured to perform various additional sample preparation steps, as described below.

At steps 1608 and 1610, the extracted sample, which is now disposed in a sample chamber within the cartridge, is purified and lysed. These steps may be performed at different times, simultaneously, or approximately simultaneously. Furthermore, purification may be performed either before or after lysing, and in some instances two or more separate purification steps may be performed, one before lysing and one after lysing. Purification generally includes some form of filtering to remove unwanted components from the sample while leaving the desired target components relatively unaffected, and lysing generally includes disruption of the sample constituents (e.g., by breaking the cellular membranes) to expose target DNA for amplification, typically involving some form of physical blending or stirring of the sample-containing mixture. For example, lysing may proceed through bulk mixing such as agitation, magnetic stirring, and/or aspiration, or through microfluidic mixing of various types such as forcing the sample through a tortuous path, electromagnetic bombardment, sonication, and/or convection. The fluid containing the contents of the lysed sample may be referred to as a lysate.

Depending on whether a particular purification step is performed before or after lysing, the method of purification may vary. For example, purification prior to lysing may be configured to capture relatively large target-containing material, such as bacteria or other cells. Purification at this stage may, for example, include filtering the sample-containing solution through an aperture-based filter with a characteristic aperture size smaller than the characteristic size of the target-containing cells, to retain the cells or other target material within the sample chamber while removing other, smaller waste material. On the other hand, purification after lysing may be configured to capture relatively small target material, such as DNA or partial nucleic acid sequences. Accordingly, post-lysing purification may include filtration through a smaller filter, and/or affinity capture of DNA or other target material, to retain target material within the sample while removing other, larger waste material. In some cases, such as when purification steps are performed both before and after lysing, two or more different types of filters, including aperture-based filters and/or affinity-based filters, may be used.

At step 1612, the partially processed sample (i.e., the lysate) is concentrated. This step is generally accomplished by separating excess fluid in the lysate from the target DNA or DNA-containing material, for example, by filtering, ethanol precipitation, butanol extraction, or affinity capture, among others. In any case, the result of the concentration step is a greater density of target material per unit volume of fluid. Concentration of the sample at this stage may result in a detectable amplified target after relatively fewer PCR amplification cycles than would be necessary without concentration.

At step 1614, a PCR reagent mixture including appropriate enzymes and DNA primers is mixed with the sample. These reagent constituents are selected to facilitate DNA amplification of a particular target in conjunction with cyclical temperature changes (i.e., thermocycling). The reagent mixture may be combined with the sample in fluid form, or it may be lyophilized (freeze-dried) and converted into a powder, a pellet, or any other convenient form. To form a lyophilized reagent, suitable stabilizing and/or sedimenting agents may be combined with the PCR enzymes and DNA primers.

Two or more reagents may be mixed with the sample at step 1614, to form either a single sample/reagent mixture containing multiple reagents, or multiple mixtures each containing a single reagent. A single mixture containing multiple reagents may, for example, allow screening for multiple targets simultaneously, whereas multiple mixtures each containing a single reagent may be configured for PCR amplification of several different DNA targets, or (when two or more of the mixtures contain the same reagent) to provide experimental control, for instance, by allowing multiple PCR amplification and/or detection techniques to be applied to the same sample/reagent mixture. When multiple sample/reagent mixtures are used, the different mixtures may be separately prepared and/or separately tracked through the system.

At step 1616, droplets containing the sample and the reagent are generated, typically in aqueous form within an oil-based emulsion. The generated droplets may contain a mixture of sample and reagent, either activated or not activated (i.e., either requiring or not requiring an additional activation step before PCR amplification begins), or the droplets each may contain sample and reagent that are separated from each other, for example, by a thin membrane, such as an oil membrane. When more than one sample/reagent mixture is present, droplets containing each of the various mixtures may be separately produced and tracked. Common modes of droplet generation include flow focusing, jetting, and shearing. Using these techniques, stable droplets may be created at throughputs of 10-1000 Hz with tunable volumes ranging from 15 picoliters (pL) to 5 nanoliters (nL). Various techniques for generating droplets are known.

At step 1618, the droplets produced in step 1616 are transferred from the disposable cartridge to a non-disposable instrument portion of the system. As noted above, the droplets may be contained within an emulsion, such as an oil-based emulsion, in which case transferring the droplets will include transferring portions or the entirety of the emulsion. When more than one sample/reagent mixture has been created, the droplets containing each type of mixture may be separately transferred in a continuous or semi-continuous manner, so that each separate droplet type can be separately processed by the instrument portion of the system. Continuous or semi-continuous droplet transfer may allow relatively rapid screening for multiple target DNA segments. Alternatively, or in addition, droplets containing various sample/reagent mixtures may be "tagged" in some manner, such as with a bar code or some other detectable component, in which case different types of droplets may in some instances be transferred to the non-disposable portion of the system together and then tracked or detected individually.

After transfer from the disposable, sample-preparation cartridge portion of the PCR system to the non-disposable instrument portion, thermocycling and analysis will occur. The following examples describe specific exemplary methods and apparatus for receiving a sample in a disposable vessel, such as a cartridge, preparing the sample for PCR amplification, and passing the prepared sample to a reusable instrument portion of a PCR amplification system. Additional pertinent disclosure may be found in the U.S. provisional patent applications listed above under Cross-References and incorporated herein by reference, particularly Ser. No. 61/277,249, filed Sep. 21, 2009.

A. Example 1: Disposable Sample Cartridge 1

Figure 42:
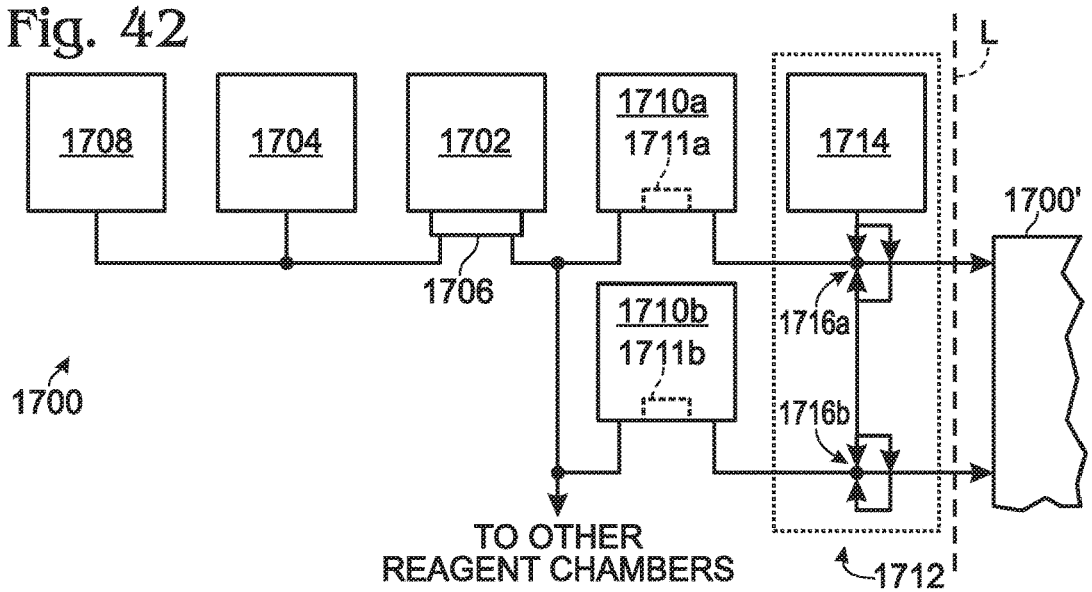
FIG. 42 is a schematic diagram depicting a disposable sample preparation cartridge and suitable fluidic connections between various components of the cartridge, in accordance with aspects of the present disclosure.

This example depicts a disposable sample preparation cartridge and suitable fluidic connections between various components of the cartridge; see FIG. 42.

FIG. 42 is a schematic view of the cartridge, generally indicated at 1700, and suitable fluidic connections between various components of the cartridge. Cartridge 1700 is configured to receive and prepare a target-containing sample for PCR thermocycling and amplification. Preparation of the sample may include some or all of the following steps (not necessarily in this order): purification, lysing, concentration, combination with one or more reagents, and/or generation of droplets suitable for PCR. Droplets containing sample and reagent may be transferred from the cartridge to an instrument, generally indicated at 1700', which is configured to heat the droplets cyclically to facilitate PCR amplification. Dashed line L in FIG. 42 represents the interface between disposable cartridge 1700 and instrument 1700'. This interface may include suitable fluidic connectors, receptors, and the like, to provide a reliable fluidic connection between the cartridge and instrument without significant leakage or contamination.

A sample chamber 1702 of cartridge 1700 is configured to receive a sample. The sample entering chamber 1702 will contain, or at least potentially contain, a target for PCR amplification, such as one or more bacteria, viruses, DNA molecules, and/or other material that contains nucleic acid sequences. For example, the sample may be loaded in the form of eluant that was prepared from a sample collection swab. In some cases, the sample transferred to chamber 1702 may already have been prepared to some extent, for example, by washing, concentrating, and/or lysing, and in other cases the sample may be substantially unprepared or "raw" when it reaches chamber 1702. In any case, sample chamber 1702 may be configured to receive and prepare the sample as described below.

A waste chamber 1704 is fluidically connected to sample chamber 1702, and cartridge 1700 is configured to transfer fluid out of sample chamber 1702, through a filter 1706, and into the waste chamber. Filter 1706 is configured to allow waste products to pass through itself and into the waste chamber, while retaining the PCR target material within the sample chamber. For example, filter 1706 may be a membrane or other similar aperture-type filter with a known characteristic size cutoff. Alternatively, or in addition, the filter may be configured to retain the PCR target within the sample chamber through a suitable form of affinity capture, such as by coating a portion of the sample chamber with an appropriate binding compound. The filter may be used to capture and pre-concentrate the target before the sample is washed, and/or it may be used to retain, additionally concentrate, and/or purify the sample after the sample is washed.

A reservoir chamber 1708 is fluidically connected to sample chamber 1702, and is configured to transfer to the sample chamber a reconstitution fluid, a wash solution, and/or any other fluid suitable for combination with the filtered sample. For example, the fluid transferred from the reservoir chamber may be water, or a buffer solution, such as TE buffer (i.e., a combination of tris(hydroxymethyl)aminomethane, hydrochloric acid, and EDTA), which may remove matrix components that could inhibit downstream PCR amplification. Fluid transferred from the reservoir chamber generally may include any agent configured to separate the target from undesirable components that may have been originally attached to the sample or that may have been used to capture the target when filter 1706 operates through affinity capture.

Sample chamber 1702 also may be configured to lyse the sample. Lysing will typically, but not necessarily, be performed after the target has been washed and/or reconstituted with fluid transferred from reservoir chamber 1708. Lysing may be performed within the sample chamber through mechanical agitation, such as blending, vibrating, shaking, and/or stirring the sample within the chamber, to release nucleic acids from the sample. In some cases, agitation elements, such as discs, rods, and/or small beads may be present in the sample chamber to facilitate lysing. The sample and/or the agitation elements may be agitated by any suitable method, such as manually, through the application of sound waves (i.e., sonication), and/or using magnetic or electromagnetic forces.

Sample chamber 1702 also may be configured to concentrate the target-containing fluid sample. This can be accomplished prior to washing, by transferring some of the original sample-containing fluid from the sample chamber, through the filter, and into the waste chamber. Alternatively, or in addition, concentration can be accomplished by transferring some of the sample-containing fluid into the waste chamber after the sample is washed, while completely or substantially retaining the target nucleic acids within the sample chamber. Concentrating the fluid sample in this manner results in a greater number of target nucleic acids per unit volume of fluid, which can lead to more efficient and faster PCR amplification in subsequent processing steps.

Cartridge 1700 includes one or more reagent chambers. Two reagent chambers 1710a, 1710b are depicted in FIG. 42, but more generally any desired number of reagent chambers, such as five or more, may be utilized. Each reagent chamber contains reagents, such as primers, polymerase, and appropriate enzymes, configured to react with a particular target nucleic acid sequence and to undergo PCR amplification if the target is present in the sample. Typically, the reagents will be pre-loaded into each reagent chamber during the cartridge manufacture, although in some embodiments the reagents may be loaded by a user or transferred from a related PCR instrument.

The reagents may be stored in or introduced into the reagent chambers in any suitable manner. For example, the reagents may take the form of lyophilized pellets 1711a, 1711b depicted in FIG. 42, or a coating (not shown) applied to a portion of the interior wall of each reagent chamber. Alternatively, a reagent coating may be applied to a stir element disposed within the reagent chamber, and/or to a plunger used to vary transfer fluid into and out of the reagent chamber. The reagent chambers of FIG. 42 are fluidically connected in parallel with the sample chamber, so that each reagent chamber can separately receive a portion of the filtered, lysed sample-containing solution, without cross-contamination. One or more stir elements (not shown) may be included in each reagent chamber to facilitate mixing the sample with the pre-loaded reagents. When stir elements are included in the reagent chambers, they may operate manually, through sonication, or using magnetic or electromagnetic forces, in a manner similar to the operation of the agitation elements used for lysing in the sample chamber.

Reagent chambers 1710a and 1710b are each fluidically connected to a droplet generator, generally indicated at 1712. Droplet generator 1712 is configured to generate discrete micro-volume droplets, each containing all of the ingredients for subsequent nucleic acid amplification via PCR. In general, droplet generator 1712 is configured to generate one or more water-in-oil emulsions, although other types of emulsions, such as oil-in-water, water-in-oil-in-water, and so forth are also possible.

Parallel fluid connections lead to droplet generator 1712 from reagent chambers 1710a and 1710b. A common oil reservoir 1714 is configured to transfer oil along the fluid paths indicated, so that oil arrives at each of intersection points 1716a and 1716b from two separate directions. At the intersection points, sample-containing solution arrives from the respective reagent chambers and combines with the oil from the oil reservoir to form water-in-oil droplets. The generated droplets are then transferred across interface L and into instrument 1700'. Each sample/reagent mixture may be transferred either serially or in parallel to droplet generator 1712. Other droplet generator configurations may be suitable, as described below.

After droplets have been generated, system 1700 is configured to facilitate transfer of the droplets through interface L to instrument 1700'. This transfer may be accomplished through the use of suitable fluidic tubing, capillaries, pumps, valves, and/or the like, which may be configured to transfer droplets to the instrument either as parallel streams or in separate (serial) batches, each of which contains droplets that include a specific reagent. The droplets then may be transferred through a multi-port valve and introduced into a thermocycler for PCR amplification.

B. Example 2: Disposable Sample Cartridge 2

This example describes an exemplary disposable cartridge that is suitable for performing some or all of the sample preparation steps described above; see FIGS. 43-45.

Figure 43:
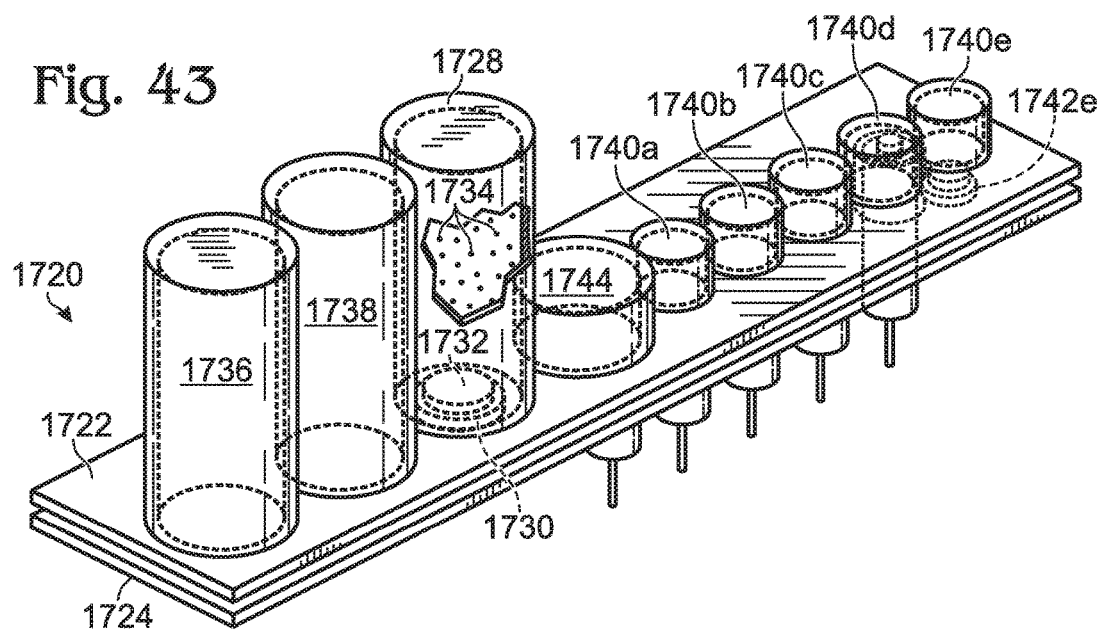
FIGS. 43-45 are isometric, side elevation, and top views, respectively, of an interior portion of an exemplary disposable cartridge, suitable for performing some or all of the sample preparation steps in FIG. 41.

FIG. 43 is an isometric view of an interior portion of the exemplary cartridge, generally indicated at 1720. The cartridge is configured to interface with an instrument (not shown), so that prepared samples can be transferred to the instrument, generally in the form of a water-in-oil emulsion, for PCR amplification and analysis. In addition to the interior portion depicted in FIG. 43, cartridge 1720 also may include a suitable exterior housing (not shown) disposed around some or the entirety of the interior portion. The exterior housing may be configured to protect the interior portion and may be shaped to facilitate storage and/or transportation of multiple cartridges.

Cartridge 1720 includes an upper section 1722 and a lower section 1724, which are configured to fit together to form the interior portion of the cartridge. For clarity, the upper and lower sections are separated by a slight gap in the drawings. These sections may be manufactured by any suitable method, such as by injection molding a thermoplastic material. The upper and lower sections may be bonded together in any suitable manner, for example, with connecting pins (or similar connectors), with an adhesive, and/or by thermal curing, to maintain the structural integrity of the assembled cartridge.

Figure 44:
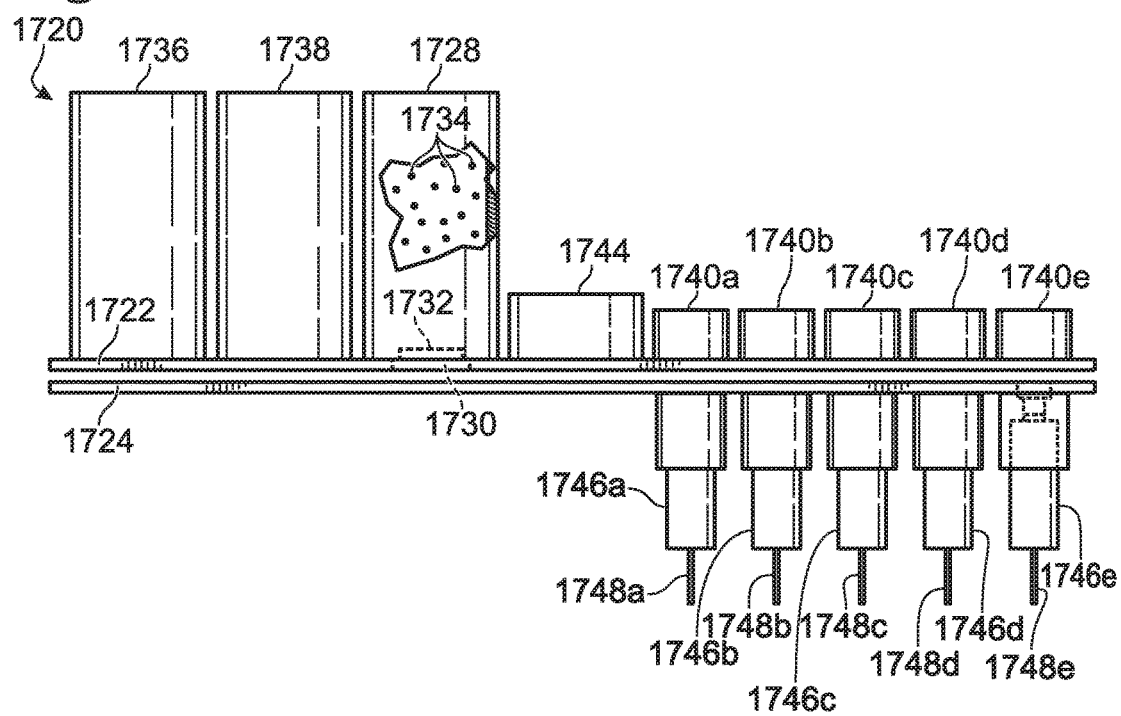
Figure 45:
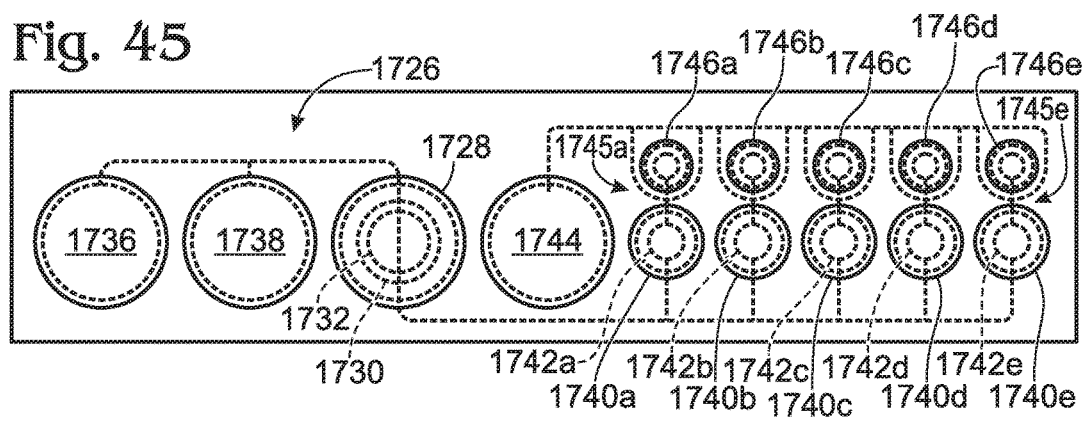

FIGS. 44 and 45 are side elevation and top views, respectively, of the interior portion of cartridge 1720. These drawings, together with FIG. 43, show that the cartridge includes a number of discrete chambers. These chambers are fluidically connected by a fluid path, which is generally indicated at 1726 in FIG. 45. Fluid path 1726 may result from joining complementary grooves formed within each of sections 1722 and 1724, so that a closed fluid path results when the sections are joined together. The grooves of each section may, for example, have an approximately hemispherical profile, so that the grooves form a substantially cylindrical fluid path when the upper and lower sections of the cartridge are assembled. In other embodiments, the grooves may have other shapes, such as rectangular, and the allocation of the total cross section between the upper and lower sections may vary.

A sample chamber 1728 of cartridge 1720 is configured to receive a sample that contains (or potentially contains) a target nucleic acid sequence. The sample may be transferred into the sample chamber as a fluid, or it may be placed in the chamber attached to a swab or some other suitable sample collection medium. The sample chamber can be constructed to have any desired shape, such as the cylindrical shape depicted in FIGS. 43 and 44, and any desired volume, such as a volume in the range of 200 microliters (µL) to 2 milliliters (mL). The volume of the sample chamber may depend in part on the number of separate nucleic acid targets for which the cartridge is configured to test, as described below.

Sample chamber 1728 may include a filter 1730. The filter will typically be disposed near or below the bottom surface of the sample chamber. Filter 1730 may be a size-exclusion filter configured to prevent passage of material larger than a particular preselected size. For example, to prevent passage of bacteria having a characteristic size of 600 nanometers (nm), the filter may be a membrane with a characteristic cutoff size of 200-400 nm. To prevent passage of other material, the filter may be chosen to have a different characteristic cutoff size, which is selected based on the material to be filtered. Membrane filtration based on size fractionation is a simple, yet effective method of capturing target cells. Once captured, the cells can be washed to remove potential PCR inhibitors that are soluble or below the size cutoff of the membrane.

Alternatively, filter 1730 may operate through affinity capture (i.e., by attracting and/or chemically binding one or more target molecules), or by solid phase extraction, such as chemical precipitation. However, membrane filtration may have certain advantages over solid phase extraction, including a reduced number of processing steps, no hazardous reagents, fast processing times, and the potential for simultaneous concentration and purification of the target organisms, as described below.

The sample chamber also may include one or more lysing elements, such as a stirring disc 1732 and/or lysis beads 1734; see FIGS. 43-44. These elements are generally configured to facilitate lysis of a fluid in the sample chamber, through agitation of the sample to release nucleic acids by breaking down surrounding material (such as cellular material). The lysing disc 1732 or other similar stirring element will typically be disposed toward the bottom of, but within, the sample chamber. Lysis beads 1734, which can take the form of beads of any desired material and diameter, such as glass beads with diameters in the range of 70-700 µm, are configured to further facilitate lysis by colliding with and disrupting material within the agitated fluid of the sample chamber.

Agitation of stirring disc 1732, which also can take the form of a rod or any other suitable shape, may be provided by magnetic or electromagnetic forces. For example, the stirring disc may be sufficiently magnetic to respond to a changing magnetic field applied to the sample chamber. Thus, variations in the applied magnetic field can cause the stirring disc to spin and/or tumble, resulting in agitation of the fluid within the sample chamber. A variable magnetic field may be provided, for example, by a single low-cost driver located on the related PCR instrument. The driver may be configured to drive the lysing elements within one, several, and/or a multitude of sample chambers simultaneously. Because the lysing elements are contained within the sample chamber and because the magnetic driver may be configured to act across a plurality of sample chambers, lysing within cartridge 1720 does not require a special interface between the disposable cartridge and the related instrument. This configuration provides a high degree of amenability to integration and automation within a low-cost single-use cartridge.

Sample chamber 1728 is configured to receive one or more fluids, such as a wash and/or a reconstitution solution, from a reservoir chamber 1736. When the sample transferred to the sample chamber is attached to a medium, such as a swab, fluid from the reservoir chamber may be used to reconstitute the sample into fluidic form. Fluid from the reservoir chamber also may be used to purify a sample, such as bacteria, by washing the sample with a buffer solution. The fluid in reservoir chamber 1736 may be provided with the cartridge, supplied by a user, and/or transferred to the cartridge from an instrument to which the cartridge attaches. In any case, fluid may be transferred from reservoir chamber 1736 to sample chamber 1728 along fluid path 1726, which connects the two chambers. This connection can be seen, for example, in FIG. 45, which is a top view of cartridge 1700. Fluid transferred from the reservoir chamber to the sample chamber passes through filter 1730, so that the fluid is filtered before entering the sample chamber.

Cartridge 1720 also includes a waste chamber 1738. The waste chamber is configured to receive waste material, such as nucleic acid fragments and other waste material either introduced to the sample chamber with the sample or fragmented during lysing, from the sample chamber. Waste chamber 1738 is fluidically connected to sample chamber 1728 through fluid path 1726, which passes through filter 1730. Accordingly, fluid and fragmentary waste products may be transferred from the sample chamber to the waste chamber, while target material having a characteristic size (or chemical affinity) suitable for capture by the filter will be retained within the sample chamber.

For example, sample-containing solution may be purified prior to lysing by filtering the fluid through filter 1730 and into waste chamber 1738. The fluid in the sample chamber then may be replenished from reservoir chamber 1736, as described previously. Similarly, sample-containing solution may be purified and/or concentrated after lysing, again by filtering the fluid through filter 1730 and into waste chamber 1738. The steps of purification, concentration, and fluid replenishment may be repeated any desired number of times by transferring fluid from the sample chamber to the waste chamber and from the reservoir chamber to the sample chamber.

FIGS. 43-45 depict five separate reagent chambers 1740a, 1740b, 1740c, 1740d and 1740e within cartridge 1720. In general, any desired number of reagent chambers, from one, two, three, four, five, six, seven, eight, nine, ten, or more, up to an arbitrarily large number, may be provided (both in this embodiment and other disposable cartridges shown herein). Each reagent chamber is configured to receive sample-containing fluid from the sample chamber, and to allow the combination of the sample-containing fluid with a particular reagent mixture. Sample-containing fluid can be transferred from the sample chamber to the reagent chambers along fluidic path 1726, which connects the sample chamber to each of the reagent chambers in parallel, as can be seen in FIG. 45.

Each reagent mixture may include, for example, primers, polymerase, and/or enzymes suitable for PCR amplification of a particular nucleic acid sequence. The reagent mixtures in two or more of reagent chambers 1740 may be the same or substantially similar (for example, to allow for experimental control), or each reagent mixture may be substantially different, to search for multiple different target nucleic acid sequences.

The reagent mixtures of cartridge 1720 are depicted as lyophilized pellets 1742a, 1742b, 1742c, 1742d, and 1742e disposed at the bottom of the associated reagent chambers; see FIG. 45. However, in general the reagent mixtures can be provided in any suitable form, such as within a fluid, as a lyophilized powder (either loose or shaped into a form other than a pellet), or as a coating applied to the interior surface of each reagent chamber, among others. Furthermore, the reagent mixtures may be supplied with the cartridge, supplied by a user, or transferred to the cartridge from a PCR instrument to which the cartridge is connected.

Cartridge 1720 also includes an oil chamber 1744, which is fluidically connected to each of reagent chambers 1740a, 1740b, 1740c, 1740d, and 1740e. Oil chamber 1744 is configured to supply the oil needed to produce a water-in-oil emulsion containing droplets of sample and reagent fluid. More specifically, oil can pass from chamber 1744 to a plurality of droplet generation regions 1745a, 1745b, 1745c, 1745d, and 1745e, each corresponding to and fluidically connected with one of the reagent chambers. Each droplet generator is configured to generate droplets of a particular sample/reagent mixture suspended in an oil background.

Specifically, as depicted in FIG. 45, oil in cartridge 1720 passes from oil chamber 1744 down a plurality of fluid pathways. These include a pair of oil pathways corresponding to each droplet generator and configured to intersect with a fluid pathway from one of the reagent chambers, to create water-in-oil droplets. The generated droplets then may pass through interface components, such as a plurality of capillary connectors 1746a, 1746b, 1746c, 1746d, and 1746e. The capillary connectors are configured to transfer fluid to a plurality of corresponding capillaries 1748a, 1748b, 1748c, 1748d, and 1748e, which are configured to interface with instrument 1700' (see, e.g., FIG. 42).

C. Example 3: Exemplary Hydraulic Mechanisms

Figure 46:
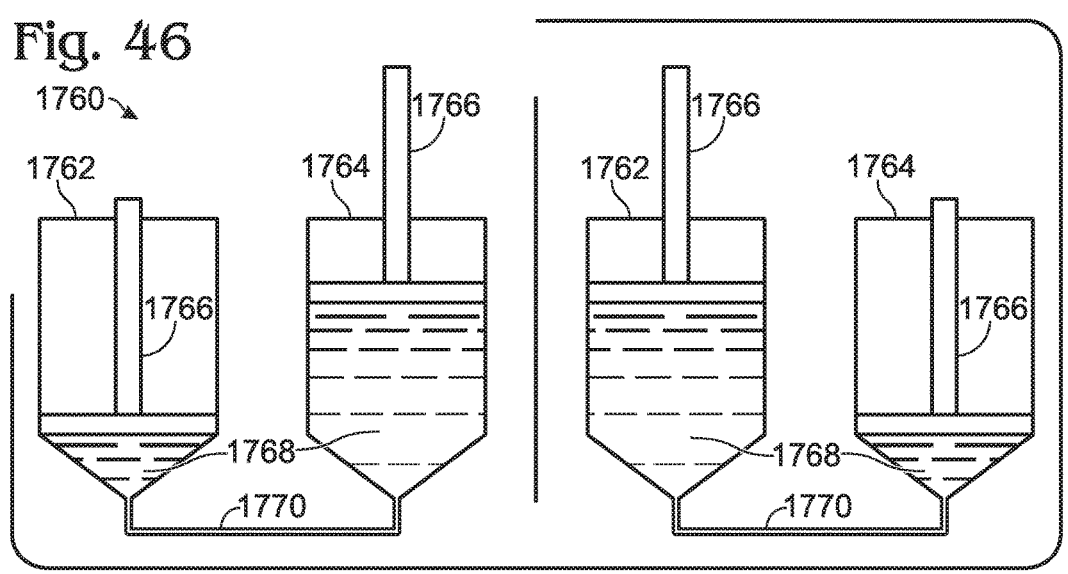
FIG. 46 is a schematic view of a two-chamber hydraulic mechanism, suitable for controlling fluid motion between the various chambers of a disposable cartridge, in accordance with aspects of the present disclosure.
Figure 47:
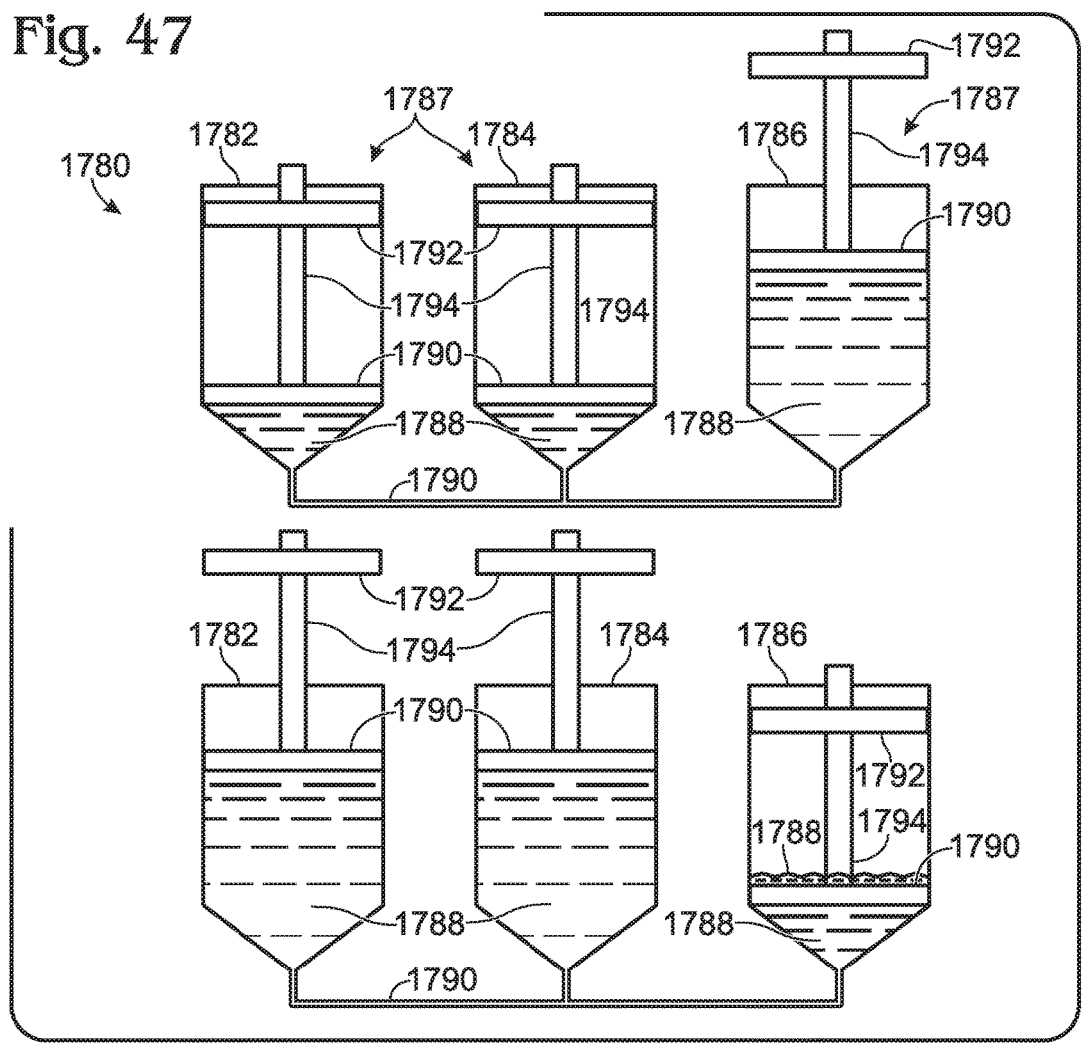
FIG. 47 is a schematic view of a three-chamber hydraulic mechanism, which is similar to two-chamber mechanism of FIG. 46, suitable for controlling fluid motion between the various chambers of a disposable cartridge, in accordance with aspects of the present disclosure.

This example describes aspects of two exemplary hydraulic mechanisms suitable for controlling fluid motion between the various chambers of a disposable cartridge; see FIGS. 46 and 47.

FIG. 46 schematically illustrates aspects of a two-chamber hydraulic mechanism, generally indicated at 1760, that is suitable for controlling fluid motion between the various chambers of a disposable cartridge, such as cartridges 1700 or 1720 described above. Each side of FIG. 46 depicts two fluid chambers 1762 and 1764. Each chamber is equipped with a plunger 1766, and a fluid 1768 is partially disposed within each chamber. In the left-hand portion of FIG. 46, the majority of the fluid is disposed in chamber 1764, and in the right-hand portion of FIG. 46, the majority of the fluid is disposed in chamber 1762. A connecting fluid pathway 1770 is provided between chambers 1762 and 1764, which allows fluid 1768 to pass between the chambers.

Fluid motion between chambers will occur when unequal forces are applied to the two plungers 1766, causing one of the plungers to move down while the other moves up. Such forces will typically be applied by a force actuator, such as a piston or a push rod, which will be contained within or otherwise integrated with an instrument configured to receive a disposable sample preparation cartridge. In this manner, fluid can be transferred between any of the previously described chambers of a disposable cartridge in a controlled manner.

More specifically, motions of plungers 1766 may be controlled directly by a user and/or by an instrument configured to receive and interact with the cartridge containing the plungers. For example, a user might manually load a sample or a sample-containing fluid into one of chambers 1762 or 1764 (which would therefore be considered a sample chamber), and then insert a plunger 1766 into the chamber, sealing the sample or sample-containing fluid within the chamber. Fluid then may be transferred hydraulically into and out of the sample chamber by depressing the appropriate plunger either manually or automatically.

Automatic plunger motions may be controlled by a processor programmed to transfer fluids between chambers of the system in a predetermined manner. For instance, if hydraulic mechanism 1760 is incorporated into cartridge 1700, then instrument 1700' may include force actuating structures complementary to the plungers of the hydraulic mechanism, such as pistons, push rods or the like. These force actuators may be configured to depress the associated plungers at particular times, in a particular order, or in response to signals sent to the instrument by a user.

FIG. 47 schematically depicts a three-chamber hydraulic mechanism, generally indicated at 1780, which is similar to two-chamber mechanism 1760 of FIG. 46. Fluid chambers 1782, 1784, and 1786 each include a plunger 1787. A fluid 1788 is partially disposed within each chamber, and the chambers are fluidically connected by a fluid pathway 1790. Accordingly, fluid will be transferred from one chamber to one or both of the other chambers when plungers 1787 are moved appropriately. For example, fluid from chamber 1786 can be transferred to chambers 1782 and 1784 by depressing the plunger of chamber 1786 and simultaneously raising the plungers of chambers 1782 and 1784.

If the chambers all have the same size and geometry, then to transfer an equal amount of fluid from chamber 1786 to chambers 1782 and 1784, each of the plungers of chambers 1782 and 1784 would be raised at half the rate with which the plunger of chamber 1786 is depressed. Alternatively, the chambers may have different sizes and/or shapes, in which case the plunger motions would be suitably modified to achieve equal fluid transfer from one chamber to the other chambers. Furthermore, fluid from one chamber can be divided among two or more other chambers according to any desired ratio of volumes, by controlling the motions of the various plungers.

Plungers according to the present disclosure may include a locking mechanism. The locking mechanism of a particular plunger may be configured to lock the plunger into a particular position, to avoid undesirable transfer of fluid to or from a particular chamber. For example, a plunger associated with a waste chamber may include a locking mechanism configured to lock the plunger in place when the plunger reaches an upper (retracted) position, corresponding to a maximum volume of fluid within the waste chamber. This can prevent waste fluid from unintentionally being transferred back into another chamber, such as a sample chamber or a reservoir chamber, after waste has been removed from a sample.

A suitable plunger locking mechanism can take various forms, each having the common property that the mechanism prevents particular unwanted plunger motions. For example, a suitable locking may include a mechanism integrated with the plunger itself, such as a spring-biased tab or the like (not shown) that snaps into place when the plunger reaches a certain position, preventing subsequent downward plunger motions. Alternatively, the locking mechanism may be associated with the instrument configured to receive the disposable cartridge, in which case the locking mechanism may include programming a controller to avoid causing downward motions of a particular plunger under certain circumstances.

Plungers according to the present disclosure also may be configured to limit or eliminate leaks. For example, as depicted in FIG. 47, plungers 1787 may include both a lower seal 1790 and an upper seal 1792, attached to a common shaft 1794 and separated by a desired distance. Seals 1790 and 1792 typically will take the form of o-rings or similar structures configured to fit in a substantially fluid-tight manner within the inner circumference of the associated chamber. Thus, as FIG. 47 depicts (see chamber 1786), any residual fluid 1788 that passes the lower seal as a plunger is depressed will still be trapped within the associated chamber by the upper seal.

D. Example 4: Exemplary Droplet Generators

This example describes various exemplary droplet generation configurations that may be suitable for generating water-in-oil droplets containing a mixture of sample and reagent; see FIGS. 48A-48F. The generated droplets then may be transported to a thermocycling instrument for PCR amplification. Each depicted configuration is compatible with continuous production of oil phase emulsions and with both pressure-controlled and positive displacement pumping. A droplet generator or droplet generation configuration according to the present disclosure may be connected to a pressure/pump source located on a complementary PCR instrument, or may include any pumps and/or pressure sources needed to facilitate droplet generation.

Each depicted droplet configuration in FIGS. 48A-48F may be capable of high-throughput droplet generation (~1,000 droplets per second) in a disposable device, such as a cartridge. Each configuration may be constructed by injection molding two layers of material that fit together to form fluid channels, such as cylindrical channels formed by complementary hemispherical grooves. The fluid channels of the droplet generation configurations depicted in FIGS. 48A-48F may have varying channel depths, such as 50, 100, 150, 200, or 250 µm, among others.

Figure 48A:
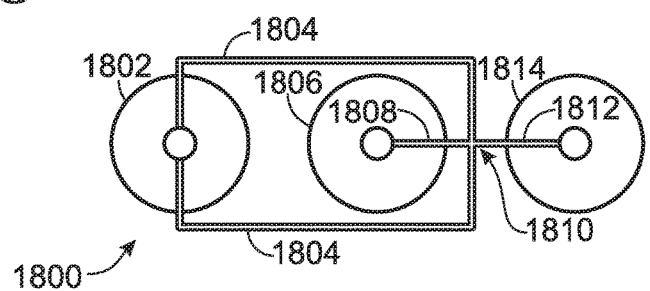
FIGS. 48A-48F are top views of various exemplary droplet generators, in accordance with aspects of the present disclosure.

FIG. 48A depicts a 3-port cross droplet generation configuration 1800 wherein oil from a first fluid well (or chamber) 1802 is transferred through two similar branches of a fluid channel section 1804. The oil from well 1802 intersects with aqueous fluid from a second fluid chamber 1806, which is transferred along a fluid channel section 1808 to an intersection area generally indicated at 1810. The oil from well 1802 arrives at intersection 1810 from two different and substantially opposite directions, whereas the aqueous solution arrives at the intersection along only a single path that is substantially perpendicular to both directions of travel of the arriving oil. The result is that at intersection 1810, aqueous droplets in an oil background (i.e., a water-in-oil emulsion) are produced and transferred along a fluid channel section 1812 to a third chamber 1814, where the emulsion can be temporarily stored and/or transferred to a thermocycling instrument.

Figure 48B:
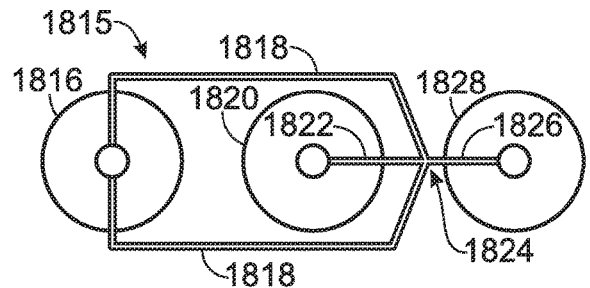

FIG. 48B depicts a configuration 1815 that is similar in most respects to droplet generation configuration 1800 depicted in FIG. 48A. Specifically, in droplet generation configuration 1815, oil from a first fluid chamber 1816 is transferred through two similar branches of a fluid channel section 1818. Fluid channel sections 1818 intersect with a fluid channel section 1822 that transfers aqueous fluid from a second fluid chamber 1820, at an intersection area generally indicated at 1824. As in configuration 1800, the oil from chamber 1816 arrives at intersection 1810 from two different directions, but unlike in configuration 1800, the oil does not arrive from substantially opposite (antiparallel) directions. Rather, channel sections 1818 each intersect channel section 1822 at a non-perpendicular angle, which is depicted as approximately 60 degrees in FIG. 48B. In general, configuration 1815 may include oil fluid channels that intersect an aqueous fluid channel at any desired angle or angles. Oil flowing through channel sections 1818 and aqueous solution flowing through channel section 1822 combine to form a water-in-oil emulsion of aqueous droplets suspended in an oil background. As in the case of configuration 1800, the droplets then may be transferred along a fluid channel section 1826 to a third fluid chamber 1828, for storage and/or transfer to a thermocycling instrument.

Figure 48C:
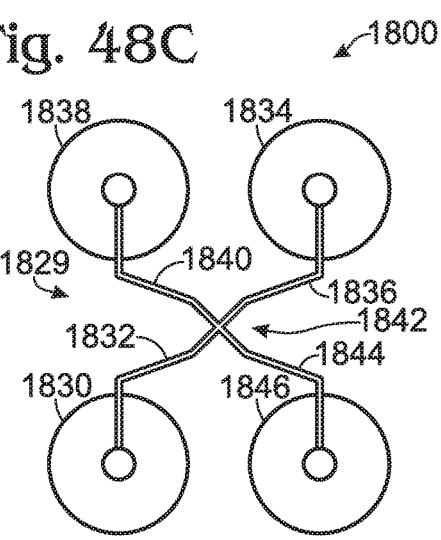

FIG. 48C depicts a four-port droplet generation configuration 1829 that includes two separate oil wells or chambers. A first oil chamber 1830 is configured to store oil and transfer the oil through a fluid channel section 1832 toward a channel intersection point generally indicated at 1842. A second oil chamber 1834 is similarly configured to store and transfer oil toward the intersection point through a fluid channel section 1836. An aqueous fluid chamber 1838 is configured to store aqueous fluid, such as a sample/reagent mixture, and to transfer the aqueous fluid through fluid channel section 1840 toward intersection point 1842. When the oil traveling through fluid channel sections 1832 and 1836 intersects with the aqueous fluid traveling through fluid channel section 1840, a water-in-oil emulsion of aqueous droplets suspended in oil is generated. Although fluid channel 1840 is depicted as intersecting with each of fluid channels 1832 and 1836 at a perpendicular angle, in general the channels may intersect at any desired angle, as described previously with respect to droplet generation configuration 1815 of FIG. 48B. The emulsion generated at intersection 1842 travels through outgoing fluid channel section 1844 toward an emulsion chamber 1846, where the emulsion may be temporarily held for transfer to an instrument, such as a thermocycling instrument.

Figure 48D:
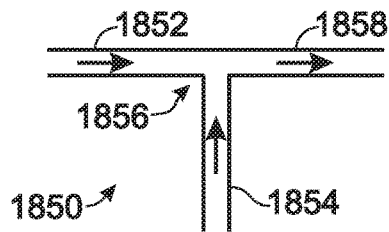
Figure 48E:
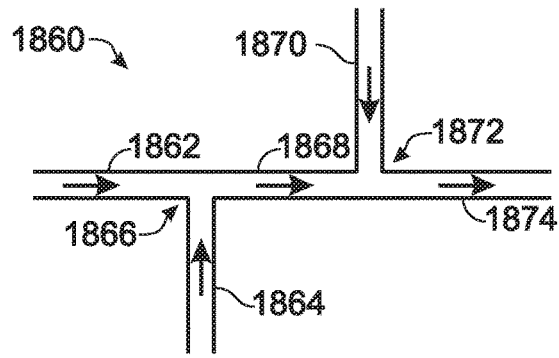
Figure 48F:
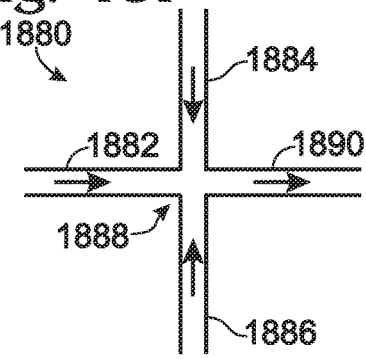

FIGS. 48D-48F schematically depict fluid channel intersection regions of several other possible droplet generation configurations, in which the arrows within the depicted fluid channels indicate the direction of fluid flow within each channel. Although fluid chambers for receiving and/or storing oil, water, and any generated emulsion are not depicted in FIGS. 48D-48F, these chambers or at least some source of oil and aqueous fluid would be present in a cartridge containing any of the depicted configurations. The fluid channels and any associated chambers may be formed by any suitable method, such as injection molding complementary sections of thermoplastic as described previously.

FIG. 48D depicts a "single T" configuration 1850 in which oil traveling in an oil channel 1852 intersects with aqueous fluid traveling in an aqueous channel 1854 at fluid channel intersection 1856, to produce a water-in-oil emulsion that travels through outgoing fluid channel 1858. This configuration differs from those of FIGS. 48A-48C in that oil arrives at the oil/water intersection from only a single direction. Accordingly, droplets may be formed by a slightly different physical mechanism than in configurations where oil arrives from two directions. For example, droplets formed in the single T configuration of FIG. 48D may be formed primarily by a shear mechanism rather than primarily by a compression mechanism. However, the physics of droplet formation is not completely understood and likely depends on many factors, including the channel diameters, fluid velocities, and fluid viscosities.

FIG. 48E depicts a "double T" configuration 1860 in which oil traveling in an oil channel 1862 intersects with aqueous fluid traveling in a first aqueous channel 1864 at a first intersection 1866, to produce a water-in-oil emulsion that travels through intermediate fluid channel 1868. Channel 1868 intersects with a second aqueous channel 1870 at a second intersection 1872, to generate additional water-in-oil droplets within the emulsion. All of the generated droplets then travel through outgoing fluid channel 1874. This configuration again differs from those of FIGS. 48A-48C in that oil arrives at the oil/water intersections from only a single direction. In addition, configuration 1860 differs from single T configuration 1850 depicted in FIG. 48D due to the presence of two oil/water intersections. This may result in a greater density of droplets in the water-in-oil emulsion generated by configuration 1860 than in the emulsion generation by configuration 1850, which includes only one oil/water intersection.

FIG. 48F depicts a droplet generation configuration 1880 in which oil traveling in an oil channel 1882 intersects with aqueous fluid traveling in first and second aqueous channels 1884 and 1886 at an intersection 1888. In this configuration, the aqueous fluid arrives at the intersection from two opposite directions, both of which are substantially perpendicular to the direction of travel of the oil in channel 1882. More generally, the aqueous fluid can intersect with the oil at any desired angles. Depending on at least the sizes of the various channels, the flow rates of the oil and the aqueous fluid, and the angle of intersection of the aqueous fluid channels with the oil channel, a configuration of this type may be suitable for producing either an oil-in-water emulsion or a water-in-oil emulsion. In either case, the emulsion will travel away from intersection 1888 through outgoing fluid channel 1890.

E. Example 5: Disposable Sample Cartridge 3

Figure 49:
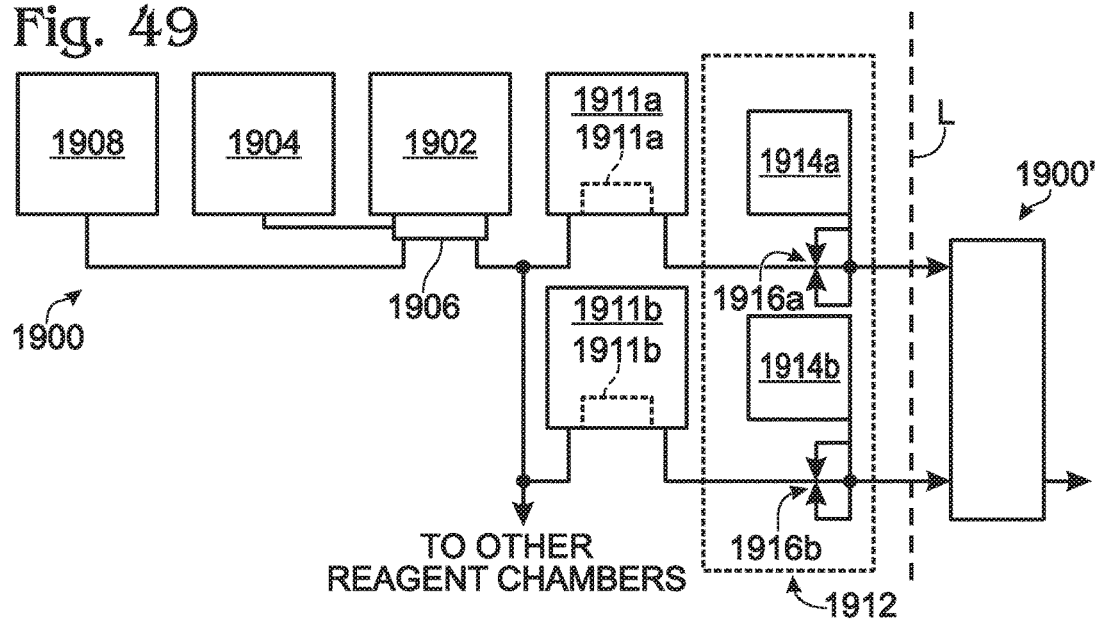
FIG. 49 is a schematic diagram depicting another disposable sample preparation cartridge and suitable fluidic connections between various components of the cartridge, in accordance with aspects of the present disclosure.
Figure 50:
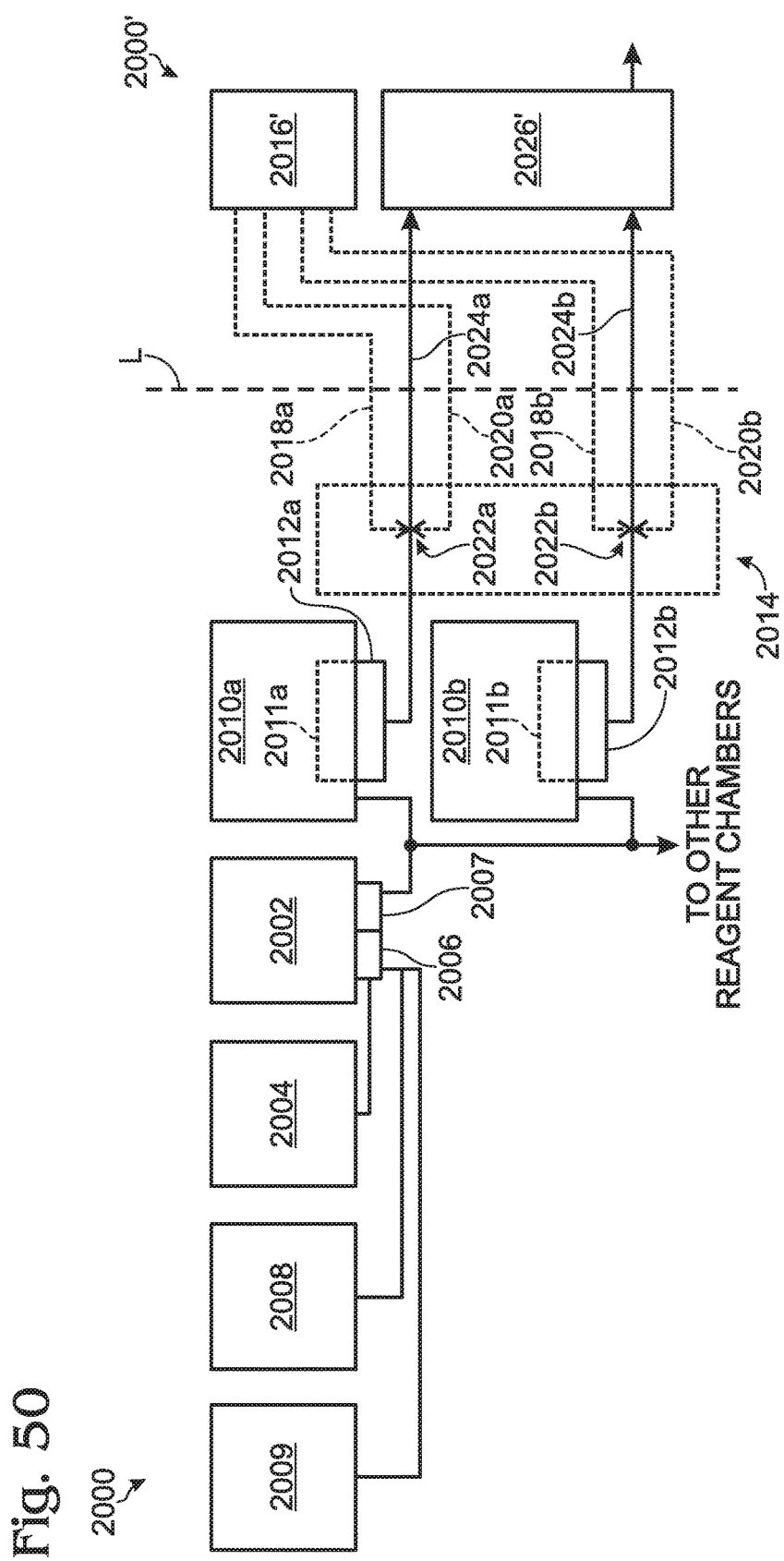
FIG. 50 is a schematic diagram depicting still another disposable sample preparation cartridge (left), portions of a complementary PCR instrument (right), and suitable fluidic connections among and between various components of the cartridge and instrument, in accordance with aspects of the present disclosure.
Figure 51:
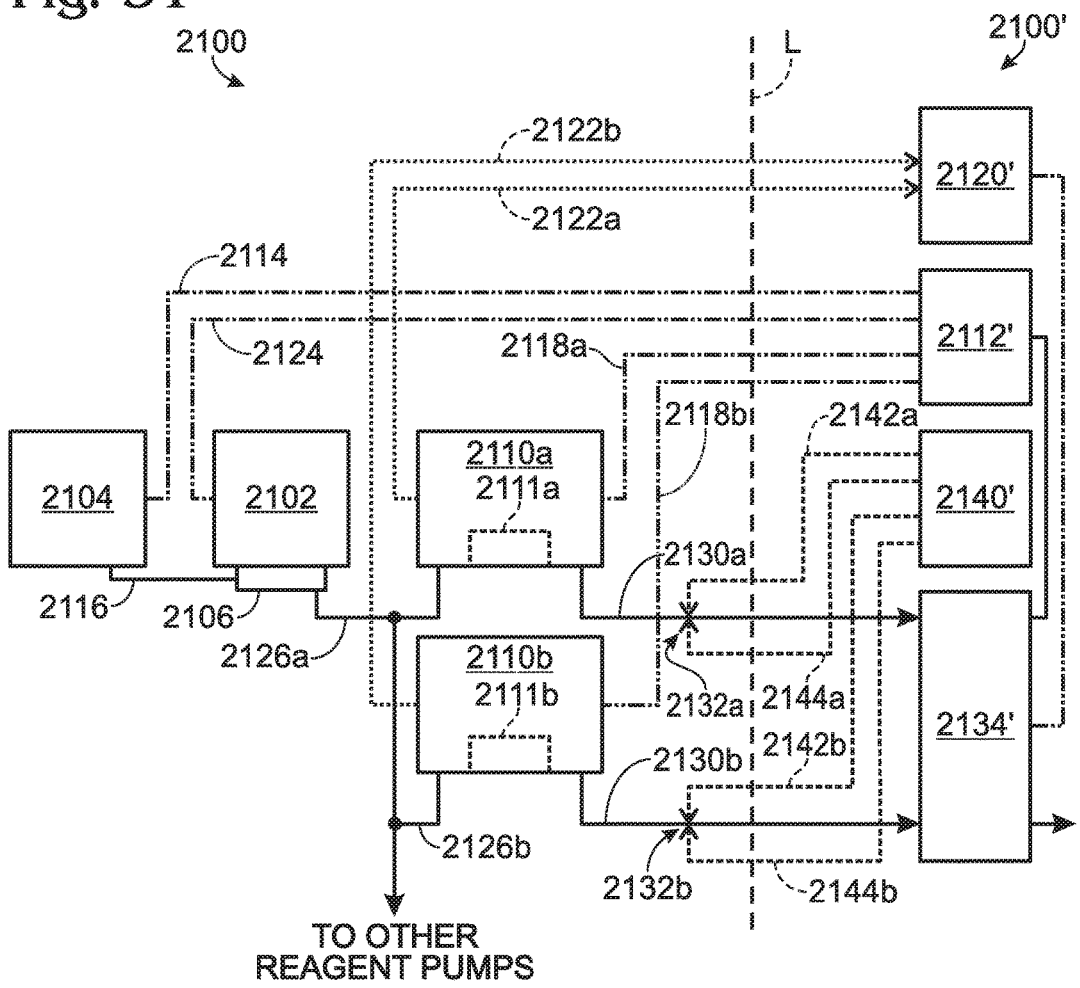
FIG. 51 is a schematic diagram depicting still another disposable sample preparation cartridge (left), portions of a complementary PCR instrument (right), and suitable fluidic connections among and between various components of the cartridge and instrument, in accordance with aspects of the present disclosure.

This example describes aspects of three alternative disposable sample preparation cartridges; see FIGS. 49-51.

FIG. 49 is a schematic diagram depicting another disposable sample preparation cartridge, generally indicated at 1900, and suitable fluidic connections between various components of the cartridge. Cartridge 1900 is configured to receive and prepare a target-containing sample for PCR thermocycling and amplification, and is substantially similar to cartridge 1700 depicted in FIG. 42 in many respects. Accordingly, cartridge 1900 includes a sample chamber 1902, a waste chamber 1904, a filter 1906, a reservoir chamber 1908, and reagent chambers 1910*a*, 1910*b* that may be pre-loaded with reagents 1911*a*, 1911*b*. These components are similar to their counterparts in cartridge 1700, and will not be described again in detail. As in the case of cartridge 1700, any desired number of reagent chambers, such as five or more, may be provided in cartridge 1900.

Cartridge 1900 also includes a droplet generator, generally indicated at 1912, which differs slightly from droplet generator 1712 of cartridge 1700. Specifically, droplet generator 1912 includes two separate oil reservoirs 1914*a*, 1914*b* corresponding to, and separately connected to, the two different reagent chambers. Thus, oil reservoir 1914*a* transfers oil to intersection point 1916*a*, where the oil combines with aqueous fluid from reagent chamber 1910*a* to form a first water-in-oil emulsion of sample/reagent droplets, and oil reservoir 1914*b* transfers oil to intersection point 1916*b*, where the oil combines with aqueous fluid from reagent chamber 1910*b* to form a second water-in-oil emulsion of sample/reagent droplets. Both emulsions then may be transferred to an instrument 1900' for thermocycling. In comparison to cartridge 1800, providing separate oil reservoirs and oil channels in the manner of cartridge 1900 may reduce any chance of cross-contamination between reagents from the separate reagent chambers.

FIG. 50 is a schematic diagram depicting still another disposable sample preparation cartridge, generally indicated at 2000, and suitable fluidic connections between various components of the cartridge. Like cartridges 1700 and 1900 depicted in FIGS. 42 and 49, respectively, cartridge 2000 is configured to receive and prepare a target-containing sample for PCR thermocycling and amplification. Cartridge 2000 includes a sample chamber 2002, a waste chamber 2004, a first filter 2006, and a first reservoir chamber 2008, which are similar to their counterparts in cartridge 1700, and will not be described again in detail.

Cartridge 2000 also includes a second reservoir chamber 2009. Filter 2006 is disposed between sample chamber 2002 and each of reservoir chambers 2008 and 2009, and serves to retain the target-containing sample in the sample chamber as fluid is transferred into and out of the sample chamber. As in the previously described exemplary cartridges, reconstitution and/or wash fluid will typically be transferred into the sample chamber from one of the reservoir chambers, and waste fluid will typically be transferred out of the sample chamber into the waste chamber.

First and second reservoir chambers 2008 and 2009 are provided so that the sample in the sample chamber may be reconstituted and/or washed twice. For example, a reconstitution solution may be transferred into the sample chamber from reservoir chamber 2008, after which the sample may be lysed as has been described previously. Waste fluid then may be transferred from the sample chamber into waste chamber 2004, while the target material is retained in the sample chamber. Next, a wash solution may be transferred into the sample chamber from reservoir chamber 2009, and waste fluid again may be transferred from the sample chamber into the waste chamber. Providing two reservoir chambers and two reconstitution/wash steps may result in a sample that contains relatively few impurities and thus a relatively high fraction of target material.

A second filter 2007 is disposed between sample chamber 2002 and reagent chambers 2010*a*, 2010*b*. The reagent chambers may be pre-loaded with reagents 2011*a*, 2011*b*, and both the reagent chambers and the reagents are similar to their previously described counterparts. Filter 2007 is configured to allow passage of target nucleotide material from the sample chamber to the reagent chambers, while preventing passage of larger material, such as lysis beads or large waste material that remains in the sample chamber after purification and lysis. As in the case of cartridges 1700 and 1900, any desired number of reagent chambers, such as five or more, may be provided in cartridge 2000.

Alternatively, or in addition, to filter 2007, additional filters 2012*a*, 2012*b* may be provided with reagent chambers 2010*a*, 2010*b*, and similar additional filters may be provided with each additional reagent chamber. These additional filters may serve a similar purpose as filter 2007, i.e., preventing relatively large waste material, such as lysis beads, from proceeding further through the cartridge. Providing both a second filter 2007 and additional filters 2012*a*, 2012*b* may result in a relatively more pure sample/reagent mixture transferred from the reagent chambers toward a droplet generation portion of the cartridge.

Cartridge 2000 includes a droplet generator, generally indicated at 2014, which is configured to generate a water-in-oil emulsion corresponding to each reagent chamber. Unlike the previously described cartridges, however, the oil for the emulsion is supplied by a related instrument 2000' rather than from within the cartridge. To describe the interaction between the cartridge and the instrument, primed reference numbers will be used to represent components of instrument 2000', whereas unprimed reference numbers will continue to be used to reference components of cartridge 2000.

To supply oil to cartridge 2000, an oil reservoir 2016' within instrument 2000' transfers the oil along oil lines 2018*a*, 2020*a*, to generate droplets corresponding to reagent chamber 2010*a*. The oil intersects aqueous solution from reagent chamber 2010*a* at an intersection region 2022*a*, to generate droplets containing a sample/reagent mixture that may be transferred into instrument 2000' for thermocycling. Similarly, oil reservoir 2016' supplies oil along lines 2018*b*, 2020*b* to generate droplets corresponding to reagent chamber 2010*b* at an intersection region 2022*b*, and oil reservoir 2016' (or additional reservoirs, not shown) may be configured to supply oil to generate droplets corresponding to any desired number of additional reagent chambers that are included in cartridge 2000.

Sample/reagent droplets generated at regions 2022*a*, 2022*b*, and at any other additional droplet generation intersection regions of cartridge 2000, all may be transferred through corresponding fluidic pathways 2024*a*, 2024*b* (and so forth) to a multi-port valve 2026' of instrument 2000'. Valve 2026' may, for example, be configured to receive droplets from multiple fluidic input channels, and to transfer the droplets to a thermocycling region of the instrument in any desired manner, such as in controlled batches of one type of sample/reagent droplets at a time.

FIG. 51 is a schematic diagram depicting yet still another disposable sample preparation cartridge, generally indicated at 2100, and suitable fluidic connections between various components of the cartridge. Like the previously described cartridges, cartridge 2100 is configured to receive and prepare a target-containing sample for PCR thermocycling and amplification. Cartridge 2100 includes several of the features of the other cartridges, including a sample chamber 2102, a waste chamber 2104, a filter 2106, and reagent chambers 2110a, 2110b (plus any desired number of additional reagent chambers). These components are similar to their previously described counterparts, and will not be described again in detail.

Cartridge 2100 is configured to be inserted into or otherwise interact with a related PCR instrument 2100', shown to the right of interface line L in FIG. 51. In this case, instrument 2100' supplies substantially all of the working fluids, other than the sample or sample-containing fluid, to the cartridge. In other words, instrument 2100' is configured to prime cartridge 2100 with fluids. As in the case of the description relating to FIG. 50, primed reference numbers will be used in the description of FIG. 51 to represent components of instrument 2100', whereas unprimed reference numbers will continue to be used to reference components of cartridge 2100.

A reservoir pump 2112' of instrument 2100' may be equipped with a selector valve or similar mechanism to allow fluid to be selectively transferred from the reservoir pump through the various fluid channels leading from the pump. After cartridge 2100 is placed in a secure position within or adjacent to instrument 2100', so that a substantially fluid tight seal is formed, the reservoir pump pumps fluid into fluid channel 2114 toward waste chamber 2104, which is typically empty of fluid when the cartridge is connected to the instrument. Reservoir pump 2112' continues pumping fluid into channel 2114 until the fluid fills channel 2114 and proceeds through channel 2116 to fill filter 2106. The reservoir pump then stops pumping fluid into channel 2114 and begins pumping fluid into channel 2118a toward reagent chamber 2110a, continuing until fluid fills channel 2118a. During operation of reservoir pump 2112', a waste pump 2120', which is fluidically connected to reagent chamber 2110a through a channel 2122a, operates to draw away air and any excess fluid.

Once fluid channels 2114, 2116, and 2118a have been primed with fluid, reservoir pump 2112' transfers a measured amount of fluid into fluid channel 2124 between the reservoir pump and sample chamber 2102, to fill channel 2124, channel 2126a between the sample chamber and reagent chamber 2110a, and channel 2122a between reagent chamber 2110a and waste pump 2120'. Waste pump 2120' operates to draw away air and fluid as channels 2124, 2126a, and 2122a are primed with fluid. Next, reservoir pump 2112' transfers additional fluid through channel 2118a to reagent chamber 2110a, into channel 2130a, through droplet generation region 2132a, and into a multi-port valve 2134' of instrument 2100'.

At this point, the fluid channels leading from reservoir pump 2112' to sample chamber 2102, waste chamber 2104, and reagent chamber 2110a, and from reagent chamber 2110a to multi-port valve 2134', have all been primed with fluid. Reservoir pump 2112' may then be used to prime the fluid channels associated with any additional reagent chambers. For example, reservoir pump 2112' may transfer a measured amount of fluid through channel 2124 to fill channel 2126b between the sample chamber and reagent chamber 2110b, and channel 2122b between reagent chamber 2110b and waste pump 2120', while waste pump 2120' operates to draw away air and fluid. Reservoir pump 2112' then may transfer fluid through channel 2128b directly to reagent chamber 2110b, into channel 2130b, through droplet generation region 2132b, and into multi-port valve 2134'. In a similar manner, reservoir pump 2112' (or in some cases, additional reservoir pumps) can be used to prime the fluid channels associated with any desired number of reagent chambers.

Once the channels of cartridge 2100 have been primed to a desired degree, a sample or sample-containing fluid may be placed in the sample chamber, and all of the previously described steps of purification, concentration, lysing, reagent combination, and/or droplet generation may be performed as described previously with respect to other cartridge embodiments. However, one additional distinction between cartridge 2100 and the previously described cartridges is that cartridge 2100 does not include an oil reservoir to supply oil for droplet generation. Rather, an oil reservoir 2140' is included in instrument 2100'. Oil reservoir 2140' is configured to supply oil through lines 2142a and 2144a to droplet generation region 2132a, and through lines 2142b and 2144b to droplet generation region 2132b. The oil reservoir can be configured to supply oil to any desired number of additional droplet generation regions, corresponding to additional reagent reservoirs beyond the two depicted in FIG. 51. After sample/reagent droplets are generated, they may be transferred to multi-port valve 2134', which is configured to transfer the droplets to a thermocycling portion of instrument 2100' for PCR amplification.

F. Example 6: Disposable Sample Cartridge 4

Figure 53:
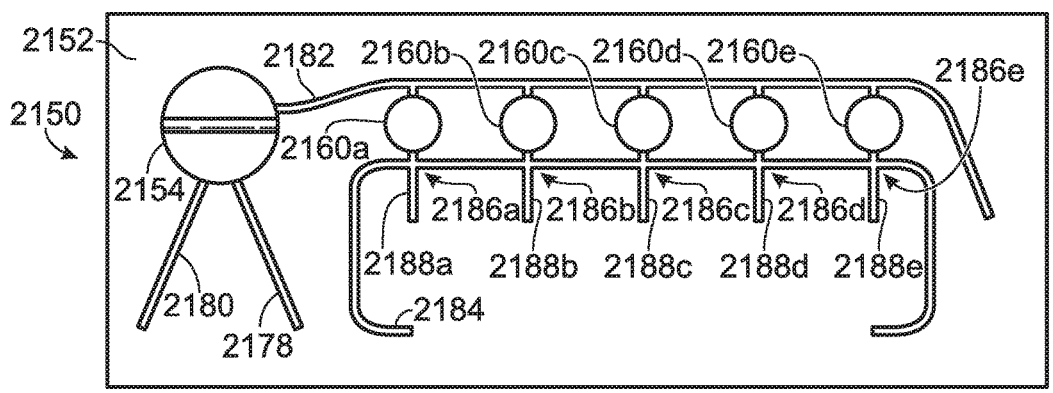
FIG. 53 is a bottom view of the cartridge of FIG. 52.
Figure 52:
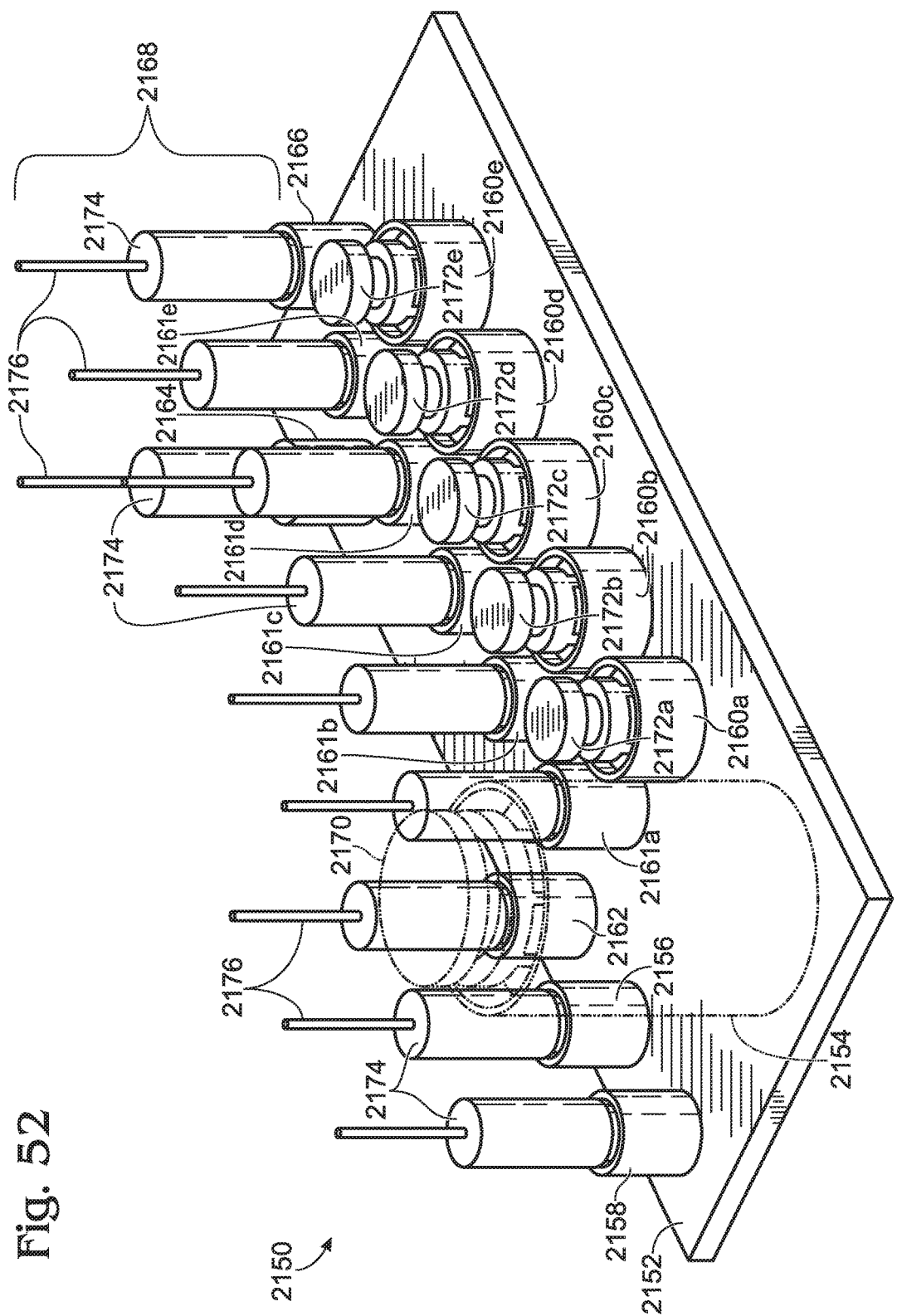
FIG. 52 is an isometric view of still another disposable sample preparation cartridge, in accordance with aspects of the present disclosure.

This example describes aspects of yet another alternative disposable sample preparation cartridge; see FIGS. 52 and 53.

FIG. 52 is an isometric view of an interior portion of the exemplary cartridge, generally indicated at 2150. Cartridge 2150 is configured to interface with an instrument (not shown), so that prepared samples can be transferred to the instrument, generally in the form of a water-in-oil emulsion, for PCR amplification and analysis. In addition to the interior portion depicted in FIG. 52, cartridge 2150 also may include a suitable exterior housing (not shown) disposed around some or the entirety of the interior portion. The exterior housing may be configured to protect the interior portion and may be shaped to facilitate storage and/or transportation of multiple cartridges.

Cartridge 2150 includes an upper body portion 2152, plus various plungers and connectors that will be described in more detail below. Body portion 2152 may be unitarily constructed, for example, by injection molding a thermoplastic or other similar material. A second, lower body portion (not shown) may be included in cartridge 2150 and connected to the upper body portion by heat sealing, gluing, or otherwise fastening the two body portions together, but this lower body portion is simply a substantially planar, featureless sheet of material and therefore will not be described further. Restricting the significant features within a unitarily constructed cartridge body portion, such as upper body portion 2152, may have advantages in cost, simplicity, structural integrity, and/or improved functionality compared to a two-piece construction where both pieces include features used for fluid manipulation and transfer, as shown and described (for example) with reference to FIGS. 43-44 above.

Body portion 2152 of cartridge 2150 includes a sample chamber 2154 configured to receive a sample that potentially contains a target nucleic acid sequence, a reservoir chamber 2156 configured to supply a wash and/or a reconstitution solution, a waste chamber 2158 fluidically connected to the sample chamber and configured to receive waste material, and various reagent chambers 2160a, 2160b, 2160c, 2160d, 2160e each fluidically connected to the sample chamber and configured to receive sample-containing fluid and to combine the sample-containing fluid with a reagent mixture prior to PCR thermocycling. In addition, body portion 2152 of cartridge 2150 includes droplet chambers 2161a, 2161b, 2161c, 2161d, 2161e, each of which is configured to receive an emulsion of water-in-oil, sample-containing droplets including the sample/reagent mixture contained in the corresponding reagent chamber. As described previously, any desired number of reagent chambers (and corresponding droplet chambers) may be included in a cartridge. The sample chamber, reservoir chamber, waste chamber, and reagent chambers are substantially similar in both structure and function to their counterparts in cartridge 1720 of FIG. 43, including any appropriate filters, stirring elements, and the like, and accordingly will not be described in detail again.

Body portion 2152 also includes an oil input chamber 2162, an oil outlet chamber 2164, and a primer outlet chamber 2166. Oil input chamber 2162 is configured to hold and transfer oil that will be used to produce sample-containing droplets in a water-in-oil emulsion, in a manner described below in more detail. Oil outlet chamber 2164 is configured to receive oil that has been transferred out of the oil input chamber, but that has not been utilized in the water-in-oil emulsion of sample-containing droplets. The excess oil received in oil outlet chamber 2164 may be either discarded or recycled (i.e., redirected to the oil input chamber). Primer outlet chamber 2166 is configured to receive one or more priming fluids during an initial cartridge priming step, in a manner that will be described in more detail below.

In addition to upper body portion 2152, cartridge 2150 also includes a fluid manipulation portion, generally indicated at 2168. The fluid manipulation portion of the cartridge includes a sample chamber plunger 2170 and various reagent chamber plungers 2172a, 2172b, 2172c, 2172d, 2172e. The plungers are configured to move up and down within their respective chambers, to cause fluid to be transferred into and out of the chambers in a desired fashion. Fluid manipulation portion 2168 of the cartridge also includes a plurality of substantially similar capillary connectors 2174, and a plurality of substantially similar capillaries 2176. The capillary connectors are configured to transfer fluid to and/or from the corresponding chamber to the corresponding capillary, which is configured to interface with an associated thermocycling instrument.

FIG. 53 is a bottom view of upper body portion 2152, illustrating a network of fluid channels forming the fluid connections between various portions of the cartridge. As noted above, a lower body portion (not shown) of cartridge 2150 will generally be disposed flush against the bottom surface of upper body portion 2152, to form a fluid tight seal so that fluid is only able to travel between portions of the cartridge through the various fluid channels shown in FIG. 53. Thus, the network of fluid channels is defined by a lower surface of the upper body portion and an upper surface of the lower body portion, although the upper surface of the lower body portion is in this example a substantially planar surface, so that the fluid channels are formed entirely in the upper body portion of the cartridge.

Specifically, a fluid channel 2178 is configured to transfer reconstitution/wash and/or priming fluid into sample chamber 2154 from reservoir chamber 2156, and another fluid channel 2180 is configured to transfer waste fluid out of sample chamber 2154 and into waste chamber 2158. Yet another fluid channel 2182 is configured to transfer sample-containing fluid from sample chamber 2154 into reagent chambers 2160a, 2160b, 2160c, 2160d, 2160e, and also to transfer priming fluid from sample chamber 2154 into primer outlet chamber 2166. Yet another fluid channel 2184 is configured to transfer oil from oil input chamber 2162 to a plurality of droplet generation regions 2186a, 2186b, 2186c, 2186d, 2186e. The droplet generation regions are each fluidically connected to one of the reagent chambers and each configured to receive sample/reagent mixture fluid from one of the reagent chambers and to combine the sample/reagent mixture fluid with a background fluid to form an emulsion of sample-containing droplets. A plurality of fluid channels 2188a, 2188b, 2188c, 2188d, 2188e are configured to transport the generated droplets from their respective droplet generation regions to corresponding droplet chambers 2161a, 2161b, 2161c, 2161d, 2161.

Typically, cartridge 2150 will be primed with fluid(s) supplied by a related instrument. For instance, when a fluid connection has been established between the cartridge and the instrument, priming fluid such as oil, water, or any other substantially incompressible fluid may be transferred from the instrument, through the appropriate capillary and capillary connector, and into reservoir chamber 2156. The priming fluid then may be transferred from the reservoir chamber, through fluid channel 2178, and into sample chamber 2154. From the sample chamber, the priming fluid may be transferred through fluid channel 2182 and into primer outlet chamber 2166 and/or the reagent chambers. Similarly, oil or some other priming fluid may be transferred from the instrument into oil input chamber 2162, through fluid channel 2184, and into oil outlet chamber 2164 and/or the droplet generation chambers. In this manner, desired priming fluids can be used to prime any desired subset of the fluid chambers and channels of cartridge 2150.

Plungers 2170, 2172a, 2172b, 2172c, 2172d, and 2172e (and any other plungers contemplated by the present disclosure) each may be configured both to direct fluids as desired through particular fluid channels, and also to selectively allow or prevent fluid flow in and out of various chambers. In other words, each plunger may be configured to operate as a valve in addition to operating as a plunger, by selectively opening or closing the entrance to one or more particular fluid channels. For example, when reagent plungers 2172a, 2172b, 2172c, 2172d, and 2172e are in their most downward positions (minimizing the volumes of the reagent chambers), the plungers may be configured to block fluid connection between fluid channel 2182 and fluid channel 2184 (see FIG. 53), so that channel 2182 can be primed with fluid independently of channel 2184. In a similar manner, the plungers of any cartridge can be used as valves, to prevent or allow fluid flow between various portions of the cartridge.

Disposable cartridge 2150 of FIGS. 52 and 53 is just one example of a disposable cartridge that is configured to be primed with fluid supplied by an associated instrument. The present disclosure contemplates other disposable cartridges that may be substantially similar except for the disposition of various chambers and/or variations in how fluids are routed between the various chambers, or between the chambers and the instrument. For example, the waste chamber and/or the reservoir chamber may be disposed on the instrument rather than on the cartridge as in FIGS. 52 and 53. A plurality of oil input chambers may be provided, with each chamber supplying oil to a single droplet generation region rather than one chamber supplying oil to multiple regions as in FIGS. 52 and 53. The droplet generation regions may take any of the various forms described previously with respect to FIGS. 48A-48F, such as a cross configuration instead of a single T configuration as in FIGS. 52 and 53. Excess oil or priming fluid may either be discarded as in FIGS. 52 and 53, recycled, or routed through the droplet generator outlet(s).

Droplets may be routed either through multiple outlets as in FIGS. 52 and 53 or through a single, common outlet. Virtually any combination of the above variations may be adopted, resulting in a modified system that may be most appropriate for a particular application.

G. Example 7: Selected Embodiments

This subsection describes additional aspects of sample preparation and sample cartridges, in accordance with aspects of the present disclosure, presented without limitation as a series of numbered sentences.

1. A method of target molecule amplification, comprising (A) purifying a fluid sample; (B) lysing the sample; (C) combining the sample with a reagent mixture; (D) generating droplets of the sample in an emulsion; and (E) transferring the emulsion to a thermocycling instrument; wherein the steps of purifying, lysing, combining, and generating are all performed within a disposable, single-use cartridge.

2. The method of paragraph 1, further comprising extracting the sample from a sample collector within the disposable cartridge.

3. The method of paragraph 1, further comprising concentrating the sample within the disposable cartridge.

4. The method of paragraph 1, wherein purifying includes purifying prior to lysing by retaining target material within the sample while removing waste material smaller than the target material.

5. The method of paragraph 1, wherein purifying includes purifying after lysing by retaining target material within the sample while removing waste material larger than the target material.

6. A single-use sample preparation cartridge, comprising a first body portion and a second body portion, wherein the first body portion includes (A) a sample chamber configured to receive a sample; (B) a reservoir chamber fluidically connected to the sample chamber and configured to supply a reconstitution fluid to the sample chamber; (C) a waste chamber fluidically connected to the sample chamber and configured to receive waste fluid from the sample chamber; (D) a plurality of reagent chambers each fluidically connected to the sample chamber and each configured to receive sample-containing fluid from the sample chamber and to combine the sample-containing fluid with a reagent mixture; and (E) a plurality of droplet generation regions, each fluidically connected to one of the reagent chambers and each configured to receive sample/reagent mixture fluid from one of the reagent chambers and to combine the sample/reagent mixture fluid with a background fluid to form an emulsion of sample-containing droplets; and wherein the sample chamber, the reservoir chamber, the waste chamber, the reagent chambers, and the droplet generation regions are fluidically connected to each other by a network of fluid channels defined by a lower surface of the first body portion and an upper surface of the second body portion.

7. The cartridge of paragraph 6, wherein the fluid channels are formed entirely in the first body portion, and wherein the upper surface of the second body portion is a substantially planar surface.

8. The cartridge of paragraph 6, wherein the background fluid is oil, and further comprising an oil input chamber configured to receive oil to be transferred to the droplet generation regions.

9. The cartridge of paragraph 8, further comprising an oil outlet chamber configured to receive oil that has been transferred out of the oil input chamber, but that has not been utilized in one of the emulsions.

10. The cartridge of paragraph 6, further comprising a plurality of droplet chambers each configured to receive one of the generated emulsions.

11. The cartridge of paragraph 6, further comprising a fluid manipulation portion including a plurality of plungers configured to cause fluid to be transferred into and out of the chambers.

12. The cartridge of paragraph 11, wherein the fluid manipulation portion further includes a plurality of connectors configured to transfer fluid between at least one chamber of the cartridge and the instrument.

13. The cartridge of paragraph 11, wherein each plunger is configured to act as a valve by selectively closing an entrance to at least one of the fluid channels when in its most downward position.

14. The cartridge of paragraph 11, wherein the sample chamber includes an agitation element configured to be agitated by magnetic forces.

15. The cartridge of paragraph 11, wherein the reagent chambers are fluidically connected to the sample chamber in parallel.

16. The cartridge of paragraph 11, wherein the background fluid is oil, and further comprising at least one oil reservoir fluidically connected to at least one of the reagent chambers and configured to supply the oil used to form the corresponding emulsion.

17. The cartridge of paragraph 16, wherein the at least one oil reservoir includes one oil reservoir corresponding to each reagent chamber and configured to supply the oil used to form the corresponding emulsion.

18. A microfluidic device having integrated lysing, separating, reagent mixing and microdroplet generating regions for extracting nucleic acid from a sample and for formation of microdroplets, comprising (A) a lysing region for lysing a cell or microorganism to release the nucleic acid; (B) a separating region for separating the nucleic acid from other parts of the cell or microorganism, wherein the separating region is connected to the lysing region; (C) a reagent mixture region for mixing the nucleic acid with at least one reagent; wherein the reagent mixture region is connected to the separating region; and (D) a droplet generating region comprising a sample inlet end, an immiscible fluid, and an outlet end, wherein the droplet generating region is connected to the reagent mixture region.

IV. DROPLET GENERATOR

This Section describes exemplary droplet generators, for example, for use in droplet-based assays.

It may be desirable, in systems such as DNA amplification systems, among others, to generate sample-containing droplets using a partially or completely disposable apparatus. This may be accomplished by a disposable cartridge configured to generate droplets as part of a series of sample preparation steps that also may include lysing, purification, and concentration, among others. However, in other cases, it may be desirable to provide a partially or completely disposable apparatus configured to perform droplet generation without performing substantial additional sample preparation steps. This may be desirable, for example, when the DNA amplification system is configured to analyze samples that are typically prepared at another location or by a practitioner. Under these circumstances, a dedicated droplet generation system may be the simplest and most economical solution.

Figure 54:
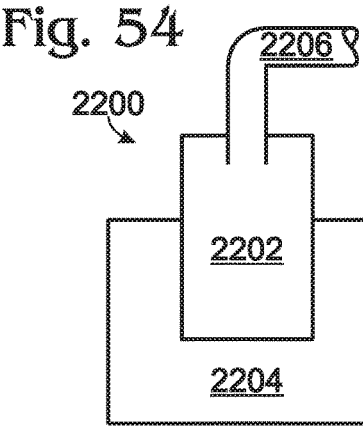
FIG. 54 is a schematic diagram of an exemplary droplet generation system, in accordance with aspects of the present disclosure.

FIG. 54 schematically illustrates a droplet generation system, generally indicated at 2200. System 2200 includes a droplet generator 2202 and a fluid reservoir 2204. Droplet generator 2202 is configured to generate sample-containing droplets, typically in the form of a water-in-oil emulsion, and to transport the generated droplets to a desired location such as a storage location or a thermocycling instrument. Fluid reservoir 2204 is configured to store and/or receive the fluids that will be used to form the emulsion, typically a background fluid such as oil and a foreground fluid such as an aqueous solution containing a DNA sample and a reagent mixture.

To generate an emulsion of droplets, droplet generator 2202 will typically be at least partially disposed within fluid reservoir 2204, as FIG. 54 indicates. To transport droplets away from reservoir 2204, droplet generator 2202 will typically either be physically removable from the reservoir, or will include suitable fluid connections, schematically indicated at 2206, configured to receive droplets from the droplet generator and to transfer them to another desired location. When droplet generator 2202 is configured to be removable from reservoir 2204, one or both of the droplet generator and the reservoir may be disposable. Disposing of any portions of the system that have come into direct contact with a sample may, for example, help to avoid the possibility of cross-contamination between multiple samples.

Many configurations of droplet generators and fluid reservoirs may be suitable as components of a droplet generation system such as system 2200. For example, suitable droplet generators include butted tubes, tubes drilled with intersecting channels, tubes partially or completely inserted inside other tubes, and tubes having multiple apertures, among others, where "tubes" means elongate hollow structures of any cross-sectional shape. Suitable fluid reservoirs include pipette tips, spin columns, wells (either individual or in a plate array), tubes, and syringes, among others. The following examples describe specific exemplary droplet generators and fluid reservoirs; see FIGS. 55-71. Additional pertinent disclosure may be found in the U.S. provisional patent applications listed above under Cross-References and incorporated herein by reference, particularly Ser. No. 61/277,204, filed Sep. 21, 2009.

A. Example 1

Figure 55:
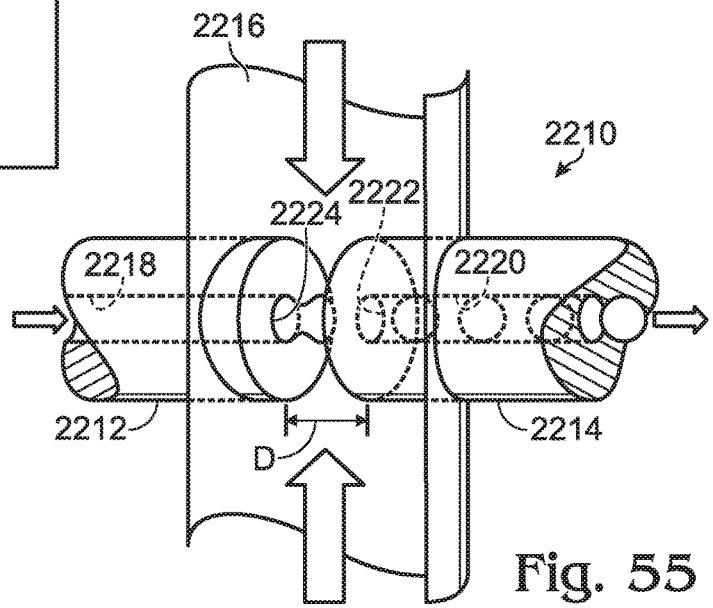
FIG. 55 is an isometric view of a portion of an exemplary droplet generator, in accordance with aspects of the present disclosure.
Figure 56:
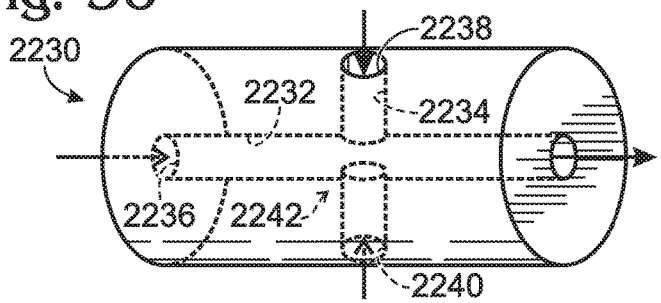
FIG. 56 is an isometric view of a portion of another exemplary droplet generator, in accordance with aspects of the present disclosure.

FIGS. 55 and 56 depict exemplary cross-type droplet generators.

FIG. 55 schematically depicts a first exemplary cross-type droplet generator, generally indicated at 2210, in the form of a pair of butted tubes. The term "cross-type droplet generator" indicates that a background emulsion fluid (typically oil) travels inward from two substantially opposite directions to intersect a foreground emulsion fluid (typically an aqueous fluid) traveling at right angles to the direction of travel of the background fluid, to form an emulsion that moves along the original direction of travel of the foreground fluid. Thus, the directions of travel of the incoming background fluid, the incoming foreground fluid, and the outgoing emulsion form a cross.

Accordingly, droplet generator 2210 includes two complementary sections of hollow fluidic tubing 2212, 2214, separated by a small distance D. Tubing sections 2212, 2214 may be constructed from a single continuous hollow tube that has been cut and separated, in which case the tubing sections will have substantially equal outer and inner diameters. Alternatively, tubing sections 2212, 2214 may be constructed separately and then disposed appropriately within droplet generator 2210, in which case the tubing sections may have substantially different outer and/or inner diameters.

Tubing sections 2212, 2214 are disposed at least partially within an oil channel 2216. Oil channel 2216 will typically be a portion of a fluid reservoir configured to supply fluids, including oil and/or sample-containing aqueous fluid, to droplet generator 2210. Various exemplary fluid reservoirs are described in Example 2 below. Oil channel 2216 may take various forms, such as a cylindrical channel formed within a tube, a rectangular channel formed between substantially planar channel walls, or simply a fluid flow path within a surrounding reservoir of fluid, among others. Tubing sections 2212, 2214 may be formed integrally with oil channel 2216, or the tubing sections may be inserted into one or more apertures of the oil channel in a substantially fluid tight manner.

Tubing section 2212 includes a hollow inner portion forming an incoming fluid channel 2218, and tubing section 2214 includes a hollow inner portion forming an outgoing fluid channel 2220. Incoming fluid channel 2218 is configured to transport sample-containing fluid from a fluid source such as a surrounding fluid reservoir or a reagent chamber into oil channel 2216, and may be pressurized relative to the oil channel to facilitate that transfer. To generate sample-containing droplets, oil in oil channel 2216 and sample-containing fluid in incoming fluid channel 2218 each may be pressurized relative to outgoing fluid channel 2220, tending to draw both oil and sample-containing fluid toward an inlet aperture 2222 of the outgoing fluid channel. As the sample-containing fluid exits an outlet aperture 2224 of incoming fluid channel 2218, aqueous droplets of sample-containing fluid may be formed in an oil background, resulting in a water-in-oil emulsion of droplets entering the outgoing fluid channel.

One of tubing sections 2212, 2214 may be fixed within a surrounding fluid reservoir, whereas the other section may be removable from the surrounding reservoir. In such cases, tubing section 2212 will typically be fixed in place, whereas tubing section 2214 will typically be removable, and may be configured to be selectively placed into position at a known, desired distance from tubing section 2214. For example, tubing section 2214 may represent the tip of a syringe, pipette, or the like, which may be inserted into a reservoir containing oil channel 2216 and used to create and store sample-containing droplets by applying suction to draw an emulsion of sample-containing droplets into inlet aperture 2222 of the outgoing fluid channel. Tubing section 2214 then may be removed from the fluid reservoir, and the emulsion transferred to another desired location such as a thermocycling instrument.

FIG. 56 depicts a second exemplary cross-type droplet generator, generally indicated at 2230. Droplet generator 2230 is constructed from a single section of fluidic tubing, through which two perpendicular and intersecting fluid channels 2232 and 2234 are formed. Droplet generator 2230 may be temporarily or permanently disposed within a fluid reservoir (not shown) configured to hold fluids used to form an emulsion of sample-containing droplets, such as a background oil and a foreground sample-containing aqueous solution. A distal aperture 2236 of fluid channel 2232 is configured to receive and transport the sample-containing solution, and intermediate apertures 2238, 2240 of fluid channel 2234 is configured to receive and transport the background oil.

At an intersection region generally indicated at 2242, sample-containing fluid traveling through channel 2232 intersects with oil traveling through channel 2234, and a water-in-oil emulsion of sample-containing droplets is generated. This emulsion then continues to travel through channel 2232 along the original direction of travel of the sample-containing fluid (from left to right in FIG. 56). The emulsion then may be transferred to a storage location and/or to a thermocycling instrument as is desired. In some cases, droplet generator 2230 may be the tip of a removable and/or disposable component such as a syringe or pipette, or alternatively, droplet generator 2230 may represent the distal portion of a fixed, nondisposable component that is configured to transport a droplet emulsion away from a fluid reservoir to a desired location.

B. Example 2

Figure 57:
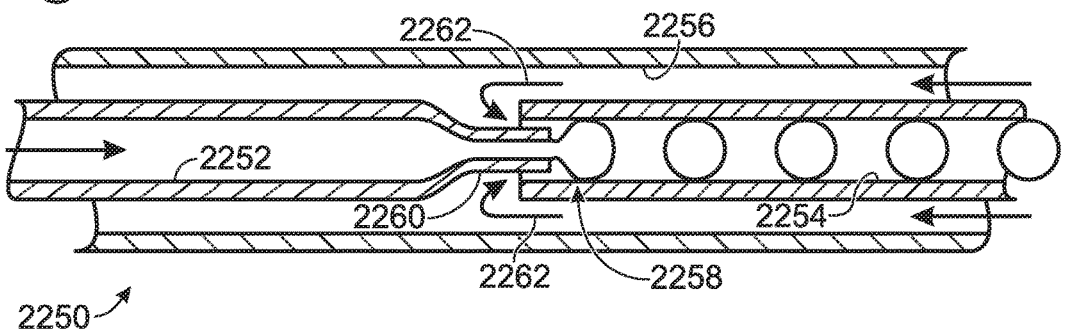
FIG. 57 is a cross-sectional side elevational view showing an inner portion of another exemplary droplet generator, in accordance with aspects of the present disclosure.
Figure 58:
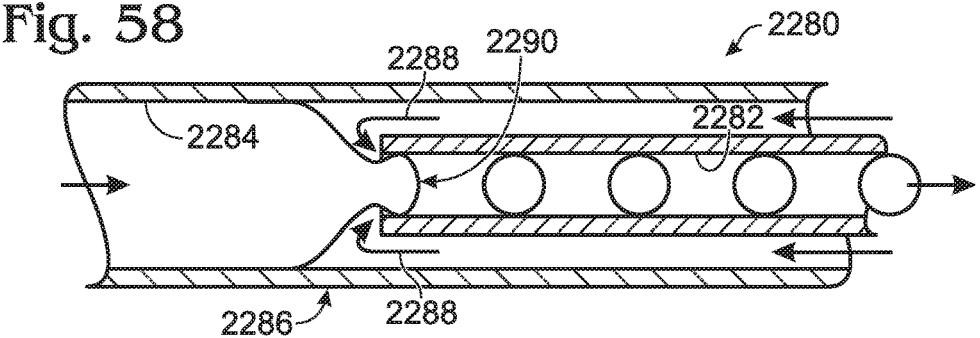
FIG. 58 is a cross-sectional side elevational view showing an inner portion of another exemplary droplet generator, in accordance with aspects of the present disclosure.

FIGS. 57 and 58 depict exemplary flow-focus droplet generators.

FIG. 57 depicts a first exemplary flow-focus droplet generator, generally indicated at 2250. The term "flow-focus droplet generator" indicates that droplets are generated when a background fluid is focused by the local geometry of its surroundings toward an intersection region where it intersects a foreground, sample-containing fluid. An emulsion of sample-containing droplets is then formed. Unlike in a cross-type droplet generator, the background and foreground fluids in a flow-focus droplet generator need not intersect at substantially right angles, as indicated in FIG. 57.

Flow-focus droplet generator 2250 includes a fluid input channel 2252, a droplet output channel 2254, and an oil reservoir 2256. Fluid input channel 2252 is configured to transport sample-containing fluid toward a fluid intersection region generally indicated at 2258. As FIG. 57 depicts, fluid input channel 2252 may be substantially cylindrical with an elongate tapered tip 2260 configured to produce fluid droplets of a desired size, although variations such as a non-tapered tip also may be suitable. Droplet output channel 2254 also may be substantially cylindrical or have any other desired shape suitable for directing the background oil toward intersection region 2258 in conjunction with tip 2260, as described below. Oil reservoir 2256 is configured to receive and/or store oil or any other suitable emulsion background fluid.

To generate droplets, a pressure differential is created to draw fluid from both input channel 2252 and oil reservoir 2256 into output channel 2254. Due to the geometry of the input channel, the output channel, and the reservoir, oil from the reservoir forms a fluid path that is focused toward intersection region 2258 with a component of fluid velocity parallel to the direction of travel of the sample-containing fluid within the fluid input channel, as indicated by arrows 2262 in FIG. 57. An emulsion of sample-containing droplets in an oil background is formed and travels away from intersection region 2258 within fluid output channel 2254, in substantially the same direction of motion as the direction of motion of the sample-containing fluid within fluid input channel 2252.

Output channel 2254 either may be fixed within oil reservoir 2256, in which case it will be configured to transfer the generated water-in-oil emulsion out of the oil reservoir to another desired location such as a storage location or a thermocycling instrument. Alternatively, output channel 2254 may be part of a removable and/or disposable component such as the tip of a syringe or a pipette, in which case it may be removed once a desired amount of emulsion has been generated. The emulsion then may be physically transported, in bulk, to another desired location.

FIG. 58 depicts a second flow-focus droplet generator, generally indicated at 2280. Droplet generator 2280 is similar to droplet generator 2250 of FIG. 57, except that droplet generator 2280 does not include a separate sample-containing fluid input channel. Instead, droplet generator 2280 includes only a droplet output channel 2282 and a fluid reservoir 2284. In this case, however, fluid reservoir 2284 is configured to receive and/or store both sample-containing fluid and a suitable emulsion background fluid such as oil. As in the embodiment of FIG. 57, the droplet output channel may be part of a removable and/or disposable component.

To generate droplets with droplet generator 2280, a pressure differential is created to draw fluid into output channel 2282. Again due to the local geometry of the area near a fluid intersection region 2286, oil from the reservoir forms a fluid path that is focused toward intersection region 2286, as indicated by arrows 2288. In addition, sample-containing fluid is drawn toward intersection region 2286, where the meniscus at the boundary between the sample-containing fluid and the oil forms a necking region 2290 adjacent to the intersection region. In the necking region, the meniscus is periodically deformed into an elongate "neck," at which point a discrete droplet is separated from the meniscus. An emulsion of sample-containing droplets in an oil background is thus formed as droplets are generated one at a time in the necking region.

C. Example 3

Figure 59:
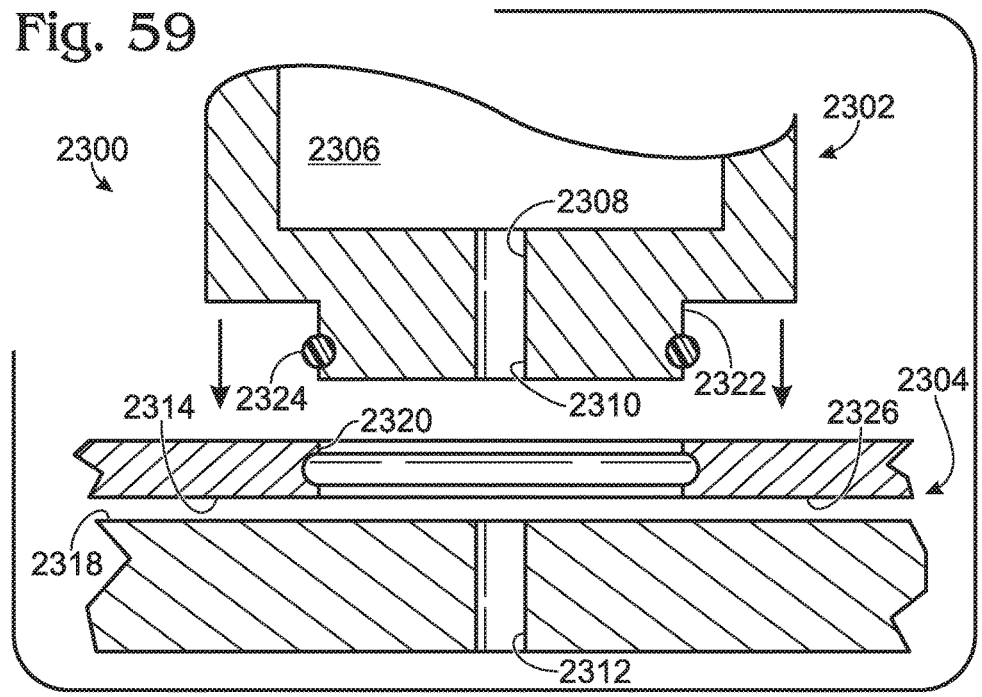
FIG. 59 is a cross-sectional side elevational view showing an inner portion of another exemplary droplet generator, in accordance with aspects of the present disclosure, showing a sample-containing portion disassembled from a droplet outlet portion.
Figure 60:
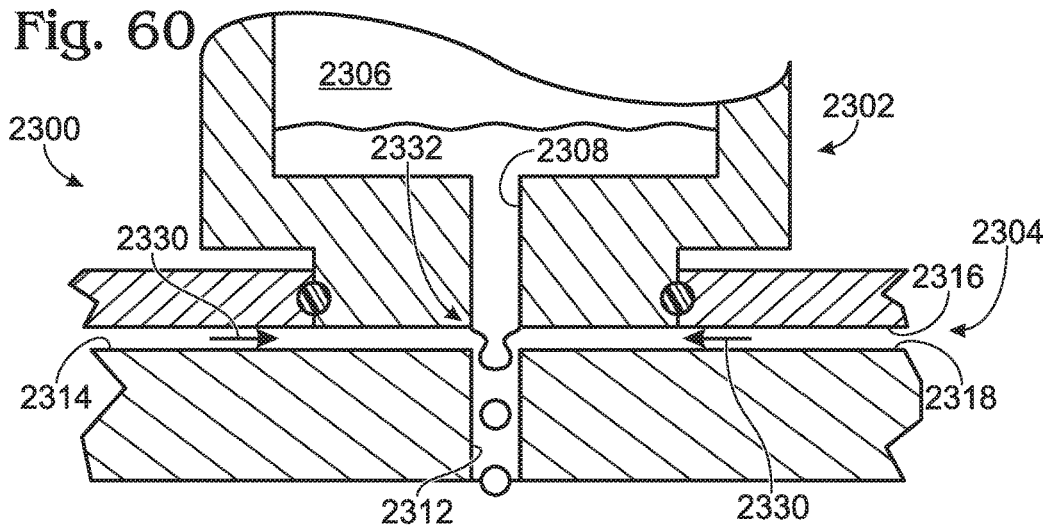
FIG. 60 is a cross-sectional side elevational view showing the sample-containing portion and the droplet outlet portion of FIG. 59 assembled together.

FIGS. 59 and 60 depict yet another cross-type droplet generator, generally indicated at 2300. Droplet generator 2300 includes a disposable sample-containing portion 2302, and a nondisposable droplet outlet portion 2304. Sample-containing portion 2302 may be configured to be a single-use, disposable component, and accordingly may be constructed of a relatively inexpensive material such as an injection-molded thermoplastic. FIG. 59 depicts droplet generator 2300 with sample-containing portion 2302 and droplet outlet portion 2304 substantially separated from each other and thus not in a position suitable for producing sample-containing droplets. FIG. 60 depicts droplet generator 2300 with sample-containing portion 2302 and droplet outlet portion 2304 disposed in close proximity to each other, in position for producing sample-containing droplets as described below.

Sample-containing portion 2302 of droplet generator 2300 includes a sample reservoir 2306 and a sample fluid channel 2308. The sample reservoir may be configured to receive sample-containing fluid through any suitable fluid input mechanism such as fluidic tubing (not shown), manual insertion of sample-containing fluid by a practitioner, or automatic insertion of sample-containing fluid by a machine. Sample fluid channel 2308 is configured to transport fluid from the sample reservoir toward a fluid outlet aperture 2310, which is configured to emit droplets of sample-containing fluid that have passed through the sample fluid channel from the sample reservoir. Sample-containing portion 2302, sample reservoir 2306, and sample fluid channel 2308 depicted in the cross-sectional view of FIGS. 59-60 are all substantially cylindrical, although other shapes may be suitable.

Droplet outlet portion 2304 of droplet generator 2300 includes an emulsion outlet channel 2312, which is configured to transport an emulsion of sample-containing droplets toward a desired location such as a storage chamber or a thermocycling instrument (not shown). Droplet outlet portion 2304 also includes an oil channel 2314, which is defined by upper and lower channel walls 2316, 2318 of the outlet portion. Oil channel 2314 may take the form of an elongate groove, a cylindrical (or alternately shaped) substantially planar reservoir, or any other desired form suitable for facilitating the transfer of oil toward droplet outlet channel 2312.

A substantially cylindrical aperture 2320 is formed in upper channel wall 2316 of the droplet outlet portion, and is configured to receive a complementary cylindrical lower part 2322 of sample-containing portion 2302. A fluid tight sealing ring 2324, such as an o-ring, may be provided to help form a substantially fluid tight seal between sample-containing portion 2302 and droplet outlet portion 2304 when the two portions are assembled together. A cylindrical groove may be formed in the exterior surface of sample-containing portion 2302 to retain the o-ring in a desired position, and another similar groove may be provided within aperture 2320. Aligning the o-ring within these grooves may help a user to locate the correct mounting position of the sample-containing portion within cylindrical aperture 2320. Alternatively or in addition, various locating pins or other similar protrusions (not shown) may be provided and attached to one or both of the sample-containing portion and the droplet outlet portion, to stop those portions at a desired separation distance from each other when the sample-containing portion is mounted to the droplet outlet portion.

FIG. 60 shows the two main portions of droplet generator 2300 assembled together and droplets being formed. Oil travels within oil channel 2314, inward toward droplet outlet channel 2312, as indicated by arrows 2330. At the same time, sample-containing fluid travels downward through sample fluid channel 2308 to intersect the oil at an intersection region generally indicated at 2332. At intersection region 2332, an emulsion of water-in-oil droplets is produced and passes into droplet outlet channel 2312. All of these fluid motions are typically caused by negative pressure introduced at a distal end of the droplet outlet channel. The generated emulsion may pass through the outlet channel and into a storage chamber, a transport chamber, or directly to a thermocycling instrument. In summary, when the droplet outlet portion and the sample-containing portion of droplet generator 2300 are assembled together, a substantially fluid tight seal is formed between the droplet outlet portion and the sample-containing portion, and droplets emitted by the fluid outlet aperture intersect oil traveling in the oil channel to produce an emulsion of water-in-oil droplets that passes into the emulsion outlet channel.

When oil channel 2314 takes the form of an elongate groove, the oil and sample-containing fluid intersect and produce droplets with the various fluid velocities forming a cross shape, as described previously. If oil channel 2314 takes the form of an extended planar channel or reservoir, the oil within the channel may approach droplet outlet channel 2312 radially from many different directions, each of which is substantially perpendicular to both the sample fluid channel and the droplet outlet channel. Accordingly, such a configuration still may be thought of as a cross-type droplet generator.

Sample-containing portion 2302 of droplet generator 2300 may be disposable, as mentioned previously. Thus, after an emulsion is created and transported to a desired location, sample-containing portion 2302 may be removed from aperture 2320 and discarded. Another sample-containing portion then may be placed into aperture 2320 and used to create another emulsion, using either the same or a different sample/reagent mixture. The internal surfaces of droplet outlet portion 2304, including the walls of outlet channel 2312 and channel walls 2316, 2318, all may be coated with a hydrophobic coating and/or washed with one or more rinse solutions, to reduce the possibility of cross contamination from one sample/reagent solution to another.

D. Example 4

FIGS. 61-63 depict exemplary droplet generation systems generally configured to generate an emulsion of relatively less dense fluid droplets in a background of relatively more dense fluid.

FIG. 61 depicts a first such droplet generation system, generally indicated at 2340, including both a droplet generator 2342 and a fluid reservoir 2344. Droplet generator 2342 includes a substantially cylindrical emulsion chamber 2346 and an elongate tip 2348, although other emulsion chamber and tip shapes are possible. The tip of the droplet generator is configured to be at least partially inserted into the fluid reservoir. Droplet generator 2342 also includes an interface portion 2350, which is configured to join emulsion chamber 2346 to a body portion of the droplet generator (not shown). The body portion of the droplet generator may, for example, be configured to be grasped by a user, and may include a pressure mechanism such as a pipettor bulb, a syringe plunger or the like, to effect pressure changes within the droplet generator.

Tip 2348 of the droplet generator is depicted as cylindrical, i.e., as having a circular cross-section, but the cross-section of the tip (and of the emulsion chamber) can take many other shapes, such as rectangular, square, or oval. The tip includes both a distal end aperture 2352 configured to receive a background fluid such as oil, and a side aperture 2354 configured to receive a foreground fluid such as an aqueous sample/reagent mixture. In some cases, distal aperture 2352 will be formed simply by leaving the distal end of tip 2348 open, and accordingly will have the same shape as a cross-section of the tip. However, the distal aperture may be given any desired shape to facilitate a desired flow rate of background fluid into the aperture. Side aperture 2354 may be formed in various shapes, such as circular, square, rectangular, star-shaped, oval, or triangular, among others. The shape of side aperture 2354 may be selected based on a desired flow rate and/or flow pattern of fluid passing through the side aperture.

Fluid reservoir 2344 is depicted substantially as a paraboloid, but virtually any three dimensional container that is closed at one end and open at another may form a suitable reservoir. The fluid reservoir may, for example, be one of many reservoirs disposed in an array on a chip or a microplate, or it may be a single freestanding reservoir such as an individual well, a test tube, a pipette body, or a spin column chamber, among others. Regardless of its precise shape, reservoir 2344 is configured to hold both a background emulsion fluid and a foreground emulsion fluid, which will be used in conjunction with droplet generator 2342 to form an emulsion of sample-containing droplets as described below.

FIG. 62 shows a magnified view of a portion of the droplet generation system of FIG. 61, illustrating how an emulsion of sample-containing droplets can be generated by the system. As shown, reservoir 2344 is configured to hold both a background emulsion fluid 2356 (such as oil) and a foreground emulsion fluid 2358 (such as an aqueous sample/reagent mixture). In system 2340, background fluid 2356 has a different and greater density than foreground fluid 2358, and thus is disposed at the bottom portion of reservoir 2344, with the foreground fluid disposed in a layer above the background fluid. Accordingly, distal aperture 2352 of droplet generator 2342 is in contact with the background fluid, whereas, side aperture 2354 of droplet generator 2342 is in contact with the foreground fluid. In other words, the distal aperture is configured to be in contact with background fluid held by the reservoir and the side aperture is configured to be in contact with foreground fluid held by the reservoir when the reservoir contains background and foreground fluids and the elongate tip is inserted into the reservoir.

To generate an emulsion of foreground-in-background fluid droplets, a negative or upward pressure is applied to an interior fluid channel 2360 of droplet generator 2342. This pressure may be applied by any suitable mechanism such as a manual or motor-driven plunger, a bulb, or a pump, among others. In any case, the applied pressure causes background fluid 2356 to flow into distal aperture 2352 of droplet generator 2342, and also causes foreground fluid to flow into side aperture 2354 of droplet generator 2342. Accordingly, foreground fluid flowing into the side aperture intersects with a stream of background fluid that enters the tip through the distal aperture, to form an emulsion of foreground fluid droplets 2362 in background fluid in the vicinity of the side aperture. An emulsion of droplets 2362 in background fluid then proceeds up channel 2360, where it is received in emulsion chamber 2346. The emulsion then may be stored and/or transported to another location such as to a thermocycling instrument for DNA amplification, as described previously. Because the directions of the incoming background fluid velocity, the incoming foreground fluid velocity, and the outgoing emulsion velocity form the shape of a "T," the system shown in FIGS. 61-62 may be described as a "single T" droplet generator configuration.

FIG. 63 shows a magnified end portion of another droplet generation system, generally indicated at 2380, which is similar to system 2340 of FIGS. 61 and 62. Specifically, system 2380 includes a droplet generator 2382 and a fluid reservoir 2384 having all the same features as the corresponding parts of system 2340, except that tip 2385 of droplet generator 2382 includes a distal end aperture 2386 and two distinct side apertures 2388, 2390, all of which provide fluid access to a fluid channel 2392 within the tip of the droplet generator. Accordingly, when upward pressure is applied to fluid channel 2392, a background fluid 2394 flows into distal aperture 2386, and a foreground fluid 2396 flows into both side apertures 2388, 2390. This may result in a greater number and/or a different distribution of droplets being produced in an emulsion, relative to systems with just a single side aperture.

Because of the directions of the various fluid velocities in the vicinity of side apertures 2388, 2390, system 2380 may be characterized as a "double T" droplet generator configuration. This configuration may be generalized in various ways. For example, a pair of side apertures may be disposed at the same longitudinal position along the tip of a droplet generator, rather than longitudinally offset as depicted in FIG. 63. Furthermore, any desired number of side apertures, such as three or more, may be disposed along the length of a droplet generator, some of which may be longitudinally aligned while others are longitudinally offset. Because the fluid velocities form a "T" at each side aperture, such generalized configurations naturally may be characterized as "multi-T" droplet generation systems. The number, location, size and shape of the various side apertures in a multi-T system typically will be selected based on the desired properties of the resulting emulsion.

E. Example 5

FIGS. 64-66 depict droplet generation systems generally configured to generate an emulsion of relatively more dense fluid droplets in a background of relatively less dense fluid. In contrast, FIGS. 61-63, in the previous example, depicted droplet generation systems generally configured to generate an emulsion of relatively less dense fluid droplets in a background of relatively more dense fluid.

FIG. 64 depicts a magnified end portion of a first such droplet generation system, generally indicated at 2400. System 2400 includes a droplet generator 2402 and a fluid reservoir 2404. Fluid reservoir 2404 is substantially similar to reservoir 2344 depicted in FIGS. 61-62, including all of the possible variations in its structure and shape, and accordingly will not be described again in detail. A foreground fluid 2406 of relatively high density is disposed at the bottom of reservoir 2404, and a background fluid 2408 of relatively low density is disposed above the foreground fluid within the reservoir.

Droplet generator 2402 includes a tip 2410, the interior of which forms a fluid channel 2412, a distal aperture 2414, and a side aperture 2416. However, tip 2410 of droplet generator 2402 includes a nonlinear u-shaped distal portion 2418, configured so that distal aperture 2414 is disposed above side aperture 2416 relative to the bottom of reservoir 2404. Accordingly, when upward pressure is applied to fluid channel 2412, the upper fluid in reservoir 2404, which is background fluid 2408, is drawn into fluid channel 2412 through distal aperture 2414. At the same time, the lower fluid in reservoir 2404, which is foreground fluid 2406, is drawn into fluid channel 2412 through side aperture 2416. Just as described previously, the intersection of the foreground and background fluids in the vicinity of the side aperture results in generation of an emulsion of foreground fluid droplets 2418 in the background fluid, and the generated emulsion proceeds upward through channel 2412 for storage and/or transport.

It should be apparent from the configuration shown in FIG. 64 that droplet generator 2402 may be characterized as a "single T" generator, based on the directions of the various incoming and outgoing fluid velocities. Other configurations, such as a "double T" configuration or a "multi-T" configuration, may be used in conjunction with a droplet generator having a u-shaped or similarly shaped tip. By altering the number of side apertures, their positions, their sizes, and their shapes, the resulting emulsion may be given essentially any desired characteristics.

FIG. 65 depicts another droplet generation system, generally indicated at 2420, which is configured to generate an emulsion of relatively more dense droplets in a background of relatively less dense fluid. System 2420 includes a droplet generator 2422 and a fluid reservoir 2424. Droplet generator 2422 is a syringe having a body 2426 that serves as a variable-volume emulsion reservoir, and an elongate sharp tip 2428 that defines a fluid channel 2430. The syringe includes a movable plunger 2431, which is configured to slide up and down to create pressure differences within the syringe and to vary the volume of the emulsion reservoir. They syringe also will include a plunger control mechanism (not shown), such as a handle or plunger head configured to allow a user to move the plunger longitudinally within the body of the syringe.

Droplet generator 2422 includes a distal aperture 2432 at the end of tip 2428, configured to receive or expel fluid in fluid channel 2430. Tip 2428 also includes a side aperture 2434, also configured to receive or expel fluid. When negative pressure is exerted (i.e., when a partial vacuum is created) within fluid channel 2430, fluid thus may be drawn into both distal aperture 2432 and side aperture 2434. When fluids of different densities are disposed in fluid reservoir 2424 (as depicted in FIG. 65), different fluids may be drawn into the two different apertures, so that tip 2428 acts as a "single T" emulsion generator as described in detail above. Also as described previously, any desired number, size and/or shape of side apertures may be used to generate an emulsion having desired properties.

Fluid reservoir 2424 is depicted in FIG. 65 as a substantially cylindrical chamber having a removable threaded top 2436, which includes a penetrable membrane such as a layered septum 2438. Thus, once a desired amount of emulsion has been produced and drawn into body 2426, droplet generator 2422 may be withdrawn from the fluid reservoir to transport the emulsion to another location such as a thermocycling instrument. The fluid reservoir is configured to contain the fluid ingredients of a desired emulsion without significant leakage, while allowing droplet generator 2422 to penetrate the reservoir and establish fluid contact with the fluids in the reservoir. Any alternative reservoir having these features may be used with droplet generator 2422, such as reservoirs of various shapes and sizes, and reservoirs having various alternative types of penetrable membranes.

Droplet generator 2422 is disposed below fluid reservoir 2424 in FIG. 65. Accordingly, a relatively high density sample-containing fluid 2440 will be disposed in the vicinity of side aperture 2434 of the droplet generator, whereas a relatively low-density background fluid 2442 (such as oil) will be disposed in the vicinity of distal aperture 2432 of the droplet generator. This results in an emulsion of sample-containing droplets in an oil background. Of course, system 2420 could be turned 180 degrees (i.e., flipped upside down relative to FIG. 65), in which case it would be configured to produce an emulsion of sample-containing droplets in an oil background when the sample-containing fluid is less dense than the background fluid.

FIG. 66 depicts a lower portion of yet another droplet generation system, generally indicated at 2450, which is configured to produce an emulsion of relatively higher density droplets in a background of relatively lower density fluid. System 2450 includes a butted tube type droplet generator 2452, and a fluid reservoir 2454. Fluid reservoir 2454 is substantially similar to the fluid reservoirs depicted in FIGS. 61-64 and described above, and accordingly will not be described further. Droplet generator 2452 includes a tube 2456 having a distal aperture 2458 and a pair of opposing side apertures 2460, 2462. When a partial vacuum is created within tube 2456 from above, higher density sample-containing fluid 2464 is drawn into distal aperture 2458 and lower density background fluid 2466 is drawn into side apertures 2460, 2462. The fluids intersect in the vicinity of the side apertures to produce droplets 2468 of sample-containing fluid that travel upward through tube 2456 in an emulsion. Due to the directions of fluid velocity near the side apertures, droplet generator 2452 may be characterized as a cross-type droplet generator.

F. Example 6

FIG. 67 depicts a lower portion of another cross-type droplet generation system, generally indicated at 2480. Droplet generation system 2480 includes an emulsion generator 2482, and an emulsion reservoir 2484 configured to receive the emulsion generated by the emulsion generator. As its name suggests, emulsion generator 2482 is configured to generate an emulsion of sample-containing droplets, typically in the form of aqueous droplets in an oil background. Emulsion reservoir 2484 is depicted in FIG. 67 as a test tube, but more generally may be any reservoir configured to receive, contain and/or transport an emulsion to a desired location.

Emulsion generator 2482 includes an inner fluid chamber 2486 configured to contain a sample-containing fluid 2488, and an outer fluid chamber 2490 surrounding portions of the inner fluid chamber and configured to contain a background fluid 2492, typically an oil. The depicted lower portions of inner fluid chamber 2486 and outer fluid chamber 2490 are substantially cylindrical and concentric, but other geometries may be chosen. Inner fluid chamber 2486 includes a distal aperture 2494, configured to allow passage of sample-containing fluid 2488 out of the inner fluid chamber at a desired rate. Outer fluid chamber 2490 includes a distal aperture 2496, configured to allow passage of an emulsion out of the outer fluid chamber at a desired rate. Accordingly, distal apertures 2494, 2496 may have any suitable size and/or shape resulting in desirable flow characteristics through the apertures.

Background fluid channels 2498, 2500 are formed between the lower external boundary of the inner fluid chamber and the lower internal boundary of the outer fluid chamber, and configured to transfer background fluid 2492 radially inward toward distal aperture 2496 of the outer fluid chamber. In some cases, the lower boundary of inner fluid chamber 2486 may rest directly upon the lower inside surface of outer fluid chamber 2490, except for a pair of grooves forming discrete fluid channels 2498, 2500. In other cases, inner fluid chamber 2486 and outer fluid chamber 2490 may be held out of direct contact with each other by some spacing mechanism (not shown). In this case, background fluid channels 2498, 2500 will be portions of a single circular background fluid channel through which background fluid can move radially inward toward aperture 2496.

System 2480 may be operated by applying positive pressure from above chambers 2486, 2490, to push sample-containing fluid 2488 and background fluid 2492 toward their respective apertures. The inner and outer fluid chambers are positioned so that oil flowing radially inward through the background fluid channels will intersect with sample-containing fluid passing out of the inner fluid chamber through distal aperture 2494 of the inner fluid chamber, to generate an emulsion of sample-containing droplets within the background fluid which will pass through distal aperture 2496 of the outer fluid chamber and into emulsion reservoir 2484, where it may be stored or transported as desired. Emulsion reservoir 2484 may at least partially surround the emulsion generator or be otherwise configured to receive the emulsion generated by the emulsion generator. Typically, emulsion generator 2492 is removable from emulsion reservoir 2484, and would likely be removed after the emulsion has been generated. The emulsion generator then may be disposed of or cleaned in preparation for the introduction of a new sample. Alternatively, inner chamber 2486 may be removable from outer chamber 2490 and disposable, while outer chamber 2490 may be reusable.

Aside from applying positive pressure to the fluids within chambers 2486 and 2490, an emulsion may be formed similarly by applying negative pressure to pull the fluids through apertures 2494 and 2496, for example, by creating a partial vacuum in the emulsion reservoir. In the case of either positive or negative pressure, the pressure may be created through any suitable mechanism such as a pump, a bulb, or a plunger. Furthermore, system 2480 may be placed in a centrifuge and spun, to create an emulsion based on the inertia of the constituent fluids. This technique may sometimes be referred to as causing fluid motions through "centrifugal force." When a centrifuge is used in this manner, system 2480 may be characterized as a "spin column" droplet generator or emulsion generator.

Figure 68:
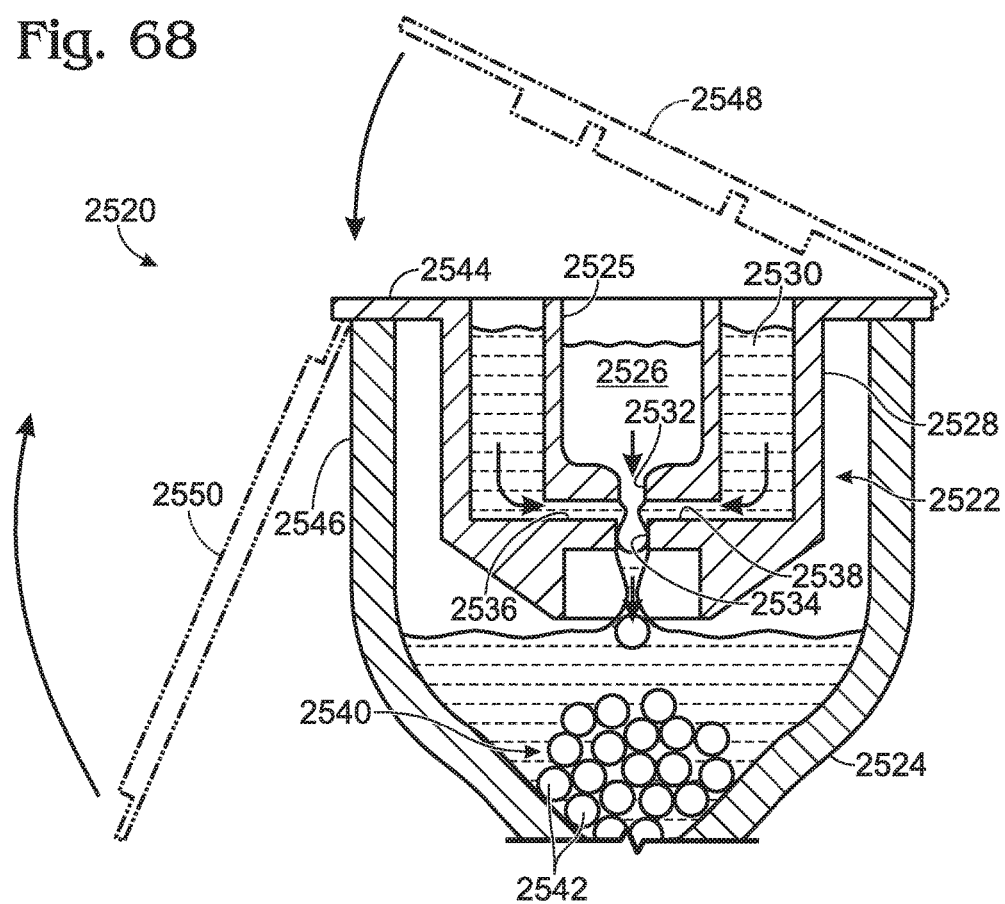
FIG. 68 is a cross-sectional side elevational view of still another droplet generation system, in accordance with aspects of the present disclosure.

FIG. 68 depicts portions of another emulsion generation system, generally indicated at 2520. System 2520 is similar in many respects to system 2480 of FIG. 67, and further illustrates the potentially removable and/or disposable nature of various parts of the system. System 2520 includes an emulsion generator 2522 and an emulsion reservoir 2524. Emulsion generator 2522 includes an inner fluid chamber 2525 configured to contain a sample-containing fluid 2526, and an outer fluid chamber 2528 configured to contain a background fluid 2530. Inner fluid chamber 2525 and outer fluid chamber 2528 are substantially cylindrical and concentric. A distal aperture 2532 of the inner fluid chamber is configured to allow passage of sample-containing fluid out of the inner fluid chamber, and a distal aperture 2534 of the outer fluid chamber is configured to allow passage of an emulsion out of the outer fluid chamber.

Fluid channels 2536, 2538 are formed between the lower boundary of the inner fluid chamber and the lower inside surface of the outer fluid chamber, and configured to transfer background fluid inward toward distal aperture 2534. An emulsion 2540 of sample-containing droplets 2542 is formed either by applying positive pressure push sample-containing fluid and background fluid toward their respective apertures, or by applying negative pressure to accomplish the same motions. Pressure may be created by any suitable mechanism such as a pump, bulb, plunger, or centrifuge, as described previously with respect to FIG. 67. The generated emulsion passes through aperture 2534 into emulsion reservoir 2524, for storage or transport to a thermocycling instrument.

Emulsion generator 2522 is a self-contained component that may be inserted and removed from emulsion reservoir 2524 as desired. A supporting lip 2544 of the emulsion generator is configured to overlap side wall 2546 of the emulsion chamber, to support the emulsion generator in a desired position with respect to the emulsion chamber. The emulsion generator includes a lid 2548 that may be rotated away from the emulsion generator to allow the addition of fluids and/or pressure, and rotated to cover the emulsion generator to form a fluid tight seal. This may allow convenient transport of the emulsion generator, and also may allow the use of a centrifuge without undesirable leaking. Similarly, the emulsion reservoir includes a lid 2550 that may be used to selectively form a fluid tight seal at the top of the emulsion reservoir. This may allow convenient transport, storage or further processing of an emulsion with substantially no loss of fluid from the reservoir.

G. Example 7

Figure 69:
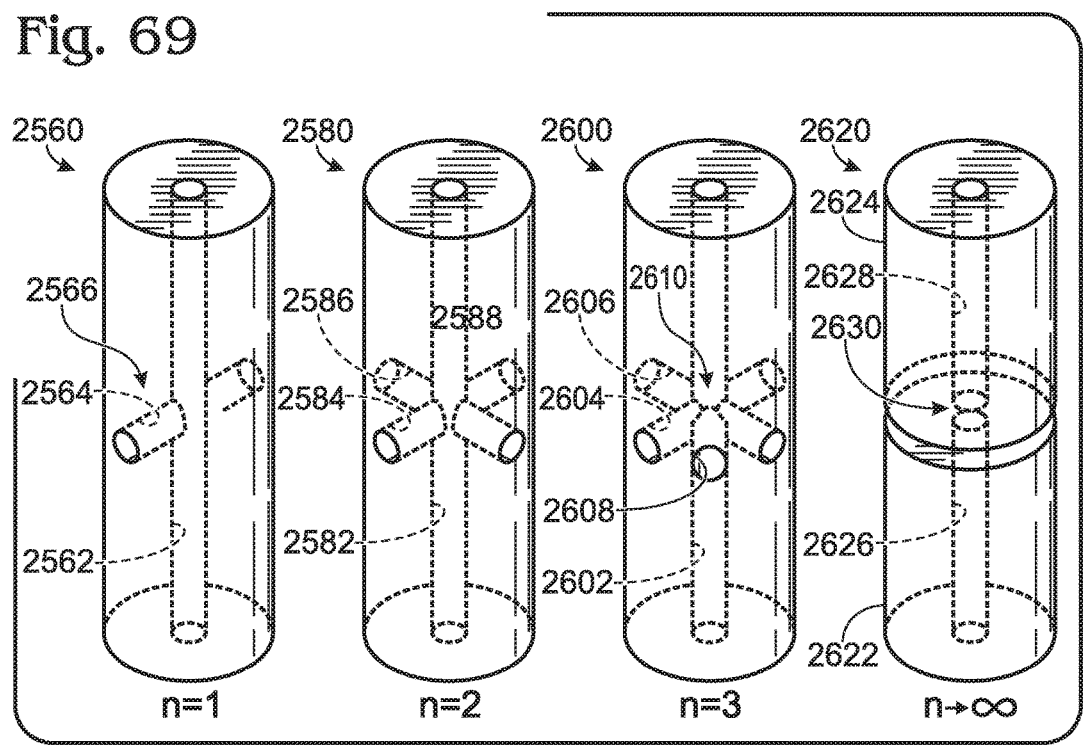
FIG. 69 is an isometric view of four different droplet generators, illustrating the relationship between various cross-type droplet generators, in accordance with aspects of the present disclosure

FIG. 69 illustrates the relationship between various cross-type droplet generators. More specifically, FIG. 69 shows a first cross-type droplet generator 2560 including a single cross, a second cross-type droplet generator 2580 including two crosses, a third cross-type droplet generator 2600 including three crosses, and a butted tube cross-type droplet generator 2620.

Droplet generator 2560 includes hollow channels 2562, 2564 that intersect at an intersection region 2566. To generate droplets, one of these channels will generally carry a foreground fluid toward intersection region 2566 from one direction, while the other channel carries a background fluid toward intersection region 2566 from both directions. Typically, channel 2562 will carry a foreground fluid such as a sample-containing solution, and channel 2564 will carry a background fluid such as oil, but the opposite is also possible. In any case, an emulsion will be created at intersection region 2566 and will continue moving through channel 2562 in the direction of travel of the foreground fluid, as described in detail above.

Droplet generator 2580 includes three hollow channels 2582, 2584, 2586 that intersect at an intersection region 2588. To generate droplets, channel 2582 will typically carry a foreground fluid such as a sample-containing solution toward intersection region 2588 from a single direction, and each of channels 2584, 2586 will typically carry a background fluid such as oil toward intersection region 2588 from two opposite directions. In that case, an emulsion will be created at intersection region 2588 and will continue moving through channel 2582 in the direction of travel of the foreground fluid. It is also possible that each of channels 2584, 2586 would carry a foreground fluid toward intersection region 2588 from a single direction, and channel 2582 would carry a background fluid toward intersection region 2588 from two opposite directions. In that case, the emulsion created at intersection region 2588 would travel through both channels 2584 and 2586, in the original directions of travel of the foreground fluid in each of those channels. Droplet generator 2580 thus may function to produce droplets that emerge from two separate channels.

Similarly, droplet generator 2600 includes four channels 2602, 2604, 2606, 2608 that intersect to generate an emulsion of foreground fluid droplets in background fluid at an intersection region 2610. By analogy to the three-channel configuration of droplet generator 2580, the four-channel configuration of droplet generator 2600 may be used either to generate a single emulsion that travels through channel 2602, or to generate multiple emulsions that travel through channels 2604, 2606, and 2608.

Droplet generator 2620 is a butted tube generator that includes a first section of hollow tube 2622 and a second section of hollow tube 2624. Tube section 2622 includes a fluid channel 2626, and tube section 2624 includes a fluid channel 2628. The tube sections are separated by a small distance, forming an intersection region 2630 between the tubes. Accordingly, if a foreground fluid flows toward intersection region 2630 through channel 2626, and a background fluid flows radially inward toward intersection region 2630 from the region outside the tubes, an emulsion can be created and flow into channel 2628.

The progression from droplet generator 2560 through droplet generator 2620 illustrates the relationship between these various droplet generators. Specifically, if the variable n is chosen to represent the number of radial fluid channels that intersect a longitudinal fluid channel at an intersection region within a tube, then droplet generator 2560 may be characterized as an "n=1" cross-type droplet generator, droplet generator 2580 may be characterized as an "n=2" cross-type droplet generator, droplet generator 2600 may be characterized as an "n=3" cross-type droplet generator, and droplet generator 2620 may be characterized as an "n=0.0" cross-type droplet generator, because the gap between tubes 2622 and 2624 may be viewed as formed from an infinite number of radial fluid channels extending continuously around the circumference of a single elongate tube.

H. Example 8

Figure 70:
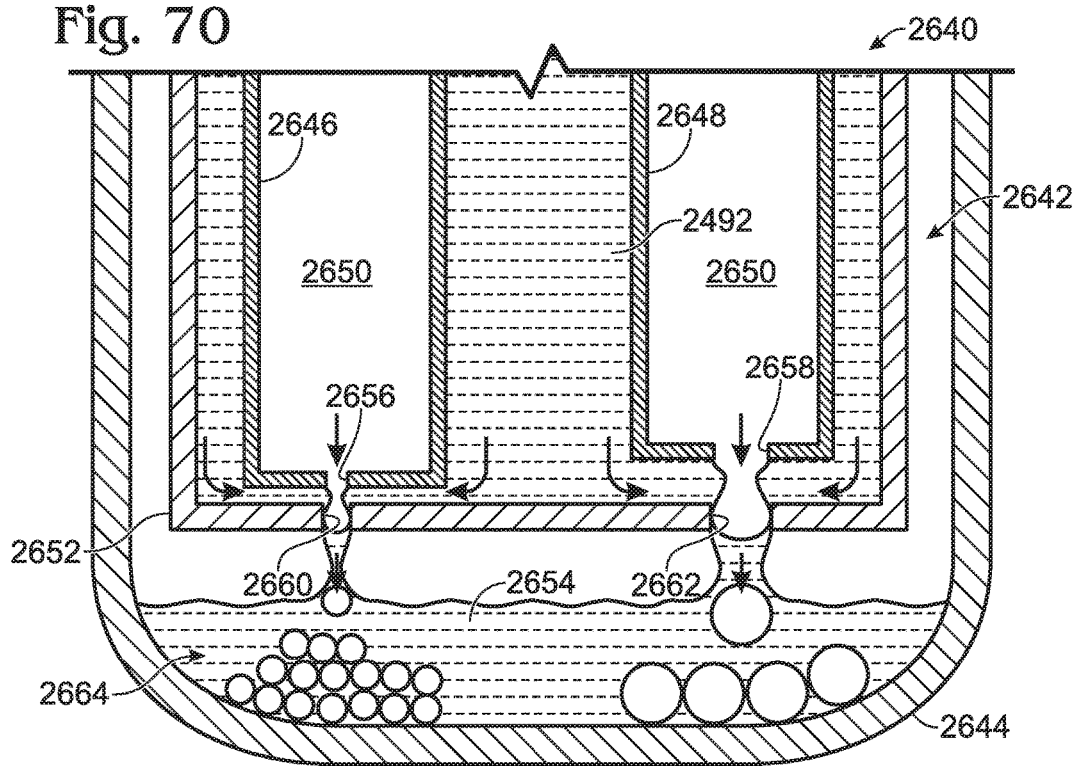
FIG. 70 is a cross-sectional side elevational view of another droplet generation system, in accordance with aspects of the present disclosure.
Figure 71:
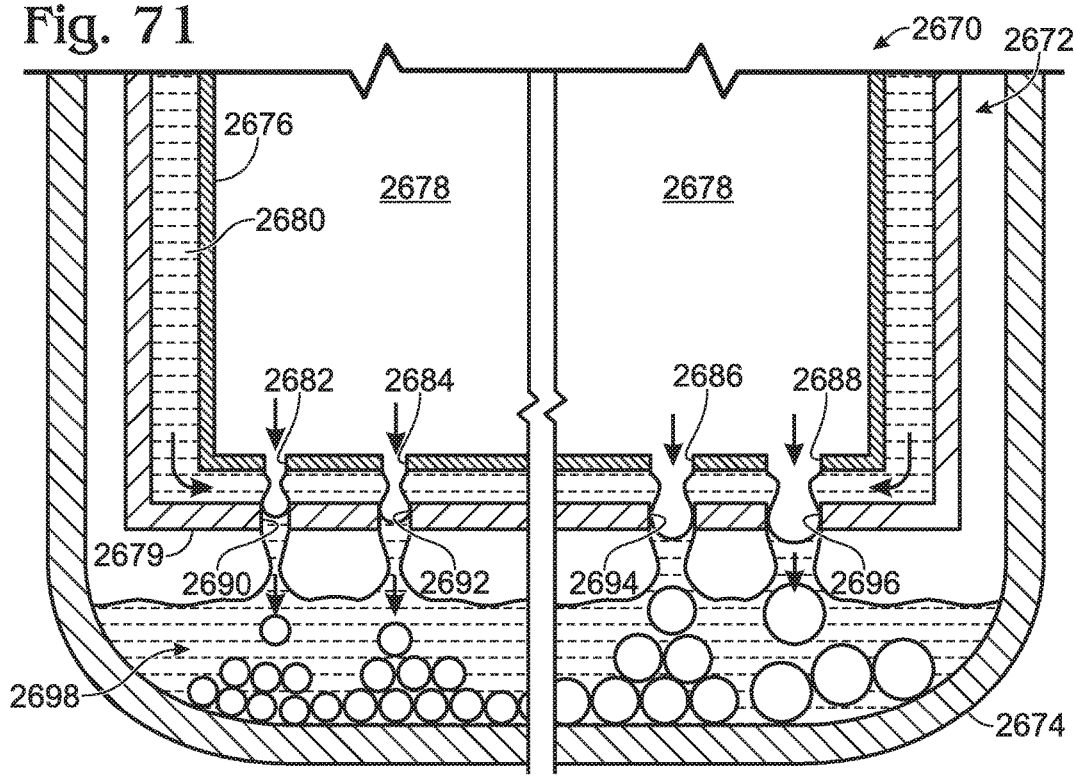
FIG. 71 is a cross-sectional side elevational view of still another droplet generation system, in accordance with aspects of the present disclosure.

FIGS. 70 and 71 depict additional cross-type droplet generation systems, which are similar to droplet generation system 2480 of Example 6, but which are configured to generate droplets of two or more substantially different sizes.

FIG. 70 shows a lower portion of a first such cross-type droplet generation system, generally indicated at 2640, which is configured to generate droplets of two substantially different sizes. Accordingly, droplet generation system 2640 includes an emulsion generator 2642, and an emulsion reservoir 2644 configured to receive the emulsion generated by the emulsion generator. Emulsion reservoir 2644 may be any reservoir configured to receive, contain and/or transport an emulsion to a desired location, such as a well, a pipette tip, a spin column or vial, or a syringe body.

Emulsion generator 2642 is configured to generate an emulsion of sample-containing droplets of two different sizes. Specifically, emulsion generator 2642 includes first and second inner fluid chambers 2646, 2648 each configured to contain a sample-containing fluid 2650, and an outer fluid chamber 2652 surrounding portions of the inner fluid chambers and configured to contain a background fluid 2654, such as an oil. Alternatively, inner fluid chambers 2646, 2648 each may contain a different fluid, in which case the generated droplets will have different constituents as well as different sizes.

Regardless of their contents, inner fluid chambers 2646, 2648 respectively include distal apertures 2656, 2658, configured to allow passage of sample-containing fluid out of each inner fluid chamber. Outer fluid chamber 2652 includes distal apertures 2660, 2662, each aligned with one of apertures 2656, 2658. Each pair of aligned apertures is configured to allow passage of droplets of a particular size, as FIG. 70 indicates. Emulsion 2664 created via the aligned apertures of system 2640 is otherwise produced in the same way emulsion 2520 is produced in droplet generation system 2480 of FIG. 67, and the details will not be repeated here.

FIG. 71 shows a droplet generation system 2670 much like droplet generation system 2640 of FIG. 70, except that system 2670 is configured to generate droplets across a range of many different sizes. Accordingly, droplet generation system 2670 includes an emulsion generator 2672, and an emulsion reservoir 2674 configured to receive the emulsion generated by the emulsion generator. As in many of the previously described embodiments, emulsion reservoir 2674 may be any reservoir configured to receive, contain and/or transport an emulsion to a desired location, such as a well, a pipette tip, a spin column or vial, or a syringe body.

Emulsion generator 2672 is configured to generate an emulsion of sample-containing droplets of a plurality of different sizes. Emulsion generator 2672 thus includes an inner fluid chamber 2676 configured to contain a sample-containing fluid 2678, and an outer fluid chamber 2679 surrounding portions of the inner fluid chamber and configured to contain a background fluid 2680. Although FIG. 71 depicts only a single inner chamber 2676, two or more separate inner chambers could alternatively be used, as in FIG. 70.

Inner fluid chamber 2676 includes a plurality of distal apertures 2682, 2684, 2686, 2688, each configured to allow passage of sample-containing fluid out of the inner fluid chamber at a particular rate. Outer fluid chamber 2678 includes distal apertures 2690, 2692, 2694, 2696, each aligned with one of the apertures of the inner chamber to allow passage of an emulsion including droplets of a particular size. Thus, droplet generation system 2670 is configured to generate an emulsion 2698 that includes droplets of a wide range of sizes. In a similar manner, a droplet generation system may be configured to produce an emulsion having any desired characteristic droplet size distribution.

I. Example 9

This example describes further aspects of exemplary droplet generators. The droplet generation systems described above generally involve multiple separate components, such as a droplet generator and a complementary reservoir. However, a droplet generation system according to the present disclosure also may take the form of an injection molded cartridge, with or without sample preparation capabilities. Such a cartridge would generally include chambers or protrusions acting as the barrels of syringes, wells, or reservoirs to contain the sample and oil for combination into an emulsion of sample-containing droplets. These chambers will require sturdy walls that can withstand the side forces expected during pumping, insertion of the disposable portion into a non-disposable portion of the system, and shipping/handling. Therefore, the walls of the chambers are envisioned to be approximately 0.020 inch thick but could range in thickness from 0.04 to 0.40 inches.

A disposable cartridge-style droplet generator also would generally include very precise microchannels to contain and direct the flow of sample-containing solution and oil. These channels could be, for example, approximately 250 microns wide and 250 microns deep, although these dimensions each could range from approximately 50 microns to approximately 350 microns. Furthermore, some areas of the droplet generator (specifically, those contacting a sample) must be biocompatible, whereas others areas of the disposable need not meet this requirement.

Integrating droplet generation into a single assembly such as a disposable cartridge may have certain efficiency advantages over a multi-component droplet generation system. Specifically, if droplet generation involves the use of two or more subassemblies manufactured separately, there will typically be more potential for (a) leakage at the connections between the subassemblies, (b) increased unswept volumes in those connections, (c) more volume in the lines connection, (d) greater complexity in the fluid circuit, and (e) increase fabrication/assembly costs. On the other hand, integrating these diverse requirements into a single assembly results in potential savings in all the areas listed.

A molded droplet generator cartridge also may have various other advantageous features. For example, moldable plastic typically has minimal or no absorption of material such as protein, DNA, RNA, lipids, or other constituents of biological samples expected to be tested. Furthermore, it is possible to mold protrusions able to withstand side forces on one side of a part and microfluidic channels on the opposite side, as part of a single molding step. A plate, thin sheet, or foil of the same or similar material is then bonded to the side of the part with microfluidic channels, resulting in tube-like channels connecting various areas of the assembly. Holes through the part connect the barrel type features to the channels. This means that all alignments between these features can be inexpensively manufactured, since they are molded into one structure.

The anticipated average operating pressures within a disposable droplet generating cartridge are 2 to 5 psi. By keeping the fluid pressures relatively low, a single molded cartridge can meet the diverse functions listed elsewhere in this disclosure. Maintaining lower internal operating pressures rather than higher pressures also means that the cartridge can have (a) thinner wall sections (i.e., less need for strong structures to withstand breakage), (b) less bulging of the walls (i.e., more uniformity in controlling fluid flows with pressure variations), and (c) thinner plates bonded to the microchannel side of the cartridge. These factors result in decreased production assembly times and deceased product cost.

Depending on whether a disposable cartridge-type droplet generator is used to generate water-in-oil emulsions or multiple emulsions, it may be desirable for the fluid contacting surfaces of the droplet generator to be either hydrophobic or hydrophilic. Either of these alternatives may be accomplished by choosing an appropriate material that is compatible with the molding process, and/or by applying a coating to alter surface properties of the chosen material.

J. Example 10

This example describes additional aspects of droplet generation, in accordance with aspects of the present disclosure, presented without limitation as a series of numbered sentences.

1. A droplet generator system, comprising (A) a droplet outlet portion including an emulsion outlet channel and upper and lower channel walls defining an oil channel; and (B) a sample-containing portion configured to be selectively assembled with the droplet outlet portion and including (i) a sample reservoir; and (ii) a fluid outlet aperture configured to emit droplets of sample-containing fluid from the sample reservoir; wherein when the droplet outlet portion and the sample-containing portion are assembled together, wherein a substantially fluid tight seal is formed between the droplet outlet portion and the sample-containing portion; and wherein droplets emitted by the fluid outlet aperture intersect oil traveling in the oil channel to produce an emulsion of water-in-oil droplets that passes into the emulsion outlet channel.

2. The system of claim 1, wherein the sample-containing portion is configured to be a single-use, disposable component of the system.

3. The system of claim 2, wherein the sample-containing portion is constructed of injection-molded thermoplastic.

4. A droplet generation system, comprising (A) a fluid reservoir configured to hold a background emulsion fluid having a first density and a foreground emulsion fluid having a second density; and (B) a droplet generator including an elongate tip configured to be at least partially inserted into the fluid reservoir and having at least one side aperture and a distal aperture; wherein the distal aperture is configured to be in contact with background fluid held by the reservoir and the side aperture is configured to be in contact with foreground fluid held by the reservoir when the reservoir contains background and foreground fluids and the elongate tip is inserted into the reservoir; and wherein the droplet generator is configured so that foreground fluid flowing into the side aperture intersects with a stream of background fluid that enters the tip through the distal aperture, to form an emulsion of foreground fluid droplets in background fluid.

5. The droplet generation system of paragraph 4, wherein the droplet generator further includes an emulsion chamber configured to receive the emulsion.

6. The droplet generation system of paragraph 4, wherein the at least one side aperture includes a plurality of side apertures.

7. The droplet generation system of paragraph 4, wherein the elongate tip includes a u-shaped distal portion.

8. A droplet generation system, comprising (A) an emulsion generator including (i) an inner fluid chamber configured to contain a sample-containing fluid and having a distal aperture configured to allow passage of the sample-containing fluid out of the inner fluid chamber; and (ii) an outer fluid chamber configured to contain a background fluid, the outer fluid chamber surrounding at least portions of the inner fluid chamber and having a distal aperture configured to allow passage of an emulsion out of the outer fluid chamber; wherein background fluid channels are formed between an external boundary of the inner fluid chamber and an internal boundary of the outer fluid chamber, and configured to transfer background fluid radially inward toward the distal aperture of the outer fluid chamber; and wherein the inner and outer fluid chambers are positioned so that oil flowing radially inward through the background fluid channels will intersect with sample-containing fluid passing out of the inner fluid chamber through the distal aperture of the inner fluid chamber, to generate an emulsion of sample-containing droplets within the background fluid which will pass through the distal aperture of the outer fluid chamber; and (B) an emulsion reservoir at least partially surrounding the emulsion generator and configured to receive the emulsion generated by the emulsion generator.

V. CONTINUOUS FLOW THERMOCYCLER

This Section describes exemplary thermocyclers, for example, for use in droplet-based assays.

It may be desirable, in systems such as DNA amplification systems, to perform temperature-dependent reactions for increasing the number of copies of a sample, or component(s) thereof. Methods of cyclically varying the temperature of a fluid or other material generally may be termed methods of "thermocycling," and an apparatus used to accomplish such cyclical temperature variations generally may be termed a "thermocycler." In the case of DNA amplification through PCR, cyclical temperature changes cause repeated denaturation (also sometimes termed DNA "melting"), primer annealing, and polymerase extension of the DNA undergoing amplification. Typically, twenty or more cycles are performed to obtain detectable amplification. In other processes, such as alternative enzymatic amplification processes, thermocycling may have other effects, and different temperature ranges and/or different numbers of temperature changes may be appropriate.

Figure 72:
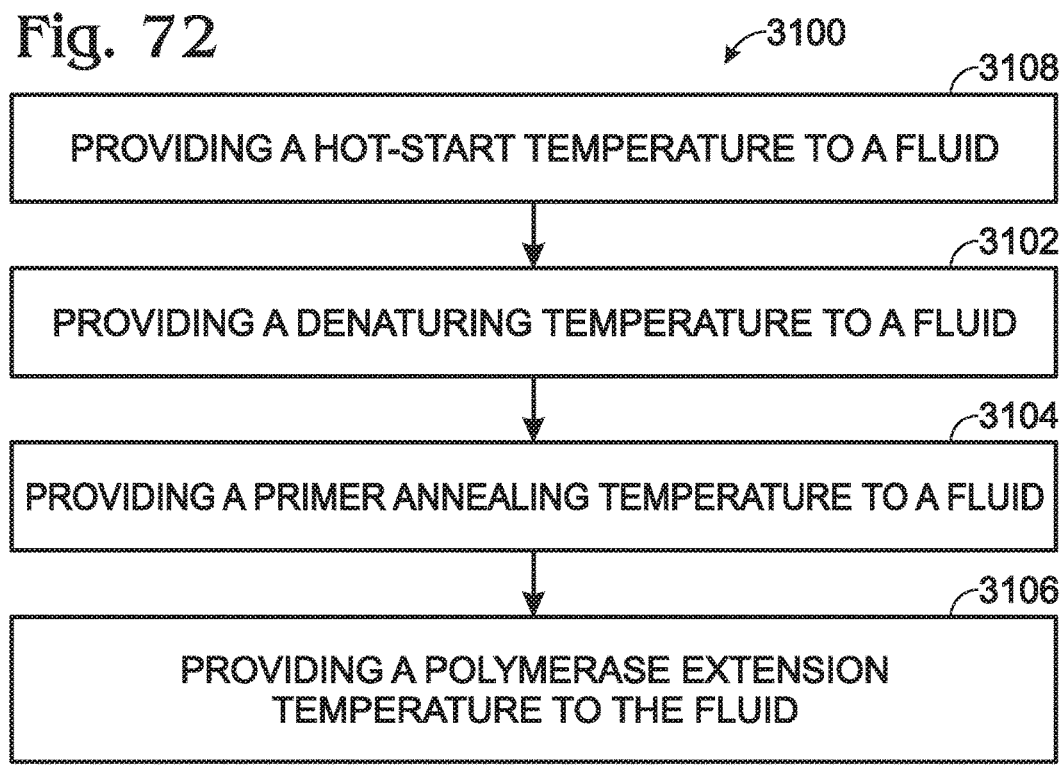
FIG. 72 is a flowchart depicting a method of thermocycling a sample/reagent fluid mixture to promote PCR.

FIG. 72 is a flowchart depicting a method, generally indicated at 3100, of thermocycling a sample/reagent emulsion or other fluid mixture to promote PCR. Typically, three separate temperatures or temperature ranges are provided to the fluid to accomplish thermocycling for PCR. Other numbers of temperature ranges, such as one, two, four, or more, may be provided for different processes. In the case of PCR, providing a first, relatively higher temperature to the fluid, as indicated at step 3102, causes the target DNA to become denatured. This denaturing temperature is typically in the range of 92-98° C. Providing a second, relatively lower temperature to the fluid, as indicated at step 3104, allows annealing of DNA primers to the single-stranded DNA templates that result from denaturing the original double-stranded DNA. This primer annealing temperature is typically in the range of 50-65° C. Finally, providing a third, middle temperature to the fluid, as indicated at step 3106, allows a DNA polymerase to synthesize a new, complementary DNA strand starting from the annealed primer. This polymerase extension temperature is typically in the range of 70-80° C., to achieve optimum polymerase activity, and depends on the type of DNA polymerase used.

In some cases, a single temperature may be provided for both primer annealing and polymerase extension (i.e., steps 3104 and 3106 above), although providing a single temperature for these processes may not optimize the activity of the primers and/or the polymerase, and thus may not optimize the speed of the PCR reaction. When provided for both annealing and extension, this single temperature is typically in the range of 55-75° C.

A PCR thermocycler also may include, in addition to the two or three temperature zones described above, an integrated or complementary "hot start" mechanism configured to provide a relatively high hot-start temperature, as indicated at step 3108. The hot-start temperature is provided to initiate PCR and/or to prepare a sample/reagent mixture for initiation of PCR upon the addition of a suitable polymerase. More specifically, providing a hot-start temperature may reverse the inhibition of a polymerase enzyme that has been added to inhibit priming events that might otherwise occur at room temperature. In this case, heating the sample/reagent mixture to a hot-start temperature initiates the onset of PCR. In other instances, providing a hot-start temperature may preheat the sample and the primers in the absence of the polymerase, in which case subsequent addition of the polymerase will initiate PCR. The hot start temperature is typically in the range of 95-98° C.

The thermocycler also may include integrated or complementary mechanisms for allowing "final elongation" and/or "final hold" steps, after thermocycling has (nominally) been completed. For example, in the former case, the thermocycler may include a mechanism configured to maintain samples at the extension temperature long enough (e.g., for 5-15 minutes) to ensure that any remaining single-stranded nucleotide is fully extended. In continuous flow systems, this mechanism may include a relatively long piece of narrow tubing to increase path length, and/or a relatively short piece of wider tubing to decrease flow rate, both maintained at an extension temperature. Alternatively, or in addition, the thermocycler may include a mechanism for holding or storing samples (e.g., for an indefinite time) at a temperature below the extension temperature (e.g., 4-15° C.).

Various methods of providing the desired temperatures or temperature ranges to a sample/reagent fluid mixture may be suitable for PCR. For example, a fluid may be disposed within one or more stationary fluid sites, such as test tubes, microplate wells, PCR plate wells, or the like, which can be subjected to various temperatures provided in a cyclical manner by an oven or some other suitable heater acting on the entire thermal chamber. However, such array-type PCR systems may be limited by the number of fluid sites that can practically be fluidically connected to the system and/or by the kinetics of changing temperatures in a large (high-thermal-mass) system (e.g., transition times between melt, anneal, and extension temperatures in commercial systems may be orders of magnitude longer than the fundamental limits of Taq polymerase processivity). Alternatively, fluid may be passed continuously or quasi-continuously through various temperature regions, in a cyclical manner. In this case, it is desirable to minimize heat transfer between the regions, to provide sharp temperature transitions between the regions. It is also desirable to monitor the temperature of each region continuously and to provide rapid feedback to maintain a relatively constant desired temperature in each region.

One type of continuous-flow PCR system involves coiling or winding fluidic tubing to form a fluid channel in a helical shape around a thermocycler that is configured to provide the various desired temperatures or temperature regions. Furthermore, various alternatives to externally wrapped fluidic tubing may be used to provide a fluid channel configured to transport an emulsion of sample-containing droplets cyclically through various temperature regions. For example, tubing may be disposed within the body of thermocycler, such as by casting the thermocycler (or the inner segments of the thermocycler) around the tubing. Alternatively, a fluid tight coating (such as a silicon coating) may be applied to external grooves or channels of the thermocycler and then wrapped with a fluid tight sheet (such as a silicon sheet), to define an integrated fluid channel passing cyclically around the thermocycler without the need for any separate tubing at all.

Thus, providing the first, second, third and/or hot-start temperatures at steps 3102, 3104, 3106, 3108 of method 3100 may include transporting an emulsion in a substantially helical path cyclically through a denaturing temperature region, a primer annealing temperature region, a polymerase extension temperature region, and/or a hot-start temperature region of the thermocycler. These various temperature regions may be thermally insulated from each other in various ways, and each region may provide a desired temperature through the use of resistive heating elements, thermoelectric coolers (TECs) configured to transfer heat between a thermal core and the temperature regions, and/or by any other suitable mechanism. Various heat sinks and sources may be used to provide and/or remove heat from the thermocycler, either globally (i.e., in substantial thermal contact with two or more temperature regions) or locally (i.e., in substantial thermal contact with only one temperature region).

The following examples describe specific exemplary methods and apparatus for cyclically heating and cooling a sample/reagent mixture to facilitate DNA amplification through PCR, i.e., exemplary thermocyclers and methods of thermocycling suitable for PCR applications. Additional pertinent disclosure may be found in the U.S. provisional patent applications listed above under Cross-References and incorporated herein by reference, particularly Ser. No. 61/277,200, filed Sep. 21, 2009.

A. Selected Embodiments 1

This Section describes a first exemplary thermocycler 3200, in accordance with aspects of the present disclosure; see FIGS. 73-80.

Figure 73:
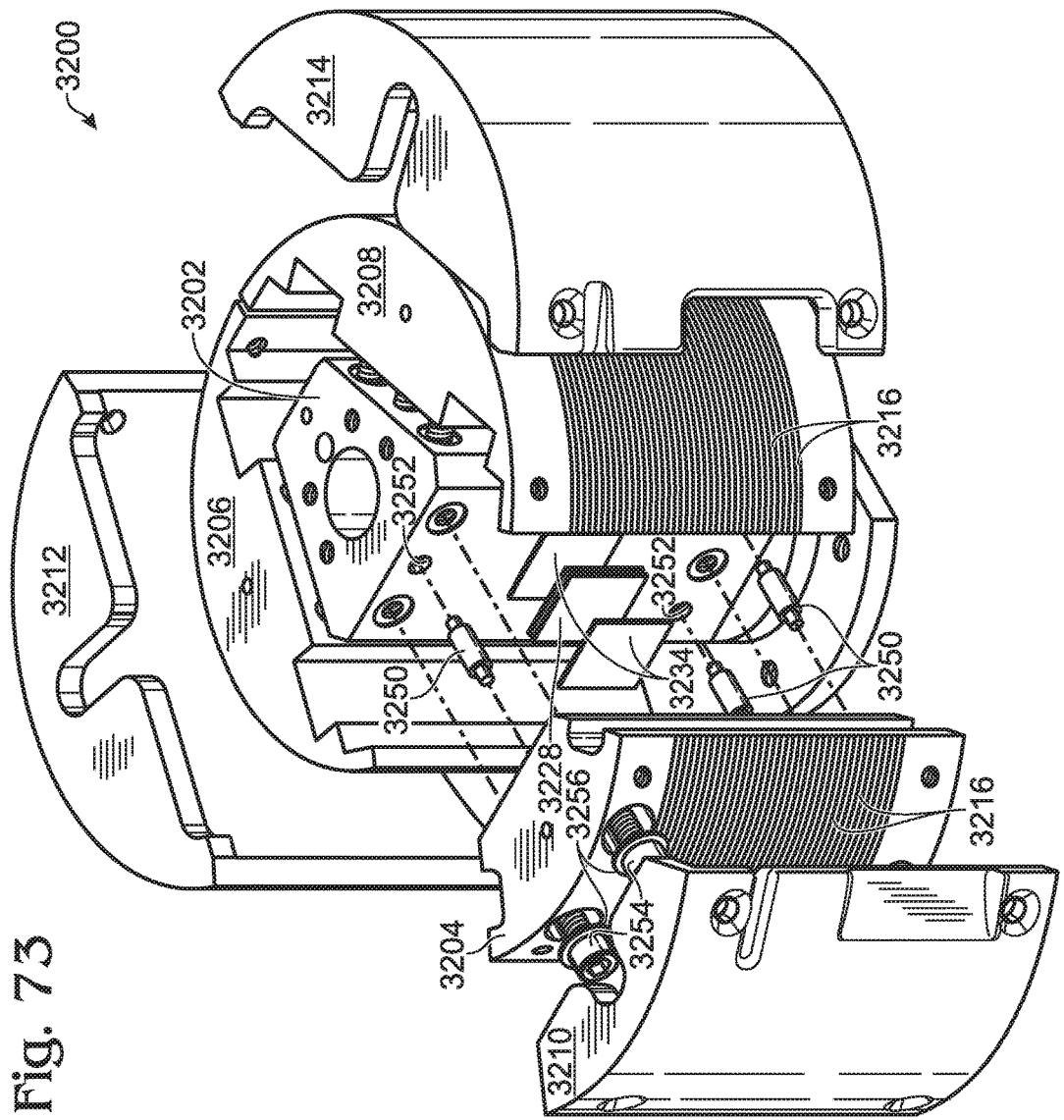
FIG. 73 is an exploded isometric view of an exemplary thermocycler, in accordance with aspects of the present disclosure.

FIG. 73 is an exploded isometric view of key components of thermocycler 3200. The thermocycler includes a core 3202 defining a central longitudinal axis, three inner segments 3204, 3206, 3208, and three outer segments 3210, 3212, 3214. The three pairs of segments correspond to the three portions of the PCR thermal cycle described above, in connection with FIG. 72, and define the corresponding temperature regions. Specifically, segments 3204 and 3210 correspond to the melt phase, segments 3206 and 3212 correspond to the anneal phase, and segments 3208 and 3214 correspond to the extension (extend) phase, respectively. In alternative embodiments, the thermocycler could include alternative numbers of segments, for example, two segments in a thermocycler in which the annealing and extension phases were combined. Collectively, portions or regions of the thermocycler involved in maintaining particular temperatures (or temperature ranges) may be termed "temperature regions" or "temperature-controlled zones," among other descriptions.

Figure 74:
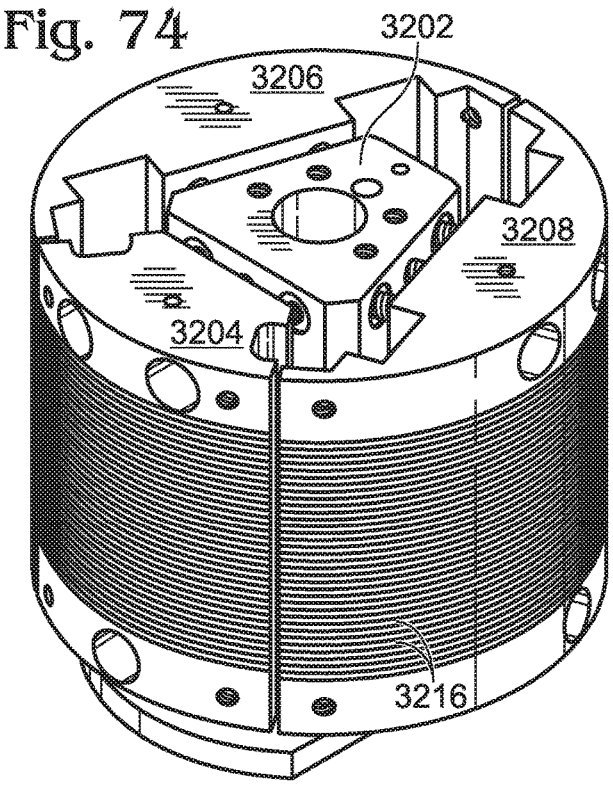
FIG. 74 is an unexploded isometric view of a central portion of the thermocycler of FIG. 73.

FIG. 74 is an unexploded isometric view of a central portion of the thermocycler of FIG. 73, emphasizing the relationship between the core and inner segments. Core 3202 is configured as both a heat source and a heat sink, which can be maintained at a constant desired temperature regardless of whether it is called upon to supply or absorb heat. For example, in some embodiments, core 3202 may be maintained at approximately 70° Celsius. However, more generally, in embodiments in which the core acts as a heat source and a heat sink between two or more segments, the core may be maintained at any suitable temperature between the temperatures of the warmest and coolest segments (e.g., between the temperature of the melt segment and the annealing segment).

Inner segments 3204, 3206, 3208 are attached to the core and configured to form an approximate cylinder when all of the inner segments are attached or assembled to the core. Inner segments 3204, 3206, 3208 are equipped with external grooves 3216 on their outer peripheral surfaces, as visible in FIGS. 73 and 74. When the inner segments are assembled to the core, these grooves form a helical pattern around the circumference of the cylindrical surface formed by the inner segments. Grooves 3216 are configured to receive fluidic tubing that can be wrapped continuously around the inner segments, as described below, to allow a fluid traveling within the tubing to travel helically around the circumference formed by the assembled inner segments. The fluidic tubing acts as a fluid channel to transport an emulsion of sample-containing droplets cyclically through the various temperature regions of the thermocycling system.

Outer segments 3210, 3212, 3214 are configured to fit closely around the inner segments, as seen in FIG. 73. Thus, the fluidic tubing may be wound between the inner and outer segments and held in a stable, fixed, environmentally controlled position by the segments.

Figure 75:
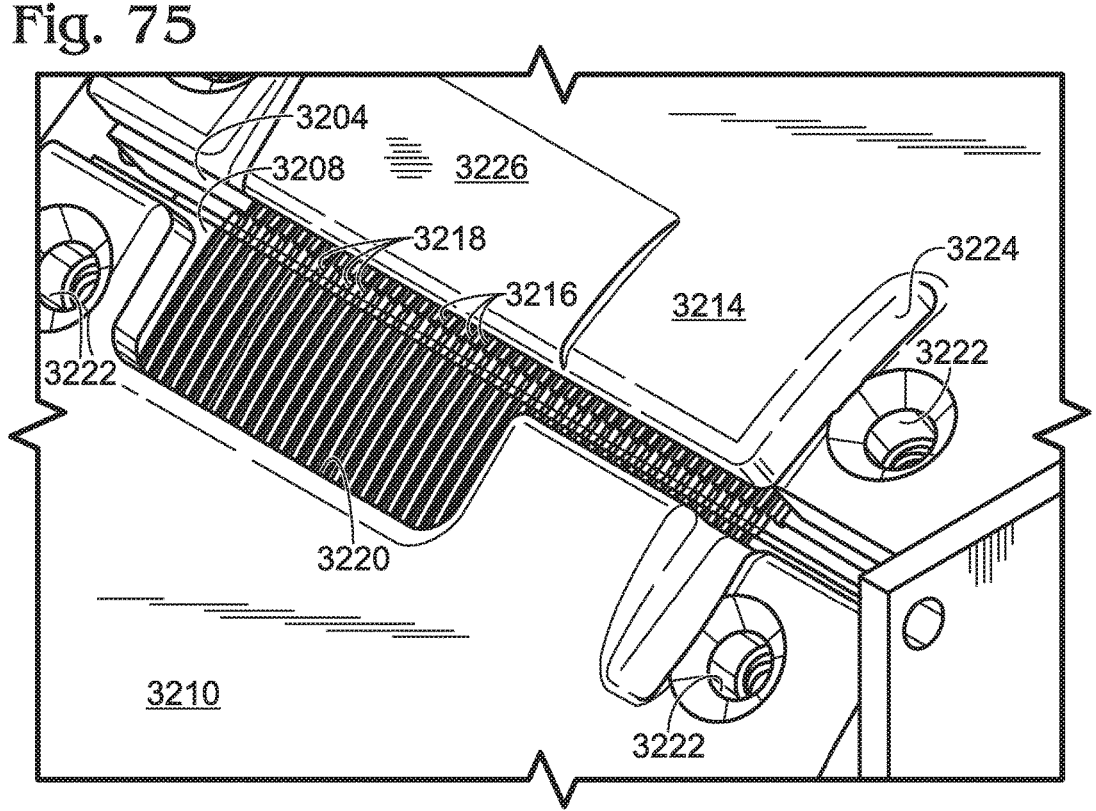
FIG. 75 is an isometric view showing a magnified portion of the assembled thermocycler of FIG. 73, which is suitable for relatively small outer diameter fluidic tubing, in accordance with aspects of the present disclosure.

FIG. 75 is an isometric magnified view of a portion of the assembled thermocycler. This embodiment is particularly suitable for relatively small outer diameter fluidic tubing. Portions of outer segments 3210, 3214 are disposed around inner segments 3204, 3208 and core 3202 (not visible). Fluidic tubing 3218 can be seen disposed in grooves 3216, which are partially visible within an aperture 3220 formed by the outer segments. Additional fastening apertures 3222 are provided in the outer segments to facilitate attachment of the outer segments to the inner segments. The tubing may pass from outside to inside thermocycler 3200 through an ingress region 3224. The tubing is then wrapped helically around the inner segments a minimum number of times, such as 20 or more times, after which the tubing may pass from inside to outside thermocycler 3200 through an egress region 3226. Egress region 3226 is relatively wide, to allow the tubing to exit thermocycler 3200 after forming any desired number of coils around the inner segments.

Figure 76:
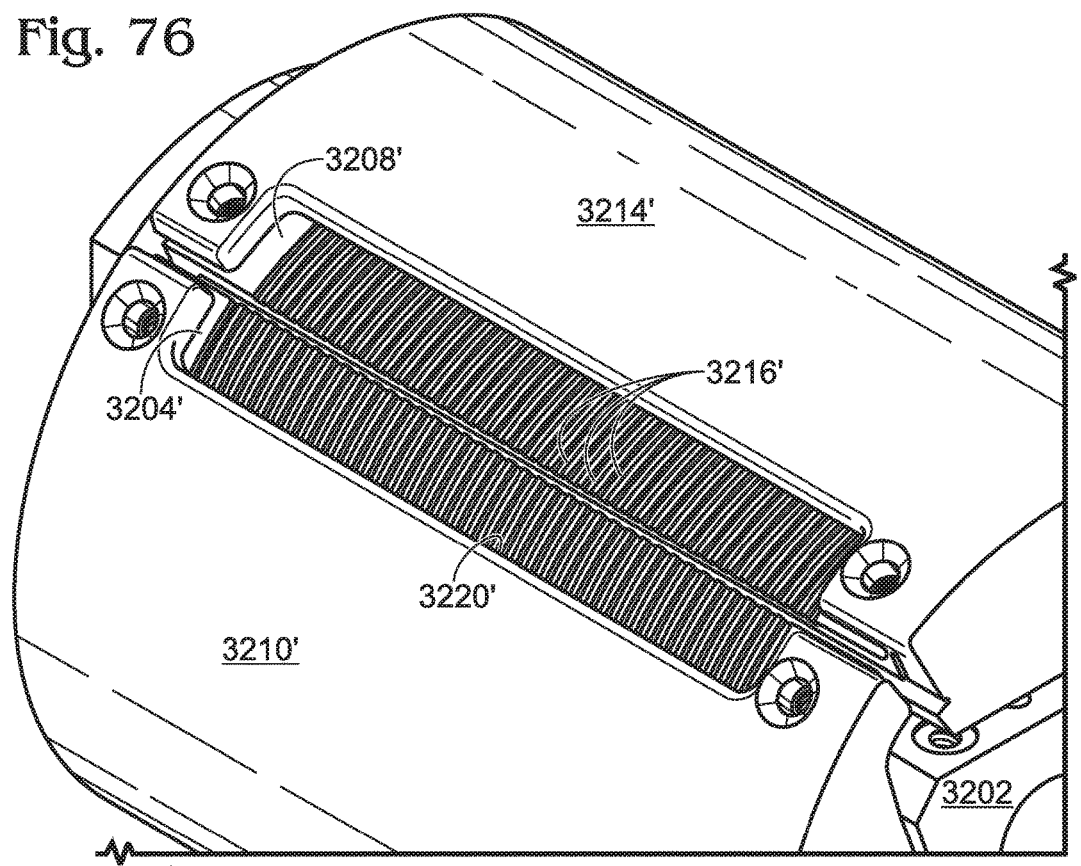
FIG. 76 is an isometric view showing a magnified portion of an alternative embodiment of the assembled thermocycler, which is suitable for relatively larger outer diameter fluidic tubing, in accordance with aspects of the present disclosure.

FIG. 76 is an isometric magnified view of a portion of an alternative embodiment of the assembled thermocycler. This embodiment, which shows a slight variation in the shape of the outer segments, is particularly suitable for relatively large outer diameter fluidic tubing. Specifically, FIG. 76 shows outer segments 3210', 3214' disposed around inner segments 3204', 3208' and core 3202. Grooves 3216', which are relatively wider than grooves 3216 of FIG. 75, are partially visible within an aperture 3220' formed by the outer segments. In FIG. 76, fluidic tubing may pass from outside to inside thermocycler 3200 and vice versa at any desired groove positions, simply by overlapping the edge of aperture 3220' with the tubing. Between the ingress and egress tubing positions, the tubing may be wrapped around the inner segments to make any desired number of helical coils around the inner segments.

Figure 77:
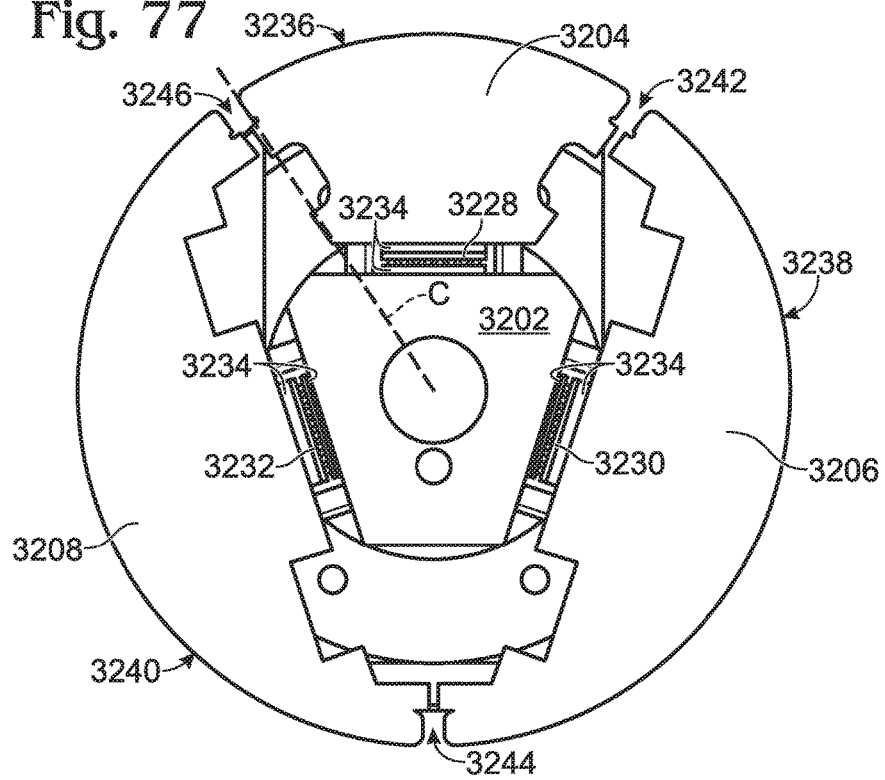
FIG. 77 is a top plan view of the thermocycler of FIG. 73, without the outer segments attached.

FIG. 77 is a top plan view of the assembled thermocycler, without the outer segments attached. This view shows three thermoelectric coolers (TECs) 3228, 3230, 3232 disposed between core 3202 and inner segments 3204, 3206, 3208. One of these, TEC 3228, can be seen in FIG. 73. Each TEC is configured to act as a heat pump, to maintain a desired temperature at its outer surface when a voltage is applied across the TEC. The TECs may be set to steady-state temperatures using a suitable controller, such as a proportional-integral-derivative (PID) controller, among others. The TECs operate according to well-known thermoelectric principles (in which, for example, current flow is coupled with heat transfer), such as the Peltier effect, the Seebeck effect, and/or the Thomson effect. The TECs may be configured to transfer heat in either direction (i.e., to or from a specific thermocycler element), with or against a temperature gradient, for example, by reversing current flow through the TEC. Thus, the TECs may be used to speed up or enhance heating of an element intended to be warm, speed up or enhance cooling of an element intended to be cool, and so on, to maintain each temperature region approximately at a different desired temperature. Suitable TECs include TECs available from RMT Ltd. of Moscow, Russia.

Each TEC, in turn, may be sandwiched between a pair of thermally conductive and mechanically compliant pads 3234, as seen in FIGS. 73 and 77. Pads 3234 may be configured to protect the TECs from damage due to surface irregularities on the outer surface of core 3202 and in the inner surfaces of inner segments 3204, 3206, 3208. Alternatively, or in addition, pads 3234 may be configured to minimize the possibility of potentially detrimental shear stresses on the TECs. Suitable pads include fiberglass-reinforced gap pads available from the Bergquist Company of Chanhassen, Minn.

Figure 78:
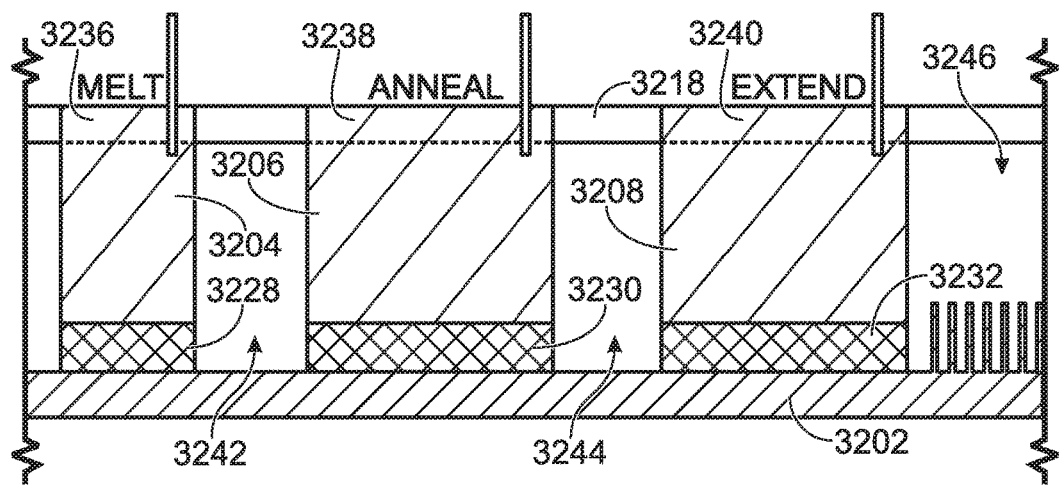
FIG. 78 is a schematic sectional view of the thermocycler of FIG. 73, depicting the relative dispositions of the core and other components, taken generally along line C in FIG. 77 as line C in swept through one clockwise revolution about the center of the thermocycler.

FIG. 78 is a schematic section diagram depicting the relative disposition of core 3202, TECs 3228, 3230, 3232, inner segments 3208, 3206, 3204, and tubing 3218. Here, the core, TECs, and inner segments are collectively configured to maintain the outer surfaces 3236, 3238, 3240, respectively, of the inner segments at any desired temperatures to facilitate PCR reactions in fluids passing through tubing disposed helically around the cylindrical perimeter of the assembled inner segments. FIG. 78 can be thought of as the top view shown in FIG. 77, cut along line C in FIG. 77 and shown "unrolled" into a representative linear configuration. FIG. 78 can be obtained from FIG. 77 by continuous deformation, making these figures topologically equivalent (homeomorphic), and meaning that FIG. 78 may simply be viewed as an alternate way of visualizing the arrangement of components shown in FIG. 77.

TECs 3228, 3230, and 3232 are configured to maintain outer surfaces 3236, 3238, 3240, respectively, of the inner segments at various temperatures corresponding to the different stages of PCR, as depicted in FIG. 78. Because tubing 3218 is in thermal contact with outer surfaces 3236, 3238, 3240, the temperature of any fluid in tubing 3218 also may be controlled via the TECs. Specifically, outer surface 3236 is maintained at a temperature $T_{melt}$ suitable for melting (or denaturing) DNA, outer surface 3238 is maintained at a temperature $T_{anneal}$ suitable for annealing primers to single-stranded DNA templates, and outer surface 3240 is maintained at a temperature $T_{extend}$ suitable for synthesizing new complementary DNA strands using a DNA polymerase.

TECs 3228, 3230, 3232 respond relatively rapidly to electrical signals and are independently controllable, so that the desired temperatures at outer surfaces 3236, 3238, 3240 may be maintained relatively accurately. This may be facilitated by temperature sensors that monitor the temperatures of the outer surfaces and provide real-time feedback signals to the TECs. Maintaining the various temperatures is also facilitated by gaps 3242, 3244, 3246, which are visible in both FIG. 77 and FIG. 78, between the inner segments. These gaps, which in this example are filled simply with air, provide insulation between the neighboring inner segments to help keep the inner segments thermally well-isolated from each other. In other embodiments, the gaps may be filled with other materials.

Figure 79:
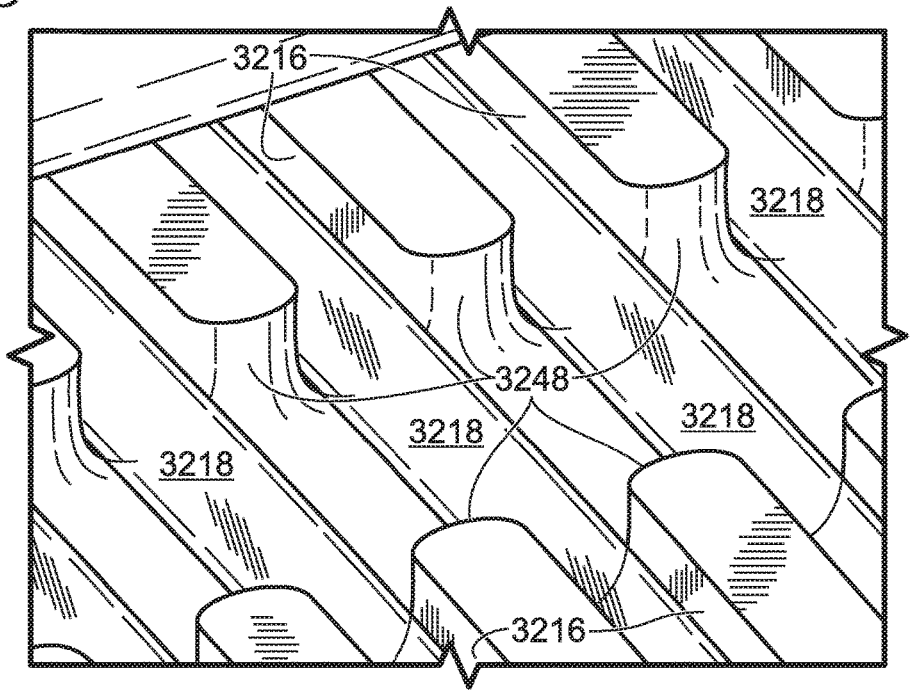
FIG. 79 is a magnified isometric view of a central portion of the thermocycler of FIG. 75.

FIG. 79 is a magnified isometric view of a central portion of grooves 3216 and tubing 3218 of FIG. 75, spanning the interface between two of the inner segments of the thermocycler. The features of the grooves shown in FIG. 79 are also present in grooves 3216' of FIG. 76. Specifically, grooves 3216 and 3216' include sloping edge contours 3248 disposed at the periphery of each inner segment 3204, 3206, 3208. Edge contours 3248 allow the tubing to be wrapped around the inner segments, even if there is a slight misalignment of two of the inner segments with respect to each other, because the edge contours do not include sharp edges that can be fracture points for tubing under stress from curvature due to potential misalignment.

The configuration of the inner segments in this example provides that each inner segment 3204, 3206, 3208 is substantially thermally decoupled from the other inner segments, as FIG. 78 illustrates schematically. This has advantages over systems in which the various temperature regions are in greater thermal contact, because in this exemplary configuration there is relatively little heat conduction between segments. One source of conduction that still exists is conduction via the fluid and fluidic tubing that passes from one inner segment to the next; however, as described below, the effects of this conduction on temperature uniformity are generally small.

Figure 80:
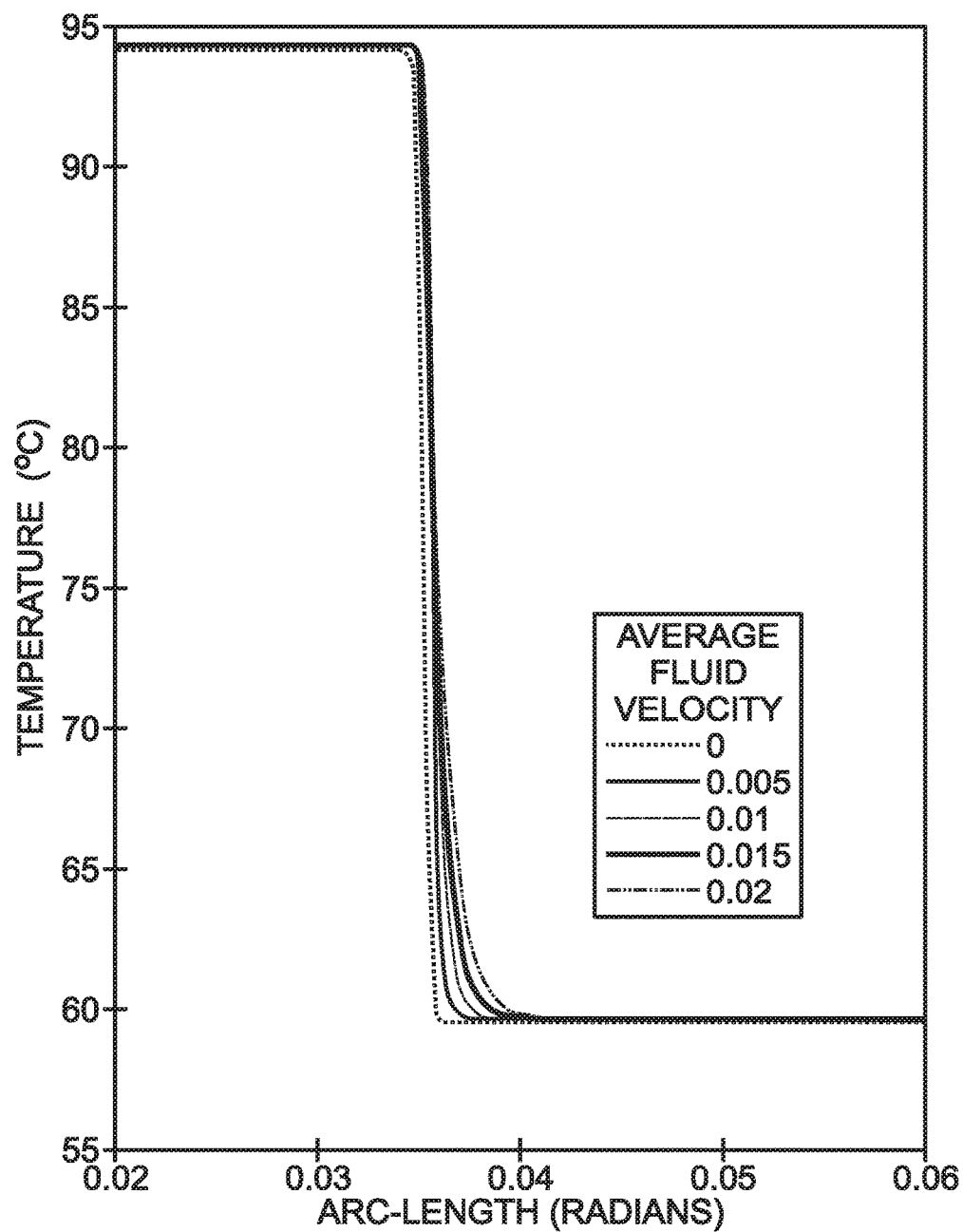
FIG. 80 is a graph of measured temperature versus arc length, as a function of average fluid velocity, near the interface between two inner segments of the thermocycler of FIG. 73.

FIG. 80 shows actual measured temperature versus arc length, as a function of average fluid velocity, near the interface between two inner segments configured according to this example. In particular, the effects of fluid heat conduction on temperature uniformity generally become insignificantly small within a few one-thousandths of a radian from the interface between inner segments, even for relatively rapid fluid velocity. Cycle times in the system can be adjusted dynamically by changing the flow rate through either software or hardware modifications (e.g., pump settings, drum radius, arc length of each segment (since length of time in a given segment or zone is proportional to the arc length of that segment), capillary internal diameter, etc.).

FIGS. 73 and 77 each show aspects of a mounting system for TECs 3228, 3230, 3232. Here, one TEC is mounted between core 3202 and each of inner segments 3204, 3206, 3208, as described previously. To attain positional accuracy when attaching each inner segment to the core, locating pins 3250 are configured to attach to both the core and one of the inner segments, to align each segment precisely with the core. Furthermore, the presence of the locating pins should reduce the likelihood that shear forces will act on the TECs and potentially damage them. The locating pins fit into complementary pin apertures 3252 disposed in both the inner segments and the core. In the exemplary embodiment of FIG. 73, a single locating pin is positioned at one end of the core (the top end in FIG. 73), and two locating pins are positioned at the other end of the core (the bottom end in FIG. 73).

FIG. 73 also shows bolts 3254 and washers 3256 configured to attach the inner segments to the core. The bolts are generally chosen to have low thermal conductivity, so that the TECs remain the only significant heat conduction path between the core and the inner segments. For instance, the bolts may be constructed from a heat-resistant plastic or a relatively low thermal conductivity metal to avoid undesirable thermal conduction. The washers may be load compensation washers, such as Belville-type washers, which are configured to provide a known compressive force that clamps each inner segment to the core. This bolt/washer combination resists loosening over time and also allows application of a known stress to both the bolts and the TECs, leading to greater longevity of the thermocycler.

B. Selected Embodiments 2

Figure 81:
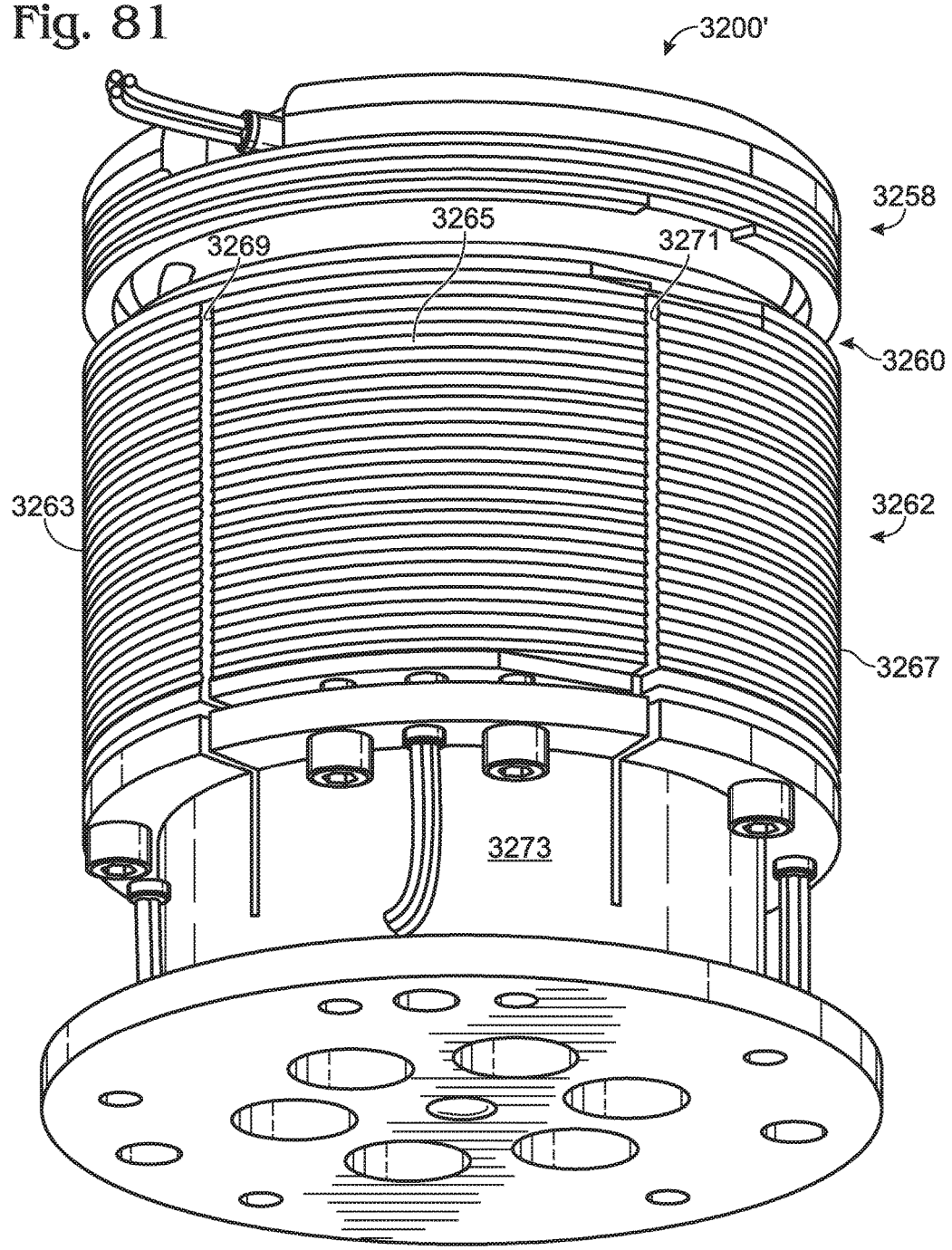
FIG. 81 is an isometric view of a central portion of a thermocycler having an optional "hot start" region, in accordance with aspects of the present disclosure.

Various modifications and/or additions may be made to the exemplary embodiments of FIGS. 73-80 according to the present disclosure. For example, a "hot start" mechanism may be added to facilitate a high-temperature PCR activation step. FIG. 81 shows a central portion (i.e., outer segments not shown) of an exemplary thermocycler 3200' including a hot start region 3258, which is separated from the remainder of the thermocycler by a gap 3260. The hot start region is configured to accept fluidic tubing just as are the inner segments, but is separated from the inner segments by gap 3260 to avoid unwanted heat conduction between the hot start region and the other portions of the thermocycler. A separate core portion (not shown) may be configured to heat region 3258 to a relatively high activation temperature, typically in the range of 95-98° C., to dissociate any polymerase inhibitors that have been used to reduce non-specific or premature PCR amplification.

Aside from hot start region 3258 and its associated gap and core portion, the remainder of thermocycler 3200', which is generally indicated at 3262, may have a similar construction to thermocycler 3200 described previously. Alternatively, instead of thermoelectric controllers, thermocycler 3200' may include an air core surrounded by a plurality of resistive section heaters (not shown) for heating various temperature regions 3263, 3265, 3267 of the thermocycler. These regions may be separated by insulating gaps 3269, 3271, which extend into an insulating base portion 3273 to help thermally isolate the temperature regions from each other. The configuration of the base portion, including the insulating gaps, can be changed to adjust thermal conductance between the different temperature regions.

C. Selected Embodiments 3

This subsection describes various alternative exemplary thermocyclers 3202a-h, in accordance with aspects of the present disclosure; see FIGS. 82-89.

FIGS. 82-89 are schematic diagrams depicting top views of the thermocyclers. These diagrams, like FIG. 78, correspond to and are topologically equivalent to three-dimensional cylindrical thermocycling units. The thermocyclers each include three inner (e.g., melt, anneal, and extend) segments 3204a-h, 3206a-h, 3208a-h in thermal contact with fluidic tubing 3218a-h for carrying samples undergoing PCR. The segments, in turn, each may (or optionally may not) be in thermal contact with respective (e.g., melt, anneal, and extend) heating elements 3252*a-h*, 3254*a-h*, 3256*a-h* (denoted by vertical bars) for delivering heat to the segments. The segments also may be in direct or indirect contact with one or more TECs (indicated by cross-hatching), one or more thermal conductive layer(s) (indicated by stippling), one or more thermal insulating layer(s) (indicated by dashed-dotted hatching), and/or one or more heated or unheated cores (indicated by hatching or stippling, respectively). These and other components of the thermocyclers may be selected and initially and/or dynamically adjusted to establish, maintain, and/or change the absolute and relative temperatures of the different segments and thus of the associated fluidic tubing and PCR samples. Specifically, the components may be selected and/or adjusted to accomplish a temperature goal by accounting for heat added to or removed from the segments via conduction through other core components (including fluidic tubing and the associated fluid) and/or convection with the environment. In particular, the TECs, where present, may transfer heat to or from the segments to facilitate more rapid and precise control over the associated segment temperatures and thus the associated reaction temperatures.

Figure 82:
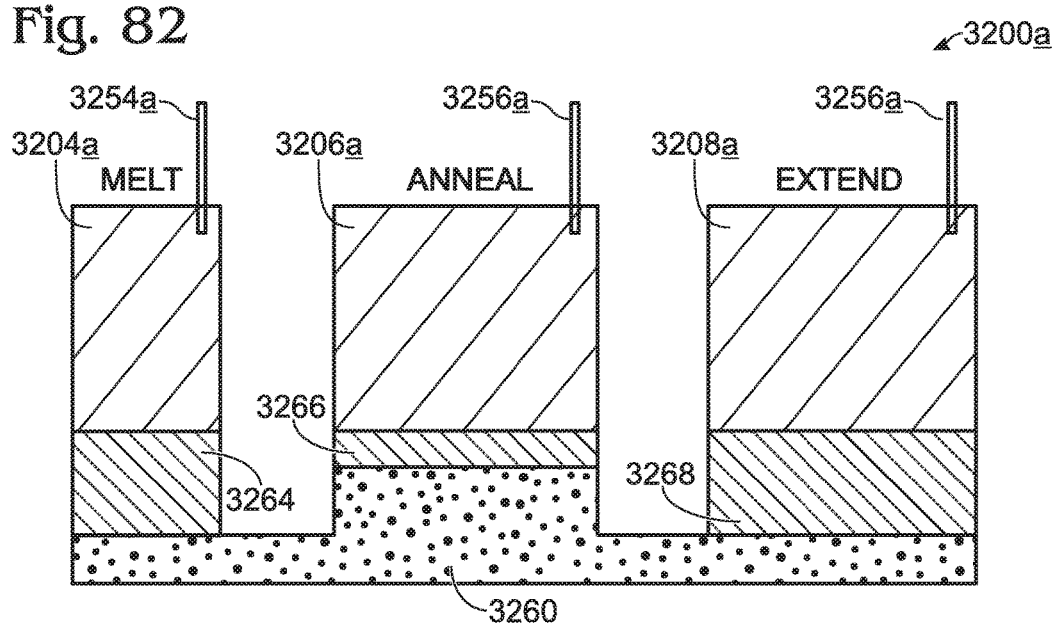

FIG. 82 depicts a first alternative thermocycler 3200*a*. In this embodiment, the melt, anneal, and extend segments 3204*a*, 3206*a*, and 3208*a* are in thermal contact with a common unheated (e.g., plastic block) core 3260 via respective thermal insulating layers 3264, 3266, 3268. The insulating layers (and insulating layers described elsewhere in this Section) independently may be made of the same or different materials, with the same or different dimensions, such that the layers may have the same or different thermal conductivities. For example, in this embodiment, the insulating layers for the melt and extend segments are made of the same material, with the same thickness, whereas the insulating layer for the anneal segment is made of a different material, with a different thickness. Heat for performing PCR is supplied to the segments by heating elements 3254*a*, 3256*a*, 3258*a*. This embodiment is particularly simple to construct, with relatively few, mostly passive components. However, it is not as flexible or responsive as the other pictured embodiments.

Figure 83:
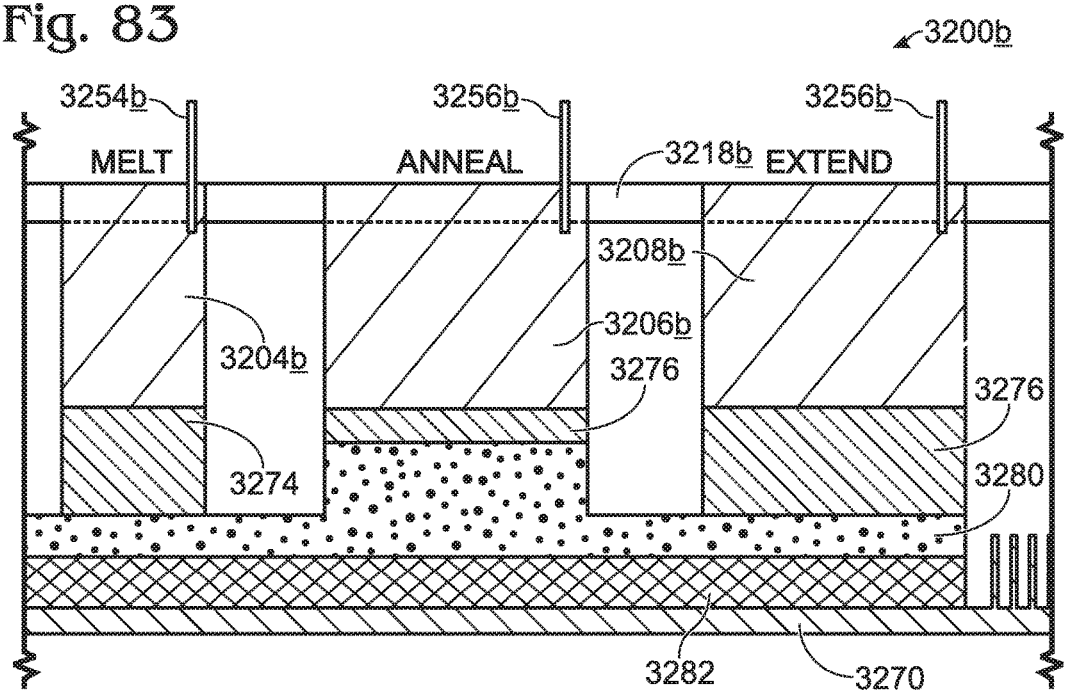

FIG. 83 depicts a second alternative thermocycler 3200*b*. In this embodiment, the melt, anneal, and extend segments 3204*b*, 3206*b*, and 3208*b* are in thermal contact with a common heated (e.g., copper) core 3270. However, disposed between the segments and the core, preventing their direct contact, are respective insulating layers 3274, 3276, 3278 (one for each segment), a common thermal conductor 3280 (in contact with all three insulating layers), and a common TEC 3282 (in contact with the common thermal conductor and with the common heated core). Heat for performing PCR is supplied to the segments by heating elements 3254*b*, 3256*b*, 3258*b* and by the common core. The TEC may be used to transfer heat to and from the inner segments and the heated core, across the intervening insulating and conducting layers, to adjust, up or down, the temperatures of the segments.

FIG. 84 depicts a third alternative thermocycler 3200*c*. In this embodiment, the melt and extend segments 3204*c* and 3208*c* are in thermal contact with a common unheated core 3290 via respective insulating layers 3294, 3298, whereas the anneal segment 3206*c* is in thermal contact with a heated core 3300 via a dedicated intervening TEC 3296. This configuration substantially thermally decouples the anneal segment from the melt and extend segments and allows the temperature of the anneal segment to be changed relatively rapidly via heating element 3256*c*, heated core 3300, and the TEC. The temperatures of the melt and extend segments, which are thermally connected through unheated core 3284, may be changed via heating elements 3254*c*, 3258*c* (to add heat) and conduction to the unheated core (to remove heat).

FIG. 85 depicts a fourth alternative thermocycler 3200*d*. In this embodiment, thermocycler 3200*c* (from FIG. 84) is further coupled to a common heated core 3302 via an intervening TEC 3304, allowing enhanced feedback and control over the temperatures of the melt and extend segments via the TEC layer.

FIG. 86 depicts a fifth alternative thermocycler 3200*e*. In this embodiment, the melt, anneal, and extend segments 3204*e*, 3206*e*, 3208*e* are in thermal contact with a common heated core 3310 via either a dedicated insulating layer 3314, 3318 (in the case of the melt and extend segments) or a dedicated TEC layer 3316 (in the case of the anneal layer). This configuration allows relatively rapid feedback and control over the temperature of the anneal segment via a combination of the heating element 3256*e* and the TEC, while still providing a measure of control over the temperatures of the melt and extend segments via heating elements 3254*e*, 3258*e*.

Figure 87:
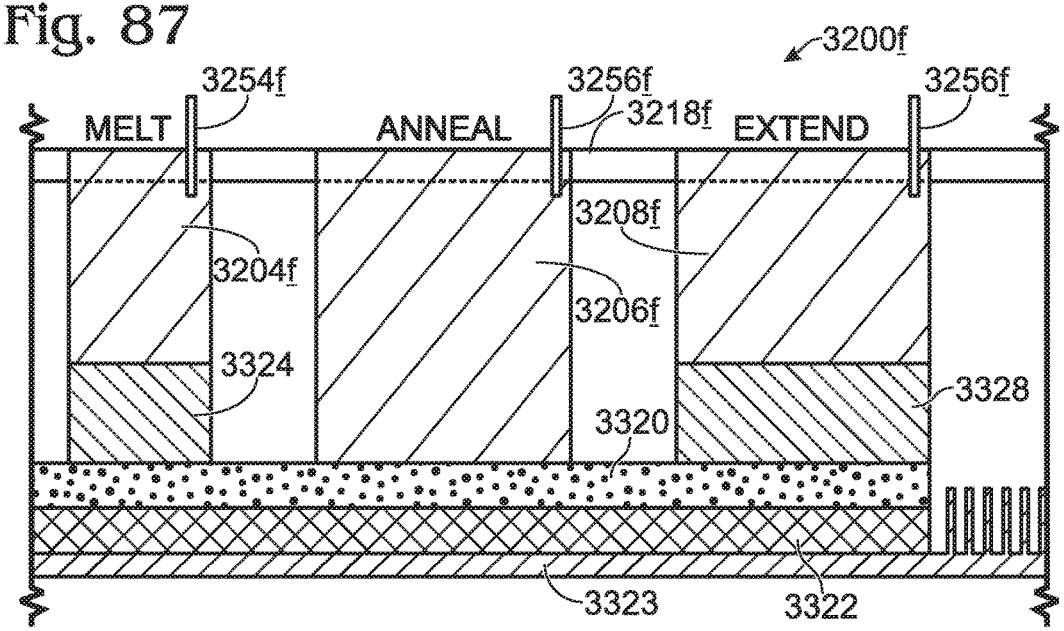

FIG. 87 depicts a sixth alternative thermocycler 3200*f*. In this embodiment, which is similar to thermocycler 3200*e* of FIG. 86, a common conducting layer 3320 and a common TEC 3322 separate the segments from the entirety of a heated thermal core 3323. The TEC is in thermal contact with the anneal segment through the conducting layer, whereas the TEC is separated from the melt and extend segments both by the conducting layer and by dedicated insulating layers 3324, 3328.

Figure 88:
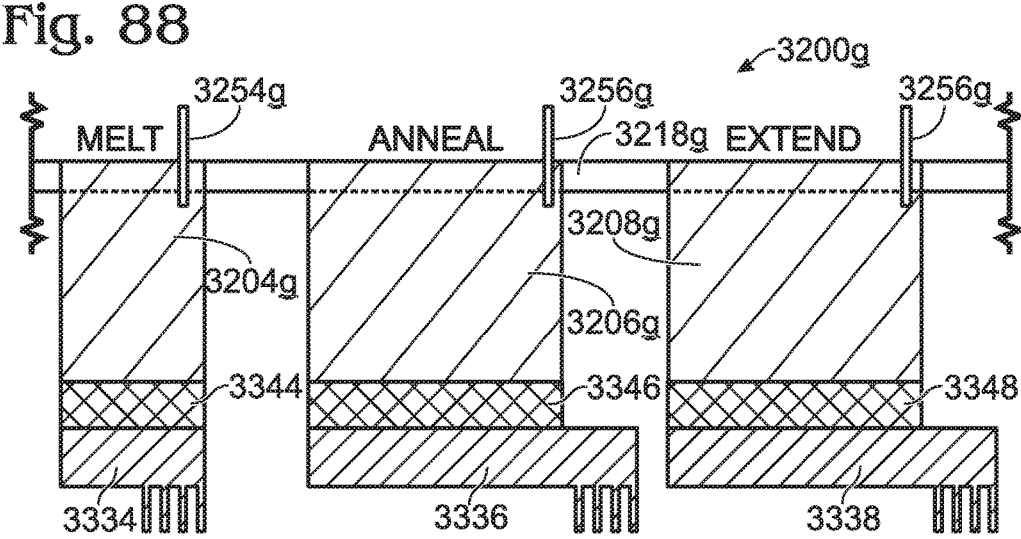

FIG. 88 depicts a seventh alternative thermocycler 3200*g*. In this embodiment, the melt, anneal, and extend segments 3204*g*, 3206*g*, 3208*g* each are in thermal contact with a respective heated core 3334, 3336, 3338 via a dedicated intervening TEC 3344, 3346, 3348 (for a total of three segments, three heated cores, and three TECs). This embodiment provides rapid feedback and separate control over the temperature of each inner segment. In particular, each segment is independently in thermal contact with dedicated heating element and a dedicated heated core, such that heat can be transferred to or from the segment from two dedicated sources or sinks. However, this embodiment also is more complicated, requiring controllers for each TEC.

Figure 89:
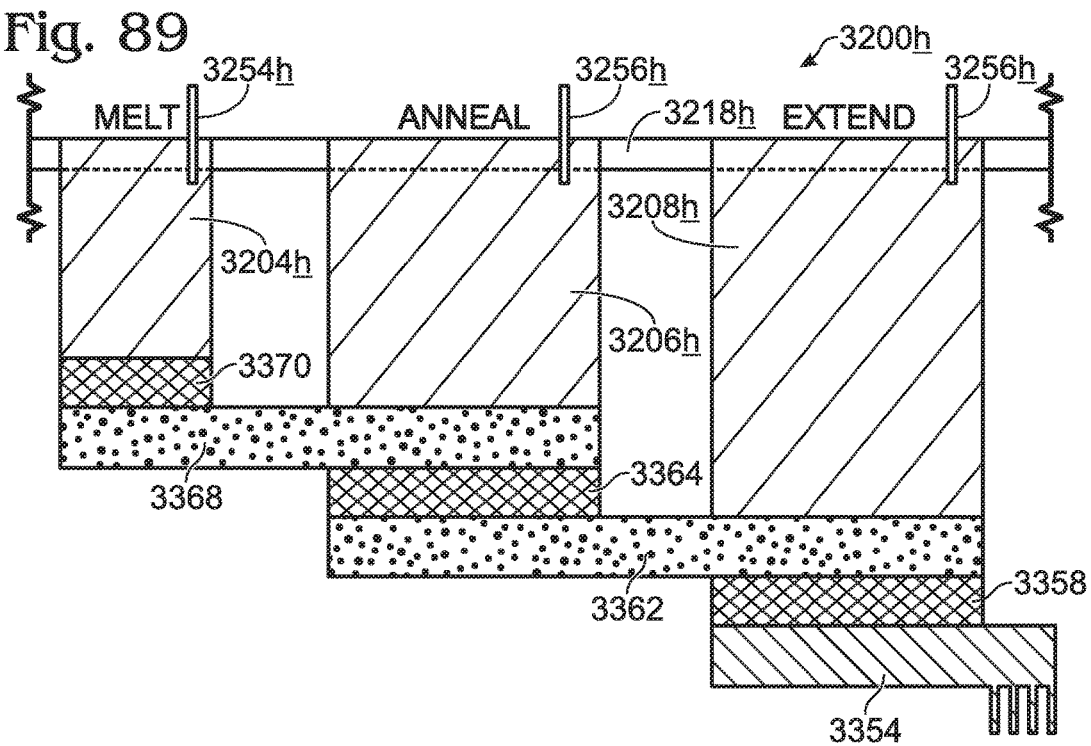

FIG. 89 depicts an eighth alternative thermocycler 3200*h*. In this embodiment, in which a single section of a heated core 3354 is aligned interior to one inner segment (e.g., the extend segment 3208*h*) of the thermocycler, separated from the segment by a TEC 3358. The extend segment, in turn, is in thermal contact with a neighboring inner segment (e.g., the anneal segment 3206*h*) via an unheated conductor 3362, which is separated from the inner segment by a second TEC 3364. The anneal segment, in turn, is in thermal contact with a neighboring inner segment (e.g., melt segment 3204*h*) via another unheated conductor 3368, which is separated from the inner segment by a third TEC 3370. Thus, core section 3354 remains available to all of the TECs as a heat source and heat sink.

D. Selected Embodiments 4

Figure 90:
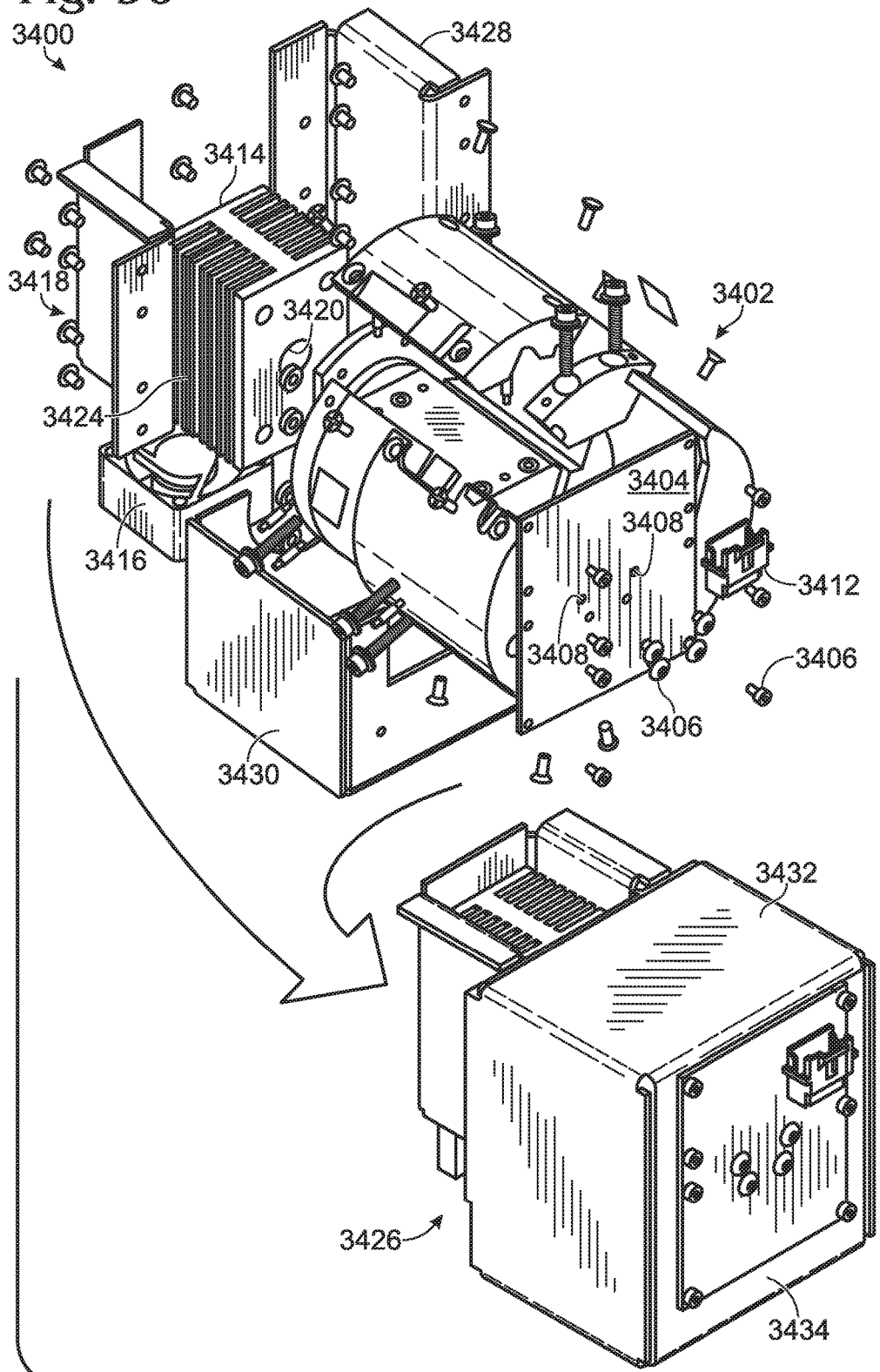
FIG. 90 is an exploded isometric view of a thermocycler, with associated heating, cooling, and housing elements, in accordance with aspects of the present disclosure.

This example describes a thermocycler disposed within an instrument that also includes other components such as a cooling mechanism and a protective housing; see FIG. 90.

FIG. 90 generally depicts an exemplary thermocycling instrument 3400 at various stages of assembly. Instrument 3400 includes a thermocycler, generally indicated at 3402, which is substantially similar to thermocycler 3200 described above, but which generally may take various forms, including one or more features of any of the thermocyclers described in the previous examples. The instrument may include additional components, such as a front plate, connection port, a heat sink, a cooling fan, and/or a housing, as described below.

A front plate 3404 is attached to the thermocycler with a plurality of fasteners 3406 that pass through central apertures 3408 in the front plate and complementary apertures in the thermocycler. The front plate helps to isolate the thermocycler from external air currents and thus to maintain controlled temperature zones within the unit.

A connection port 3412 is attached to the front plate, and is configured to supply power to the instrument and to receive sensor information obtained by the instrument. Thus, the connection port is configured to receive electrical power from outside the instrument and transmit the power to the instrument, and to receive sensor signals from within the instrument and transmit the signals outside the instrument. Transfer of power and sensor signals may be accomplished through suitable connecting wires or cables (not shown) disposed within and outside the instrument.

A heat sink 3414 and a cooling fan 3416, which will be collectively referred to as a cooling mechanism 3418, are shown attached to a side of the thermocycler opposite the front plate. One or both components of cooling mechanism 3418 will generally be mounted to the thermocycler using suitable fasteners such as bolts, pins and/or screws. In FIG. 90, heat sink 3414 is attached directly to the thermocycler, and cooling fan 3416 is attached to the heat sink. Heat sink 3414 includes a central aperture 3420, which is aligned with a central aperture of the thermocycler core that defines a central longitudinal axis (see, e.g., FIGS. 73, 74, and 77). These aligned apertures facilitate heat transfer from the central (axial) portion of thermocycler 3402 into the heat sink. The heat sink also may be formed of a relatively thermally conductive material to facilitate conduction of excess heat away from the thermocycler, and includes convection fins 3424 to facilitate convection of heat away from the thermocycler.

Cooling fan 3416 is configured to blow cooling air through fins 3424 and aperture 3420 of the heat sink, to increase convective heat transfer away from the heat sink. Air from fan 3416 also may flow or be directed through the heat sink and into the central aperture of thermocycler 3402, to provide a convection current within the thermocycler. Dedicated structures such as baffles, angled walls or canted fins (not shown) may be provided to facilitate the transfer of air from the cooling fan into the thermocycler.

Thermocycler 3402 and cooling mechanism 3418 are mounted within an external housing, generally indicated at 3426. Housing 3426 may include several discrete sections 3428, 3430, 3432, 3434, which are configured to conform to various portions of the thermocycler and the cooling mechanism, and which are further configured to fit together and interface with front plate 3404 to form housing 3426. The various discrete sections and the front plate of housing 3426 are collectively configured to insulate the thermocycler from external air currents and other factors that could lead to uncontrolled temperature variations within the thermocycler.

E. Selected Embodiments 5

Figure 91:
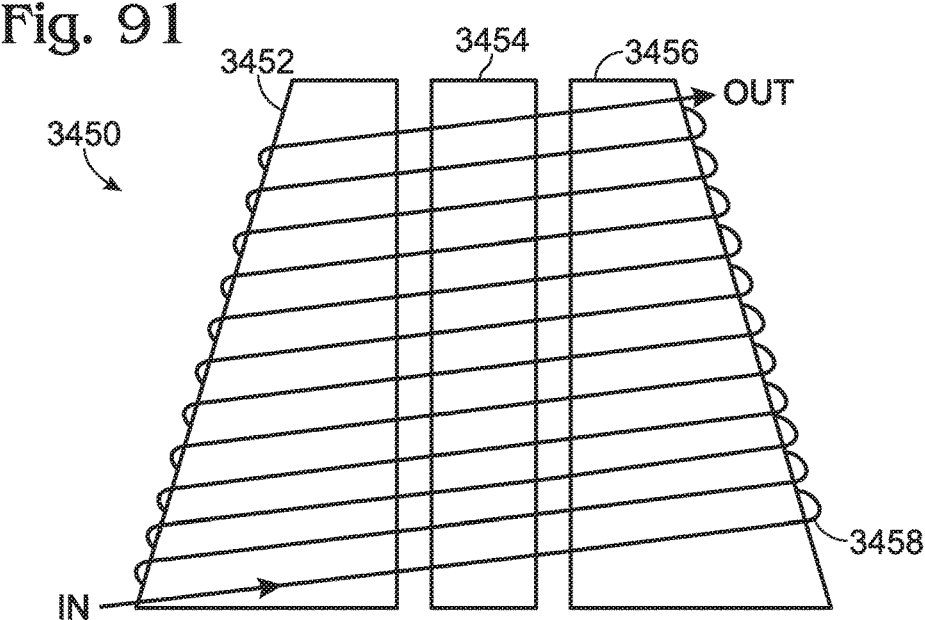
FIG. 91 is a side elevational view of an exemplary thermocycler having temperature regions that vary in size along the length of the thermocycler, in accordance with aspects of the present disclosure.
Figure 92:
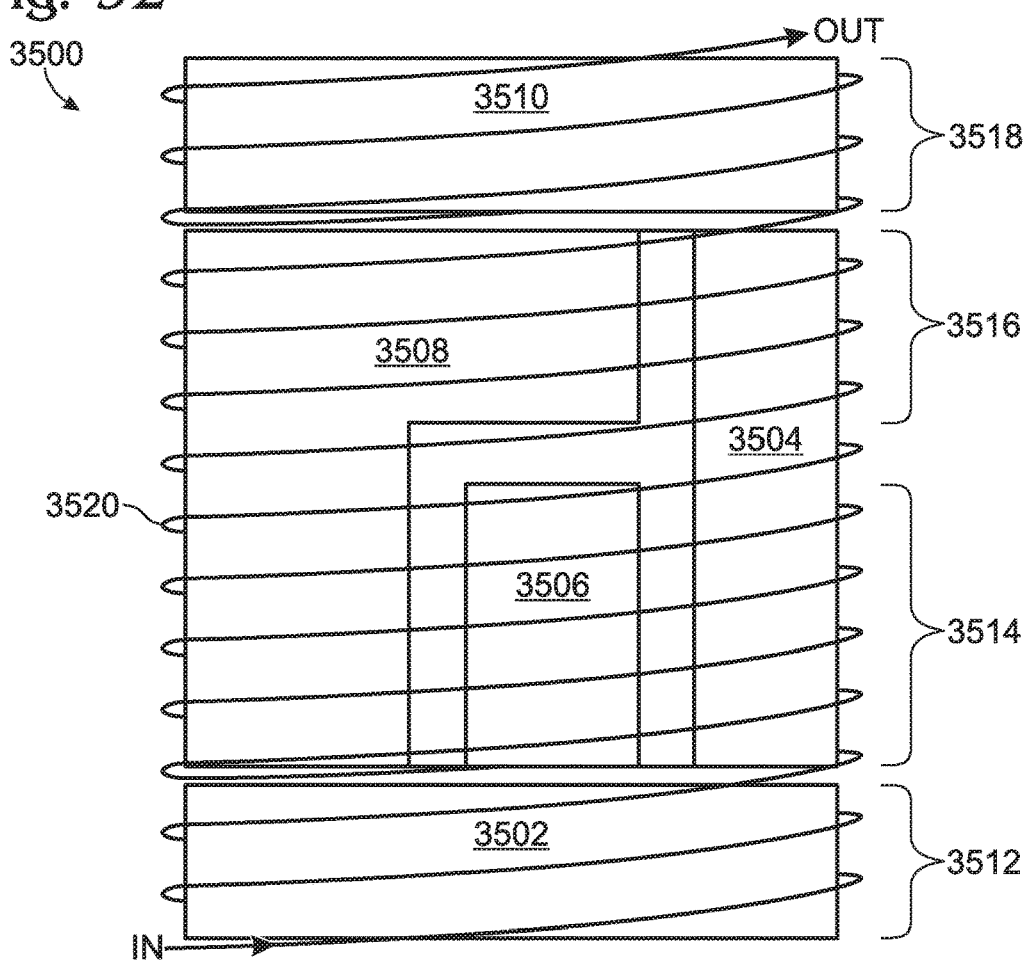
FIG. 92 is a side elevational view of an exemplary thermocycler having temperature regions that vary in number along the length of the thermocycler, in accordance with aspects of the present disclosure.

This example describes exemplary thermocyclers having temperature regions that vary in size and/or number along the length of the thermocycler, in accordance with aspects of the present disclosure; see FIGS. 91-92.

FIG. 91 shows a side elevational view of portions of an exemplary thermocycler, generally indicated at 3450, having three connected segments 3452, 3454, 3456, each defining a different temperature region. Segments 3452, 3454, 3456 may be connected via a common core or through materials (typically thermally insulating materials), not shown, disposed between the segments. Segments 3452, 3454, 3456 are angled along the length of the thermocycler (i.e., along the longitudinal axis), so that the inner segments of thermocycler 3450 collectively form a generally frustoconical shape as FIG. 91 depicts. Accordingly, each winding of fluidic tubing 3458 wrapped around the exterior of thermocycler 3450 will be progressively shorter from top to bottom in FIG. 91, so that the helical path followed by the tubing decreases in length over successive cycles. Assuming fluid flows through tubing 3458 at a uniform speed, fluid within the tubing will therefore spend progressively less time in the temperature regions defined by segments 3452 and 3456. On the other hand, segment 3454 has a substantially constant width, so that fluid flowing through tubing 3458 will spend a substantially constant amount of time in the corresponding temperature region with each successive cycle, again assuming the fluid flows with a uniform speed.

The thermocycler depicted in FIG. 91 may be useful, for example, when it is desirable to begin a thermocycling operation with relatively long time duration cycles, and subsequently to decrease the cycle duration to speed up the overall thermocycling process. In applications such as PCR, this may be the case because efficient target molecule replication becomes increasingly less important with each successive thermocycle. For instance, if a single target molecule fails to replicate during the first cycle and then replicates with perfect efficiency in the subsequent 19 cycles, the result after 20 cycles will be $2^{19}$ target molecules. However, if a single target molecule replicates with perfect efficiency for the first 19 cycles, but one molecule fails to replicate during the twentieth cycle, the result after 20 cycles will be $(2^{20}-1)$ target molecules.

Aside from a frustoconical shape, many other thermocycler configurations can be used to affect the time of passage of a sample fluid through the various temperature regions of a thermocycler. For example, the sizes of various temperature regions may be decreased in discrete steps, by sequentially decreasing the radius of a cylindrical thermocycler in discrete steps. In general, any configuration that results in a changing path length traveled by successive windings of fluidic tubing may be suitable for altering the time a fluid spends at each desired temperature over the course of the entire thermocycling process.

FIG. 92 shows a side elevational view of portions of an exemplary thermocycler, generally indicated at 3500, having temperature regions that vary in number along the length of the thermocycler, in accordance with aspects of the present disclosure. Specifically, thermocycler 3500 includes a plurality of inner segments 3502, 3504, 3506, 3508, 3510 that each may be configured to define a separate temperature region. These segments may be attached to a common core (not shown) or bound together in any suitable manner, and may be separated by air or any other suitable medium, typically a thermally insulating material. The gaps between segments, if any, may have any chosen widths to generate a desired temperature profile in both the longitudinal direction and the tangential direction. As FIG. 92 depicts, the plurality of inner segments includes a different number of inner segments attached to the core at different positions along the longitudinal axis.

Fluid traveling through fluidic tubing 3520 would encounter a first portion 3512 of the thermocycler having just a single temperature region defined by segment 3502. Subsequently, the fluid would encounter a second portion 3514 of the thermocycler having three temperature regions defined by segments 3504, 3506, and 3508. Next, the fluid would encounter a third portion 3516 of the thermocycler having two temperature regions defined by segments 3504, 3508, and finally the fluid would encounter a fourth portion 3518 of the thermocycler having a single temperature region defined by section 3510.

Any desired number of longitudinal portions, instead of or in addition to portions 3512, 3514, 3516 and 3518, may be included in a thermocycler, to alter the number of temperature regions encountered by a fluid as it proceeds through a thermocycling process. Furthermore, any desired number of tangential segments may be included within each longitudinal portion, so that particular windings of fluidic tubing may be configured to encounter essentially any number of temperature regions. By combining the features of thermocycler 3500 with the features of thermocycler 3450 depicted in FIG. 91, a thermocycler can be constructed to provide virtually any temporal temperature profile to a moving fluid, making the disclosed thermocyclers suitable for a wide range of applications.

F. Selected Embodiments 6

This example describes various additional aspects and possible variations of a thermocycler, in accordance with aspects of the present disclosure.

Whereas thermocyclers are primarily described above as including a single "strand" of fluidic tubing wrapped substantially helically around the circumference of heated sections of the thermocycler, many variations are possible. For example, more than one strand of tubing may be provided, and the various strands all may be wrapped around a portion of the thermocycler. In some cases, the strands may be braided in some fashion so that they cross each other repeatedly, whereas in other cases the strands all may be configured to directly contact the heated thermocycler sections for substantially the entirety of their wrapped length. In addition, one or more tubes may be configured to pass through the heated sections of a thermocycler, rather than wrapped around their exteriors. For instance, the heated sections may be cast, molded, or otherwise formed around the tubes. In some cases, fluid tight channels may be formed in this manner, so that tubes are not necessary.

In some cases it may be desirable to vary the number of thermocycles provided by a thermocycling instrument, either dynamically or by providing several varying options for the number of cycles a particular fluid will encounter. Dynamic changes in the number of thermocycles may be provided, for example, by unwinding or additionally winding the fluidic tubing around the thermocycler. Optional numbers of cycles may be provided, for example, by providing multiple fluidic tubes that are wound a different number of times around the instrument, or by creating various optional bypass mechanisms (such as bypass tubes with valves) to selectively add or remove cycles for a particular fluid.

Although the heated segments of the thermocyclers described above are generally shown separated from each other by thermally insulating air gaps, any desired thermally insulating material may be placed between the heated segments of a thermocycler according to the present disclosure. For example, the use of a low-density polymer or a silica aerogel may provide increased thermal isolation of neighboring segments, both by reducing the thermal conductivity of the insulating regions and by decreasing convective heat transfer.

The disclosed thermocyclers may be used for PCR, any other molecular amplification process, or indeed any process involving cyclical temperature changes of a fluid sample, whether or not the sample includes discrete droplets. For example, potentially target-containing samples may be separated into discrete units other than droplets, such as by binding sample molecules to a carrier such as a suitable bead or pellet. These alternative carriers may be placed in a background fluid and thermocycled in much the same way as droplets in an emulsion. Alternatively, a plurality of thermocyclers may be used simultaneously to cycle different bulk fluid samples in parallel or in an overlapping sequence, without separating the fluid samples into many discrete units.

G. Selected Embodiments 7

This example describes additional aspects of a thermocycler, in accordance with aspects of the present disclosure, presented without limitation as a series of numbered sentences.

1. A method of thermocycling a sample-containing fluid to promote target molecule amplification, comprising (A) transferring an emulsion of sample-containing droplets into a thermocycling instrument; (B) providing a denaturing temperature to the emulsion; (C) providing a primer annealing temperature to the emulsion; and (D) providing a polymerase extension temperature to the emulsion; wherein providing the denaturing temperature, the primer annealing temperature, and the polymerase extension temperature respectively include transporting the emulsion in a substantially helical path cyclically through a denaturing temperature region, a primer annealing temperature region, and a polymerase extension temperature region.

2. The method of paragraph 1, further comprising providing a hot-start temperature to the emulsion, prior to providing the denaturing temperature to the emulsion, by transporting the emulsion in a substantially helical path through a hot-start temperature region.

3. The method of paragraph 1, wherein the temperatures are provided through the use of thermoelectric coolers configured to transfer heat between a thermal core and the temperature regions.

4. The method of paragraph 1, wherein the helical path decreases in length over successive cycles.

5. A thermocycling system configured to promote molecular amplification, comprising (A) a core defining a central longitudinal axis; (B) a plurality of inner segments attached to the core and defining a plurality of temperature regions; (C) a plurality of heating elements configured to maintain each temperature region approximately at a different desired temperature; and (D) a fluid channel configured to transport an emulsion of sample-containing droplets cyclically through the temperature regions.

6. The system of paragraph 5, further comprising a plurality of outer segments attached to the inner segments, and wherein the fluid channel is disposed between the inner and outer segments.

7. The system of paragraph 5, wherein the fluid channel is configured to transport the emulsion in a substantially helical path.

8. The system of paragraph 5, wherein the fluid channel includes fluidic tubing wrapped around the inner segments.

9. The system of paragraph 8, wherein the fluidic tubing is disposed in grooves of the inner segments that define a substantially helical path around the inner segments.

10. The system of paragraph 5, wherein the fluid channel is disposed within the inner segments.

11. The system of paragraph 5, wherein the inner segments include external grooves, and wherein the fluid channel is defined by the grooves and by a fluid tight sheet wrapped around the inner segments.

12. The system of paragraph 5, wherein the core is configured as a heat source and as a heat sink, and wherein the heating elements include at least one thermoelectric cooler disposed between one of the inner segments and the core.

13. The system of paragraph 12, wherein at least one independently controllable thermoelectric cooler is disposed between each of the inner segments and the core.

14. The system of paragraph 12, wherein the core is maintained at an operating temperature that falls between two of the desired temperatures.

15. The system of paragraph 12, wherein the at least one thermoelectric cooler is disposed between a pair of thermally conductive and mechanically compliant pads.

16. The system of paragraph 5, wherein the core is unheated, and further comprising a thermal insulating layer disposed between the core and each inner segment.

17. The system of paragraph 5, wherein the core includes a plurality of core sections, each independently in thermal contact with one of the inner segments.

18. The system of paragraph 5, wherein at least a portion of each inner segment is angled along the longitudinal axis so that the inner segments collectively form an approximately frustoconical shape.

19. The system of paragraph 5, wherein the plurality of inner segments includes a different number of inner segments attached to the core at different positions along the longitudinal axis.

20. A thermocycling instrument configured to promote molecular amplification, comprising (A) a core including a central aperture defining a central longitudinal axis; (B) a plurality of inner segments attached to the core and defining a plurality of temperature regions; (C) a plurality of heating elements configured to maintain each temperature region approximately at a different desired temperature; (D) a fluid channel configured to transport an emulsion of sample-containing droplets cyclically through the temperature regions; and (E) a thermally conductive heat sink including a central aperture aligned with the central aperture of the core.

21. The instrument of paragraph 20, further comprising a cooling fan configured to blow air through the central aperture of the heat sink and the central aperture of the core.

22. An apparatus for performing reactions in droplets, comprising (A) a droplet generator that produces droplets disposed in an immiscible carrier fluid; (B) a heater assembly comprising at least two temperature-controlled zones maintained at respective distinct temperatures (C) a coiled tube that receives droplets from the droplet generator and that traverses the temperature-controlled zones serially and repeatedly; and (D) a pump that drives travel of droplets through the coiled tube such that the droplets are cyclically heated and cooled by the temperature-controlled zones.

23. The apparatus of paragraph 22, wherein the distinct temperature of at least one of the temperature-controlled zones is regulated by a thermoelectric cooler.

24. The apparatus of paragraph 22, further comprising a controller in communication with the thermoelectric cooler and programmed to actively adjust electrical power supplied to the thermoelectric cooler to maintain a set point temperature of at least one of the temperature-controlled zones under varying thermal loads.

25. The apparatus of paragraph 22, wherein a pair of the temperature-controlled zones are thermally coupled to each other by a thermoelectric cooler.

26. The apparatus of paragraph 4, wherein the thermoelectric cooler is disposed between the pair of temperature-controlled zones.

27. The apparatus of paragraph 22, wherein the heater assembly includes a thermally conductive core, and wherein each of the temperature-controlled zones includes a conductive segment disposed at least generally radially from the thermally conductive core.

28. The apparatus of paragraph 22, wherein the distinct temperature of each member of a pair of the temperature-controlled zones is regulated by a respective thermoelectric cooler, and wherein the heater assembly includes a thermally conductive core that is connected to the respective thermoelectric coolers and is maintained at a temperature intermediate to the distinct temperatures of the pair of temperature-controlled zones.

29. The apparatus of paragraph 22, wherein the tube wraps around the heater assembly a plurality of times.

30. The apparatus of paragraph 22, wherein the heater assembly includes a thermally conductive core and a heating element coupled to the thermally conductive core.

31. The apparatus of paragraph 22, wherein the heater assembly comprises at least three temperature-controlled zones maintained at three or more respective distinct temperatures, wherein the coiled tube comprises a plurality of coils, and wherein each coil thermally couples to each of the at least three temperature-controlled zones.

32. The apparatus of paragraph 31, wherein two or more coils of the coiled tube thermally couple to a same temperature-controlled zone at a same range of angular positions on each of the coils.

33. The apparatus of paragraph 22, further comprising one or more other discrete, coiled tubes that traverse the temperature-controlled zones serially and repeatedly.

34. The apparatus of paragraph 33, wherein the at least one other coiled tube is interspersed with the coiled tube.

35. The apparatus of paragraph 22, further comprising at least one thermally controlled incubation region maintained at a predefined incubation temperature, the incubation region being located upstream from the temperature-controlled zones thereby causing a temperature of droplets flowing through the tube to at least substantially reach the incubation temperature prior to being heated and cooled cyclically by the temperature-controlled zones.

36. The apparatus of paragraph 35, wherein heat for the incubation region is supplied by a heater or a thermoelectric cooler.

37. An apparatus for performing reactions in droplets, comprising (A) a heater assembly comprising at least two temperature-controlled zones maintained at respective distinct temperatures, a temperature of at least one of the temperature-controlled zones being regulated by a thermoelectric cooler; (B) a coiled tube that traverses the temperature zones serially and repeatedly; and (C) a pump that drives fluid flow through the coiled tube such that the fluid is cyclically heated and cooled by the temperature-controlled zones.

38. The apparatus of paragraph 37, wherein a pair of the temperature-controlled zones are thermally coupled to each other by the thermoelectric cooler.

39. The apparatus of paragraph 38, wherein the thermoelectric cooler is disposed between the pair of temperature-controlled zones.

40. The apparatus of paragraph 37, wherein the heater assembly includes a thermally conductive core, and wherein each of the temperature-controlled zones includes a conductive segment disposed at least generally radially from the thermally conductive core.

41. The apparatus of paragraph 37, wherein the distinct temperature of each member of a pair of the temperature-controlled zones is regulated by a respective thermoelectric cooler, and wherein the heater assembly includes a thermally conductive core that is connected to each of the respective thermoelectric coolers and is maintained at a temperature intermediate to the distinct temperatures of the pair of temperature-controlled zones.

42. The apparatus of paragraph 37, wherein the tube wraps around the heater assembly a plurality of times.

43. The apparatus of paragraph 42, wherein the heater assembly includes a thermally conductive core and a heating element coupled to the thermally conductive core.

44. The apparatus of paragraph 37, wherein the heater assembly comprises at least three temperature-controlled zones maintained at three or more respective distinct temperatures, wherein the coiled tube forms a plurality of coils, and wherein each coil thermally couples to each of the at least three temperature-controlled zones.

45. The apparatus of paragraph 44, wherein two or more coils of the coiled tube thermally couple to a same temperature-controlled zone at a same range of angular positions on each of the coils.

46. The apparatus of paragraph 37, further comprising one or more other discrete, coiled tubes that traverse the temperature-controlled zones serially and repeatedly.

47. The apparatus of paragraph 37, further comprising at least one thermally controlled incubation region maintained at a predefined incubation temperature, the incubation region being located upstream from the temperature-controlled zones thereby causing a temperature of droplets flowing through the tube to at least substantially reach the incubation temperature prior to being heated and cooled cyclically by the temperature-controlled zones.

48. The apparatus of paragraph 47, wherein heat for the incubation region is supplied by a heater or a thermoelectric cooler.

49. A method of nucleic acid analysis, comprising (A) generating droplets disposed in an immiscible carrier fluid, each droplet including a partition of a sample disposed in an amplification reaction capable of amplifying a nucleic acid target, if present in the droplet; (B) driving the droplets through a coiled tube that traverses two or more temperature-controlled zones serially and repeatedly, to thermally cycle the droplets under conditions promoting amplification of the nucleic acid target; (C) detecting one or more signals from one or more of the droplets; and (D) determining a presence of the nucleic acid target in the sample based on the signals.

50. A thermocycling apparatus comprising a coiled tube traversing a plurality of temperature controlled regions in at least one substantially helical winding, each of the regions including at least a first zone maintained at a first temperature and a second zone maintained at a second temperature thereby causing the temperature of one or more droplets in an immiscible carrier fluid flowing through the tube to cycle between the first and the second temperatures.

51. The apparatus of paragraph 50, wherein the plurality of regions includes between two and fifty regions.

52. The apparatus of paragraph 50, wherein the temperature of at least one of the temperature controlled zones is regulated by a thermoelectric controller.

53. The apparatus of paragraph 52, wherein at least two temperature controlled zones are separated by a thermoelectric controller.

54. The apparatus of paragraph 50, wherein the temperature of the first temperature controlled zone is regulated by a first thermoelectric controller and the temperature of the second temperature controlled zones is regulated by a second thermoelectric controller.

55. The apparatus of paragraph 53, wherein the first and second thermoelectric controllers are connected to a common conductor, and wherein the common conductor is maintained at a temperature intermediate to the first and second zone temperatures.

56. The apparatus of paragraph 50, wherein the droplets include at least one of water, salt, DNA, RNA, proteins, prions, fluorescent dyes, probes, primers, surfactants sample, and nucleotides.

57. The apparatus of paragraph 50, wherein the immiscible carrier fluid includes at least one of vegetable oil, fluorocarbon oil, mineral oil, and surfactants.

58. The apparatus of paragraph 50, wherein the coiled tube comprises a plurality of loops, and wherein the first and the second temperature controlled zones extend across at least two of the loops, thereby causing the temperature of fluid flowing through the tube to cycle between the first and the second cycling temperatures at the same relative angular position on each of the loops.

59. The apparatus of paragraph 58, wherein each winding comprises a plurality of separately controlled temperature controlled regions and the temperature of any of the first and second zones of any member of the plurality of regions can be maintained at the same temperature thereby allowing the angular section of the winding regulated at the first temperature and the angular section of the winding regulated at the second temperature to be set to independent predetermined values.

60. The apparatus of paragraph 50, wherein the coiled tube further comprises at least one thermally controlled incubation region maintained at a predefined incubation temperature, the incubation region located upstream from the temperature controlled regions thereby causing the temperature of the fluid flowing through the tube to reach the incubation temperature prior to entering the cycling regions.

61. The apparatus of paragraph 60, wherein the heat for the incubation region is supplied by either a thermoelectric controller or a resistive heater.

62. The apparatus of paragraph 50, wherein the heat to maintain the temperatures of the temperature controlled regions is provided by at least one of conduction, convection, radiation, electric heaters, circulating liquid heaters, air blowers, incandescent light sources, lasers, LEDs, and microwaves.

63. The apparatus of paragraph 52, wherein the thermoelectric controller is actively adjusted to maintain a substantially constant temperature under varying thermal loads caused by changes in advective heat flux, including at least one of the following changes: turning fluid flow on and off within the tube, changing flow rate of a fluid within the tube, alternating oil and droplet packets within the tube, receiving a plug of cleaning solution within the tube, a change in density of fluid within the tube, a change in heat capacity of fluid within the tube, a change in thermal conductivity of fluid within the tube, and a change in thermal diffusivity of fluid within the tube.

64. An apparatus for performing a continuous-flow reaction, comprising (A) at least one capillary tube having a first open end for fluid inlet and a second open end for fluid outlet to permit a continuous flow; and (B) at least two solid heating blocks, wherein the temperature of at least one heating block is controlled by a thermoelectric controller.

65. The apparatus of paragraph 64 wherein at least one heating block is controlled by a resistive heater.

66. The apparatus of paragraph 64 wherein the heating blocks are in direct contact with each other.

67. The apparatus of paragraph 64 wherein the heating blocks are maintained at different temperatures.

68. The apparatus of paragraph 64 wherein the apparatus comprises three heating blocks, wherein a first heating block is maintained at a temperature between 85 and 99° C., a second heating block is maintained at a temperature between 50 and 65° C., and a third heating block is maintained at a temperature between 60 and 80° C.

69. The apparatus of paragraph 64 wherein the capillary tube is looped around the heating blocks.

70. The apparatus of paragraph 64 wherein the capillary tube contacts the heating blocks sequentially and repetitively.

71. The apparatus of paragraph 64 wherein the capillary tube contacts each heating block at least 20 times.

72. An apparatus for performing a continuous-flow reaction, comprising (A) at least one capillary tube having a first open end for fluid inlet and a second open end for fluid outlet to permit a continuous flow; and (B) at least two solid heating blocks, wherein at least one heating block is resistively heated and the capillary tube is looped around the heating blocks.

73. An apparatus for performing high-throughput nucleic acid amplification, comprising (A) a microdroplet generator comprising an orifice, wherein the orifice connects a sample flow pathway to a tube comprising an immiscible fluid; (B) at least one capillary tube having a first open end for fluid inlet and a second open end for fluid outlet to permit a continuous flow; and (C) a thermal cycling device, wherein the device has a plurality of fixed heating blocks, wherein the capillary tube is looped around the heating blocks and contacts the heating blocks sequentially.

VI. DETECTION

This Section describes exemplary detection systems, for example, for detecting sample-containing droplets. The systems may involve sensing or detecting the droplets themselves and/or contents of the droplets. The detection of droplets themselves may include determining the presence or absence of a droplet (or a plurality of droplets) and/or a characteristic(s) of the droplet, such as its size (e.g., radius or volume), shape, type, and/or aggregation state, among others. The detection of the contents of droplets may include determining the nature of the contents (e.g., whether or not the droplet contains a sample(s)) and/or a characteristic of the contents (e.g., whether or not the contents have undergone a reaction, such as PCR, the extent of any such reaction, etc.).

The detection of droplets and their contents, if both are detected, may be performed independently or coordinately, in any suitable order. For example, the detection may be performed serially (one droplet at a time), in parallel, in batch, and so forth.

The detection of droplets and their contents may be performed using any technique(s) or mechanism(s) capable of yielding, or being processed to yield, the desired information. These mechanisms may include optical techniques (e.g., absorbance, transmission, reflection, scattering, birefringence, dichroism, fluorescence, phosphorescence, etc.), electrical techniques (e.g., capacitance), and/or acoustic techniques (e.g., ultrasound), among others. The fluorescence techniques, in turn, may include fluorescence intensity, fluorescence polarization (or fluorescence anisotropy) (FP), fluorescence correlation spectroscopy (FCS), fluorescence recovery after photobleaching (FRAP), total internal reflection fluorescence (TIRF), fluorescence resonance energy transfer (FRET), fluorescence lifetime, and/or fluorescence imaging, among others.

The remainder of this Section describes exemplary detection systems, including droplet sensors and reaction sensors. In these exemplary systems, the droplet sensor may generate and detect scattered light, and the reaction sensor may generate and detect fluorescence, among other approaches. These systems are described, for convenience, in the context of a PCR reaction; however, the techniques apply more generally to any reaction, such as a biochemical reaction, capable of generating, or being modified to generate, a detectable signal.

In an exemplary PCR assay (or other nucleic acid amplification assay), the sample is first combined with reagents in a droplet, and the droplet is then thermocycled to induce PCR. It may then be desirable to measure the fluorescence of the droplets to determine which, if any, contained one or more target nucleotide sequences. This generally involves illuminating the droplets with radiation at a wavelength chosen to induce fluorescence, or a change in a characteristic of the fluorescence, from one or more fluorescent probes associated with the amplified PCR target sequence(s). For example, in an exemplary fluorescence intensity assay, if a relatively large intensity of fluorescence is detected, this indicates that PCR amplification of the target nucleotide occurred in the droplet, and thus that the target was present in that portion of the sample. Conversely, if no fluorescence or a relatively small intensity of fluorescence is detected, this indicates that PCR amplification of the target nucleotide did not occur in the droplet, and thus that a target was likely not present in that portion of the sample. In other fluorescence-based embodiments, the extent of reaction could be determined from a decrease in fluorescence intensity, instead of a decrease, and/or a change in one or more other fluorescence parameters, including polarization, energy transfer, and/or lifetime, among others.

The following examples describe specific exemplary detection systems, in accordance with aspects of the invention. Additional pertinent disclosure may be found in the U.S. provisional patent applications listed above under Cross-References and incorporated herein by reference, particularly Ser. No. 61/277,203, filed Sep. 21, 2009.

A. Example 1: Detection System 1

This example describes an optical detection system based on measuring the end-point fluorescence signal of each sample/reagent droplet after a PCR amplification process is complete. The exemplary system is suitable for making both qualitative and quantitative measurements; see FIGS. 93 and 94.

Figure 93:
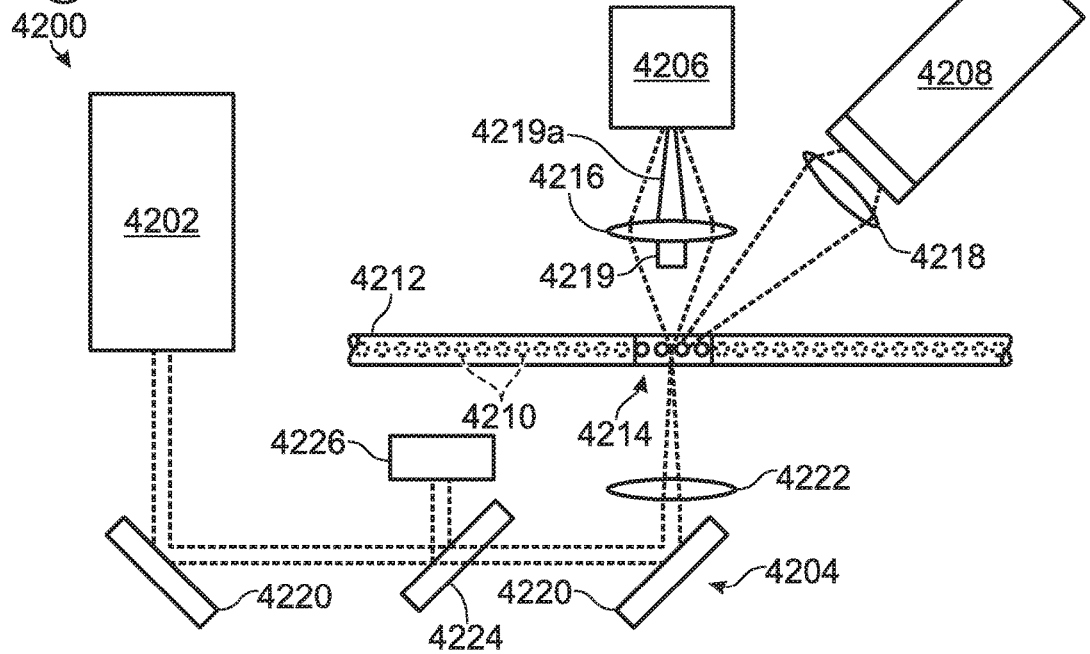
FIG. 93 is a schematic depiction of an optical detection system for irradiating sample-containing droplets and detecting fluorescence subsequently emitted by the droplets, in accordance with aspects of the present disclosure.

FIG. 93 depicts a cytometry-type optical detection system, generally indicated at 4200. The term "cytometry" refers to the fact that the detection system is configured to detect both scattered and fluorescence radiation. Detection system 4200 includes a radiation source 4202, transmission optics generally indicated at 4204, a forward scatter detector 4206, and a fluorescence detector 4208. The forward scatter detector may be replaced or augmented, in some embodiments, by side and/or back scatter detectors, among others, configured to detect light detected to the side or back of the sample, respectively. Similarly, the fluorescence detector may be replaced or augmented, in some embodiments, by an epi-fluorescence detector, among others, configured to detect fluorescence emitted anti-parallel to the excitation light (e.g., back toward transmission optics 4204 (which could, in such embodiments, include a dichroic or multi-dichroic beam splitter and suitable excitation and emission filters)).

Sample-containing droplets 4210, which have already undergone at least some degree of PCR thermocycling, are transferred through a capillary tube or other similar fluid channel 4212, which intersects the path of radiation from radiation source 4202 at an intersection region generally indicated at 4214. An optical element 4216, such as a converging lens, may be placed between intersection region 4214 and forward scatter detector 4206, to focus scattered radiation on the scatter detector. Similarly, an optical element 4218 may be placed between intersection region 4214 and fluorescence detector 4208, to focus fluorescence radiation on the fluorescence detector. The system may include an obscuration bar 4219, operatively positioned between the sample and detector, which reduces the amount of direct (unscattered) excitation radiation (light) that falls on the detector. The obscuration bar, shown here as a small square object in front of optical element 4216, may create a triangular-shaped shadow 4219a behind the optical element. This arrangement makes it easier for detector 4206 to detect changes in index of refraction that have scattered (at small angles) the normal beam.

Radiation from source 4202 may be partially scattered when it encounters a droplet, and the scattered radiation may be used to determine one or more properties of the droplet. For example, scattered radiation indicating the presence of a droplet in intersection region 4214 may be sensed by scatter detector 4206, and this information may be used to activate fluorescence detector 4208, which may otherwise remain deactivated (i.e., when a droplet is not present in the intersection region) to conserve power within the system. Even if the fluorescence detector remains continuously active, detecting the presence of a droplet may be useful for other purposes. For example, tracking the droplets passing through intersection region 4214 may be desirable because some droplets passing through the intersection region may not be detected by the fluorescence detector (e.g., if the droplets do not contain reaction product). In addition, tracking the droplets may allow background noise (i.e., the signal received by the detector in the absence of a droplet) to be removed, improving the signal-to-noise ratio. Furthermore, as described below, various properties of a detected droplet may be estimated from data sensed by forward or side scatter detector 4206.

Radiation detected by scatter detector 4206 may be used to infer the size (or other properties) of a detected droplet. Specifically, a measurement of the duration of a scattering event representing the presence of a droplet within intersection region 4214, in conjunction with knowledge of the average speed of droplet passage through the intersection region, can be used to determine the width of the droplet in a plane normal to the direction of the incident radiation from source 4202. If this width is less than the diameter of channel 4214, then it can be inferred that the droplet is an approximate sphere with a diameter less than the diameter of channel 4214, and the volume of the droplet can be calculated. If, on the other hand, the width of the droplet exceeds the diameter of channel 4214, this indicates that the droplet is likely contacting the walls of the channel and is not spherical. However, the droplet volume still may be estimated by modeling the droplet as a cylinder or other similar shape passing through the channel. As described below, a determination of droplet volume may be useful for normalizing the results of any corresponding fluorescence detection.

In some cases, radiation from source 4202 also may be scattered from intersection region 4214 even if it does not encounter a droplet, for instance, if it encounters a partially reflective surface such as a fluid interface or a wall of fluid channel 4212. This type of scattered radiation will generally have a different signature than radiation scattered from a droplet, so that it generally serves merely as a background for droplet scattering events. Whether scattering occurs in the absence of a droplet depends on the particular configuration of system 4200, as will be described below. Similarly, scattering may occur when droplets outside a desired size range pass through the intersection region, and the signature of radiation scattered from such droplets may be used to affect the subsequent treatment of such droplets. For example, the fluorescence signals received from unusually small or large droplets may be removed from a statistical sample, to increase statistical accuracy. In any case, after passing through intersection region 4214, scattered and/or unscattered radiation from radiation source 4202 is directed toward forward scatter detector 4206.

Radiation from source 4202 that is absorbed by droplets within intersection region 4214 may stimulate the emission of fluorescence radiation that can be detected by fluorescence detector 4208. More specifically, radiation intersecting a droplet may excite a fluorescent probe, such as a TAQMAN probe, that is configured to fluoresce significantly only if the fluorescent portion of the probe becomes separated from a quencher molecule. This separation, or cleaving, typically occurs only when polymerase replicates a sequence to which the probe is bound. In other words, a probe will fluoresce significantly only in droplets within which a target nucleotide sequence has been amplified through PCR. Accordingly, radiation source 4202 will generally be configured to emit radiation at a wavelength that stimulates fluorescent emission from one or more probes known to be present in the sample, and fluorescence detector 4208 will be configured to detect such stimulated radiation.

Radiation source 4202 may take any form suitable for transmitting radiation at one or more desired wavelengths or wavelength bands. For example, radiation source 4202 may be a laser, such as a diode laser, emitting substantially monochromatic light at a wavelength of 488 nanometers (nm) or at some other desired wavelength. Radiation source 4202 also may include multiple separate lasers, emitting light at either a single wavelength or at multiple different wavelengths. One or more (or all) of the lasers of radiation source 4202 may be replaced by an alternate source of light, such as a light-emitting diode (LED) configured to emit a directed beam of radiation at one or more desired wavelengths. In yet other embodiments, white light illumination, for example, from a Halogen lamp, may also be used to provide the radiation source.

Transmission optics 4204 may include any optical components suitable for directing, focusing, or otherwise desirably affecting radiation from source 4202. For example, as depicted in FIG. 93, the transmission optics may include one or more steering mirrors 4220, each configured to direct incident radiation in a desired direction such as toward another optical component or toward intersection region 4214. Also as depicted in FIG. 93, the transmission optics may include a converging lens 4222, which is configured to focus radiation from source 4202 onto intersection region 4214 to maximize scattering and fluorescence caused by the radiation. The transmission optics may further include additional components such as aperture stops, filters, diverging lenses, shaped mirrors, and the like, to affect the transmission path and/or properties of the radiation from source 4202 before it arrives at intersection region 4214. In addition, the transmission optics further may include (in this and other embodiments) a mechanism for monitoring properties of the incident (excitation) radiation. For example, the transmission optics may include a partial mirror 4224 for reflecting a portion of the incident radiation to a detector 4226, such as a photodiode, for monitoring the intensity of the incident light. This would allow correction of the detected scattering and fluorescence for changes that simply reflect changes in the intensity of the incident light.

Forward scatter detector 4206 is configured to receive and detect radiation scattered from droplets passing through intersection region 4214, as described previously. Various types of detectors may be suitable, depending on the desired cost and/or sensitivity of the detector. In approximate order of decreasing sensitivity, exemplary types of scatter detectors that may be suitable include photodiodes, avalanche photodiodes, multi-pixel photon counters, and photomultiplier tubes. The presence of optical element 4216, which typically will be a converging lens used to refocus scattered radiation toward scatter detector 4206, may decrease the necessary sensitivity of the forward scatter detector for a given application, by increasing the intensity per unit area of scattered radiation incident on the detector.

Fluorescence detector 4208 is configured to receive and detect fluorescence radiation emitted by droplets at or near the time they pass through intersection region 4214. Various types of fluorescence detectors may be suitable, depending on factors such as desired cost and/or sensitivity, including photodiodes, avalanche photodiodes, multi-pixel photon counters, and photomultiplier tubes. Also as in the case of the forward scatter, utilizing an optical element 4218, typically a converging lens, between intersection region 4214 and fluorescence detector 4208 may decrease the necessary sensitivity of the fluorescence detector by increasing the intensity per unit area of fluorescence radiation incident on the detector.

Figure 94:
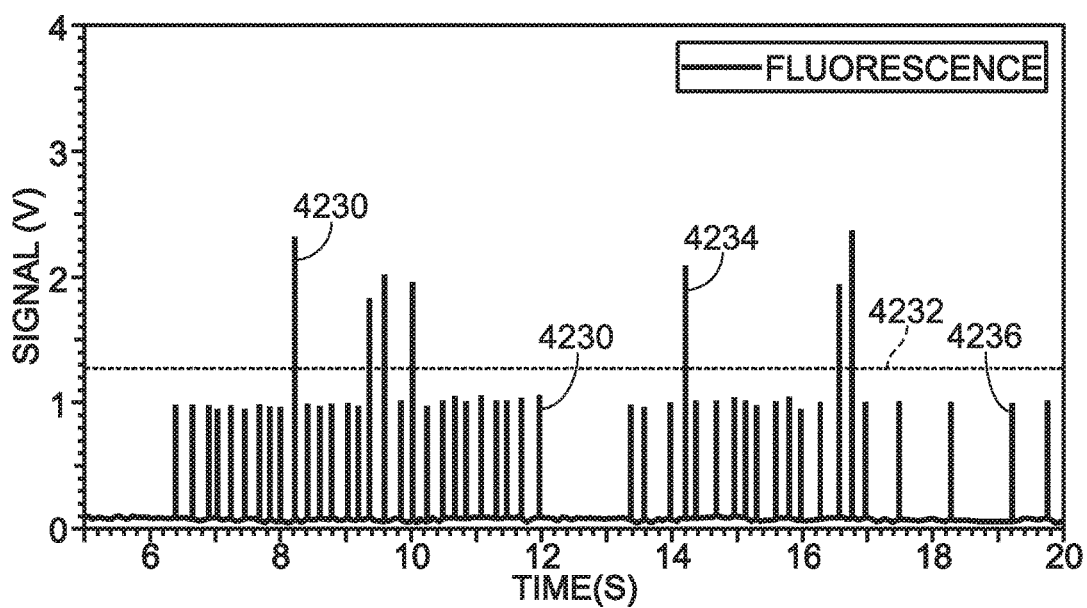
FIG. 94 is a graph of intensity versus time for fluorescence detected by an optical detection system such as the system of FIG. 93, illustrating the distinction between fluorescence emitted by droplets containing a target and droplets not containing a target.

FIG. 94 depicts exemplary fluorescence measurements made by fluorescence detector 4208. More specifically, FIG. 94 shows a post-PCR end-point fluorescence trace from droplets, in which each "peak" 4230 represents the intensity of detected fluorescence emitted by an individual droplet flowing through intersection region 4214. As FIG. 94 indicates, the resulting histogram can be used to identify positive from negative signals. Specifically, the signals depicted in FIG. 94 each may be compared to a cut-off or threshold fluorescence level, as indicated by dashed line 4232. Signals exceeding the threshold level will be interpreted as positive for PCR amplification, and thus for the presence of the target nucleotide sequence in the corresponding droplet, as indicated for an exemplary signal at 4234. On the other hand, signals falling below threshold level 4232 will be interpreted as negative outcomes, indicating that the corresponding droplet did not contain the target.

An example of a negative signal is indicated at 4236, where the detection of a sub-threshold amount of fluorescence is due to the presence of uncleaved fluorescent probe in the droplet. As described previously, the fluorescence of such probes is generally not completely quenched even in the absence of cleavage by a binding polymerase. Also, the differences in fluorescent intensity of a positive, as seen in the signal voltage peak heights between the positive peak at 4230 and positive peak 4234, can be attributed to different amounts of starting nucleic acid target originally in the droplet prior to PCR (e.g., one versus two starting targets). The ratio of different amounts of starting target amounts may be governed by Poisson statistics.

Typically, hundreds to millions of droplets are analyzed per run. In any case, after a desired number of signals have been detected by fluorescence detector 4208, i.e., after a desired number of droplets have passed through intersection region 4214, the positive and negative signals are counted and analyzed. Analysis is typically performed using receiver-operator characteristic curves and Poisson statistics to determine target presence and target concentration, respectively. Running analysis using Poisson statistics can also be performed to give an estimate of target concentration prior to processing all the droplets (i.e., subsets of the total droplets are used in the statistical analysis). The analysis of droplets is further described in Section VII.

B. Example 2: Detection Systems Using Optical Fibers

This example describes fluorescence detectors configured to measure the end-point fluorescence signal of sample/reagent droplet after PCR, and which utilize one or more optical fibers to transmit radiation to and/or from an intersection region within which illuminating radiation intersects the path of the sample-containing droplets. The exemplary systems are suitable for making both qualitative and quantitative measurements; see FIGS. 95-99.

FIG. 95 depicts an optical detection system, generally indicated at 4250, which is similar to system 4200 depicted in FIG. 93 except that transmission optics 4204 of system 4200 have been replaced by an optical fiber 4254. Optical fiber 4254 may be constructed from a glass, a plastic, and/or any other material that is substantially transparent to radiation of one or more particular desired wavelengths and configured to transmit that radiation along the length of the fiber, preferably with little or no loss of intensity.

Replacing the transmission optics with optical fiber 4254 may allow system 4254 to be constructed relatively inexpensively and in a more space-saving manner than systems using optical elements such as mirrors and lenses. This results from the fact that the cost and space associated with the other optical elements is no longer necessary, and also from the fact that optical fiber 4254 may be shaped in any desired manner, allowing significant design flexibility. Aside from optical fiber 4254, detection system 4250 otherwise includes a radiation source 4252, a forward scatter detector 4256, and a fluorescence detector 4258, all of which are similar to their counterparts in system 4200 and will not be described again in detail.

Optical fiber 4254 is depicted in FIG. 95 as ending a short distance from droplets 4260 traveling in fluid channel 4262 through an intersection region generally indicated at 4264, in which radiation emitted from the end of the optical fiber intersects with the droplets traveling through the fluid channel. Other configurations are possible in which, for example, the optical fiber is configured to focus radiation more precisely toward the intersection region and/or is integrated directly into the fluid channel. These possibilities are described below in more detail; see FIGS. 98 and 99 and accompanying discussion.

FIG. 96 depicts an optical detection system, generally indicated at 4270, which is similar to system 4200 depicted in FIG. 93 except that optical elements 4216 and 4218 of system 4200 have been replaced by optical fibers 4286 and 4288 in system 4270 of FIG. 96. As in the case of optical fiber 4254 shown in FIG. 95 and described above, optical fibers 4286 and 4288 each may be constructed from a glass, a plastic, and/or any other material that is substantially transparent to radiation of one or more particular desired wavelengths and configured to transmit that radiation along the length of the fiber, preferably with little or no loss of intensity.

In the case of system 4270, optical fiber 4286 will be configured to transmit at least scattered radiation having a wavelength equal to the wavelength of light emitted by radiation source 4272 (which generally does not change during scattering), and optical fiber 4288 will be configured to transmit at least fluorescence radiation emitted by any fluorescent probes within droplets 4280 that are excited by incident radiation from source 4272. Accordingly, optical fibers 4286 and 4288 may in some cases be constructed from different materials. The use of optical fibers 4286 and 4288 may result in cost and space savings for the same reasons described previously with respect to the use of optical fiber 4254 in system 4250.

Aside from the use of optical fibers 4286 and 4288, system 4270 is similar to system 4200, including radiation source 4272, transmission optics 4274, a forward scatter detector 4276, and a fluorescence detector 4278, which are similar to their previously described counterparts and will not be described further. Radiation from source 4272 passes through transmission optics 4274 and encounters droplets 4280 traveling through fluid channel 4282, at an intersection region 4284. Some of the forward scattered radiation is transmitted through optical fiber 4286 to forward scatter detector 4276. Similarly, some of the fluorescence radiation emitted from droplets 4280 is transmitted through optical fiber 4288 to fluorescence detector 4278. As in the case of optical fiber 4254 in FIG. 95, optical fibers 4286 and 4288 are shown starting at a distance from fluid channel 4282, but as noted above, other configurations are possible and will be described below with reference to FIGS. 98 and 99.

FIG. 97 depicts an optical detection system, generally indicated at 4300, in which optical fibers are used to transmit both incident and outgoing radiation. More specifically, system 4300 includes a radiation source 4302, an optical fiber 4204 for transmitting emitted radiation away from source 4302, a forward scatter detector 4306, and a fluorescence detector 4308. Post-PCR sample-containing droplets 4310 are transferred through fluid channel 4312 toward intersection region 4314. Optical fiber 4316 transmits scattered radiation from intersection region 4314 to forward scatter detector 4306, and optical fiber 4318 transmits fluorescence radiation from intersection region 4314 to fluorescence detector 4308.

As described previously, the use of optical fibers may result in various cost and space savings. These savings may be further amplified, relative to systems 4250 and 4270, by the use of fiber optics for all of the radiation transfer in system 4300. Aside from the use of optical fibers for radiation transfer and any associated efficiencies, system 4300 is similar in both its components and its operation to the previously described systems, and accordingly will not be described further.

Figure 98:
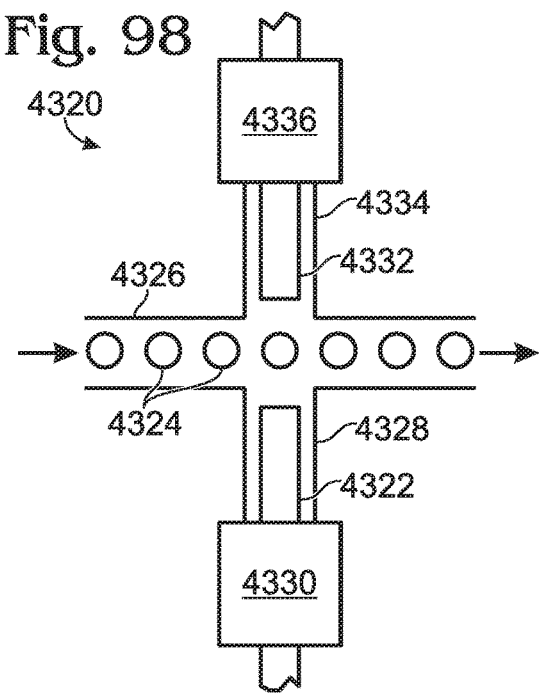
FIG. 98 depicts an intersection region where incident radiation intersects with sample-containing droplets traveling through a fluid channel, illustrating how optical fibers may be integrated with sections of fluidic tubing.

FIG. 98 shows a magnified view of an intersection region, generally indicated at 4320, in which incident radiation from a radiation source (not shown) is transmitted through an optical fiber 4322 to intersect with sample-containing droplets 4324 traveling through a droplet input fluid channel 4326. Intersection region 4320 differs from the intersection regions described previously in that optical fiber 4322 is integrated into a radiation input fluid channel 4328 that is fluidically connected with fluid channel 4326. Thus, radiation is emitted from optical fiber 4322 directly into the fluid within the connected fluid channels, so that it encounters droplets 4324 without crossing either an interface between air and the fluid channel material (typically some form of glass) or an interface between the fluid channel material and the fluid within the channel.

By configuring the intersection region in this manner and avoiding two interfaces between media with different indices of refraction, undesirable reflections of the incident radiation may be decreased, resulting in a greater intensity of radiation reaching droplets 4324. Furthermore, embedding optical fiber 4322 within a connected fluid channel may allow for more convenient and stable placement of the optical fiber at a small distance from fluid channel 4326 and at a desired orientation relative to fluid channel 4326, again potentially resulting in a greater intensity of radiation reaching the droplets. To secure optical fiber 4322 in place within channel 4328, a fluidic fitting 4330 may be placed at an end of channel 4328, and configured so that optical fiber 4322 passes through an aperture of the fitting in a fluid tight manner.

Intersection regions of the type depicted in FIG. 98 may take various forms. For example, as depicted in FIG. 98, optical fiber 4322 may have a slightly smaller outer diameter than the inner diameter of fluid channel 4328. Alternatively, optical fiber 4322 may have an outer diameter approximately equal to the inner diameter of fluid channel 4328, which may lead to an even more secure placement of the optical fiber within the fluid channel. In addition, FIG. 98 depicts an outgoing optical fiber 4332 disposed within a fluid channel 4334 that is also fluidically connected with fluid channel 4326. Optical fiber 4332, which is secured within channel 4334 by a fluidic fitting 4336, is configured to transmit scattered radiation to a forward scatter detector (not shown). In some embodiments, one of incoming optical fiber 4322 and outgoing optical fiber 4332 may be used, but not the other. Furthermore, one or more additional optical fibers, such as an outgoing optical fiber leading to a fluorescence detector (not shown) may be fluidically coupled into intersection region 4320.

Figure 99A:
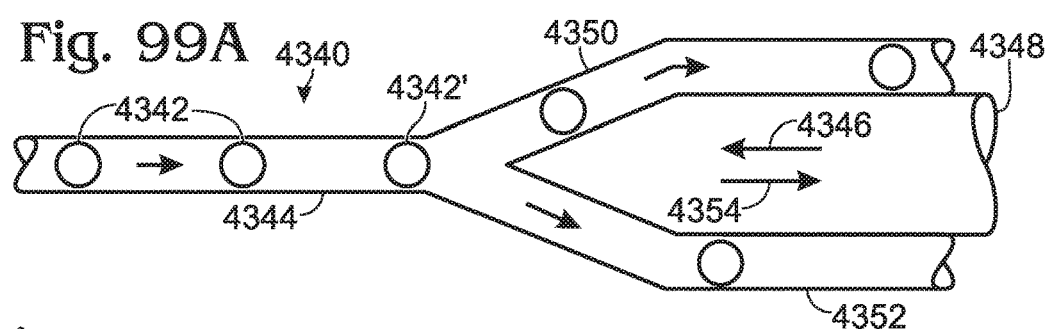
FIG. 99A depicts another intersection region where incident radiation intersects with sample-containing droplets traveling through a fluid channel, illustrating how a single optical fiber may be used to transmit both incident radiation and stimulated fluorescence.

FIG. 99A depicts another intersection region, generally indicated at 4340, between sample-containing droplets 4342 traveling through a fluid channel 4344 and excitation radiation 4346 emitted from a radiation source (not shown). Excitation radiation 4346 is transmitted to intersection region 4340 through an optical fiber 4348, which is oriented with its long axis parallel to fluid channel 4344. As depicted in FIG. 99A, optical fiber 4348 may come to a point or otherwise be tapered in the region proximal to fluid channel 4344, to focus excitation radiation 4346 (through internal reflections within the optical fiber) into channel 4344 and toward droplets 4342. This may allow the excitation radiation to be directed primarily at a single droplet 4342', despite the collinear disposition of optical fiber 4348 with multiple droplets.

Fluid channel 4344, which is configured to transport the droplets to intersection region 4340 where the droplets encounter stimulating radiation transmitted by optical fiber 4348, is shown splitting into two (or more) outgoing fluid channels 4350 and 4352 after droplets 4342 pass through the central part of intersection region 4340. This allows the sample-containing droplets to continue their motion through the PCR system while still allowing a collinear arrangement of fluid channel 4344 and optical fiber 4348. As FIG. 99A illustrates, the outgoing fluid channels and the optical fiber may be given complementary shapes, so that the optical fiber fits snugly between outgoing channels 4350 and 4352. This may lead to a relatively stable collinear configuration of the optical fiber and fluid channel 4344 (to help self-align the fiber and channel).

The intersection region shown in FIG. 99A is configured so that optical fiber 4348 transmits both excitation radiation 4346 and also fluorescence radiation 4354 emitted by the droplets. The fluorescence radiation is then transmitted back through the optical fiber and toward a fluorescence detector (not shown), which may be integrated with a radiation source into a single component. Due to the shape of the proximal end of optical fiber 4348, emitted fluorescence radiation from stimulated droplet 4342' may enter optical fiber 4348 both "head on" and also from a subsequent position along one side of the optical fiber. This effectively lengthens the integration time of the fluorescence detection, resulting in better detection with a given detector sensitivity.

Figure 99B:
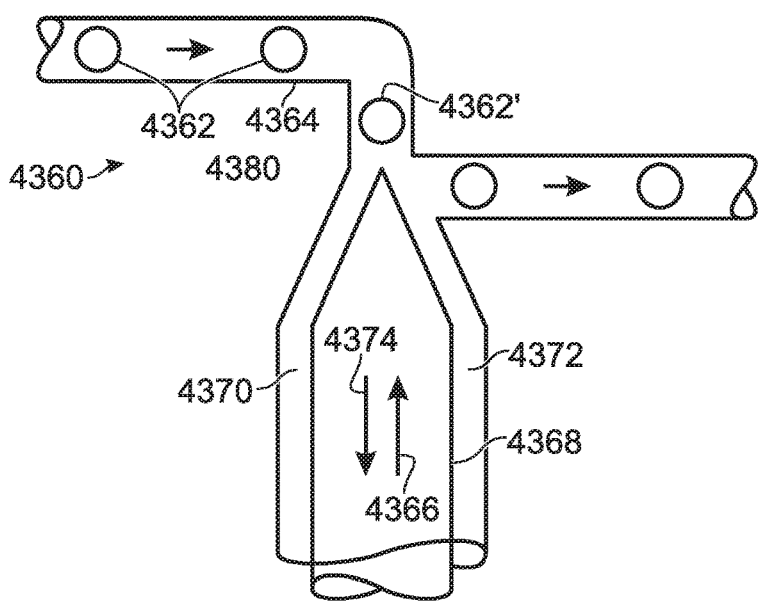
FIG. 99B depicts another intersection region configured to transmit both incident radiation and stimulated fluorescence through a single optical fiber, and also configured to transfer radiation to and from substantially one droplet at a time.

FIG. 99B depicts another intersection region, generally indicated at 4360, which is similar in some respects to intersection region 4340 of FIG. 99A. Specifically, an optical fiber 4368 in FIG. 99B is configured to transmit excitation radiation 4366 from a radiation source (not shown) toward sample containing droplets 4362 traveling in a fluid channel 4364, and fluorescence radiation 4374 from an excited droplet 4362' back through the optical fiber and toward a fluorescence detector (not shown). Unlike intersection region 4340, however, fluid channel 4364 of intersection region 4360 is oriented mostly perpendicular to the long axis of optical fiber 4368, except for a "dog leg" or side-facing region 4380 in the central portion of intersection region 4360.

Side-facing region 4380 of intersection region 4360, which is configured to transport the droplets to intersection region 4360 where the droplets encounter stimulating radiation transmitted by optical fiber 4368, is configured to allow only a small number of droplets, such as one droplet at a time, to travel parallel to the long axis of optical fiber 4368. This configuration may result in relatively more accurate detection of fluorescence radiation, because only one droplet (or a small number of droplets) is stimulated with incident radiation at a time, and only the stimulated droplet(s) emits substantial fluorescence radiation back into optical fiber 4368 for detection.

Optical fiber 4368 of FIG. 99B may be partially or completely surrounded by fluid, and this surrounding fluid may be in fluid communication with fluid channel 4364. However, unlike fluid channels 4350 and 4352 of FIG. 99A, fluid regions 4370 and 4372 surrounding optical fiber 4368, which may in some cases constitute a single continuous fluid region, are too small to allow passage of any sample-containing droplets. Rather, these surrounding fluid region(s) are configured primarily to remove unnecessary interfaces between the optical fiber and the droplets, increasing the intensity of the incident radiation as described previously.

C. Example 3: Detection Systems with Plural Radiation Channels

In some cases, a detection system according to the present disclosure may include multiple separate incident radiation channels to illuminate sample-containing droplets that have undergone PCR thermocycling. This example describes two such systems and some of their potential uses; see FIGS. 100 and 101.

Figure 100:
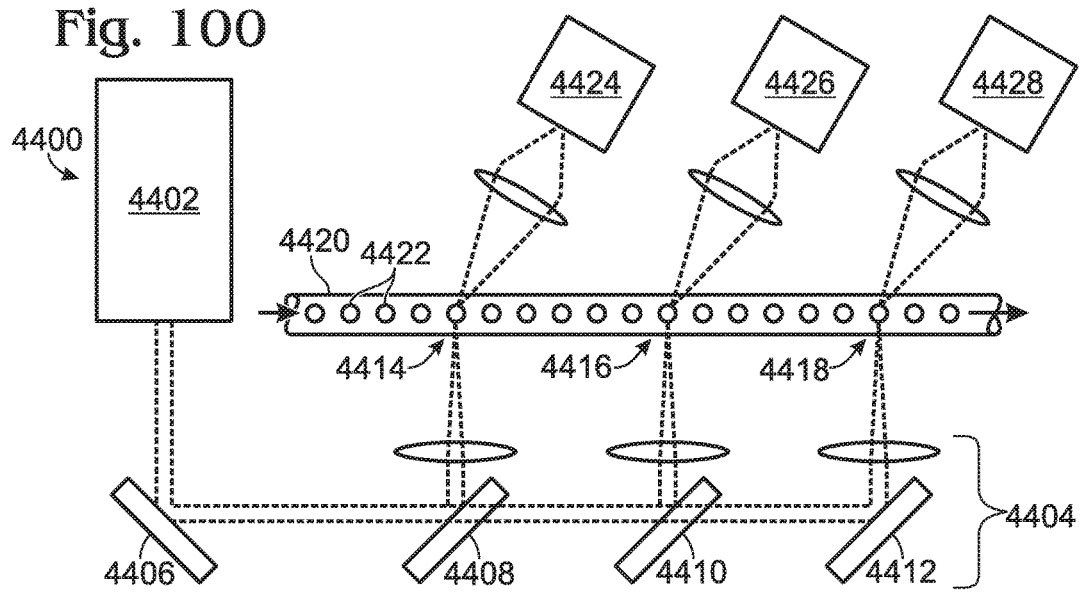
FIG. 100 is a schematic depiction of an optical detection system in which the incident radiation is split into a plurality of separate beams, in accordance with aspects of the present disclosure.

FIG. 100 depicts a multi-channel cytometry-type optical detection system, generally indicated at 4400. Detection system 4400 includes a radiation source 4402, configured to emit radiation at one or more desired wavelengths. As described previously, a radiation source according to the present disclosure may be of various types, such as an LED source or a laser source, and may emit radiation substantially at a single wavelength, at a plurality of substantially discrete wavelengths, or within one or more ranges of wavelengths.

Radiation from source 4402 passes from the source toward transmission optics, as generally indicated at 4404. Transmission optics 4404 may include one or more optical elements, such as a mirror 4406, configured primarily to redirect radiation emitted by source 4402 in a desired direction. Transmission optics 4404 also may include one or more optical elements, such as reflective elements 4408, 4410, 4412, configured to split the radiation emitted by source 4402 into several different portions, each of which may be redirected in a particular manner, such as the manner shown in FIG. 100. Alternatively, radiation source 4402 may be omitted, and reflective elements 4408, 4410, 4412 each may be replaced by a separate radiation source. In some cases, providing plural radiation sources in this manner may be simpler than splitting the radiation from a single source.

In some instances, reflective elements 4408, 4410, 4412 may be configured to transmit and reflect incident radiation in different ways. For example, reflective element 4408 may be configured to reflect approximately one-third of the radiation incident upon it and to transmit approximately two-thirds of the radiation incident upon it, reflective element 4410 may be configured to reflect approximately one-half of the radiation incident upon it and to transmit approximately one-half of the radiation incident upon it, and reflective element 4412 may be configured to reflect substantially all of the radiation incident upon it. In this manner, radiation emitted by radiation source 4402 may be split into three portions of approximately equal intensity.

In cases where it is desirable to split the radiation emitted by source 4402 into a number of channels other than three, a plurality of reflective surfaces may be configured appropriately. Specifically, when n channels are desired, n reflective elements may be used, with the first reflective element configured to reflect fraction $1/n$ and to transmit fraction $(n-1)/n$ of the radiation incident upon it, the second reflective element configured to reflect fraction $1/(n-1)$ and to transmit fraction $(n-2)/(n-1)$ of the radiation incident upon it, the third reflective element configured to reflect fraction $1/(n-2)$ and to transmit fraction $(n-3)/(n-2)$ of the radiation incident upon it, and so forth, until the last reflective element in the sequence is a pure mirror that reflects all of the radiation incident upon it and transmits none. This results in each of the n reflective elements reflecting an equal fraction $1/n$ of the radiation emitted by the radiation source.

An arrangement configured to split radiation from a source into several portions of either approximately equal intensity or differing intensities may be useful, for example, when it is desirable to search for various targets, each of which is bound to a fluorescent probe configured to be excited by the same wavelength of incident radiation but to fluoresce at a different wavelength. For instance, reflective surfaces 4408, 4410 and 4412 may be configured to reflect radiation toward intersection regions 4414, 4416 and 4418, respectively, which may be viewed as different adjacent portions of a single, larger intersection region. Similarly, when a plurality of radiation sources are used instead of reflective surfaces, each radiation source may be configured to transmit fluorescence stimulating radiation to a different adjacent portion of the intersection region.

In the intersection region(s), the arriving radiation will intersect a fluid channel 4420 (such as a capillary tube) through which sample-containing droplets 4422 are moving. Each droplet thus may be irradiated a plurality of times, and accordingly may be stimulated to emit fluorescence radiation a plurality of times if the irradiated droplet contains any of several desired target nucleic acid sequences. However, the droplet may emit a different wavelength of stimulated radiation depending upon which target it contains (and thus which fluorescent probe has been cleaved from its associated quenching molecule by replication of the target).

To detect stimulated fluorescence radiation corresponding to the various targets, a plurality of fluorescence detectors 4424, 4426, 4428 may be used, with each detector positioned and oriented to receive fluorescence radiation produced at a different one of intersection regions 4414, 4416, 4418 (or at a different portion of the larger intersection region encompassing regions 4414, 4416, 4418). Furthermore, each fluorescence detector may be configured to detect fluorescence at a different wavelength, corresponding to one or more (but not all) of the varieties of target molecules or target nucleic acid sequences. Thus, a given irradiated droplet may emit stimulated fluorescence that is detected by just one of detectors 4424, 4426, 4428, resulting in a "positive" detection of just one (or a subset) of the target sequences. In this manner, system 4400 may be used to search for multiple targets simultaneously.

Splitting incident radiation in the manner of system 4400 also may be useful when it is desirable to illuminate sample-containing droplets for more time than it takes the droplet to pass through the unsplit beam of the source. For instance, as described above, system 4400 may be configured so that droplets 4422 passing through a fluid channel 4420 intersect radiation from source 4402 at several intersection regions 4414, 4416, 4418 corresponding to the various split beams. If these intersection regions are disposed relatively near each other, then each droplet may essentially be continuously illuminated in an area spanning all of the intersection regions 4414, 4416, 4418. The resulting relatively long integration time (i.e., the time of exposure of a droplet to illuminating radiation) may result in greater fluorescence from each target-containing droplet, and thus in greater accuracy of the detection system. Another way to obtain a similar result is illustrated in FIG. 101 and will be described in detail below.

Still considering FIG. 100, detection system 4400 also may be used to search for multiple different nucleic acid targets in cases where various probes that respond to different incident wavelengths of excitation radiation have been combined with a sample. For example, radiation source 4402 may be configured to emit radiation at a plurality of discrete wavelengths or wavelength ranges, by using a plurality of radiation emitters or a single emitter configured to produce radiation at all of the desired wavelengths. In this case, each of reflective surfaces 4408 and 4410 (and possibly 4412) may be dichroic and configured to reflect substantially all of the radiation at a particular wavelength (or within a particular wavelength range) and to transmit the remaining incident radiation. Alternatively, as described above, a plurality of radiation sources may be provided and configured to transmit fluorescence stimulating radiation at a different wavelength.

When dichroic reflective surfaces are provided, reflective surface 4408 may be configured to reflect a particular wavelength or wavelength range toward intersection region 4414, reflective surface 4410 may be configured to reflect another particular wavelength or wavelength range toward intersection region 4416, and reflective surface 4412 may be configured to reflect yet another particular wavelength or wavelength range toward intersection region 4418. Alternatively, reflective surface 4412 may be configured to reflect all radiation toward region 4418, since this will include any desired radiation that was not already reflected by surfaces 4408 and 4410. Accordingly, different wavelengths of incident radiation will arrive at each intersection region 4414, 4416, 4418, and stimulated fluorescence emission will occur only if a probe sensitive to a particular arriving wavelength has been activated due to polymerase cleaving of its associated quenching molecule, i.e., only if a particular target is present. Detectors 4424, 4426, 4428 may be used to monitor the activation of droplets within the various intersection regions, as described previously.

Figure 101:
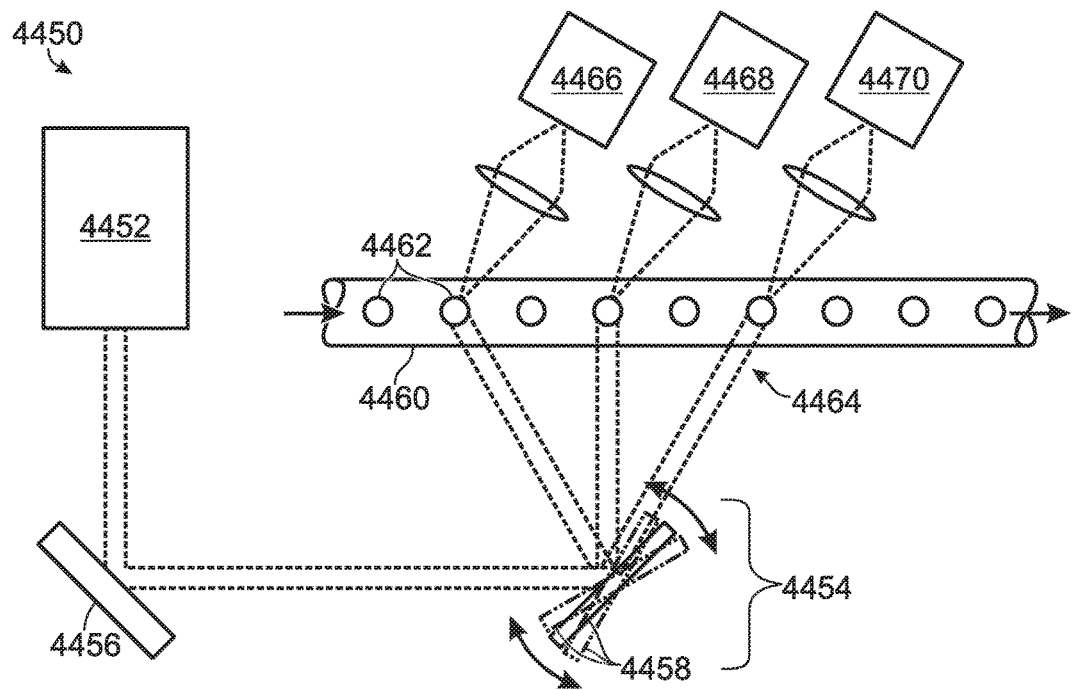
FIG. 101 is a schematic depiction of an optical detection system in which the incident radiation is spread by an adjustable mirror into a relatively wide intersection region, in accordance with aspects of the present disclosure.

FIG. 101 depicts another multi-channel cytometry-type optical detection system, generally indicated at 4450. System 4450 is generally similar to system 4400, including a radiation source 4452 and transmission optics generally indicated at 4454. In the case of system 4450, the transmission optics may include first and second mirrors 4456, 4458 configured to redirect radiation emitted by source 4452 in a desired manner. Transmission optics 4454 also may include one or more other optical elements (not shown) for focusing radiation from source 4452, as described previously.

As indicated in FIG. 101, mirror 4458 may be adjustable so that it is configured to reflect radiation at a range of different angles, to direct it toward a range of different positions along a fluid channel 4460 through which sample-containing droplets 4462 are being transferred. Thus, the reflected radiation defines an intersection region, generally indicated at 4464, which is substantially wider than it would be if mirror 4458 was fixed in a single orientation. If mirror 4458 is adjusted relatively rapidly, this configuration may allow radiation from source 4452 to illuminate more than one droplet at a time, or may cause a single droplet to fluoresce at various positions within fluid channel 4460. In this case, a plurality of detectors 4466, 4468, 4470 may be oriented to look for radiation at particular wavelengths corresponding to various target probes.

Alternatively, if the adjustment speed of mirror 4458 is chosen to correspond to the known approximate speed of sample-containing droplets traveling within fluid channel 4460, then the mirror may effectively increase the illumination time of each droplet by "tracking" the droplet through the channel. In this case, it may be appropriate to use only a single fluorescence detector, with a field of view that spans the entire path traveled by a droplet during its illumination.

D. Example 4: Separation of Droplets

Figure 103:
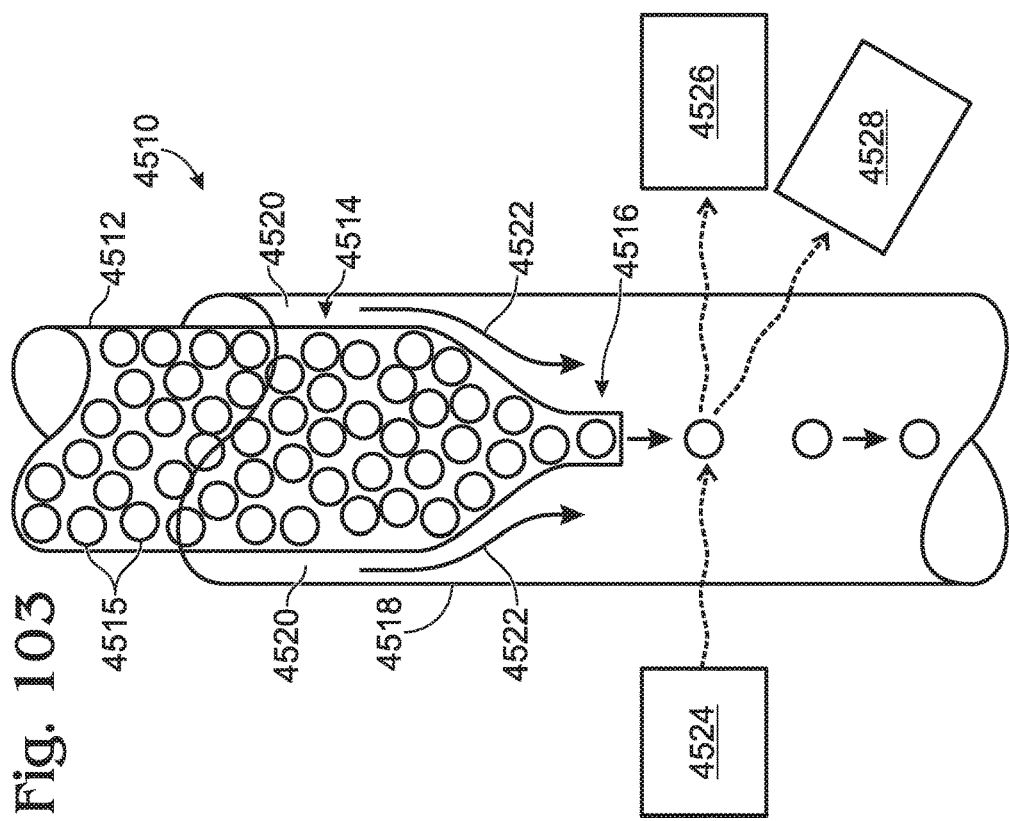
FIG. 103 depicts another flow focus mechanism for separating sample-containing droplets from each other by a desired distance, in accordance with aspects of the present disclosure.
Figure 102:
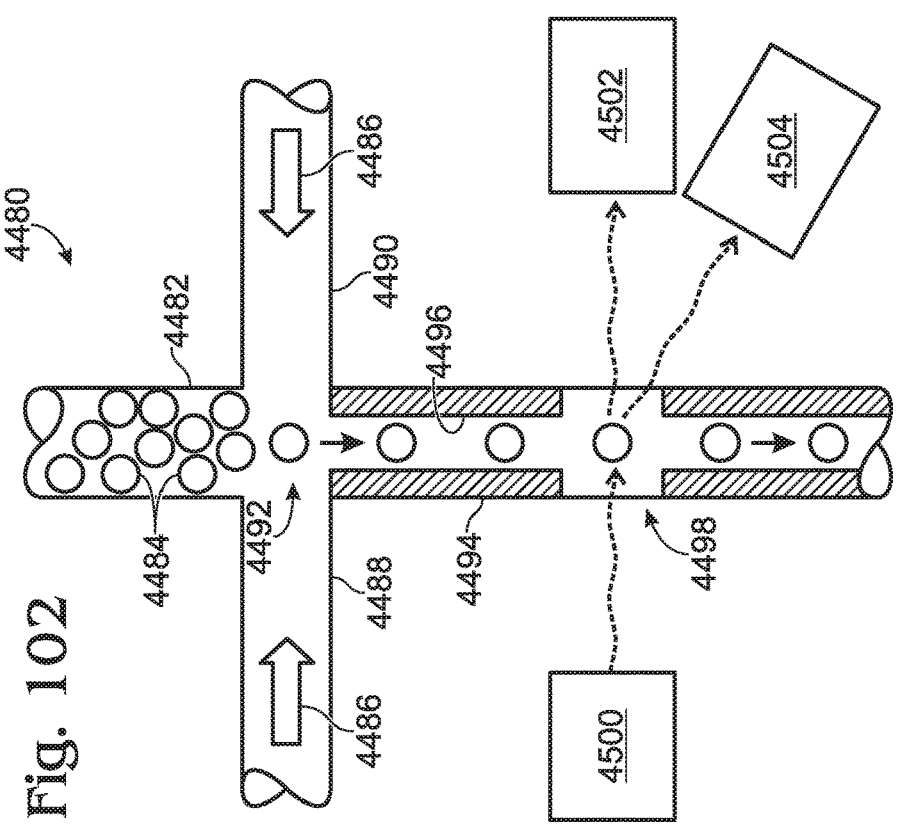
FIG. 102 depicts a flow focus mechanism for separating sample-containing droplets from each other by a desired distance, in accordance with aspects of the present disclosure.
Figure 104:
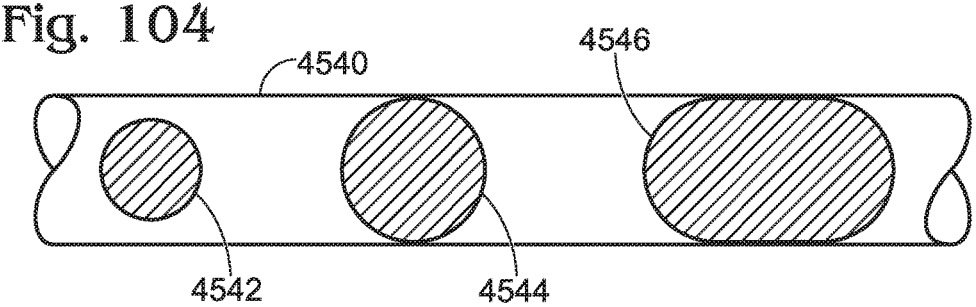
FIG. 104 depicts a section of fluidic tubing, illustrating how an appropriate choice of fluid channel diameter can facilitate proper spacing between droplets, in accordance with aspects of the present disclosure.

This example describes fluid focus mechanisms for achieving a desired separation between sample-containing droplets as they pass through a fluorescence detection system; see FIGS. 102-104. As the discussion above indicates, it may be desirable for droplets within a detection region to be separated by some known average distance, or at least by some approximate minimum distance. For example, adequate spacing may permit split beams of radiation and/or detectors to be disposed most appropriately, and may allow a suitable choice of adjustment range for an adjustable mirror, when one is used.

In addition, proper spacing can help to avoid unintentionally detecting radiation from two or more droplets simultaneously, which can result in false positives and other errors in the detection system. For instance, as described previously, an uncleaved probe within a droplet still emits some amount of fluorescence even though the nucleic acid target is not present in the droplet. Thus, the intensity of fluorescence emitted from two or more droplets, neither of which contains a target, may be sufficient to trigger a positive detection result if the fluorescence from those multiple droplets is mistakenly thought to come from a single droplet. Other errors, such as errors in determining droplet volume and target concentration, also may result when droplets are spaced too closely together.

FIG. 102 shows a fluid focus mechanism, generally indicated at 4480, which is configured to separate sample-containing droplets from each other by some desired amount of distance. This mechanism may be used, for example, to separate droplets prior to transferring them toward a detector intersection region such as intersection region 4214 of FIG. 93, intersection region 4264 of FIG. 95, or any of the other intersection regions described above. Focus mechanism 4480 includes a droplet input channel 4482, which contains sample-containing droplets 4484 that are spaced closely together. Focusing fluid, indicated by arrows 4486, is transferred through focus fluid input channels 4488, 4490, so that it encounters droplets from the droplet input channel at a focus region generally indicated at 4492.

A droplet entering focus region 4492 will be channeled into droplet egress channel 4494, which is the only channel through which fluid can exit the focus region. Egress channel 4494 may be configured to have regions with a smaller inner diameter 4496 than the inner diameter of some or all of droplet input channel 4482 and focus fluid input channels 4488, 4490, although in some instances this may not be the case. Because fluid is flowing into focus region 4492 from focus fluid input channels 4488 and 4490 as well as from droplet input channel 4482, and/or because egress channel 4494 has a smaller cross sectional area than the other channels, fluid will flow more rapidly through the egress channel than through the other channels.

Because of the increase in fluid speed as fluid approaches the egress channel, droplets will accelerate as they enter the egress channel, and will become separated from each other as FIG. 102 indicates. By appropriate choices of channel inner diameters and focus fluid input velocity, essentially any desired average spacing between droplets can be achieved. Within egress channel 4494, there may be an irradiation zone, generally indicated at 4498. The irradiation zone may have features, such as increased transparency and/or thinner channel walls, which are conducive to irradiating droplets with radiation from a radiation source 4500. A forward scatter detector 4502 and a fluorescence detector 4504 may be positioned appropriately to detect scattered and fluorescence radiation, as described previously.

FIG. 103 shows another fluid focus mechanism, generally indicated at 4510. As in the case of fluid focus mechanism 4480 of FIG. 102, fluid focus mechanism 4510 is configured to increase the distance between closely spaced sample-containing droplets to some desired minimum average value. Fluid focus mechanism 4510 includes a droplet input channel 4512 that has a body portion 4514 and a neck portion 4516. Body portion 4514 may be configured to contain a relatively large number of closely spaced sample-containing droplets 4515, as FIG. 103 depicts, or in some cases it may contain a stream of continuously flowing droplets. In either case, the diameter of neck portion 4516 may be chosen to substantially match, or to be just slightly larger than, the expected average droplet diameter, so that only one droplet at a time will typically be able to travel through the neck portion.

Mechanism 4510 also includes an outer fluid channel 4518, which surrounds at least a portion of droplet input channel 4512, including neck portion 4516. In conjunction with droplet input channel 4512, outer fluid channel 4518 defines a focus fluid input channel 4520 between the droplet input channel and the outer fluid channel. Typically, droplet input channel 4512 and outer fluid channel 4518 will be cylindrical, so that focus fluid input channel 4520 will take the form of a concentric cylindrical shell. Focusing fluid, generally indicated by arrows 4522, may be transferred through focus fluid input channel 4520 at a desired velocity. Accordingly, as each droplet 4515 exits neck portion 4516, it will accelerate away from the neck portion due to the flow of the focusing fluid. Through careful selection of the geometry of the system and the focusing fluid velocity, any desired separation between adjacent droplets exiting the neck portion can be attained. A radiation source 4524, a forward scatter detector 4526, and a fluorescence detector 4528 may be provided to irradiate, track, and analyze droplets as described previously.

FIG. 104 is a section of fluidic tubing 4540 illustrating how an appropriate choice of fluid channel diameter(s) can contribute to an appropriate separation between droplets. This point was discussed above, in the description of neck portion 4516 of fluid focus mechanism 4510. This description applies not only to a neck portion of a droplet input channel, but also more generally to any fluid channel through which droplets pass within a detection system according to the present disclosure. For example, the same considerations apply to fluid channel 4512 of FIG. 93, fluid channel 4262 of FIG. 95, etc.

As FIG. 104 depicts, fluidic tubing 4540 may be selected to have an inner diameter that is correlated with the expected average droplet diameter. Accordingly, a droplet 4542 having a slightly smaller than average diameter will be relatively unlikely to be in close proximity to additional droplets in the tubing. Similarly, a droplet 4544 having the expected average diameter will move freely within tubing 4540, and will maintain its spherical shape. Finally, a droplet 4546 having a diameter slightly greater than the expected average diameter will take on a partially cylindrical shape, the volume of which may be estimated accordingly. Thus, an appropriate choice of fluid tubing size can help to ensure proper separation between droplets.

E. Example 5: Batch Fluorescence Detection

In some cases, it may be desirable to irradiate and/or detect fluorescence from sample-containing droplets in relatively large batches rather than one droplet at a time. This example describes a system for detecting fluorescence emitted from a plurality of droplets that have been transferred to a chamber for batch detection; see FIG. 105.

Figure 105:
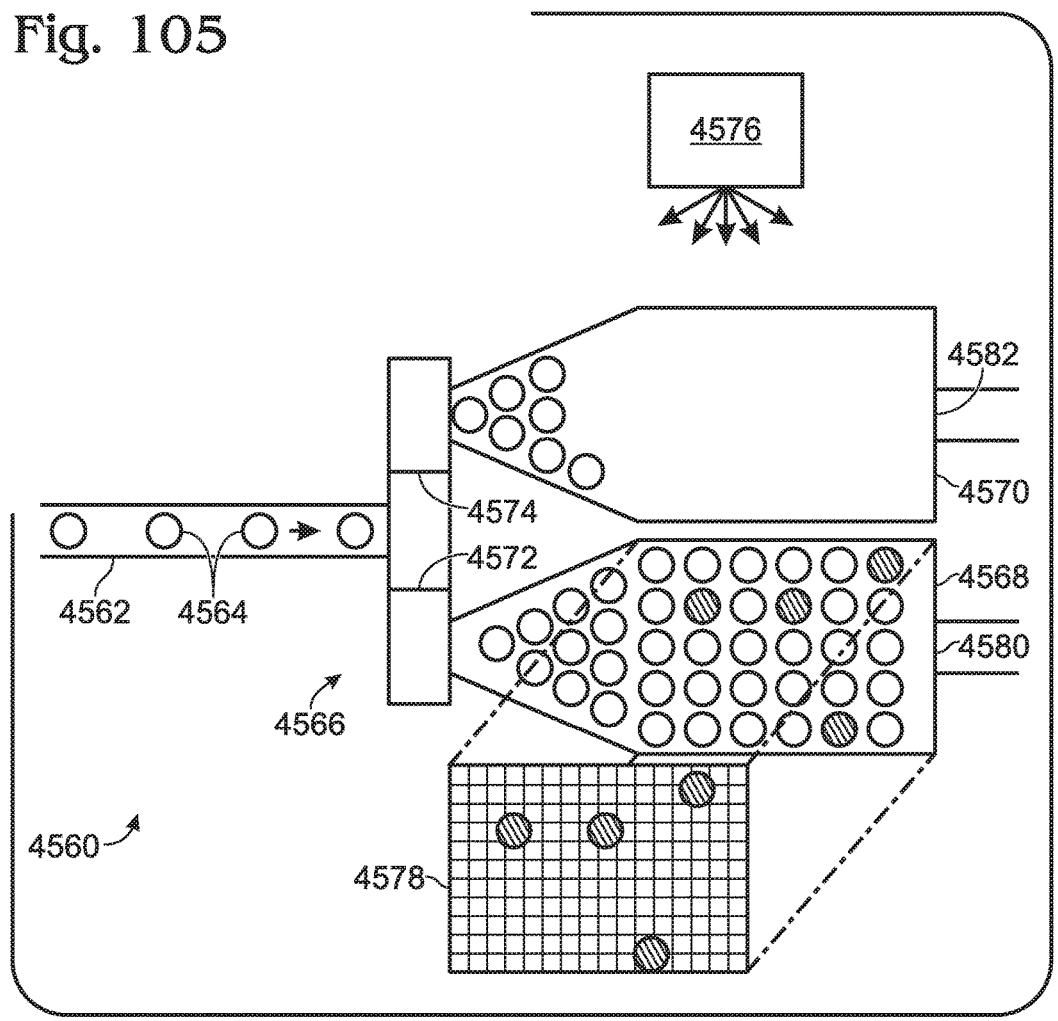
FIG. 105 depicts a batch fluorescence detection system, in accordance with aspects of the present disclosure.

FIG. 105 schematically depicts a batch optical detection system, generally indicated at 4560. In contrast to the previously described continuous flow detection systems, in which sample-containing droplets flow continuously through an intersection region where excitation radiation intersects the path of the moving droplets, system 4560 is configured to detect radiation from a plurality of droplets that have been collected in a detection region, and in some cases temporarily stopped from flowing through the system. This allows the fluorescence level of many droplets to be detected in a single detection operation, which may be advantageous in some applications.

Batch detection system 4560 includes a droplet input channel 4562, within which sample-containing droplets 4564 may be caused to flow in an emulsion (such as a water-in-oil emulsion), just as in the previously described detection systems. System 4560 also includes a valve mechanism, generally indicated at 4566, which is configured to selectively direct droplets toward either of two fluorescence detection chambers 4568, 4570. For example, valve mechanism 4566 may include a first valve 4572 disposed between droplet input channel 4562 and detection chamber 4568, and a second valve 4574 disposed between droplet input channel 4562 and detection chamber 4570. Thus, by opening and closing valves 4572 and 4574 appropriately, droplets may be transferred selectively into chambers 4568, 4570. This may allow a substantially continuous flow of emulsion to be transferred from the droplet input fluid channel to the fluorescence detection chambers.

Chambers 4568, 4570 may be configured to have a relatively shallow depth, to allow substantially only a monolayer of droplets within each chamber, so that only one droplet is disposed within each portion of the line of sight of a detector and is confined to the focal plane of the detector. Alternatively, various three-dimensional detection configurations, such as confocal imaging or wide-field imaging with deconvolution, may be used with non-monolayer samples.

A radiation source 4576 is configured to illuminate droplets within chambers 4568, 4570, and after a desired number of droplets are transferred into one of the detection chambers, the chamber may be illuminated with radiation from source 4576. Source 4576 may be configured in various ways to illuminate substantially all of the droplets within a chamber. For example, radiation source 4576 may include a single radiation emitting element, configured to illuminate substantially the entire chamber either by emitting a broad beam of radiation or by emitting radiation toward intermediate optics (not shown) that spread the emitted beam to cover the entire chamber. The radiation source also may include a plurality of radiation emitting elements, such as lasers, LEDs, and/or lamps, among others, each configured to illuminate a portion of the appropriate detection chamber. Alternatively or in addition, one or more radiation emitting elements of radiation source 4576 may be configured to scan the chamber, to sequentially illuminate droplets within the chamber, or the chamber itself may be configured to move so that all portions of the chamber intersect a substantially stationary beam of radiation. In some cases, a combination of two or more of the above techniques may be effective.

A fluorescence detector 4578 is provided and configured to detect fluorescence emitted from droplets 4564. As has been described previously, the amount of fluorescence emitted by a particular droplet is expected to be significantly higher if the droplet contains a target nucleotide sequence, because in that case the corresponding fluorescent probe will typically have been cleaved from its associated quenching molecule. Thus, after the droplets within a detection chamber have been illuminated with stimulating radiation or in some cases while illumination is occurring, detector 4578 may be configured to receive fluorescence from the detection chamber. As in the case of illumination, detection may proceed in various ways. For example, a large format detector such as a CCD focal plane array may be used to detect radiation emitted from an entire detection chamber simultaneously. Alternatively, a smaller detector such as a photodiode or a photomultiplier may be scanned across the chamber, or the chamber may be repositioned with respect to the detector, to detect fluorescence radiation from various portions of the detection chamber sequentially.

System 4560 may be configured to allow substantially continuous flow through droplet input channel 4562, by transferring droplets into two or more detection chambers, such as chambers 4568, 4570, sequentially. For example, FIG. 105 depicts the system at a time when chamber 4568 has already been filled with droplets and is being illuminated and/or imaged, whereas chamber 4570 is in the process of being filled. Accordingly, valve 4572 will be in its closed position, and valve 4574 will be in its open position, to allow droplets to flow into chamber 4570.

Upon completion of the detection process on the droplets within chamber 4568, valve 4574 may be closed, valve 4572 may be opened, and another valve 4580 at the distal end of chamber 4568 also may be opened. This stops the flow of droplets into chamber 4570 and restarts the flow of droplets into chamber 4568, while allowing the droplets already in chamber 4568 to escape through distal valve 4580. Another distal valve 4582 may be disposed at the end of chamber 4570 for a similar purpose. Alternatively, before the flow of droplets into a given chamber is resumed, and while droplets are still flowing into the other chamber, the chamber not receiving droplets may be washed with a fluid that enters through another fluid channel (not shown). This may help to avoid the possibility of mistakenly illuminating and detecting the same droplet twice. With or without a wash step, coordinated motions of valves as described above may allow an emulsion of sample-containing droplets to be continuously transferred in and out of any desired number of detection chambers.

Batch fluorescence detection may be performed without actually stopping droplets within the detection chambers of the system. For example, even if valves 4580, 4582 are not provided or are left open, droplets entering one of chambers 4568, 4570 may slow sufficiently to allow batch detection, and the lateral width of the detection chambers may be chosen to facilitate this. Alternatively or in addition, various particle tracking algorithms may be used to track droplets as they move within the detection chambers. Furthermore, a batch detection system may be partially or completely fluidically decoupled from other portions of a molecular amplification system. For example, a simple array of droplet-containing wells or reservoirs (such as a plate array) may be placed in a fluorescence detection region and imaged as described above.

F. Example 6: Detection Methods

Figure 106:
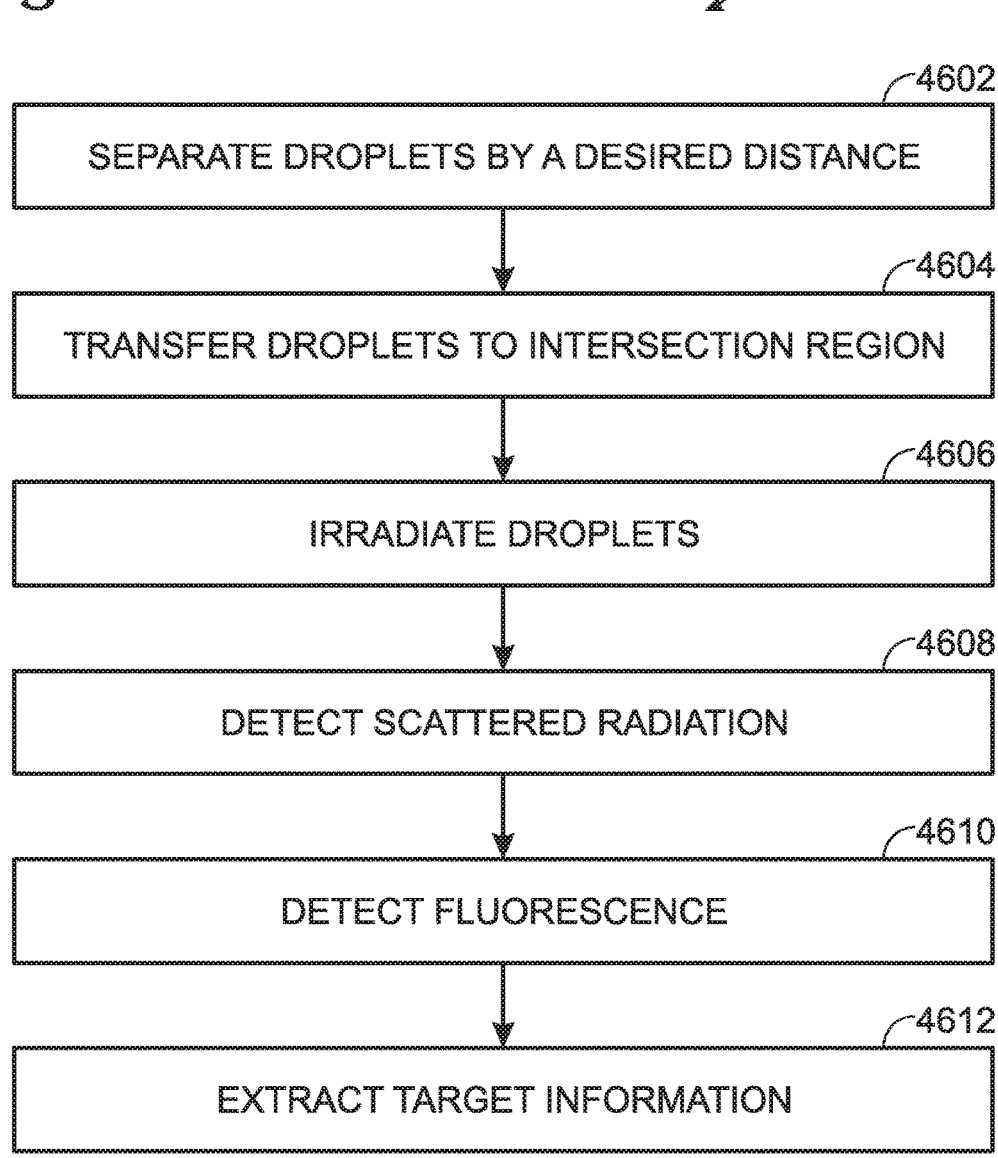
FIG. 106 is a flow chart depicting a method of detecting fluorescence from sample-containing droplets, in accordance with aspects of the present disclosure.

This example describes a method of detecting fluorescence from sample-containing droplets that have undergone PCR thermocycling; see FIG. 106.

FIG. 106 is a flowchart depicting the steps of a fluorescence detection method, generally indicated at 4600, which may be performed in conjunction with a PCR system of DNA amplification according to the present disclosure. Although various steps of method 4600 are described below and depicted in FIG. 106, the steps need not necessarily all be performed, and in some cases may be performed in a different order than the order shown in FIG. 106.

At step 4602, sample-containing droplets are separated by a desired average distance. This may be accomplished, for example, by various flow focusing techniques such as those described above (i.e., by flow focusing the droplets as they are generated), and/or by generating droplets at a suitable rate. In cases of batch detection such as in a stop-flow system, it may be appropriate for droplets to remain closely spaced during fluorescence detection, and accordingly a droplet separation step may not be performed.

At step 4604, the sample-containing droplets are transferred into a radiation intersection region, within which they will be exposed to illuminating radiation chosen to stimulate emission of fluorescence radiation from one or more fluorescent probes within the droplets, with an intensity that depends in part on whether or not a quenching moiety has been cleaved from the probe due to polymerase binding of the associated nucleotide target primer. In the case of continuous flow detection, the intersection region may be disposed within a fluid channel such as a capillary tube. In the case of batch detection, the intersection region may be disposed within one or more detection chambers. In this case, transferring droplets into the intersection region may include steps such as opening and closing one or more valves to allow a continuous flow of droplets into and out of the intersection region.

At step 4606, the droplets in the radiation intersection region encounter and are irradiated with stimulating radiation, which includes at least one wavelength chosen to excite the fluorescent probe(s) known to be present in the reagents within the droplets. As described above, the illuminating radiation may be produced by a laser, and LED, or any other suitable radiation source, and may be transferred to the intersection region through free space or through one or more optical fibers. Furthermore, the radiation may be focused, diverged, split, filtered, and/or otherwise processed before reaching the intersection region, to efficiently irradiate the droplets in the most suitable manner for a particular detector system configuration.

At step 4608, radiation scattered from the droplets in the intersection region may be detected by a forward scattering detector. This step will typically not be performed in a batch detection system, where each droplet is approximately stationary or at least relatively slow moving in a detection chamber that serves as the radiation intersection region. However, detecting scattered radiation in a continuous flow detection system may help to correlate simultaneous or subsequent fluorescence detection with the presence of droplets in the intersection region, and may allow the volume and target molecule concentration of each droplet to be estimated, as described above. More generally, step 4608 may include performing any measurement to enable an estimation of the volume of each droplet, such as the amount of radiation scattered from the droplet, the time of flight of the droplet as it passes through the intersection region, an electrical property of the droplet, or a thermal property of the droplet. Method 4600 also may include estimating the volume of each droplet based on the measurement performed in step 4608.

At step 4610, fluorescence emitted by droplets irradiated in the intersection region is detected by a fluorescence detector. As described in the preceding examples, the emitted radiation may be transferred to the fluorescence detector with or without passing through one or more intermediate optical elements such as lenses, apertures, filters, or the like. The emitted radiation also may or may not be transferred to the fluorescence detector through one or more optical fibers. In batch detection applications, the detector and/or the intersection region may be configured to move in a manner that allows an optical scan of the intersection region by a detector having a smaller field of view than the entire intersection region.

At step 4612, detected fluorescence is analyzed to determine whether or not a particular target nucleotide sequence was present in the droplets. Additional information, including but not limited to an estimate of the number or fraction of droplets containing a target molecule, the average concentration of target molecules in the droplets, an error margin, and/or a statistical confidence level, also may be extracted from the collected data.

Using the data collected from each droplet in an analysis may be conditional and may depend, for example, on whether the estimated volume of the droplet falls within a particular predetermined range. More specifically, if the estimated volume of a droplet falls within a predetermined range, then the fluorescence intensity emitted by that droplet may be used in a determination of target molecule concentration in the sample, whereas if the estimated volume of the droplet falls outside the predetermined range, then the fluorescence intensity emitted by the droplet may be excluded from a determination of target molecule concentration in the sample.

G. Example 8: Additional Embodiments

This example describes additional aspects of sample detection, in accordance with aspects of the present disclosure, presented without limitation as a series of numbered sentences.

1. A method of detecting target molecule concentration in a sample, comprising (A) generating sample-containing droplets with a droplet generator; (B) amplifying target molecules within the droplets; (C) transferring the droplets through an intersection region where the droplets encounter radiation from a radiation source; (D) estimating the volume of each droplet based on a measurement performed as the droplet passes through the intersection region; (E) detecting fluorescence intensity emitted by each droplet; and (F) for each droplet, if the estimated volume of the droplet falls within a predetermined range then using the fluorescence intensity emitted by the droplet in a determination of target molecule concentration in the sample, and if the estimated volume of the droplet falls outside the predetermined range then excluding the fluorescence intensity emitted by the droplet from a determination of target molecule concentration in the sample.

2. The method of paragraph 1, wherein the measurement is an amount of radiation scattered from the droplet.

3. The method of paragraph 1, wherein the measurement is time of passage of the droplet through a detector field of view.

4. The method of paragraph 1, wherein the measurement is an electrical property of the droplet.

5. The method of paragraph 1, wherein the measurement is a thermal property of the droplet.

6. The method of paragraph 1, further comprising separating the droplets by a desired average distance prior to transferring them through the intersection region.

7. A fluorescence detection method, comprising (A) generating sample-containing droplets; (B) separating the droplets by a desired average distance; (C) transferring the droplets to a radiation intersection region; (D) exposing the droplets to radiation configured to stimulate emission of fluorescence radiation from a fluorescent probe within the droplets; and (E) detecting fluorescence radiation emitted by the droplets.

8. The method of paragraph 7, wherein separating the droplets includes flow focusing the droplets as they are generated.

9. The method of paragraph 7, further comprising analyzing the detected fluorescence radiation to determine whether or not each droplet contains a target molecule.

10. A target molecule detection system, comprising (A) a droplet generator configured to generate sample-containing droplets; (B) a molecular amplifier configured to replicate target molecules within the droplets; (C) a radiation source configured to stimulate emission of fluorescence radiation from droplets containing target molecules; (D) a fluorescence detector configured to detect fluorescence radiation emitted by the droplets; and (E) a first optical fiber configured to transmit stimulating radiation from the radiation source to the droplets.

11. The system of paragraph 10, wherein the first optical fiber has a long axis oriented substantially parallel to a droplet input fluid channel configured to transport the droplets to an intersection region where the droplets encounter stimulating radiation transmitted by the first optical fiber.

12. The system of paragraph 10, wherein the first optical fiber has a long axis oriented substantially parallel to a side-facing region of a droplet input fluid channel configured to transport the droplets to an intersection region where the droplets encounter stimulating radiation transmitted by the first optical fiber, and wherein the side-facing region is configured to allow substantially only one droplet at a time to travel parallel to the long axis of the first optical fiber.

13. The system of paragraph 11 or 12, wherein the first optical fiber is further configured to transmit fluorescence radiation from the droplets to the fluorescence detector.

14. The system of paragraph 10, further comprising a second optical fiber configured to transmit fluorescence radiation from the droplets to the fluorescence detector.

15. The system of paragraph 14, further comprising a scattering detector configured to detect radiation scattered from the droplets, and a third optical fiber configured to transmit the scattered radiation to the scattering detector.

16. The system of paragraph 10, further comprising (F) a droplet input fluid channel; and (G) a radiation input fluid channel; wherein the droplet input fluid channel is configured to transport a fluid containing the droplets through an intersection region, the first optical fiber is configured to emit radiation from the radiation source directly into fluid within the radiation input fluid channel, the radiation input fluid channel is configured to transmit radiation from the first optical fiber to the intersection region, and the droplet input fluid channel is fluidically connected to the radiation input fluid channel.

17. A target molecule detection system, comprising (A) a droplet generator configured to generate sample-containing droplets; (B) a molecular amplifier configured to replicate target molecules within the droplets; (C) a fluid channel configured to transport the droplets through a radiation intersection region; (D) a plurality of radiation sources, each configured to transmit fluorescence stimulating radiation to a different adjacent portion of the intersection region; and (E) at least one fluorescence detector configured to detect fluorescence radiation emitted by droplets disposed within the intersection region.

18. The system of paragraph 17, wherein the at least one fluorescence detector includes a plurality of fluorescence detectors, each configured to detect fluorescence radiation emitted by droplets within one of the different portions of the intersection region.

19. The system of paragraph 18, wherein each fluorescence detector is configured to detect fluorescence radiation at a different wavelength, each wavelength corresponding to at least one variety of target molecule.

20. The system of paragraph 19, wherein each radiation source is configured to transmit fluorescence stimulating radiation at a different wavelength.

21. A target molecule detection system, comprising (A) a droplet generator configured to generate an emulsion of sample-containing droplets; (B) a molecular amplifier configured to replicate target molecules within the droplets; (C) a droplet input fluid channel configured to transfer the emulsion to at least one fluorescence detection chamber; (D) a radiation source configured to illuminate droplets within the at least one detection chamber with stimulating radiation; and (E) a fluorescence detector configured to detect fluorescence radiation emitted by the illuminated droplets.

22. The system of paragraph 21, wherein the at least one detection chamber is configured to contain substantially only a monolayer of droplets.

23. The system of paragraph 21, wherein the at least one detection chamber includes two detection chambers and a valve mechanism configured to selectively direct droplets toward one of the two detection chambers.

24. The system of paragraph 23, wherein the valve mechanism is configured to allow a substantially continuous flow of emulsion to be transferred from the droplet input fluid channel to the fluorescence detection chambers.

VII. QUANTIFICATION/ANALYSIS

This Section describes exemplary systems for analyzing reaction data and, optionally, for using results of the analysis to adjust system parameters to improve the quality of subsequent data, for example, for use with droplet-based assay systems. The systems are described, for convenience, in terms of fluorescence intensity data obtained in connection with PCR; however, the systems apply more generally to discrete data obtained in connection with any suitable reaction. Additional pertinent disclosure may be found in the U.S. provisional patent applications listed above under Cross-References and incorporated herein by reference, particularly Ser. No. 61/277,216, filed Sep. 21, 2009.

It may be desirable, once a sample-containing emulsion has been created, thermocycled by an enzymatic amplification system such as a PCR thermocycler, and passed through a detection system, to analyze the data gathered by the detection system to extract desired information about the sample. As described previously, the gathered data will typically include at least a fluorescence intensity level emitted by each detected droplet under excitation from a radiation source. The fluorescence intensity emitted by a given droplet typically will reflect the number of replicated target nucleic acid molecules in the droplet, and thus will be a measure of the target molecule concentration in the original, unamplified sample. Fluorescence intensity will be measured by one or more fluorescence detectors such as a photomultiplier tube or a photodiode or a digital camera. For example, the fluorescence signals from the detector may be digitized and a peak intensity determined as each droplet passes within the field of view of the detector. The peak intensity may be determined using a curve fitting technique such as a local parabolic fit or any other suitable method.

Aside from fluorescence intensities, various other data may be gathered during the detection phase. For example, the time of passage of each droplet in front of either a fluorescence detector or a forward scatter detector may be measured. In conjunction with knowledge of the emulsion fluid velocity as it passes through the detection region, and the geometry of each droplet, this may allow an estimate of each droplet's volume. Droplet volume also can be estimated by measuring various one or more other properties of the droplets, such as thermal or electrical conductivity, capacitance, and/or dielectric permittivity, among others.

In any event, it is expected that there will be data, at least including fluorescence intensity, available for each of a relatively large number of sample-containing droplets. This will generally include thousands, tens of thousands, hundreds of thousands of droplets, or more. Statistical tools generally may be applicable to analyzing this data. For example, statistical techniques may be applied to determine, with a certain confidence level, whether or not any target molecules were present in the unamplified sample. This information may in some cases be extracted simply in the form of a digital ("yes or no") result, whereas in other cases, it also may be desirable to determine an estimate of the concentration of target molecules in the sample, i.e., the number of target molecules per unit volume.

Because target molecule concentration depends not just on the number of target molecules within the emulsion but also on the volume of each droplet, determining the target concentration generally also involves either an explicit or an implicit determination of the volume distribution of the droplets. In some cases, a droplet volume distribution may be determined by measuring parameters such as time of passage of the droplets in the field of view of a detector, or various thermal or electrical properties of each droplet, as noted above. In other cases, the droplet sizes may be assumed to have a certain uniform value, for instance based on knowledge of the underlying characteristics of the droplet generator(s) used in the system. Knowledge of droplet volumes generally facilitates a determination of the concentration of target molecules per unit volume of sample-containing fluid.

Using statistical methods, it is possible to estimate target molecule concentration even when the droplet volumes are unknown and no parameter is measured that allows a direct determination of droplet volume. More specifically, because the target molecules are assumed to be randomly distributed within the droplets, the probability of a particular droplet containing a certain number of target molecules may be modeled by a Poisson distribution function, with droplet concentration as one of the parameters of the function.

If the droplets are assumed to have a known average size but an unknown size distribution, the detected fluorescence data, or a quantity calculated from that data, may be compared to the results predicted by various concentration values. The actual concentration value then may be estimated using an error minimization technique such as a least mean squares (LMS) fit.

Even when the droplets are not assumed to be uniform in size, target concentration may be estimated in a similar manner. To accomplish this, a particular functional form, such as a Gaussian distribution with a particular mean and standard deviation, may be assumed for the probability distribution of droplet volumes. A new Poisson-type distribution function for the probability of finding a given number of target molecules in a droplet then may be calculated, again assuming a random distribution of target molecules throughout the sample. An estimate of the target concentration again may be obtained by comparing one or more quantities determined from the actual fluorescence data with the same quantities predicted by various concentration values, and applying an error minimization technique as described previously.

Statistical techniques also may be applied to improve the accuracy of the data analysis in various ways. For example, statistical analysis of fluorescence data may help to determine an appropriate choice of a threshold fluorescence level between negative and positive detection of a target molecule within a given droplet. Applying this detection threshold to the data then may result in a more accurate determination of target concentration than simply choosing a threshold value a priori. Alternatively, the detection threshold may be left as a variable, and information may be extracted from the data across a range of different threshold values spanning a portion of (or all of) the range of detected fluorescence intensities.

Furthermore, the confidence level of the detection threshold fluorescence level may be increased (or equivalently, the confidence interval for a given confidence level may be narrowed) using various statistical resampling techniques such as random sampling with replacement (known in the field of statistics as "bootstrapping") of subsets of the fluorescence data (known as "jackknifing" or "jackknife bootstrapping"). In either case, an improved confidence level in the detection threshold may be obtained by analyzing the variability of the threshold level across replacement data sets.

Similarly, statistical methods may be used to provide other forms of feedback that can result in more efficient use of the amplification system and/or more accurate data analysis. For example, an initial determination of target molecule concentration in the unamplified sample-containing droplets may reveal that the concentration is either too high or too low to be optimal, and this information may be used to adjust various parameters of the system. More specifically, if the target concentration is too low (but nonzero), many droplets may contain no target molecules at all, resulting in poor statistics and wasted resources in preparing and processing large numbers of "empty" droplets despite the fact that some target molecules are present in the sample. On the other hand, if the target concentration is too high, virtually all of the droplets will be saturated with target molecules after amplification, and it will not be possible to determine the target concentration of the original sample accurately because there will be no significant fluorescence variation among droplets. Either of these situations may result in an undesirably large confidence interval for the determination of target concentration.

Several system parameters may be adjusted in response to a determination that the concentration of target molecules in the unamplified sample-containing droplets is not optimal for the existing parameters. For example, the sample-containing solution may be diluted or concentrated prior to droplet generation, to respectively decrease or increase target concentration. Similarly, the size range of the generated droplets may be increased to lower the probability of droplets becoming saturated with the target molecule after amplification, or decreased to increase the likelihood of finding a target molecule (and the average number of target molecules) in each droplet. In addition, various characteristics of the amplification system, such as the thermocycling temperatures and/or the number of thermocycles, may be increased in response to a determination that too little amplification is occurring, or decreased in response to a determination that too much amplification is occurring.

Figure 107:
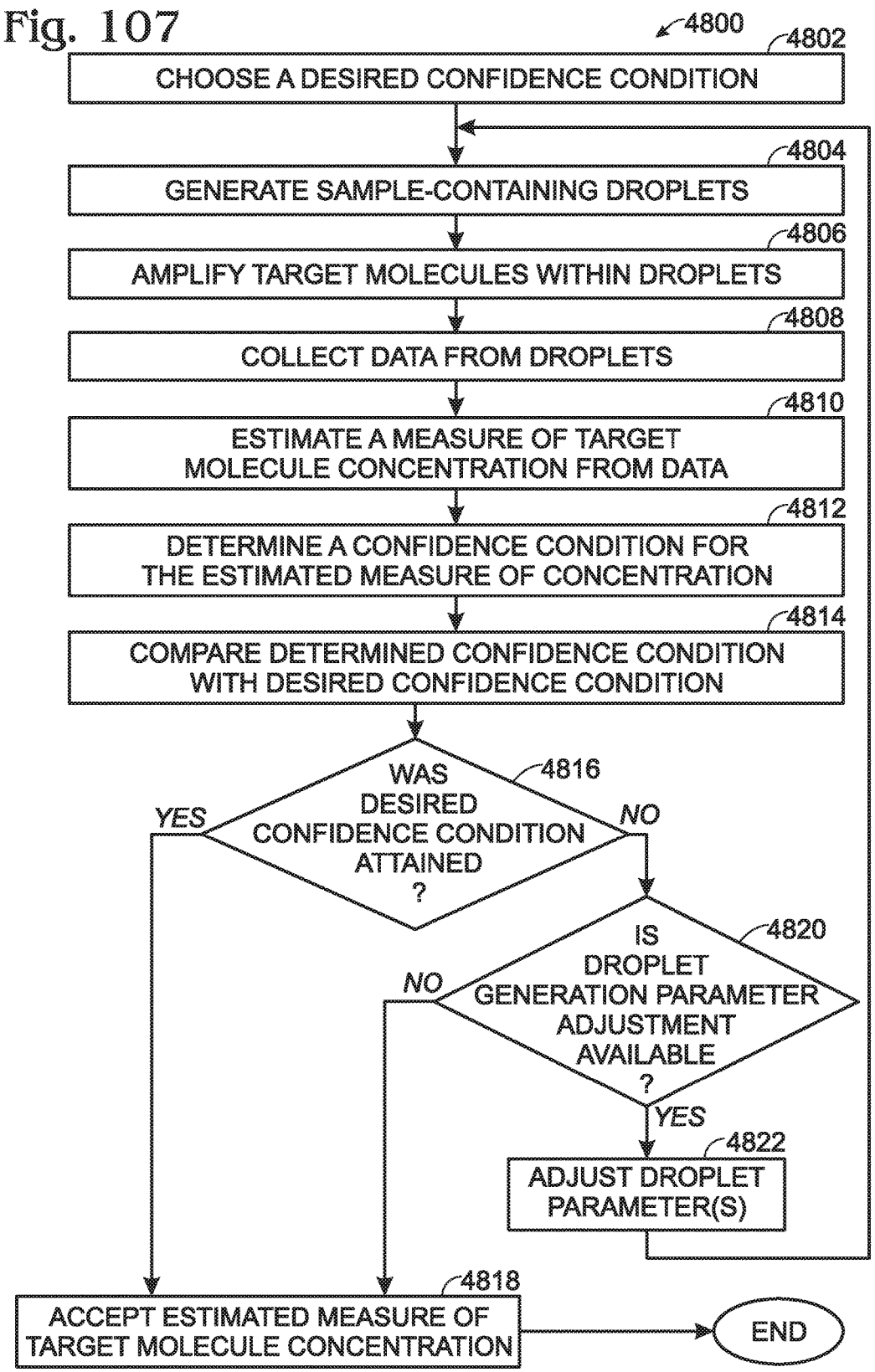
FIG. 107 is a flowchart depicting a method of determining target molecule concentration in a plurality of sample-containing droplets, in accordance with aspects of the present disclosure.

FIG. 107 is a flowchart depicting a method, generally indicated at 4800, of determining target molecule concentration in a plurality of sample-containing droplets. As described below, method 4800 includes a feedback mechanism that can be used to adjust one or more parameters of droplet generation in response to an undesirably low confidence condition in the concentration value.

At step 4802, a confidence condition is chosen. This condition can include, for example, a desired confidence level and/or an associated confidence interval.

At step 4804, sample-containing droplets are generated. Various methods and apparatus for generating such droplets are described elsewhere herein, for example, in Sections III and IV.

At step 4806, target molecules within the droplets are amplified by PCR or some other enzymatic amplification technique. Methods and apparatus for amplifying target nucleotide sequences are described elsewhere herein, for example, in Section V.

At step 4808, data such as fluorescence intensity, time of passage, one or more thermal properties, and/or one or more electrical properties, are collected from the droplets. Methods and apparatus for detecting properties of sample-containing droplets are described elsewhere herein, for example, in Section VI.

At step 4810, a measure of target molecule concentration (i.e., the number of target molecules per unit volume) in the unamplified sample is estimated from the collected data. The estimated measure may include the fraction of droplets containing one or more target molecules, and/or an estimate of the actual concentration.

At step 4812, a confidence condition for the measure estimated in step 4810 is determined. Typically, this will include a confidence level and/or an associated confidence interval, which can be compared to the desired confidence condition received at step 4802.

At step 4814, the determined confidence condition is compared with the desired confidence condition, and at step 4816, a determination is made as to whether the desired confidence condition has been attained.

At step 4818, if the desired confidence condition was attained by the estimated measure of step 4810, then the measure is accepted.

At step 4820, if the desired confidence condition was not attained by the estimated measure of step 4810, then a determination is made as to whether a suitable droplet generation parameter adjustment is available. Suitable adjustments may include adjusting the number of droplets generated (i.e., generating more droplets), changing the sample chemistry, diluting or concentrating the sample prior to droplet generation, generating droplets of different sizes, adjusting thermocycling temperatures, and/or adjusting the number of thermocycles applied to the droplets, among others.

At step 4822, if step 4820 determines that a suitable droplet generation parameter adjustment is available, then one or more droplet generation parameter adjustments is made, and the process returns to step 4804 to generate additional droplets using the adjusted parameter(s). The parameter adjustment may in some cases be simply to generate more droplets to improve statistical confidence, without changing any other parameter of the system. In other cases, a sufficient number of appropriate droplets already may have been created, and the parameter adjustment may relate entirely to the thermocycler. In that case, step 4804 need not be performed again, but rather the method may proceed directly from step 4822 back to step 4806. In any event, the method then proceeds cyclically as FIG. 107 depicts, until either the desired confidence condition is met or until no further parameter adjustments can be made. In some cases, it may not be possible to further adjust any droplet generation parameters even if the desired confidence condition has not been attained, for example, because of chemical, physical, and/or technological limitations. In this case, i.e., if step 4820 determines that a suitable droplet generation parameter adjustment is not available, then the measure of step 4810 is again accepted at step 4818, although it was not possible to meet the desired confidence condition.

Given a set of droplet fluorescence data, there are various techniques that can be used to estimate concentration measures and a confidence condition such as confidence level and confidence interval. The following examples describe several specific statistical techniques that may be applied to the data to extract useful information to a desired degree of accuracy under various circumstances.

A. Example 1

This example describes techniques for estimating the concentration per droplet (average number of target molecules per droplet) with the use of some pre-determined calibration or knowledge on the data set, nominally a characteristic such as a fluorescence threshold that may be used to distinguish target-containing droplets from empty droplets, and the statistical characterization of the confidence of this determination. This example assumes that a collection of values representing the fluorescence intensity for each droplet is available. The techniques described in this example can be applied to peak fluorescence data (i.e., the maximum fluorescence intensity emitted by a droplet containing a particular number of target molecules), but are not limited to this type of data. The described techniques may be generalized to any measurements that could be used to distinguish target-containing droplets from empty droplets.

If C is the target concentration of a sample (number of target molecules per unit volume), $V_d$ is the volume of a droplet (assumed constant in this example), and $\lambda = CV_d$ is the average number of copies per droplet, the probability that a given droplet will contain k target molecules is given by the Poisson distribution:

$$P(k; \lambda) = \frac{\lambda^k \operatorname{Exp}(-\lambda)}{k!} \qquad (1)$$

If, for example, there is an average of 3 copies of target nucleic acid per droplet, Poisson's distribution would indicate that an expected 5.0% of droplets would have zero copies, 14.9% would have one copy, 22.4% would have 2 copies, 22.4% would have 3 copies, 16.8% would have 4 copies, and so on. It can be reasonably assumed that a droplet will react if there is one or more target nucleic acid molecules in the volume. In total, 95% of the droplets should be positive, with 5% negative. Because the different numbers of initial copies per droplet can, in general, be distinguished after amplification, a general description of the analysis taking this into account can provide improved accuracy in calculating concentration.

Figure 108:
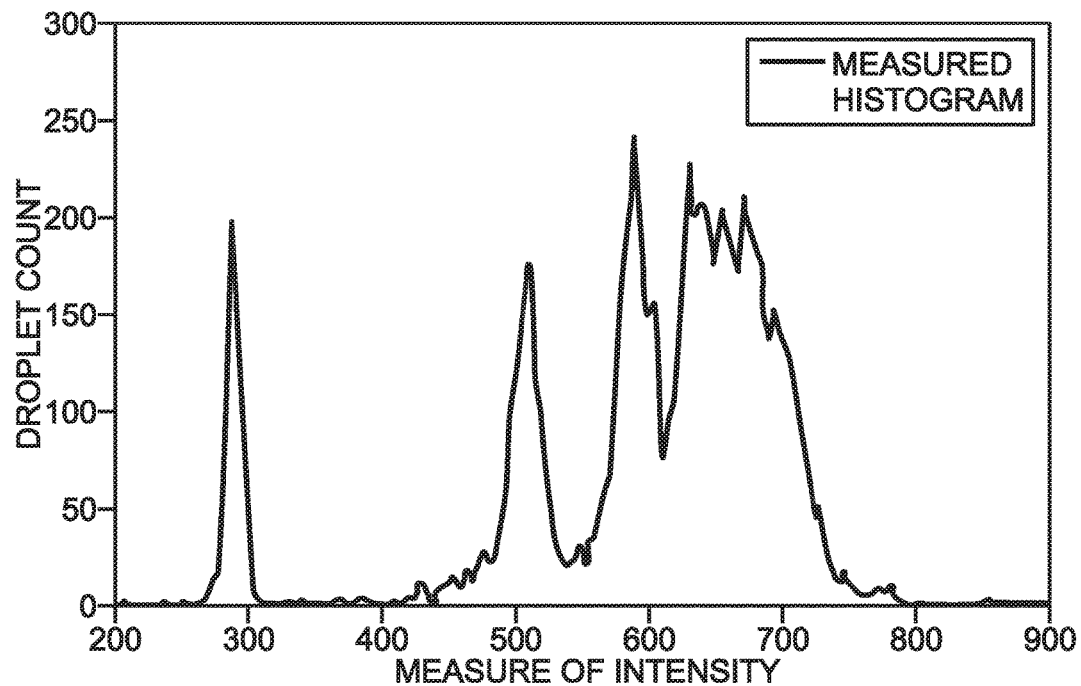
FIG. 108 is a histogram showing exemplary experimental data in which the number of detected droplets is plotted as a function of a measure of fluorescence intensity.

FIG. 108 displays a sample data set where the number of detected droplets is plotted as a histogram versus a measure of fluorescence intensity. The data indicates a peak in droplet counts at an amplitude of just less than 300, and several peaks of different intensity positives from about 500 to 700.

The different intensity of the positives is the result of different initial concentrations of target molecules. The peak at about 500 had one initial copy, the peak at about 600 had two initial copies, and so on until the peaks become indistinguishable.

We can define an initial number of copies K after which there is no difference in detection probability. We can now define a variable, X, describing the probability that a given fluorescence measurement will be defined as a positive detection (X=1). As equation (2) below indicates, this is defined to be the sum of the probabilities of a droplet containing any fluorescently distinguishable positive (first term right hand side) plus the fluorescently saturated positives (second term right hand side), plus the negatives that are incorrectly identified as positives (third term right hand side):

$$P_{measurement}(X=1) = \sum_{1 \leq i < K} P_{d_i} P(k=i) + P_{d_K} P(k \geq K) + P_{fa} P(k=0) \quad (2)$$

This can also be written in terms of $\lambda$ by substituting equation (1) for the Poisson probabilities:

$$P_{measurement}(X=1) = \quad (3)$$
$$\sum_{1 \leq i < K} P_{d_i} \frac{\lambda^i \text{Exp}(-\lambda)}{i!} + P_{d_K}\left\{1 - \sum_{0 \leq i < K} \frac{\lambda^i \text{Exp}(-\lambda)}{i!}\right\} + P_{fa}\text{Exp}(-\lambda)$$

The probability that a given measurement will be defined as a negative (X=0) can also be defined as:

$$P_{measurement}(X=0) = 1 - P_{measurement}(X=1) \quad (4)$$

The equations above are simplified for an apparatus where K=1, i.e., where one or more target copies per droplet fall within the same fluorescence peak or the separation between positive and negatives is so clear that $P_{fa}$ can be neglected. In some cases, however, there may be significant overlap between fluorescence peaks of the negative droplets and the positive droplets, so that $P_{fa}$ is not negligible. This example applies in either case.

The mean of the variable X is the sum of the product of the realizations and the probabilities:

$$M_{measurement} = 1(P(X=1)) + 0(P(X=0)) = P(X=1) \quad (5)$$
or $$M_{measurement} = \quad (6)$$
$$\sum_{1 \leq i < K} P_{d_i} \frac{\lambda^i \text{Exp}(-\lambda)}{i!} + P_{d_K}\left\{1 - \sum_{0 \leq i < K} \frac{\lambda^i \text{Exp}(-\lambda)}{i!}\right\} + P_{fa}\text{Exp}(-\lambda)$$

and its standard deviation is given by $$E_{measurement} = \sqrt{P_{measurement}(X=1)(1-M_{measurement})^2 + P_{measurement}(X=0)M_{measurement}^2} \quad (7)$$

Because the definition of X is such that a negative droplet corresponds to X=0 and a positive droplet corresponds to X=1, the mean of X is also the fraction of positive droplets:

$$M_{measurement} = \frac{N_+}{N} \quad (8)$$

Equation 6 and 7 can then be rewritten:

$$\frac{N_+}{N} = \quad (9)$$
$$\sum_{1 \leq i < K} P_{d_i} \frac{\lambda^i \text{Exp}(-\lambda)}{i!} + P_{d_K}\left\{1 - \sum_{0 \leq i < K} \frac{\lambda^i \text{Exp}(-\lambda)}{i!}\right\} + P_{fa}\text{Exp}(-\lambda)$$

and $$E_{measurement} = \sqrt{\left(1 - \frac{N_+}{N}\right)\frac{N_+}{N}} \quad (10)$$

Because of their high degree of non-linearity, equations (9) and (10) cannot be readily used to find $\lambda$ without prior knowledge of the probabilities $P_{di}$ and $P_{fa}$. A special case occurs when all droplets are detected ($P_{di}=1$), only one fluorescent state is distinguishable (K=1), and the positive and negative peaks are easily discernible so that the probability of a false detection is negligible ($P_{fa}=0$). In this case, equation (9) can be solved for $\lambda$:

$$\lambda = \ln\left(1 + \frac{N_+}{N_-}\right) \quad (11)$$

B. Example 2

This example describes extension of the previous example to situations where the simplifying assumptions $P_{di}=1$, K=1, and $P_{fa}=0$ are not made. It allows processing the data without the use of some pre-determined calibration or knowledge on the data set. This example relies on a least mean squares (LMS) or similar fit of the data to the general theory as outlined by equation (9). We define F as a function describing the difference between the theoretical ratio of droplets (see equation (9) above) and the measured equivalent:

$$F = \sum_{1 \leq i < K} P_{d_i} \frac{\lambda^i \text{Exp}(-\lambda)}{i!} + \quad (12)$$
$$P_{d_K}\left\{1 - \sum_{0 \leq i < K} \frac{\lambda^i \text{Exp}(-\lambda)}{i!}\right\} + P_{fa}\text{Exp}(-\lambda) - \frac{N_+}{N}$$

This difference should be equal to zero if the proper probabilities and $\lambda$ can be found. F is, in general, a function of the threshold value set to distinguish positives from negatives, and the distribution of fluorescence signals from a set of droplets with the same initial number of target copies, each of which under basic assumptions can be described by Gaussian distribution, although other distributions are possible and are conceptually simple extensions of the described method. More specifically, due to droplet size variation, PCR efficiency, flow rate variability through the detector, electrical noise and other such random factors, for each number i of initial target molecules in equation (12), there will be a distribution of fluorescence values characterized by a mean value, $M_i$ and standard deviation $\sigma_i$:

$$P_i(t) = \frac{1}{\sigma_i\sqrt{2\pi}} \text{Exp}\left(-\frac{\{t-M_i\}^2}{2\sigma_i^2}\right) \quad (13)$$

The droplets detected as positive from these distributions would be dependent on the chosen threshold:

$$P_{d_i} = \int_{Threshold}^{\infty}\left[\frac{1}{\sigma_i\sqrt{2\pi}}\text{Exp}\left(-\frac{\{t-M_i\}^2}{2\sigma_i^2}\right)\right]dt \quad (14)$$

The function F then becomes:

$$F(\text{Threshold}, \lambda, M_i, \sigma_i) = \quad (15)$$
$$\sum_{1\le i<K}\left\{\int_{Threshold}^{\infty}\left[\frac{1}{\sigma_i\sqrt{2\pi}}\text{Exp}\left(-\frac{\{t-M_i\}^2}{2\sigma_i^2}\right)\right]dt\right\}\frac{\lambda^i\text{Exp}(-\lambda)}{i!} +$$
$$\left\{\int_{Threshold}^{\infty}\left[\frac{1}{\sigma_K\sqrt{2\pi}}\text{Exp}\left(-\frac{\{t-M_K\}^2}{2\sigma_K^2}\right)\right]dt\right\}\left\{1 - \sum_{0\le i<K}\frac{\lambda^i\text{Exp}(-\lambda)}{i!}\right\} +$$
$$\left\{\int_{Threshold}^{\infty}\left[\frac{1}{\sigma_0\sqrt{2\pi}}\text{Exp}\left(-\frac{\{t-M_0\}^2}{2\sigma_0^2}\right)\right]dt\right\}\text{Exp}(-\lambda) - \frac{N_+}{N}$$

Equation (15) is a general example that applies to a Gaussian distribution of droplet fluorescence including multiple states of detectable positives. A least mean squares fit of equation (15) to a particular data set may be found through iterative numerical methods, resulting in best fit estimates of $\lambda$, $M_i$, and $\sigma_i$ for all possible threshold settings. The same technique may be applied to any other well-defined distribution of target molecules. For example, the configuration may be assumed to follow a distribution that takes into account the number of PCR cycles and/or the PCR efficiency.

Figure 109:
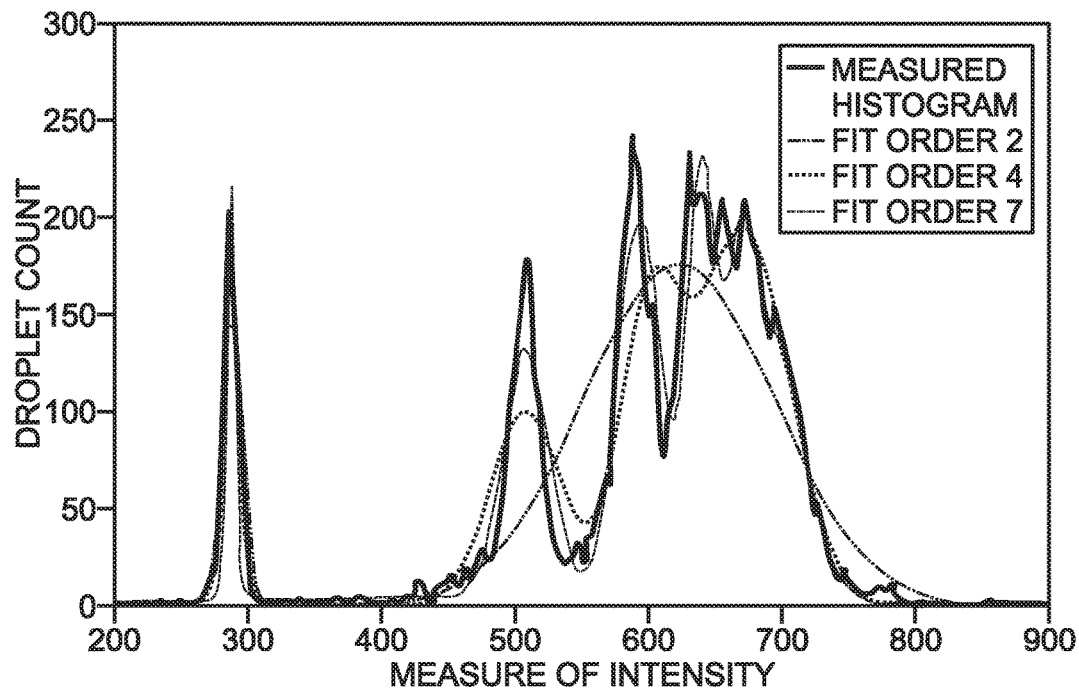
FIG. 109 is a histogram comparing the experimental data in FIG. 108 (solid line) with fluorescence distributions recreated numerically using various fit orders (dotted and dashed lines).
Figure 110:
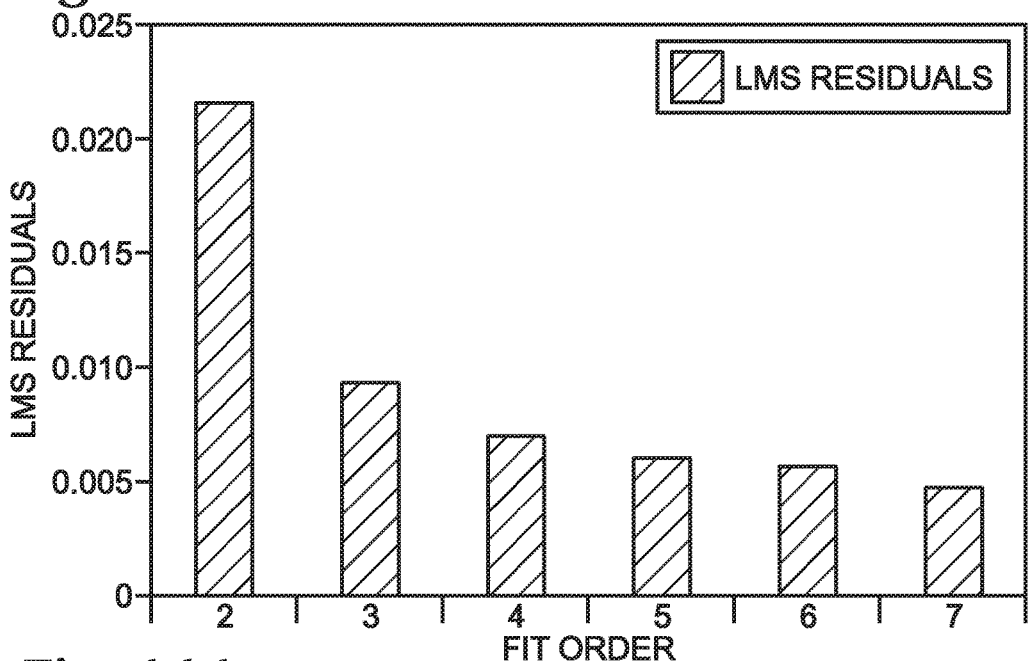
FIG. 110 is a histogram showing values of least mean square residuals for the fluorescence distributions of FIG. 108 recreated numerically using various fit orders.

FIG. 109 shows both the same fluorescence data shown in FIG. 108, again displayed as a histogram of the number of droplets detected versus a measure of fluorescence intensity, and the fluorescence distribution recreated numerically from equation (15) with several values of K. As FIG. 109 indicates, the numerically determined function recreates the actual data well, indicating an accurate determination of $\lambda$, $M_i$, and $\sigma_i$. To determine the numerically optimal fit order, the least mean square residual between the measured fluorescence data and the numerically recreated function may be calculated for each fit order, and the fit order corresponding to the lowest residual may be adopted. For example, FIG. 110 is a histogram showing the least mean square residual for fit orders two through seven obtained with equation (15), showing that the numerical method becomes increasingly accurate at least up to seven fit orders.

Figure 111:
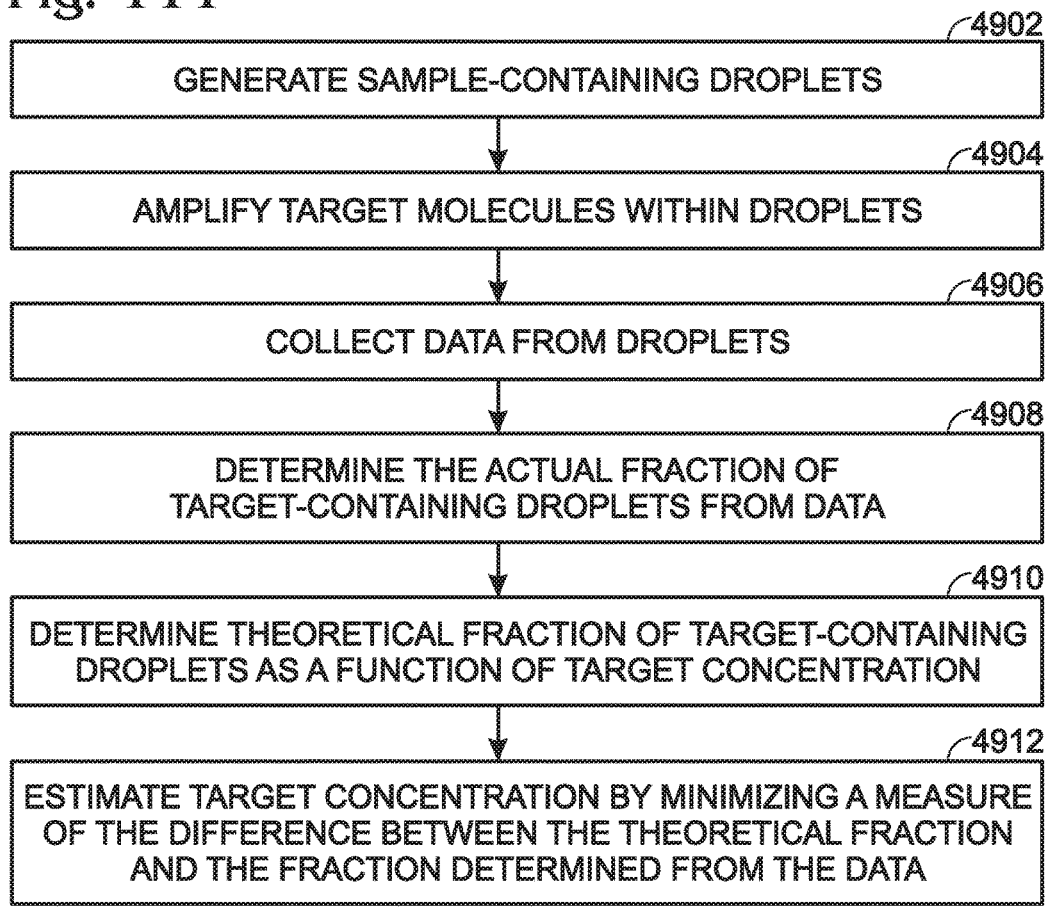
FIG. 111 is a flowchart depicting a method of numerically estimating target molecule concentration in a sample, in accordance with aspects of the present disclosure.

FIG. 111 is a flowchart depicting a method, generally indicated at 4900, for numerically estimating target molecule concentration in a sample based on aspects of this example. At step 4902, sample-containing droplets are generated. Various methods and apparatus for generating such droplets are described elsewhere herein, for example, in Sections III and IV. At step 4904, target molecules within the droplets are amplified by PCR or some other enzymatic amplification technique. Methods and apparatus for amplifying target nucleotide sequences are described elsewhere herein, for example, in Sections V. At step 4906, data such as fluorescence intensity, time of passage, one or more thermal properties, and/or one or more electrical properties, are collected from the droplets. Methods and apparatus for detecting properties of sample-containing droplets are described elsewhere herein, for example, in Section V.

The remaining steps of method 4900 are generally computationally intensive, and accordingly are typically performed with the aid of a digital processor programmed with suitable instructions. At step 4908, a measured fraction of droplets containing one or more target molecules is determined from the data collected at step 4906. As described above, this fraction will generally be a function of the threshold fluorescence value chosen to distinguish a positive (target-containing) droplet from a negative droplet. At step 4910, a theoretical value of the fraction of droplets containing one or more target molecules is determined as a function of target molecule concentration in the original, unamplified sample. This theoretical value will, like the value determined from the data, generally also be a function of the chosen detection threshold. A suitable theoretical value is provided, for example, by the integral terms of equation (15) above. At step 4912, the target concentration is estimated by minimizing a measure of the difference between the theoretical fraction determined in step 4910 and the fraction determined in step 4908 from the collected data. More generally, this step may be performed by comparing the measured fraction to the theoretical fraction in some manner.

C. Example 3

This example describes methods that may be used to estimate the confidence interval in an estimated value of target concentration that has been obtained, for example, using the methods of Examples 1 and 2 described above. The confidence interval cannot be directly estimated when a non-linear least mean square is used (as in Example 2). The bootstrap method, on the other hand, can provide some idea of the error of the estimation. The principle is based on estimating a plurality of values of target molecule concentration, where each value is estimated based on a subset of the collected fluorescence intensity values, and then determining a mean value and a standard deviation of the estimated concentration from the plurality of estimated concentration values. The subsets of the samples (here the droplet intensities) are chosen randomly (Monte Carlo). The standard deviation and mean can then provide an estimated concentration as well as a confidence interval defined from the standard deviation (if the assumption is that the estimation follows a Gaussian distribution) or directly from the actual results.

One particular type of bootstrap method, which is sometimes referred to as a form of the jackknife bootstrap method, uses data subsets each chosen to include the total number of data points minus 1. This maximizes the statistics available for the estimation while allowing up to the total number of point subsets. This works particularly well for a large data set. In the case of droplet-based detection, the number of measurements is expected to be on the order of thousands or more, so the jackknife bootstrap technique may be particularly appropriate. In the present application of the jackknife bootstrap, this means that each subset includes all but one of the collected fluorescence intensity values.

The confidence interval obtained using the jackknife bootstrap method may be characterized by its dependence on the following factors:

the number of droplet intensities used in the analysis;
the number of data subsets used (the upper limit is the total number of intensities);
the number of threshold values used for the fit; and
the fit order.

Numerical studies using sample droplet fluorescence data suggest the following conclusions regarding these factors:
the more droplets, the smaller the confidence interval, with the confidence interval decreasing approximately as the inverse square root of the number of droplets;
100 jackknife data subsets is typically sufficient to find the smallest confidence interval for a given set of other parameters;
using a number of different fluorescence thresholds greater than or equal to approximately a factor of 3 times the number of unknowns (which equals 2 times the fit order plus one) is typically sufficient to find the smallest confidence interval for a given set of other parameters; and
the fit order providing the lowest least mean square residuals should be used.

D. Example 4

This example describes how the methods of the previous examples may be extended to situations in which droplet size is not uniform, but rather varies among the droplets according to a Gaussian distribution function. The application of equation (15) above relies on the assumption of a constant droplet volume to calculate the initial concentration, $C$, from the calculated value of $\lambda$ and the assumed droplet volume $V$:

$$\lambda = CV \quad (16)$$

If the droplet volume varies significantly, the same principles can be applied to solving for the concentration for a given droplet size distribution. Equation (2) can be restated as a function of volume:

$$P_{measurement}(X=1, V) = \quad (17)$$
$$P(V) \sum_{1 \leq i < K} P_{d_i} P(k=i, V) + P_{d_K} P(k \geq K, V) + P_{fa} P(k=0, V)$$

For a Gaussian distribution of droplet volumes with mean $M_V$ and standard deviation $\sigma_V$, equation (15) can be placed into the more general form:

$$F(\text{Threshold}, \lambda, M_V, \sigma_V, M_i, \sigma_i) = \quad (18)$$
$$\int_0^\infty \left[ \frac{1}{\sigma_V \sqrt{2\pi}} \text{Exp}\left(-\frac{(V-M_V)^2}{2\sigma_V^2}\right) \right]$$
$$\left( \sum_{1 \leq i < K} \left\{ \int_{\text{Threshold}}^\infty \left[ \frac{1}{\sigma_i \sqrt{2\pi}} \text{Exp}\left(-\frac{(t-M_i)^2}{2\sigma_i^2}\right) \right] dt \right\} \right.$$
$$\frac{(CV)^i \text{Exp}(-CV)}{i!} +$$
$$\left\{ \int_{\text{Threshold}}^\infty \left[ \frac{1}{\sigma_K \sqrt{2\pi}} \text{Exp}\left(-\frac{(t-M_K)^2}{2\sigma_K^2}\right) \right] dt \right\}$$
$$\left\{ 1 - \sum_{0 \leq i < K} \frac{(CV)^i \text{Exp}(-CV)}{i!} \right\} +$$
$$\left\{ \int_{\text{Threshold}}^\infty \left[ \frac{1}{\sigma_0 \sqrt{2\pi}} \text{Exp}\left(-\frac{(t-M_0)^2}{2\sigma_0^2}\right) \right] dt \right\}$$
$$\left. \text{Exp}(-CV) \right] dV = \frac{N_+}{N}$$

Equation (18) can be solved with the same basic principles of least mean squares as equation (15). A knowledge of the mean droplet volume by alternate measurements as described previously, as well as a knowledge of the standard deviation, will help the least mean square process to converge to a stable solution. However, the least mean square process can also be tried without that knowledge, in which case the mean and standard deviation of the droplet volume will be additional unknown variables. Additionally, theoretical studies have shown that a standard deviation of less than 7% of the mean value has a negligible effect on the results. Therefore, extension of equation (15) to the more general case of equation (18) may not be needed for large required confidence intervals For the special case where all droplets are detected, $P_{di}=1$, only one fluorescence state is distinguishable, $K=1$, and the positive and negative peaks are easily discernible so that the probability of a false detection is negligible, $P_{fa}=0$, equation (17) will give $$M_{measurement} = \int_0^\infty P(V)(1 - \text{Exp}(-CV)) dV \quad (19)$$

and the standard deviation becomes:

$$E_{meas} = \sqrt{\int_0^\infty P(V)(1 - \text{Exp}(-CV))(1 - M_{meas})^2 dV + \int_0^\infty P(V) \text{Exp}(-CV)(M_{meas})^2 dV} \quad (20)$$

In general, for any known or measured droplet volume distribution $P(V)$, the mean and standard deviation can be calculated.

E. Example 5

This example describes various alternative methods of estimating droplet concentration, assuming uniform droplet volume and perfect detectability (i.e., all positive droplets detected, and no false detections). Under these assumptions, an analysis can be performed on the volume spacing between positives in the data. It is straightforward to derive the probability of detecting n negative droplets (i.e., droplets containing no target molecules) before detecting a positive. Applying the Poisson distribution of equation (1), the probability of a droplet containing no target molecules is:

$$P(0;\lambda) = \text{Exp}(-\lambda) \equiv N_-/N \quad (21)$$

Therefore, the probability of n consecutive droplets containing no target molecules is:

$$[P(0;\lambda)]^n = [\text{Exp}(-\lambda)]^n = \text{Exp}(-n\lambda) \quad (22)$$

Furthermore, the probability of a droplet containing one or more target molecules is:

$$\Sigma_{k=1}^{K=\infty} P(k;\lambda) = 1 - \text{Exp}(-\lambda) \equiv N_+/N \quad (23)$$

Thus, the theoretical probability distribution of detecting n consecutive droplets containing no target molecules before detecting a droplet containing at least one target molecule is:

$$[P(n;\lambda)] = [P(0;\lambda)]^n \Sigma_{k=1}^{k=\infty} P(k;\lambda) = (1-e^{-\lambda})e^{-n\lambda} \quad (24)$$

Accordingly, the target molecule concentration may be estimated by comparing the measured probability distribution to this theoretical probability distribution. For example, taking the natural log of both sides, $$\ln [P(n;\lambda)] = \ln(1-e^{-\lambda}) - n\lambda \quad (25)$$

Accordingly, a plot of [P(n;λ)] versus n will be a line with slope −λ and y-intercept ln [1−e$^{-\lambda}$], and P(n;λ) as determined from the data may be used to generate different estimate of λ.

Using equation (24), a related estimator for λ may be derived using a maximum likelihood analysis. Specifically, the value of λ that maximizes the probability of a spacing of n droplets before detecting a positive droplet will correspond to the average spacing value. This value may be found by setting the derivative of P with respect to λ equal to zero:

$$0 = \frac{\partial P}{\partial \lambda} \quad (26)$$
$$= -ne^{-n\lambda}(1-e^{-\lambda}) + e^{-n\lambda}(e^{-\lambda})$$
$$n = e^{-\lambda}(1+n)$$
$$\lambda = \lambda_{MLE} = \ln\left(1 + \frac{1}{\langle n \rangle}\right)$$

where <n> is the average value of the spacing calculated from the observed data, i.e., the average number of droplets containing no target molecules before detecting a droplet containing at least one target molecule.

F. Example 6

This example describes how the confidence interval for the fraction of positive detections can be determined analytically for the case K=1 using the central limit theorem. Recall from above that the mean value of the positive detection ratio may be expressed as:

$$M_{measurement} = \quad (6)$$
$$\sum_{1 \leq i < K} P_{d_i} \frac{\lambda^i \text{Exp}(-\lambda)}{i!} + P_{d_K}\left(1 - \sum_{0 \leq i < K} \frac{\lambda^i \text{Exp}(-\lambda)}{i!}\right) + P_{fa}\text{Exp}(-\lambda)$$

and its standard deviation is given by $$E_{measurement} = \sqrt{\frac{P_{measurement}(X=1)(1-M_{measurement})^2 + }{P_{measurement}(X=0)M_{measurement}^2}} \quad (7)$$

where the positive detection ratio is measured by the ratio of positively detected droplets to the total number of measurements:

$$M_{measurement} = \frac{N_+}{N} \quad (8)$$

The central limit theorem then states that the standard deviation of N measurements is given by $E_{measurement}/\sqrt{N}$. Therefore, with 95% confidence (2 standard deviations), we have:

$$\frac{N_+}{N} \pm 2\frac{E_{measurement}}{\sqrt{N}} = \quad (27)$$
$$\sum_{1 \leq i < K} P_{d_i} \frac{\lambda^i \text{Exp}(-\lambda)}{i!} + P_{d_k}\left(1 - \sum_{0 \leq i < K} \frac{\lambda^i \exp(-\lambda)}{i!}\right) + P_{fa}\exp(-\lambda)$$

with $$E_{measurement} = \sqrt{\left(1 - \frac{N_+}{N}\right)\left(\frac{N_+}{N}\right)} \quad (28)$$

For simple cases (here shown with K=1, $P_{di}=P_{dk}=1$, and $P_{fa}=0$), λ can be derived by inverting the previous equation and the result with a confidence interval at 95% confidence (2 standard deviations) can be expressed as:

$$\frac{N_+}{N} - 2\frac{E_{measurement}}{\sqrt{N}} \leq 1 - \sum_{0 \leq i < 1} \frac{\lambda^i \exp(-\lambda)}{i!} \leq \frac{N_+}{N} + 2\frac{E_{measurement}}{\sqrt{N}} \quad (29)$$

$$\frac{N_+}{N} - 2\frac{E_{measurement}}{\sqrt{N}} \leq 1 - \exp(-\lambda) \leq \frac{N_+}{N} + 2\frac{E_{measurement}}{\sqrt{N}}$$

$$1 - \frac{N_+}{N} - 2\frac{E_{measurement}}{\sqrt{N}} \leq \exp(-\lambda) \leq$$

$$1 - \frac{N_+}{N} + 2\frac{E_{measurement}}{2N} - \ln\left(1 - \frac{N_+}{N} + 2\frac{E_{measurement}}{\sqrt{N}}\right) \leq$$

$$\lambda \leq -\ln\left(1 - \frac{N_+}{N} - 2\frac{E_{measurement}}{\sqrt{N}}\right) -$$

$$\ln\left(1 - \frac{N_+}{N} + 2\frac{\sqrt{\left(1 - \frac{N_+}{N}\right)\left(\frac{N_+}{N}\right)}}{\sqrt{N}}\right) \leq$$

$$\lambda \leq -\ln\left(1 - \frac{N_+}{N} - 2\frac{\sqrt{\left(1 - \frac{N_+}{N}\right)\left(\frac{N_+}{N}\right)}}{\sqrt{N}}\right)$$

G. Example 7

This example describes additional aspects of systems for analyzing data and improving data collection, in accordance with aspects of the present disclosure, presented without limitation as a series of numbered sentences.

1. A method of determining target molecule concentration in a sample to a desired degree of confidence, comprising (A) generating sample-containing droplets with a droplet generator; (B) amplifying target molecules within the droplets; (C) collecting data from the droplets including at least values of fluorescence intensity emitted by a plurality of the droplets; (D) estimating target molecule concentration in the sample based on the collected data; (E) comparing a confidence condition for the estimated concentration with a desired confidence condition; and (F) if the desired confidence condition has not been attained, then adjusting at least one droplet generation parameter.

2. The method of paragraph 1, wherein the droplet generation parameter is the number of droplets generated.

3. The method of paragraph 1, wherein the droplet generation parameter is sample chemistry.

4. The method of paragraph 1, wherein the droplet generation parameter is droplet concentration.

5. The method of paragraph 1, wherein the droplet generation parameter is droplet size.

6. The method of paragraph 1, wherein the droplet generation parameter is a thermocycling temperature.

7. The method of paragraph 1, wherein the droplet generation parameter is a number of thermocycles.

8. The method of paragraph 1, wherein the droplet generator is a single-use droplet generator.

9. The method of paragraph 1, wherein collecting data includes measuring time of passage of each of the plurality of droplets in a field of view of a detector.

10. The method of paragraph 1, wherein collecting data includes measuring an electrical property of each of the plurality of droplets sufficient to estimate a volume of each droplet.

11. The method of paragraph 1, wherein collecting data includes measuring a thermal property of each of the plurality of droplets sufficient to estimate a volume of each droplet.

12. A method of determining target molecule concentration in a sample, comprising (A) generating sample-containing droplets with a droplet generator; (B) amplifying target molecules within the droplets; (C) collecting data from the droplets including fluorescence intensity emitted by each of a plurality of the droplets; (D) determining from the collected data a measured fraction of droplets containing at least one target molecule; (E) determining a theoretical fraction of droplets containing at least one target molecule, as a function of target molecule concentration; and (F) determining the concentration by comparing the measured fraction to the theoretical fraction.

13. The method of paragraph 12, wherein the theoretical fraction is determined by assuming that the target molecules are randomly distributed in the droplets.

14. The method of paragraph 12, wherein the theoretical fraction is determined by assuming that all droplets are detected, only one fluorescent state is distinguishable, and there are no false detections.

15. The method of paragraph 12, wherein the theoretical fraction is determined by assuming that the droplet fluorescence intensities follow a Gaussian distribution.

16. The method of paragraph 15, wherein comparing the measured fraction to the theoretical fraction includes minimizing a measure of the difference between the theoretical fraction and the measured fraction.

17. The method of paragraph 15, wherein comparing the measured fraction to the theoretical fraction includes applying a least mean squares fit of the theoretical fraction to the collected data.

18. The method of paragraph 12, wherein the measured fraction and the theoretical fraction are both functions of a detection threshold fluorescence value, and wherein determining the concentration includes comparing the measured fraction to the theoretical fraction for a plurality of detection threshold values.

19. The method of paragraph 12, wherein the theoretical fraction is determined by assuming that the droplets have a uniform volume.

20. The method of paragraph 12, wherein the theoretical fraction is determined by assuming that the droplets have a Gaussian distribution of volumes.

21. A method of determining target molecule concentration in a sample, comprising (A) generating sample-containing droplets with a droplet generator; (B) amplifying target molecules within the droplets; (C) collecting data from the droplets including a value of fluorescence intensity emitted by a plurality of the droplets; (D) estimating a plurality of values of target molecule concentration, wherein each value is estimated based on a subset of the collected fluorescence intensity values; and (E) determining a mean value and a standard deviation of the estimated concentration from the plurality of estimated concentration values.

22. The method of paragraph 21, wherein the subsets are chosen randomly.

23. The method of paragraph 22, wherein each subset includes all but one of the collected fluorescence intensity values.

24. A method of determining target molecule concentration in a sample, comprising (A) generating sample-containing droplets with a droplet generator; (B) amplifying target molecules within the droplets; (C) collecting data from the droplets including a value of fluorescence intensity emitted by a plurality of the droplets; (D) determining from the collected data a measured probability distribution of detecting a particular number of droplets containing no target molecules before detecting a droplet containing at least one target molecule; and (E) estimating target molecule concentration by comparing the measured probability distribution to a theoretical probability distribution.

25. The method of paragraph 24, wherein determining the measured probability distribution includes determining the average number of droplets containing no target molecules before detecting a droplet containing at least one target molecule, and wherein estimating target molecule concentration includes estimating a maximum likelihood value of target molecule concentration.

26. A system for determining target molecule concentration in a sample, comprising (A) a droplet generator configured to generate sample-containing droplets; (B) a thermocycler configured to amplify target molecules within the droplets; (C) a fluorescence detector configured to collect values of fluorescence intensity emitted by a plurality of the droplets; and (D) a digital processor configured to estimate target molecule concentration in the sample based on the collected data, compare a confidence condition for the estimated concentration with a desired confidence condition, and send a signal to adjust at least one parameter of the droplet generator or the thermocycler if the desired confidence condition has not been attained.

27. A method of analyzing a sample for a nucleic acid target, comprising (A) removing a portion of a sample; (B) creating an assay mixture from the portion for amplification of the nucleic acid target, if present; (C) generating a packet of droplets from the assay mixture, the packet having an at least substantially predetermined number of the droplets; (D) subjecting the packet to conditions for nucleic acid amplification; (E) performing one or more measurements on each of a plurality of droplets of the packet; (F) using the one or more measurements to determine a number of the plurality of droplets in which amplification of the nucleic acid target occurred; and (G) estimating the total presence of molecules of the nucleic acid target in the sample based on the number of droplets determined.

28. A method of analyzing a sample for a nucleic acid target, comprising (A) generating a first packet of droplets from a sample, each droplet having a composition capable of amplification of the nucleic acid target, if present, in the droplet; (B) subjecting the first packet to conditions for nucleic acid amplification; (C) performing one or more measurements on each of a plurality of droplets of the first packet; (D) using the one or more measurements to determine a first fraction of droplets in which amplification of the nucleic acid target occurred; (E) determining whether the first fraction satisfies a predefined confidence condition for estimating the total presence of target in the sample and, if not, repeating the steps of subjecting, performing, and using with a second packet of droplets having a different average droplet volume and/or a different concentration of the sample relative to the first packet, to determine a second fraction of droplets in which amplification of the nucleic acid target occurred; and (F) estimating the total presence of the nucleic acid target in the sample based on the first fraction, the second fraction, or both.

29. A method for quantifying nucleic acid concentration and/or confidence interval, comprising (A) providing a sample having a given starting volume, the sample to be analyzed for the presence of a target nucleic acid molecule, (B) removing a sub-sample of a predetermined volume from the sample; (C) creating an assay mix by performing the steps of any of combining the sub-sample with any of primers and or probes for replicating the target nucleic acid molecule, diluting the subsample, concentrating the subsample, and combinations thereof; (D) creating a droplet packet having a pre-determined number of droplets from the assay mix, the droplets having a droplet volume distribution; (E) subjecting the packets to conditions for nucleic acid replication; (F) performing one or more measurements on at least one droplet from the packets; (G) using the one or more measurements to determine the number of droplets comprising replicated target nucleic acid molecules and optionally droplet volume if the volume distribution is unknown; and (H) using the number of droplets comprising replicated target nucleic acid molecules to estimate any of the number of target nucleic acid molecules in the sample volume and the confidence interval thereof and combinations thereof.

30. The method of paragraph 29, wherein droplet volume is measured using optical (e.g., scattering, fluorescence) or electrical (e.g., conductivity, dielectric permittivity) methods.

31. The method of paragraphs 29 or 30, wherein nucleic assay replication is measured using optical (e.g., luminescence, fluorescence) or electrical (e.g., conductivity, dielectric permittivity) methods.

32. A method for determining concentration by changing droplet volume, comprising (A) adjusting the sample partition volume and measuring the percentage of partitions that amplified at least until finding the responsive range at which point the concentration can be determined, (B) creating a predetermined number of droplets at first volume that has a concentration range spanning a responsive range, (C) subjecting the droplets to conditions that support amplification, (D) measuring a signal (physical property) to determine if amplification has occurred and if DNA was present in the droplets prior to amplification, (E) counting droplets and determining the percentage of droplets that amplified, (F) estimating the concentration range using the percentage droplets amplified from Poisson curve or derivative thereof, and (G) if the estimated concentration is outside the optimal range then performing analysis using a second droplet volume.

33. A method of determining concentration by diluting or concentrating droplet solution, by analogy with paragraph 32.

VIII. CONTROLS AND CALIBRATIONS FOR DROPLET-BASED ASSAYS

This Section describes exemplary control and calibration systems, including methods and apparatus, for example, for performing droplet-based assays, such as tests of nucleic acid amplification, that are controlled and/or calibrated using signals detected from droplets. Additional pertinent disclosure may be found in the U.S. provisional patent applications listed above under Cross-References and incorporated herein by reference, particularly Ser. No. 61/275, 731, filed Sep. 1, 2009.

A. INTRODUCTION

Droplet-based tests for amplification generally need to be accurate. If inaccurate, these tests can generate erroneous results, that is, false negatives and false positives. Each type of erroneous result can have detrimental consequences. False negatives related to detection of a disease could mean that the disease is not treated early and is permitted to spread. In contrast, false positives could cause unnecessary alarm, potentially triggering an unnecessary response that may be costly and disruptive. To avoid problems associated with false negatives and false positives, inaccurate amplification tests must be repeated to improve their reliability, which increases cost and uses more sample and reagent, each of which may be precious.

Figure 112:
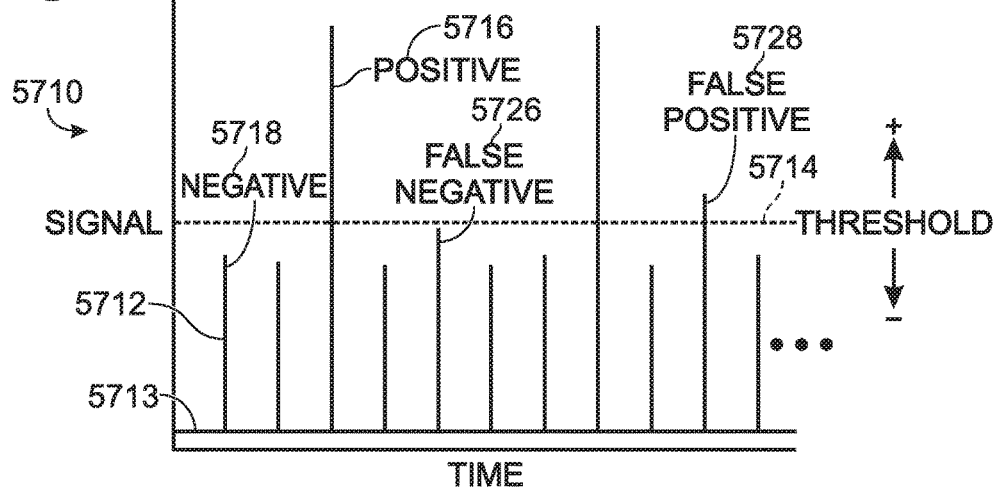
FIG. 112 is an exemplary graph of fluorescence signals that may be measured with respect to time from a flow stream of droplets, with the graph exhibiting a series of peaks representing droplet signals, and with the graph indicating a signal threshold for assigning droplet signals as corresponding to amplification-positive and amplification-negative droplets, in accordance with aspects of the present disclosure.

FIG. 112 shows a graph 5710 illustrating an exemplary approach for using fluorescence to measure amplification of a nucleic acid target in droplets formed by partitioning a sample. The graph plots, with respect to time, fluorescence signals that may be detected from a flow stream containing the droplets. Each droplet may be detected as a transient change (e.g., a transient increase) in intensity of the fluorescence signal, such as a peak or spike 5712 (i.e., a wave) formed by the fluorescence signal.

To improve clarity, the illustrative data shown here and in other figures of this Section are presented as serial data detected from a flow stream containing droplets. However, the methods disclosed in this Section also may be applied to droplet image data, which may be collected from a set of droplets in parallel (e.g., see Sections II and VI). Also, to improve clarity, the illustrative data are presented in a simplified form: each peak has no width and projects from a constant background signal 5713 formed by detection of a continuous phase carrying the droplets. However, a signal peak may have any suitable shape based on, for example, the frequency of detecting signals, the shape of each droplet, the size and geometry of a channel carrying the flow stream, the flow rate, and the like. Moreover, the signal peaks may have any suitable temporal distribution, for example, occurring at relatively constant intervals, as shown here, or at varying intervals. A droplet signal provided by and/or calculated from the peak (e.g., a signal corresponding to peak height or peak area, among others) may be used to determine whether amplification occurred in the corresponding droplet, and thus whether the droplet received at least one molecule of the nucleic acid target when the sample was partitioned.

Each droplet signal may be compared to a signal threshold 5714, also termed a cutoff. This comparison may provide a determination of whether each droplet signal represents a positive signal (target is present) or a negative signal (target is absent and/or not detected), for amplification in the droplet. For example, droplet signals greater than (and, optionally, equal to) the threshold may be considered as representing positive droplets. Conversely, droplet signals less than (and, optionally, equal to) the threshold may be considered as representing negative droplets. (A positive droplet signal above threshold 5714 is indicated at 5716, and a negative droplet signal below threshold 5714 is indicated at 5718 in FIG. 112.) Comparison to the threshold thus may transform each droplet signal to a digital value, such as a binary value (e.g., a "1" for a positive droplet and "0" for a negative droplet). In any event, the fraction of droplets that are positive can be determined. For a given droplet size, the fraction of positive droplets can be used as an input to an algorithm based on Poisson statistics to determine the number of copies (molecules) of the nucleic acid target present in the initial sample volume. In some embodiments, more than one threshold may be used to categorize results (e.g., negative, positive, or inconclusive; or no copies, one copy, two copies, three or more copies; etc.).

Figure 113:
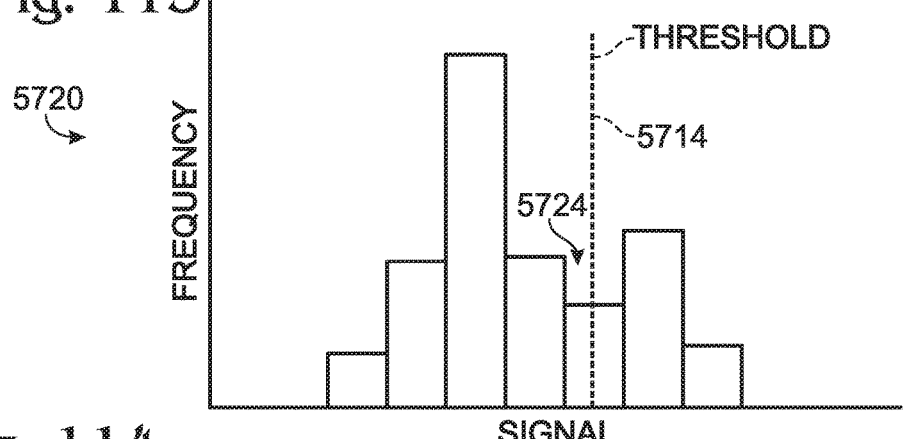
FIG. 113 is an exemplary histogram of ranges of droplet signal intensities that may be measured from the flow stream of FIG. 112, with the relative frequency of occurrence of each range indicated by bar height, in accordance with aspects of the present disclosure.

FIG. 113 shows an exemplary histogram 5720 of ranges of droplet signal intensities that may be measured from the flow stream of FIG. 112. The relative frequency of occurrence of each range is indicated by bar height. The distribution of positive and negative signal intensities may be larger than the modest difference in signal intensity produced by amplification (a positive droplet) relative to no amplification (a negative droplet). Thus, the distributions of droplet signals from positive droplets and negative droplets may produce a problematic overlap between the amplification-positive and amplification-negative droplet signals, indicated at 5724. Accordingly, as shown in FIG. 112, some amplification-positive droplets may provide relatively weak droplet signals, such as false-negative signal 5726, that are less than threshold 5714, resulting in incorrect identification of these positive droplets as negative. Conversely, some amplification-negative droplets may provide relatively strong droplet signals, such as false-positive negative signal 5728, that are greater than threshold 5714, resulting in incorrect identification of these negative droplets as positive. Since either type of erroneous result may be costly and harmful, it is desirable to minimize their occurrence.

There are many factors that can lead to variation in signals detected from droplets. Examples of physical parameters that may affect the signals may include droplet position when detected (e.g., relative to the "sensed volume" of the detector), droplet volume and shape, optical alignment of detection optics (including excitation source, filters, and detector), detector response, temperature, vibration, and flow rate, among others. Examples of reaction chemistry parameters that may affect the fluorescence signal include the number of target molecules and/or the amount of background nucleic acid present in each droplet, amplification efficiency, batch-to-batch variations in reagent concentrations, and volumetric variability in reagent and sample mixing, among others. Variations in these physical and chemical parameters can increase the overlap in the distribution of positive and negative droplet signals, which can complicate data interpretation and affect test performance (e.g., affect the limit of detection). The variations can occur within a run and/or between runs, within a test on a target and/or between tests on different targets, on the same instrument and/or different instruments, with the same operator and/or different operators, and so on.

Thus, there is a need for improved accuracy and reliability in droplet-based assays. For example, it would be desirable to have droplet-based controls for these tests, optionally, droplet-based controls that can be incorporated into test droplets (for performing assays) or incorporated into control droplets (for controlling assays) that can be intermixed with test droplets. Such integrated controls may have the benefit of reducing cost by processing control reactions in parallel with test reactions, which may speed the analysis. It also would be useful to have one or more controls that can be used in system calibration (e.g., to verify hardware, reagent, and/or software (e.g., algorithm) performance, among others).

B. DEFINITIONS

Technical terms used in this disclosure have the meanings that are commonly recognized by those skilled in the art. However, the following terms may have additional meanings, as described below.

Signal—detectable and/or detected energy and/or information. Any of the signals detected, after detection, may be described as signals and/or data. For example, detected droplet signals may provide test signals and test data, control signals or control data, reference signals and reference data, calibration signals and calibration data, transformed signals and transformed data, or any combination thereof, among others.

Transform—to change one or more values, and/or the number, of signals of a data set using one or more mathematical and/or logical operations. Transformation of a set of signals may produce a transformed set of the signals by changing values of one or more of the signals and/or by deleting/invalidating any suitable subset of the signals. Signal transformation may include reducing signal variation, deleting/invalidating outlier signals, subtracting a baseline value from signals, reducing the frequency of outliers, reducing the overlap of distributions of positive and negative droplet signals, modifying signals according to a regression line, assigning new values to signals based on comparing signal values to a threshold or range, or any combination thereof, among others.

Run—an operating period during which a set of droplets, generally droplets of about the same size and including partitions of a sample, are tested.

Oligonucleotide—a nucleic acid of less than about one-hundred nucleotides.

Exogenous—originating externally. For example, a nucleic acid exogenous to a sample is external to the sample as originally isolated. As another example, a nucleic acid exogenous to an organism or cell is not native to the organism or cell, such as a nucleic acid introduced into the organism or cell by infection or transfection.

Endogenous—originating internally, such as present in a sample as originally isolated or native to a cell or organism.

C. SUMMARY

The present disclosure provides a system, including methods and apparatus, for performing droplet-based tests of nucleic acid amplification that are controlled and/or calibrated using signals detected from droplets.

The present disclosure provides a method of sample analysis. Droplets may be obtained. The droplets may be generated on-line or at least a subset of the droplets may be pre-formed off-line. At least a subset or all of the droplets may include a partition of a sample to be tested and may be capable of amplification of at least one test nucleic acid target, if present, in the partition. In some embodiments, the droplets may be capable of amplification of a test nucleic acid target and a control nucleic acid target. The droplets collectively or each may include a dye, or at least a first dye and a second dye. In some embodiments, the droplets may be of at least two types, such as two or more types of test droplets, test droplets and calibration droplets, or test droplets and control droplets, among others. In some embodiments, the two or more types of droplets may be distinguishable based on distinct temporal positions of the droplet types in a flow stream (or distinct times of exit from the flow stream, e.g., distinct times at which the droplets are collected in one or more detection chambers for imaging), the presence of respective distinct dyes in the droplet types, distinguishable signal intensities of the same dye (or different dyes), or a combination thereof, among others.

Signals, such as fluorescence signals, may be detected from the droplets. The signals may include test signals, calibration signals, control signals, reference signals, or any combination thereof. In some embodiments, test signals and control signals may indicate respectively whether amplification of a test nucleic acid target and a control nucleic acid target occurred in individual droplets. In some embodiments, detection may include (a) exciting first and second dyes with a same wavelength of excitation light and (b) detecting emitted light from the first and second dyes at least substantially independently from one another in respective first and second detector channels.

The signals detected may be analyzed to determine a test result related to a presence (number, concentration, etc.), if any, of a test nucleic acid target in the sample. In some embodiments, analysis may include transforming test signals based on reference signals to reduce variation in the test signals. The test signals and the reference signals may be detected in respective distinct detector channels or in the same detector channel. In some embodiments, the reference signals may be provided by a second dye that is not coupled to an amplification reaction and thus serves as a passive reference. In some embodiments, the reference signals may be provided by control signals detected from a control amplification reaction. The control amplification reaction may measure amplification of an exogenous or endogenous template. In some embodiments, analysis may include (a) comparing test signals, or a transformed set of the test signals, to a signal threshold to assign individual droplets as positive or negative for a test nucleic acid target, and (b) estimating a number of molecules of the test nucleic acid target in the sample based on the comparison. In some embodiments, analysis may include (a) analyzing control signals to determine a control value corresponding to a number and/or fraction of the droplets that are amplification-positive for a control nucleic acid target, and (b) interpreting a test result, such as determining its validity, based on the control value.

The systems disclosed herein may offer improved instrument calibration and/or substantial improvements in the accuracy and/or reliability of droplet-based amplification tests. Exemplary capabilities offered by the present disclosure may include any combination of (1) correcting/minimizing variations in the fluorescence signal to increase the accuracy of droplet PCR results; (2) providing an internal indicator of whether nucleic acid amplification failed (e.g., PCR inhibition from interfering components in the sample, incorrect sample and reagent mixing, incorrect thermal cycling, incorrect droplet formation); (3) providing measurement of droplet volumes without having to add additional hardware components; (4) providing measurement of changes in the baseline fluorescence signal (i.e., baseline drift); (5) providing calibration of a droplet detector before and/or during a run; (6) monitoring the performance of quantitative droplet PCR measurements and data processing algorithms before and/or during a run; (7) verification of droplet integrity (e.g., absence of coalescence); (8) obtaining information on droplet generation and detection frequency (spatially and temporally) using an in-line detector; (9) measuring variations and comparing them to predefined tolerances; (10) processing of raw droplet PCR data to correct for variations and increase test accuracy and performance; (11) incorporating control assays preferably using a single excitation source; and/or (12) quantifying more than one species of genetic target by amplifying and detecting more than one species of genetic target in individual droplets.

D. SYSTEM OVERVIEW

Figure 114:
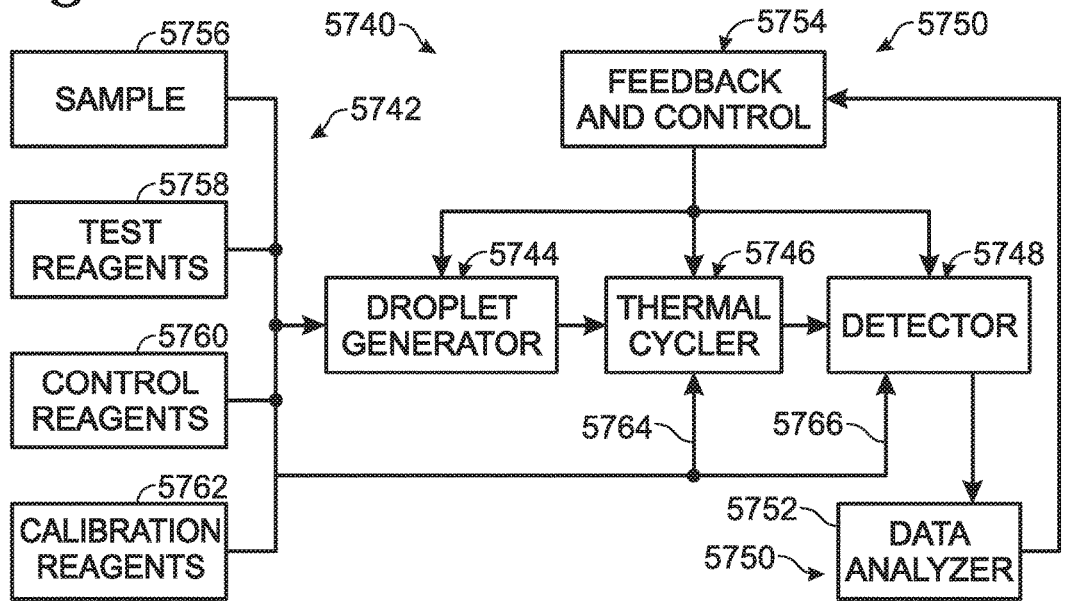
FIG. 114 is a schematic view of an exemplary system for performing droplet-based tests of nucleic acid amplification with the aid of controls and/or calibrators, in accordance with aspects of the present disclosure.

FIG. 114 shows an exemplary system 5740 for performing droplet-based tests of with the aid of controls and/or calibrators. Other exemplary systems that may be suitable are described elsewhere herein, such as in Section II, among others. System 5740 may include any combination of a sample preparation station 5742, at least one droplet generator 5744, a heating station, such as a thermal cycler 5746, a detection station 5748, and a controller 5750 incorporating a data analyzer 5752 and a feedback and control portion 5754, among others.

The system may provide at least one flow stream that carries at least one sample and reagents from one or more upstream positions and in a downstream direction to detection station 5748. Signals detected from the flow stream (or detected with stopped flow, such as by imaging), and particularly droplet signals, may be communicated to data analyzer 5752. The data analyzer may analyze the signals to determine one or more test results, control results, calibration results, a quality (e.g., validity, reliability, confidence interval, etc.) of any of the results, or a combination thereof. Any of the results may be communicated to feedback and control portion 5754, which may control and/or adjust control of any of sample preparation station 5742, droplet generator 5744, thermal cycler 5746, detection station 5748, and data analyzer 5752, based on the results determined.

Preparation station 5742 may contain and/or supply at least one sample 5756, at least one set of test reagents 5758 (also termed target reagents), one or more control reagents 5760, one or more calibration reagents 5762, or any combination thereof. Any of the samples and/or reagents may be stored and/or supplied separately, may be stored and/or supplied as one or more pre-formed mixtures, and/or may be mixed selectably before they are supplied to a downstream region of the system (e.g., droplet generator 5744, thermal cycler 5746, or detection station 5748). Furthermore, any of the samples and/or reagents may travel sequentially from sample preparation station 5742 to droplet generator 5744, thermal cycler 5746, and then detection station 5748 for detection of droplet signals. Alternatively, any of the samples and/or reagents may reach the detection station without travel through the droplet generator, as indicated at 5764, the thermal cycler, or both, as indicated at 5766. Accordingly, any of the samples and/or reagents disclosed herein may be stored and/or supplied in pre-formed droplets. Droplets may, for example, be pre-formed off-line, either locally or remotely. Pre-formed droplets may be intermixed randomly with droplets formed by droplet generator 5744 before reaching detection station 5748, or distinct types of droplets may be detected as spatially and/or temporally separated packets of droplets.

Test reagents 5758 may be any reagents used to test for amplification of one or more targets, such as one or more primary targets, in partitions of a sample. Primary targets generally comprise any targets that are of primary interest in a test. Primary targets may be present at an unknown level in a sample, prior to performing tests on the sample. Test reagents 5758 generally include one or more sets of target reagents conferring specificity for amplification of one or more particular nucleic acid targets to be tested in a sample. Thus, the test reagents may include at least one pair (or two or more pairs) of primers capable of priming amplification of at least one (or two or more) nucleic acid target(s). The test reagents also may comprise at least one reporter to facilitate detecting amplification of each test target, a polymerase (e.g., a heat stable polymerase), dNTPs, and/or the like. The test reagents enable detection of test signals from droplets.

Control reagents 5760 are any reagents used to control for test signal variation (generally, variation other than that produced by differences in amplification) and/or to interpret results obtained with the test reagents (such as a reliability and/or validity of the results). The control reagents permit control signals and/or reference signals to be detected from droplets, either the same or different droplets from the test signals. Control reagents may be mixed with test reagents prior to droplet formation and/or control droplets containing control reagents may be produced separately from the test droplets and introduced independently of the sample.

The control reagents may provide instrument controls, that is, controls for variation introduced by the system (and/or its environment). Thus, instrument controls may control for variation in droplet volume, droplet detection efficiency, detector drift, and the like. Reference signals may be detected from droplets containing control reagents that function as instrument controls.

The control reagents also or alternatively may provide amplification controls, that is, controls that test for secondary/control amplification in droplets. The control reagents thus may include reagents used to test for amplification of at least one secondary or control target in droplets. The secondary/control target may be of secondary interest in a test, and/or may be present at a known or expected level in the sample, among others. In any event, the control reagents may include one or more sets of target reagents conferring specificity for amplification of one or more control nucleic acid targets to be tested in droplets. The control reagents may include at least one pair (or two or more pairs) of primers capable of priming amplification of at least one (or two or more) control nucleic acid target(s). The control reagents also may comprise at least one reporter to facilitate detecting amplification of each control target, a polymerase (e.g., a heat stable polymerase), dNTPs, and/or the like, or any suitable combination of these control reagents may be supplied by the test reagents. Control signals may be detected from control reagents that function as amplification controls.

Calibration reagents 5762 are any reagents used to calibrate system operation and response. Droplets containing a calibration reagent (i.e., calibration droplets) may be introduced into a flow stream of the system, at any position upstream of the detection station, for the purpose of calibrating the system (e.g., calibrating flow rates, excitation power, optical alignment, detector voltage, amplifier gain, droplet size, droplet spacing, etc.). Calibration droplets may be introduced into a flow stream of the system before, during, and/or after introduction of test droplets into the flow stream. In some embodiments, the level of a dye within control droplets may be used to calibrate and/or validate detector response, such as by using a pair of dye concentrations providing calibration signals that bracket an intended measuring range and/or that are disposed near upper and lower ends of the measuring range. For example, droplets of known size and containing one or more known dye concentrations may be prepared off-line and introduced into the system, and/or may be generated by the system. In some embodiments, calibration droplets may comprise fluorescent particles such as quantum dots, polymer beads, etc.

System 5740 may used to perform a method of analyzing one or more samples. The method may include any suitable combination of the steps disclosed herein, performed in any suitable order.

Droplets may be obtained. The droplets may be of one type or two or more types. At least a subset, or all, of the droplets may be generated by the system or may be pre-formed off-line. At least a subset of the droplets may include test reagents for testing amplification of a test nucleic acid target. At least a subset of the droplets may include control reagents and/or calibration reagents for testing amplification of a control nucleic acid target. The droplets may contain one or more dyes.

The droplets may be introduced into a flow stream upstream of a detector. All of the droplets may be introduced into the flow stream at the same position or the droplets, particularly droplets of different types, may be introduced at two or more distinct positions.

The droplets, in the flow stream, may be subjected to conditions that facilitate amplification. For example, the droplets may be heated and/or may be heated and cooled repeatedly (thermally cycled).

Signals may be detected from the droplets. The signals may include test signals, control signals, reference signals, calibration signals, or any combination thereof.

The signals may be analyzed. Analysis may include transforming test signals. Analysis also or alternatively may include comparing test signals and/or transformed test signals to a signal threshold to assign individual droplets as being positive or negative for amplification of a nucleic acid target. A number and/or fraction of target-positive droplets may be determined based on results of the comparison. Analysis further may include estimating a presence of a nucleic acid target in the sample. The estimated presence may be no target in the sample. Estimation of the presence may (or may not) be performed using Poisson statistics.

E. EXEMPLARY INSTRUMENT CONTROLS AND CALIBRATIONS

Figure 115:
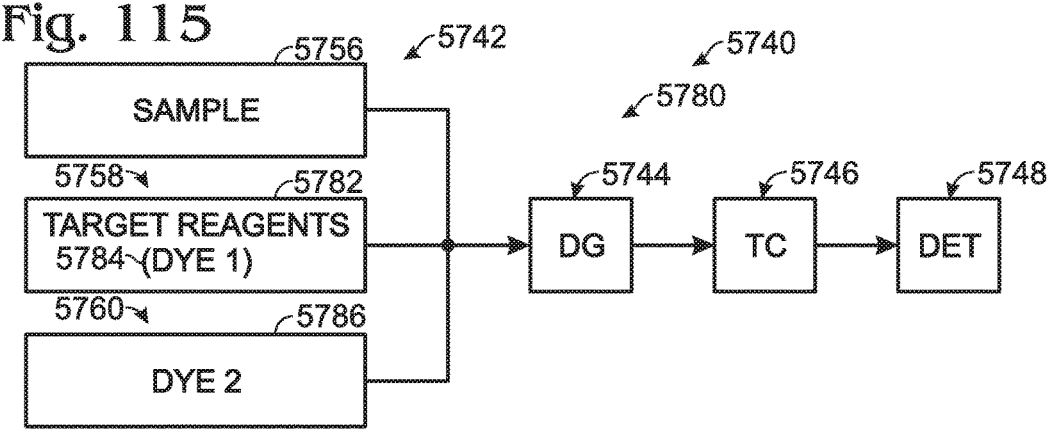
FIG. 115 is a schematic view of selected aspects of the system of FIG. 114, with the system in an exemplary configuration for detecting amplification of a nucleic acid target using a first dye, and for controlling for system variation during a test using a second dye, in accordance with aspects of present disclosure.

FIG. 115 shows selected aspects of system 5740 in an exemplary configuration 5780 for detecting amplification of a nucleic acid target using a first dye and for controlling for system variation during a test using a second dye. In FIG. 115 and in other system configurations presented in succeeding figures of the present disclosure, the terms "droplet generator," "thermal cycler," and "detection station" are abbreviated "DG," "TC," and "DET."

Sample preparation station 5742 may supply an amplification mixture to droplet generator 5744. The amplification mixture may incorporate a sample 5756, target reagents 5782 (i.e., test reagents 5758) including a first dye 5784 (dye 1), and a second dye 5786 (dye 2). The second dye and the target reagents may be mixed with one another before introduction into system 5740 or may be mixed within the system. Target reagents 5782 may provide primers for amplification of a nucleic acid target, and the first dye may enable detection of whether amplification occurred. The first and second dyes may be fluorescent dyes that are distinguishable optically. The second dye may be a passive reference or instrument control. In other words, the second dye may provide a detectable signal having an intensity that is at least substantially independent of the extent of amplification, if any, of any nucleic acid target.

Droplet generator 5744 may form droplets of the amplification mixture. The droplets may travel through thermal cycler 5746, to promote amplification of the nucleic acid target, if any, in each droplet. The droplets then may travel to detection station 5748. Station 5748 may detect, for each droplet, a test signal from the first dye and a reference signal (also termed a control signal) from the second dye.

Figure 116:
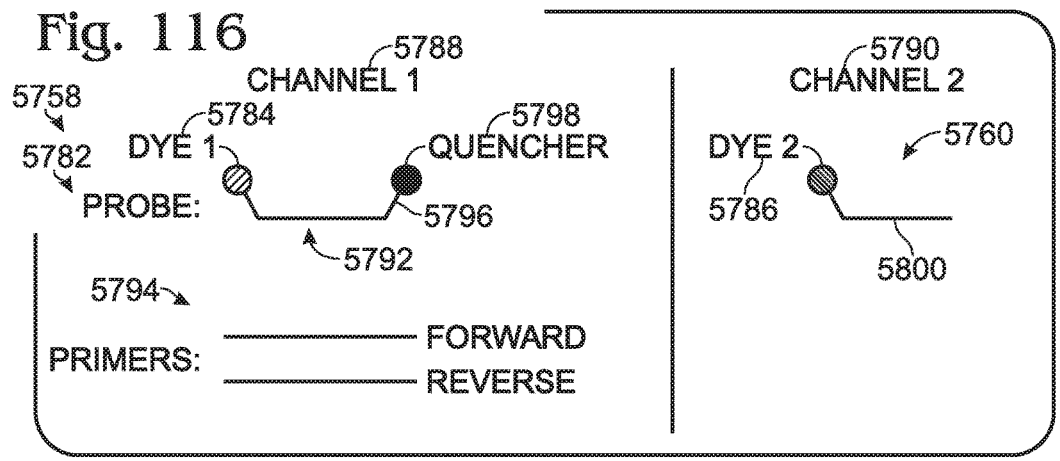
FIG. 116 is a schematic view of exemplary reagents that may be included in the system configuration of FIG. 115, to permit detection of amplification signals in a first detector channel and detection of a passive control signals in a second detector channel, in accordance with aspects of present disclosure.

FIG. 116 shows exemplary target reagents 5782 and a control reagent 5760 that may be included in system configuration 5780 of FIG. 115. The target and control reagents may permit detection of test signals in a first detector channel 5788 ("channel 1") and detection of reference signals in a second detector channel 5790 ("channel 2"). The first and second channels may represent distinct wavelengths and/or at least substantially nonoverlapping wavelength ranges.

Target reagents may include a reporter, such as a probe 5792, and target-specific forward and reverse primers 5794. Probe 5792 may be an energy transfer probe (e.g., a TAQMAN probe) including a nucleic acid, such as an oligonucleotide 5796, that binds to amplified target, and an energy transfer pair connected to strand 5796. The energy transfer pair may, for example, be formed by first dye 5784 and a quencher 5798.

Control reagent 5760 may include second dye 5786. The second dye may (or may not) be connected to a nucleic acid, such as an oligonucleotide 5800. Connection to the oligonucleotide may be covalent and/or through a binding interaction. Connection of the second dye to an oligonucleotide or other water-soluble molecule may improve retention of the second dye in the aqueous phase of a droplet and/or may facilitate distribution of the dye throughout the aqueous phase, among others.

Figure 117:
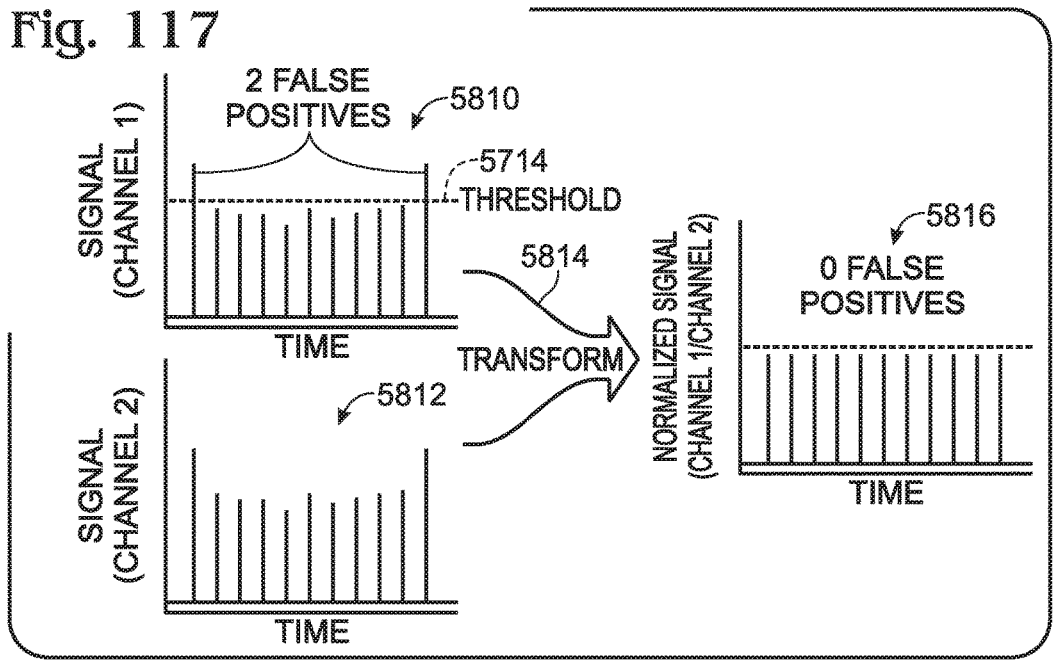
FIG. 117 a flowchart of an exemplary approach to correcting for system variation using the system configuration of FIG. 115, in accordance with aspects of the present disclosure.

FIG. 117 shows a flowchart illustrating of an exemplary approach to correcting for system variation using system configuration 5780 (FIG. 115), and, optionally, the reagents illustrated in FIG. 116. Test signals (i.e., target signals) and reference signals may be detected from the same droplets. For example, test signals may be detected in a first channel and reference signals may be detected in a second channel. Graphs illustrating coincident detection of test signals and reference signals are shown at 5810, 5812, respectively.

Test signal variation may introduce errors in data processing. For example, graph 5810 shows substantial variation in the intensity of the test signals detected. As a result, some of the test signals may be erroneously classified as positives or negatives. In the present illustration, two false positives are marked. However, variation of the test signals may be mirrored by variation of the reference signals detected from the same droplets. Accordingly, the test signals may be transformed based on the reference signals, indicated at 5814, to correct for variation in the test signals, as shown in a graph 5816, which plots the transformed test signals. The test signals may be transformed by any suitable operation or set of operation involving the reference signals. For example, the test signals may be transformed through dividing test signals by reference signals, such as dividing each test signal by its corresponding reference signal, which may be described as normalizing the test signals. Alternatively, the test signals may be transformed based on the reference signals by, for example, baseline subtraction, distance from the regression line, or the like. A transformation may compensate for variations in the test channel. This compensation or correction may make the test signals (i.e., negative test signals and/or positive test signals) more uniform in value and/or more Gaussian. The transformation also or alternatively may reduce the frequency of outliers and/or the overlap of the distributions of positive and negative signals.

Figure 118:
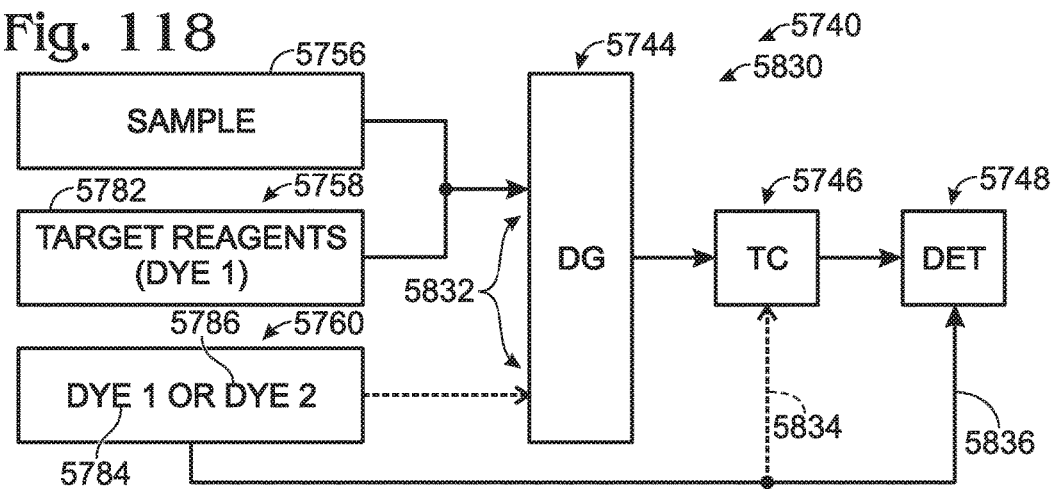
FIG. 118 is a schematic view of selected aspects of the system of FIG. 114, with the system in an exemplary configuration for detecting amplification of a nucleic acid target using a first dye in a set of droplets, and for (a) calibrating the system before, during, and/or after a test or (b) controlling for aspects of system variation during a test using either the first dye or a second dye in another set of droplets, in accordance with aspects of present disclosure.

FIG. 118 shows selected aspects of system 5740 in an exemplary configuration 5830 for (a) detecting amplification of a nucleic acid target in a set of droplets and (b) system calibration and/or correction for system variation in another set of droplets. Configuration 5830 is similar to configuration 5780 of FIG. 115, except that target reagents 5782 and control reagent 5760 are not in the same droplets. Accordingly, the target reagents and the control reagent may be supplied to respective distinct droplet generators of the system, indicated at 5832, may be supplied to the sample droplet generator at different times, or the control reagent may be supplied in pre-formed droplets that do not pass through the droplet generator, indicated at 5834, 5836. Since the target reagents and the control reagent are not in the same droplets in this configuration, the control reagent may include the same dye as the target reagent (i.e., first dye 5784) or may include a distinct dye (such as second dye 5786).

Figure 119:
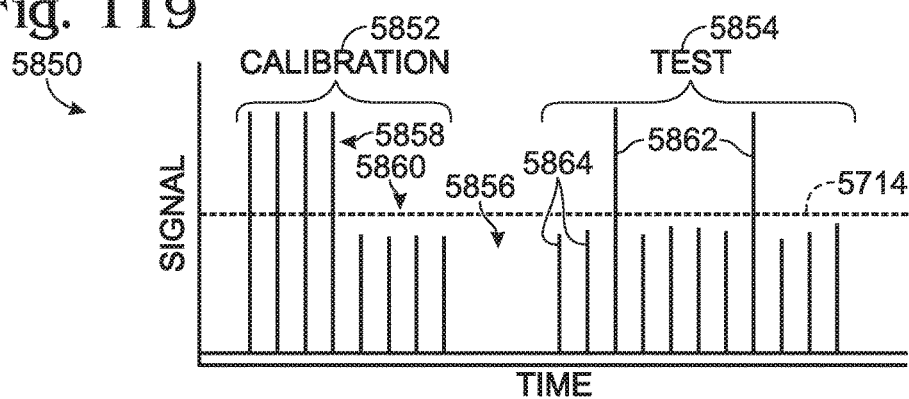
FIG. 119 is an exemplary graph of fluorescence signals that may be detected over time from a flow stream of the system configuration of FIG. 118 during system calibration and sample testing performed serially, in accordance with aspects of present disclosure.

FIG. 119 shows an exemplary graph 5850 of fluorescence signals that may be detected over time from a flow stream of system configuration 5830 (FIG. 118) during system calibration, indicated at 5852, and sample testing, indicated at 5854. Calibration and sample testing may be performed without or with mixing of calibration and test droplets.

Calibration and sample testing may be performed serially, without mixing of droplet types, using the same dye (and/or detection of the same wavelength(s)). By keeping calibration and test droplets separate, the distributions of test and calibration signal intensities may overlap. For example, calibration droplets and test droplets may be separated temporally in the flow stream, such that each type of droplet is identifiable based on its time of arrival at the detection station. The time of arrival may be calculated based on the relative time of introduction of each droplet type into the flow stream and the velocity of the flow stream. Thus, the calibration and test droplets may not (or may) be distinguishable based on signal intensity, but may be distinguishable temporally. In particular, the test and calibration droplets may be separated by a temporal (and spatial) gap 5856, which may identify a transition between droplet types. The use of temporal gaps also may permit introduction of a set of calibration droplets within a set of test droplets (i.e., within a test run), with a gap preceding and following the set of calibration droplets, to provide identification of each transition to a different droplet type. Stated differently, calibration may be performed during sample testing, by inserting calibration droplets into a train of test droplets, such that the train of test droplets is divided into two or more discrete groups.

Calibration droplets may include two or more types of droplet, which may be introduced separately or intermixed. For example, FIG. 119 shows a set of stronger calibration signals 5858 followed by a set of weaker calibration signals 5860 produced by distinct types of calibration droplets. Stronger and weaker calibration signals 5858, 5860 may correspond generally in intensity to respective positive test signals 5862 and negative test signals 5864. In other embodiments, only one type or three or more types of calibration droplet may be used, and may be configured respectively to provide one or three or more intensities of calibration signals.

Calibration and sample testing alternatively may be performed with calibration and test droplets randomly intermixed and thus not distinguishable temporally. Intermixed calibration and test droplets may be distinguishable by incorporating distinguishable dyes into the respective droplet types and, optionally, by detection of the distinguishable dyes at respective distinct wavelengths. Alternatively, or in addition, calibration droplets and test droplets may be distinguishable according to signal intensity detected at the same wavelength(s) and optionally from the same dye. In particular, calibration droplets may be designed to have one or more signal intensities outside the signal range of test droplets (i.e., the signal range provided by the collective distribution of signal intensities from negative and positive test droplets (e.g., see FIG. 113)). Thus, calibration droplets may be identified based on their calibration signals having signal intensities above and/or below the signal range of test droplets.

Figure 120:
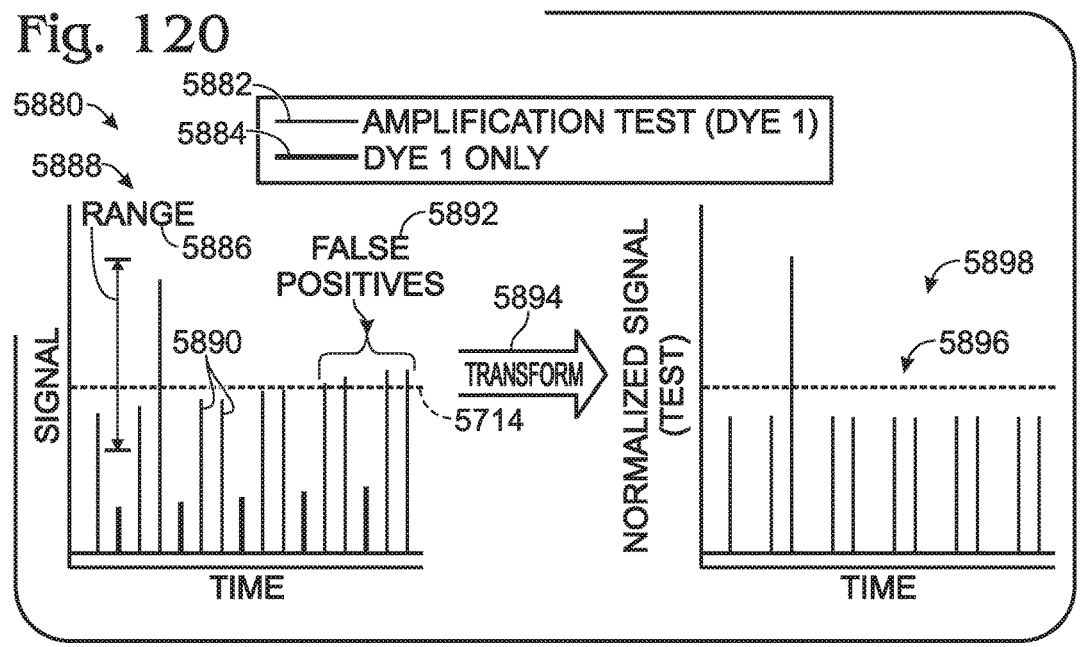
FIG. 120 is a flowchart of an exemplary method of correcting for system variation produced during a test using the system configuration of FIG. 118, in accordance with aspects of the present disclosure.

FIG. 120 shows a flowchart 5880 of an exemplary approach to correcting for signal variation during an amplification test using system configuration 5830 of FIG. 118. The approach illustrated in FIG. 120 distinguishes types of droplet signals, namely, test droplet signals 5882 and reference droplet signals 5884, based on differences in signal intensity detected in the same detector channel, as described above for calibration droplets. In particular, test droplets may produce a range 5886 of signal intensities, and reference signals 5884 may have intensities below (or above) the range. Accordingly, the distinct types of droplets may be interspersed randomly in the flow stream.

The reference droplets may be formed with the same amount (or two or more discrete amounts) of dye. Accordingly, without signal variation generated by the system, the reference droplets should produce reference signals of the same intensity. Variation in reference signal intensity may be mirrored by corresponding changes in the intensity of test signals. For example, in graph 5888, the intensity of reference signals 5884 and negative test signals 5890 show a gradual increase with respect to time. As a result, test signals from amplification-negative droplets may produce false positives 5892.

Variation in test signals 5882 may be reduced by transforming the test signals, indicated at 5894, based on reference signals 5884, to produce normalized test signals 5896 presented in graph 5898. Transformation may, for example, be performed by transforming each test signal based on one or more reference signals temporally proximate to the test signal, a weighted average of reference signals temporally proximate to the test signal, a sliding window of averaged reference signals that overlaps the test signal, or the like. Transformation before comparing test signals to a threshold may reduce the incidence of false positives, as shown here, the incidence of false negatives, or both.

F. EXEMPLARY AMPLIFICATION CONTROLS

Figure 121:
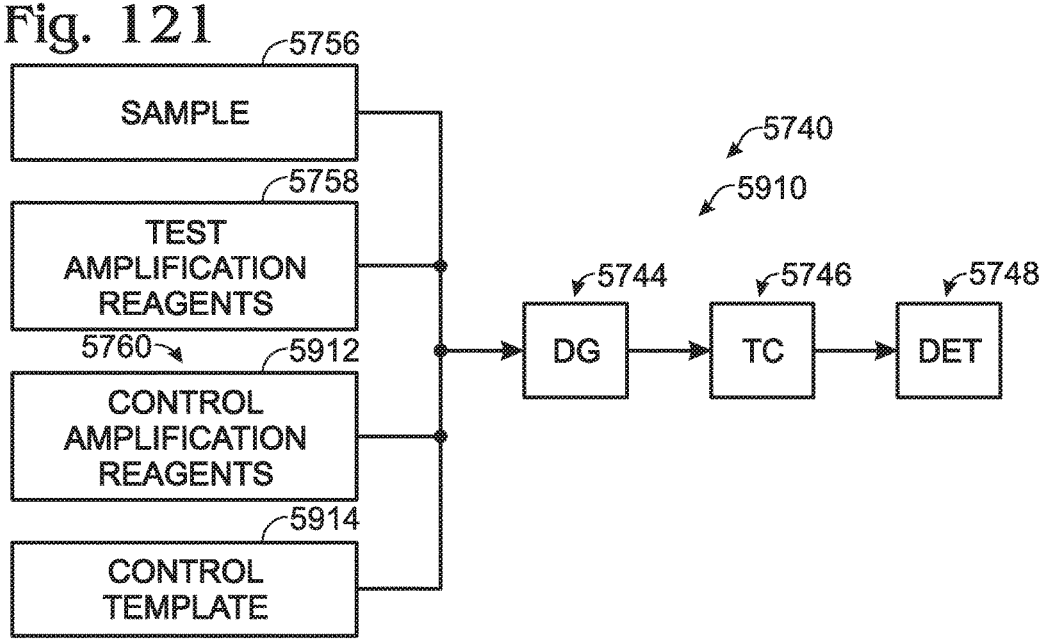
FIG. 121 is a schematic view of selected aspects of the system of FIG. 114, with the system in an exemplary configuration for testing amplification of a pair of nucleic acid targets in the same droplets, in accordance with aspects of present disclosure.

FIG. 121 show selected aspects of system 5740 of FIG. 114, with the system in an exemplary configuration 5910 for testing amplification of at least a pair of nucleic acid targets in the same droplets. System configuration 5910 may form an amplification mixture, which is supplied to droplet generator 5744. The amplification mixture may incorporate a sample 5756, test amplification reagents 5858, control amplification reagents 5912, and at least one control template 5914. Any combination of the sample, test reagents, control reagents, and control template may be mixed with one other before introduction into system 5740, or may be mixed within the system. Test reagents 5758 and control reagents 5912 may provide primers for respective amplification of at least one test target and at least one control target.

Amplification of the test and control targets may, for example, be detected via a first dye and a second dye, respectively, which may be included in respective first and second reporters (e.g., first and second probes). Signals from the first and second dyes may be detected in distinct (e.g., at least substantially nonoverlapping) first and second channels (i.e., a test channel and a control channel) as test signals and control signals, respectively.

Control template 5914 may comprise exogenous molecules of the control target. In contrast, the sample may be tested for a presence of endogenous molecules of the test target. The control template 5914 may be present in any suitable amount to provide any suitable average number of control template molecules per droplet, to generate a desired fraction of droplets positive for the control template. For example, the number of template molecules provided by template 5914 may be substantially less than an average of one per droplet, such as an average of about 0.1, 0.05, 0.02, or 0.01 molecule per droplet. Accordingly, the number/concentration of control template molecules may be selected such that the frequency of amplification of both test and control targets in the same droplet is low, which may minimize competition that may be caused by amplification of both test and control targets. For example, the control template may be present in no more than about one in five droplets.

The frequency of amplification of the control target may be determined by performing an analysis with the system. In some embodiments, this frequency may be compared with one or more previously determined frequencies of amplification for the control target and/or may be compared with an expected value for the frequency provided by a manufacturer. In any event, a control value may be determined, with the control value corresponding to a number and/or fraction of the droplets that are amplification-positive for the control nucleic acid target.

Control signals acquired in the control channel may be used to measure and/or verify the quantitative accuracy of a run and/or the measurement precision of the system during two or more runs. The control signals also or alternatively may be used to interpret a test result, such as the quality of test data measured from a sample, for example, to verify the quantitative accuracy of the test data and/or to determine the validity and/or reliability of the test data. The test result may be interpreted based on control value determined. For example, the test result may be determined as being invalid if the control value is less than a threshold value. Furthermore, data acquired from the control channel, such as signals from amplification-negative control droplets, may provide reference signals, as described above in relation to FIG. 117. In other words, test signals may be transformed using control signals that functions as reference signals, to normalize the test signals.

Figure 122:
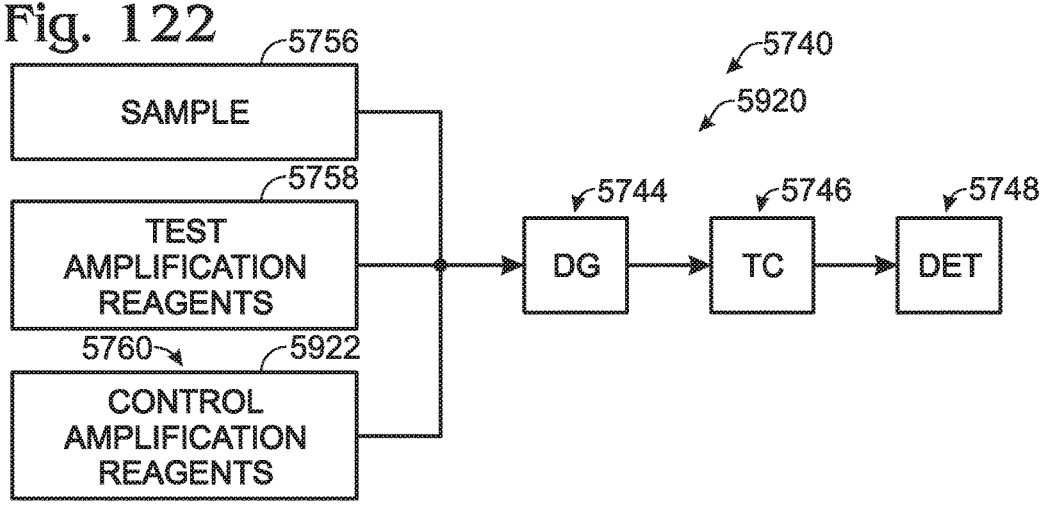
FIG. 122 is a schematic view of selected aspects of the system of FIG. 114, with the system in another exemplary configuration for testing amplification of a pair of nucleic acid targets in the same droplets, in accordance with aspects of present disclosure.

FIG. 122 shows selected aspects of system 5740 of FIG. 114, with the system in another exemplary configuration 5920 for testing amplification of at least a pair of nucleic acid targets in the same droplets. System configuration 5920 differs from configuration 5910 of FIG. 121 by including a different set of control amplification reagents 5922 (or a second set of test amplification reagents) and by the absence of an exogenous control template. Control reagents 5922 may amplify a control target that is known or expected to be present in sample 5756, and/or that has a known or expected representation with respect to a bulk nucleic acid population present in the sample (e.g., total DNA, total genomic DNA, genomic DNA from a particular species of organism, total RNA, total mRNA, etc.). In contrast, target reagents 5758 may amplify a test target that has an unknown presence in the sample and/or an unknown presence in with respect to the bulk nucleic acid population. In any event, amplification of the control target may be used to determine the quality of test data measured from a sample, such as to verify the quantitative accuracy of the test data and/or to determine the reliability of the test data. Furthermore, an amount of control target determined to be present in the sample may provide a standard against which an amount of test target determined to be present in the sample can be compared and/or normalized. In some embodiments, a control target is selected that is rare in the sample, such as a target representing a particular gene mutation. By selecting a rare control target, amplification of the control target can indicate the limit of detection of a test target and/or whether amplification of a low-abundance test target can occur. In some embodiments, the control target may be replaced by a second test target with an unknown presence in the sample (before testing).

Figure 123:
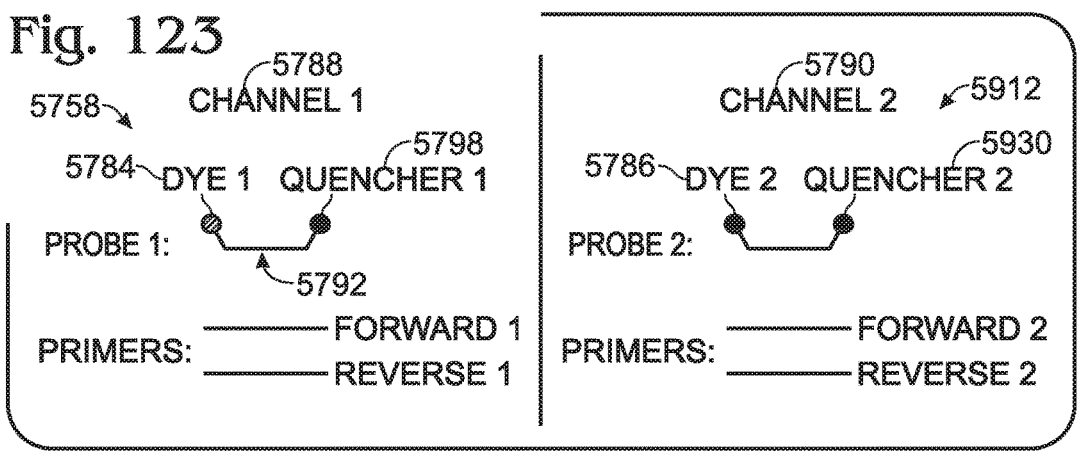
FIG. 123 is a schematic view of exemplary target-specific reagents that may be included in the system configurations of FIGS. 121 and 122, to permit detection of amplification signals in a different detector channel (i.e., a different detected wavelength or wavelength range) for each nucleic acid target, in accordance with aspects of present disclosure.

FIG. 123 shows exemplary test target reagents 5758 and control target reagents 5912 (or 5922) that may be included in system configuration 5910 (or 5920) of FIG. 121 (or 122), to permit detection of amplification signals in a different detector channel (i.e., channels 1 and 2, respectively) for each nucleic acid target. Test target reagents for channel 1 are described above in relation to FIG. 116. Control target reagents 5912 (or 5922) may be similar in general structure to the test target reagents, but different with respect to the nucleic acid sequences of the primers and probes, to provide test target and control target specificity, respectively. Also, the test and control probes may include distinct dyes 5784, 5786 and/or distinct energy transfer partners 5798, 5930 (e.g., distinct quenchers suitable for the respective dyes). In other embodiments, at least one of the probes may be replaced by a reporter including an intercalating dye, such as SYBR Green.

Figure 124:
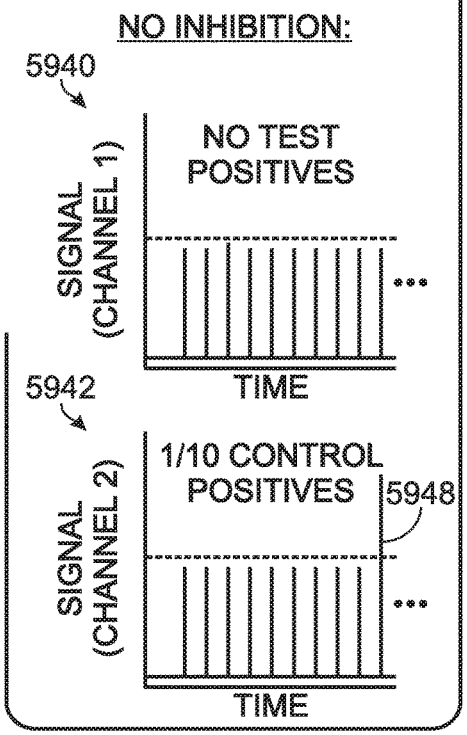
FIG. 124 is a pair of exemplary graphs of fluorescence signals that may be detected over time from a flow stream of the system configuration of FIG. 121 or 122 using different detector channels, with one of the channels detecting successful amplification of a control target, thereby indicating no inhibition of amplification, in accordance with aspects of present disclosure.
Figure 125:
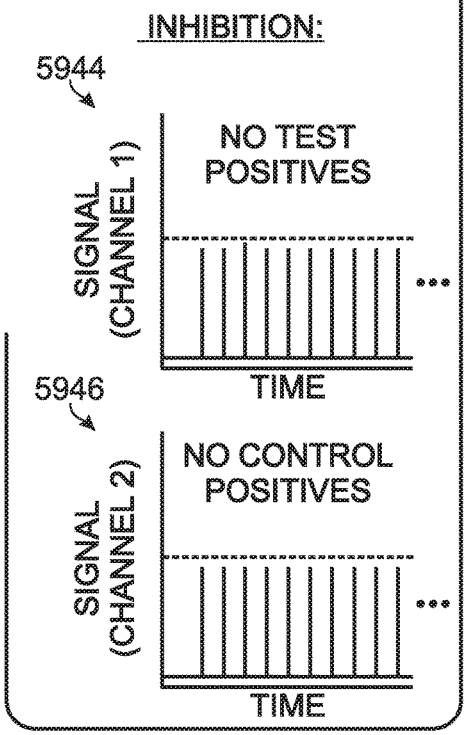
FIG. 125 is a pair of exemplary graphs with fluorescence signals detected generally as in FIG. 124, but with control signals indicating that amplification is inhibited, in accordance with aspects of present disclosure.

FIGS. 124 and 125 show representative portions of exemplary data that may be obtained using system configuration 5910 or 5920 and the reagents of FIG. 123. The figures show exemplary graphs 5940-5946 of fluorescence signals that may be detected over time from a flow stream of the system using different detector channels, namely, a test channel (channel 1) that detects test data and a control channel (channel 2) that detects control data. In FIG. 124, graph 5940 of the test data contains no positive droplet signals. In contrast, graph 5942 of the control data identifies positive droplet signals, such as a positive signal 5948, at a frequency of about one in ten. Thus, the control data demonstrates that amplification in the droplets is not inhibited substantially and suggests that the lack of positive signals from the test data is due to an absence or undetectable level of the test target in the sample. Accordingly, the control data supports and helps to validate the negative result in the test data. In contrast, control graph 5946 of FIG. 125 shows no amplification of the control target (a substantially larger data set may be analyzed to demonstrate that the control result holds). The control data of graph 5946 thus indicates that amplification of the test target also is inhibited (or the sample is defective, such as too dilute (configuration 5920)), and that the negative test result is not valid.

Figure 126:
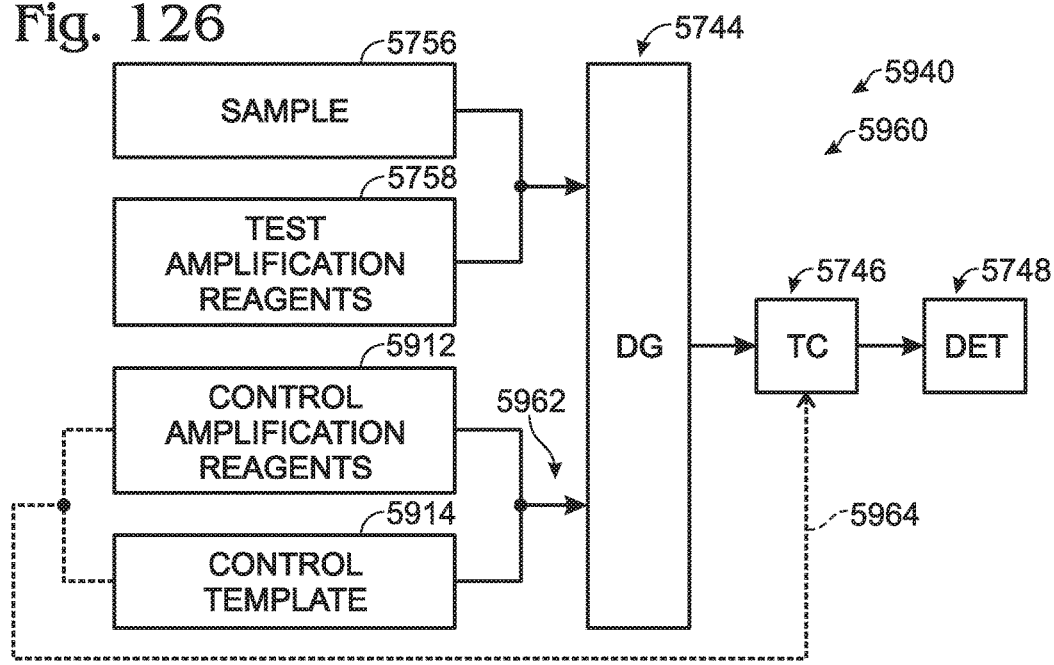
FIG. 126 is a schematic view of selected aspects of the system of FIG. 114, with the system in an exemplary configuration for testing amplification of a pair of nucleic acid targets using a different set of droplets for each target, in accordance with aspects of present disclosure.

FIG. 126 shows selected aspects of system of FIG. 114, with the system in an exemplary configuration 5960 for testing amplification of a pair of nucleic acid targets in respective different (i.e., nonoverlapping) sets of droplets. Configuration 5960 may be similar to that of configuration 5910, except that control reagents 5912 and control template 5914 are not mixed with sample 5756 and test target reagents 5758. Instead, droplets containing the control reagents and the control template may be formed separately in the system, indicated at 5962, or may be supplied as pre-formed droplets that are introduced into the flow stream downstream of droplet generator 5744, indicated at 5964.

Figure 127:
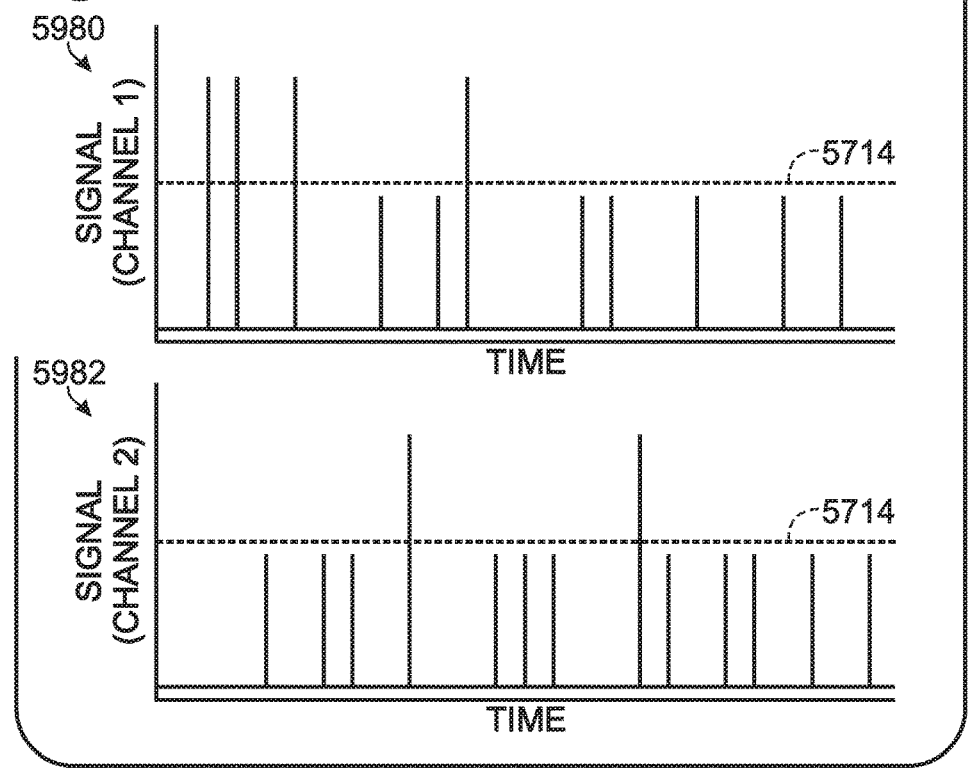
FIG. 127 is a pair of exemplary graphs of fluorescence signals that may be detected over time from a flow stream of the system configuration of FIG. 126 using different detector channels, with each channel monitoring amplification of a distinct nucleic acid target, in accordance with aspects of present disclosure.

FIG. 127 shows a pair of exemplary graphs 5980, 5982 of fluorescence signals that may be detected over time from a flow stream of system configuration 5960 of FIG. 126 using different detector channels. Graph 5980 plots fluorescence signals detected from a first channel, which detects amplification, if any, of a test target. Graph 5982 plots fluorescence signals detected from a second channel, which detects amplification, if any, of a control target. Successful amplification of the control target, as shown here, may, for example, verify and/or measure aspects of the system, such as operation of the thermal cycler and/or the detection station, the quality of the reagents, fraction of amplification-positive droplets, or any combination thereof, among others.

In configuration 5960, the test and control reagents are disposed separately in distinct droplets, so droplet signals in the first and second channels are not coincident, that is, they are not detected at the same time. In other embodiments, the control target may, instead, be a second test target and the control template may, instead, be another sample (or the same sample). Thus, the use of at least two detector channels permits droplets for distinct amplification tests to be interspersed in the flow stream.

G. EXEMPLARY MULTI-CHANNEL DETECTION

Figure 128:
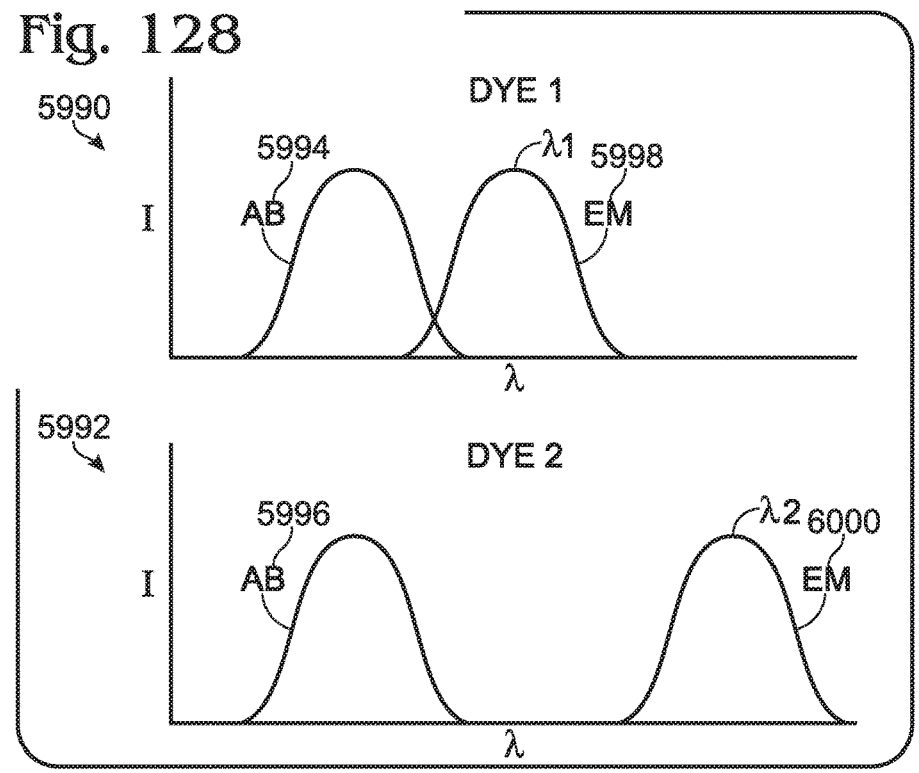

FIG. 128 shows a pair of graphs 5990, 5992 illustrating exemplary absorption and emission spectra of fluorescent dyes that may be used in the system of FIG. 114. The dyes are arbitrarily labeled dye 1 and dye 2, respectively. However, either dye may be used to detect test signals or control signals in the various system configurations disclosed herein. Moreover, while illustrated here for two distinguishable dyes, the system may be used for detection and analysis with three, four, or more distinguishable dyes.

Each graph plots the intensity of absorption ("AB"), indicated at 5994, 5996, and emission ("EM"), indicated at 5998, 6000, for the corresponding dye. The dyes may have substantially overlapping absorption spectra, such that the same wavelength of light may be utilized to excite both dyes. In contrast, the dyes may exhibit Stokes shifts (i.e., the difference (in wavelength or frequency units) between the maxima of the absorption and emission spectra) of different magnitudes. For example, dye 1 may exhibit a smaller Stokes shift and dye 2 a larger Stokes shift, or vice versa. Accordingly, the emission spectra of the dyes may be substantially shifted with respect to one another. As a result, emission from the two dyes may be detected at least substantially independently of one another in different detector channels, such as a detector channel that detects light of a first wavelength or wavelength range (e.g., $\lambda 1$) and another detector channel that detects light of a second wavelength or wavelength range (e.g., $\lambda 2$).

Figure 129:
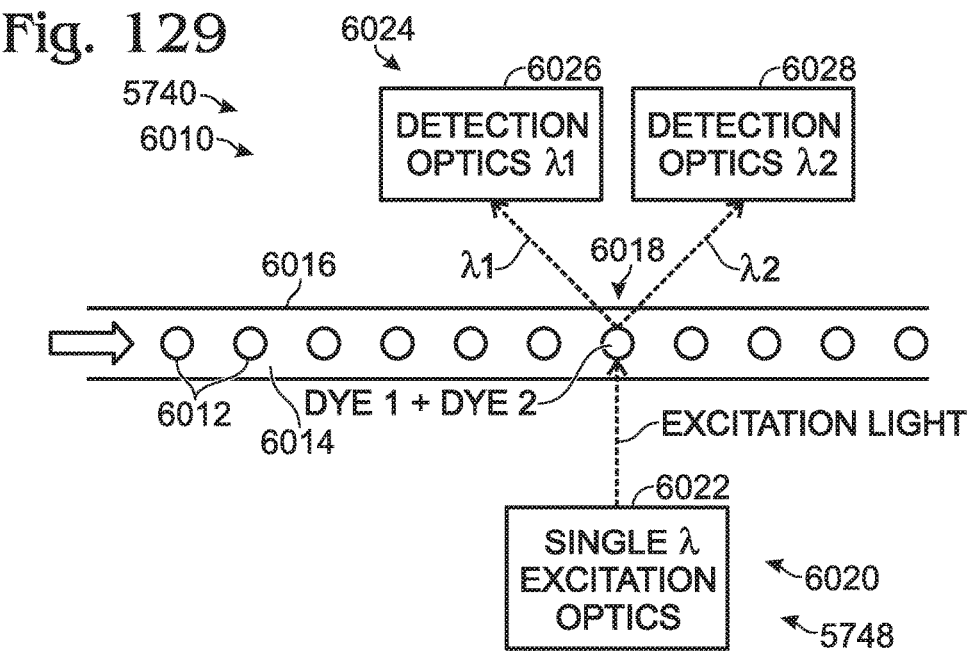

FIG. 129 is a schematic diagram illustrating exemplary use of the fluorescent dyes of FIG. 128 in an exemplary embodiment 6010 of system 5740 of FIG. 114. Droplets 6012 containing dyes 1 and 2, either in the same droplets or different sets of droplets, may be carried in a flow stream 6014 in a channel 6016. Flow stream 6014 may pass through a detection area 6018 established by an embodiment 6020 of detection station 5748.

Detection station 6020 may include a light source 6022 for exciting the fluorescent dyes in the droplets and at least one detector 6024 for detecting light emitted from the droplets. Light source 6022 may, for example, include an LED or laser that emits at least substantially a single wavelength of excitation light. Alternatively, or in addition, the light source may include at least one excitation optical filter that excludes other wavelengths of light emanating from the light source. Detector 6024 may be equipped with detection optics 6026, 6028 (e.g., beamsplitters, emission optical filters, separate detectors) that permit emitted light from the dyes to be detected separately.

Exemplary fluorescent dyes that may detected using system 6010 include a fluorescein derivative, such as carboxyfluorescein (FAM), and a PULSAR 650 dye (a derivative of $Ru(bpy)_3$). FAM has a relatively small Stokes shift, while Pulsar® 650 dye has a very large Stokes shift. Both FAM and PULSAR 650 dye may be excited with light of approximately 460-480 nm. FAM emits light with a maximum of about 520 nm (and not substantially at 650 nm), while PULSAR 650 dye emits light with a maximum of about 650 nm (and not substantially at 520 nm). Carboxyfluorescein may be paired in a probe with, for example, BLACK HOLE Quencher™1 dye, and PULSAR 650 dye may be paired in a probe with, for example, BLACK HOLE Quencher™2 dye.

H. EXEMPLARY SELF-NORMALIZATION OF DROPLET SIGNALS

Test signals may be normalized using methods different from those described above in relation to FIGS. 117 and 120. In particular, the methods illustrated in FIGS. 117 and 120 involve transformation of test data with reference data detected (a) in a different detector channel (FIG. 117) or detected (b) in different droplets (FIG. 120). This subsection describes methods that transform test data using aspects of itself rather than another data set.

Figure 130:
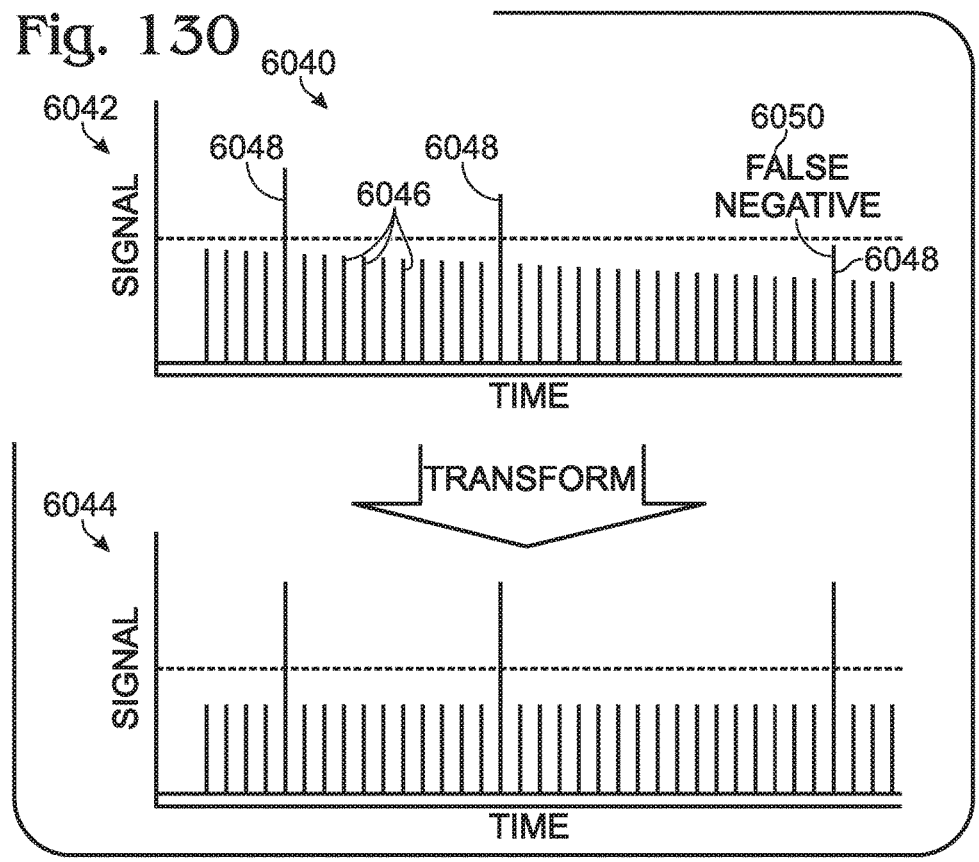

FIG. 130 shows a flowchart 6040 illustrating an exemplary method of correcting for system fluctuations during a test. The method involves processing a set of droplet test signals, shown in a first graph 6042, to produce a transformed set of test signals, shown in a second graph 6044. Negative test signals 6046 and positive test signals 6048 each should have respective constant values over time if there is no system variation. However, system variation, such as the negative drift over time illustrated in graph 6042, may produce false negatives, such as a false negative signal 6050, and/or false positives. Transformation of the test signals may be performed to correct for system variation before the test signals are used to estimate a presence of a test target in sample being tested. In particular, individual test signals may be transformed differently using the test data, accordingly to the temporal position of each test signal. For example, each test signal may be transformed using temporally proximate test data, such as normalization of each test signal with respect to a sliding window that averages a subset of the test signals including or adjacent the test signal. The subset of the test signals used may be provisionally negative, positive, or negative plus positive test signals, any of which may be re-assigned as negative/positive after transformation. For example, graph 6044 shows re-assignment of false negative signal 6050 as positive after transformation.

FIG. 131 shows a flowchart 6060 illustrating an exemplary method of transforming droplet signals based on the width of respective signal peaks providing the droplet signals. The flowchart involves graphs 6062, 6064, which represent test data before and after transformation, respectively.

Graph 6062 presents test data in which the width and height of each droplet peak is shown. (Here, each droplet peak is presented as a square wave to simplify the presentation. However, in other embodiments, each droplet peak may be detected as having any suitable shape, such as a wave with sloped leading and trailing sides.) The width of a droplet fluorescence peak may be used to determine the size and volume of each droplet, if droplet signals are detected in a flow stream with known flow rate, generally within a channel of fixed geometry. Knowing the volume of sample that is tested for amplification in droplets may be required for accurately determining the concentration/number of target molecules in the sample. If droplets of uniform size are desired, peak width may be used to identify droplets of sizes that are outside the desired range. For example, in FIG. 131, peaks 6066, 6068 having widths outside a predefined range are excluded from the data set. The droplet signals also may be transformed based on width, to provide transformed test data (i.e., graph 6064), that has been corrected for volume variation and/or variation in peak width.

I. SELECTED EMBODIMENTS

This subsection describes additional aspects of methods of using controls and calibrations for droplet-based amplification tests, in accordance with aspects of the present disclosure, presented without limitation as a series of numbered sentences.

1. A method of sample analysis, comprising: (A) generating droplets, each droplet including first and second dyes and a partition of a sample and being capable of amplification of a test nucleic acid target, if present, in the partition; (B) detecting respective test signals and control signals from the first and second dyes in the droplets, the test signals and the control signals respectively indicating whether amplification of the test nucleic acid target and a control nucleic acid target occurred in individual droplets; (C) analyzing the test signals to determine a test result related to a presence, if any, of the test nucleic acid target in the sample; (D) analyzing the control signals to determine a control value corresponding to a number and/or fraction of the droplets that are amplification-positive for the control nucleic acid target; and (E) interpreting the test result based on the control value.

2. The method of paragraph 1, wherein the step of generating droplets includes a step of forming droplets that contain primers conferring specificity for amplification of the control nucleic acid target.

3. The method of paragraph 2, wherein the step of forming droplets includes a step of forming one or more droplets that contain a control template corresponding to the control nucleic acid target, and wherein the control template is exogenous to the sample.

4. The method of paragraph 2, wherein the step of forming droplets includes a step of forming one or more droplets that contain a control template corresponding to the control nucleic acid target, and wherein the control template is endogenous to the sample.

5. The method of paragraph 1, wherein the step of detecting includes a step of exciting the first and second dyes with a same wavelength of excitation light and a step of detecting emitted light from the first and second dyes in respective first and second detector channels.

6. The method of paragraph 1, further comprising a step of transforming the test signals based on the control signals to reduce variation of the test signals.

7. The method of paragraph 6, wherein the step of transforming the test signals includes a step of transforming two or more test signals individually with corresponding control signals each detected from a respective same droplet as each of the two or more test signals.

8. The method of paragraph 7, wherein the step of transforming two or more test signals includes a step of dividing each test signal by its corresponding control signal.

9. The method of paragraph 1, wherein no more than about one in five droplets contain the control template.

10. The method of paragraph 1, wherein the step of analyzing the test signals includes a step of comparing the test signals, or a transformed set of the test signals, to a signal threshold to assign individual droplets as positive or negative for amplification of the test nucleic acid target, and a step of estimating a number of molecules of the test nucleic acid target in the sample based on results of the step of comparing.

11. The method of paragraph 1, wherein the step of interpreting the test result includes a step of determining a quality of the test result.

12. The method of paragraph 11, wherein the step of determining a quality includes a step of determining the test result as being invalid if the control value is less than a threshold value.

13. A method of sample analysis, comprising: (A) generating droplets, each droplet including first and second dyes and a partition of a sample and being capable of amplification of a test nucleic acid target, if present, in the partition; (B) detecting respective test signals and reference signals from the first and second dyes in the droplets, the test signals indicating whether amplification of the test nucleic acid target occurred in individual droplets; (C) transforming the test signals based on the reference signals to reduce variation of the test signals and to produce a set of transformed test signals; and (D) analyzing the transformed test signals to determine a test result related to a presence, if any, of the test nucleic acid target in the sample.

14. The method of paragraph 13, wherein the step of transforming the test signals includes a step of transforming two or more test signals individually with corresponding reference signals each detected from a respective same droplet as each of the two or more test signals.

15. The method of paragraph 14, wherein the step of transforming two or more test signals includes a step of dividing each test signal by its corresponding reference signal.

16. The method of paragraph 13, wherein the step of detecting includes a step of exciting the first and second dyes with a same wavelength of excitation light and a step of detecting emitted light from the first and second dyes at least substantially independently from one another in respective first and second detector channels.

17. The method of paragraph 13, wherein the step of generating droplets includes a step of forming droplets that contain primers conferring specificity for amplification of a control nucleic acid target, wherein the step of detecting includes a step of detecting control signals from the second dye, and wherein the control signals include the reference signals and indicate whether amplification of the control nucleic acid target occurred in individual droplets.

18. The method of paragraph 17, wherein the reference signals and the control signals are a same set of signals.

19. The method of paragraph 13, wherein the step of analyzing the test signals includes a step of comparing the transformed test signals to a signal threshold to assign individual droplets as positive or negative for amplification of the test nucleic acid target, and a step of estimating a number of molecules of the test nucleic acid target in the sample based on results of the step of comparing.

20. A method of sample analysis, comprising: (A) generating droplets, each droplet including first and second dyes and a partition of a sample and being capable of amplification of a test nucleic acid target, if present, in the partition; (B) exciting the first and second dyes with a same wavelength of excitation light; (C) detecting emitted light from the first and second dyes at least substantially independently from one another in respective first and second detector channels to provide respective test signals and other signals measured from the first and second dyes in the droplets, the test signals indicating whether amplification of the test nucleic acid target occurred in individual droplets; and (D) analyzing the test signals to determine a test result related to a presence, if any, of the test nucleic acid target in the sample, wherein the other signals are utilized to determine the test result, to interpret the test result, to generate another test result, or any combination thereof.

21. The method of paragraph 20, wherein the other signals include reference signals, and wherein the step of analyzing includes (a) a step of transforming the test signals based on the reference signals to reduce variation of the test signals and to produce a set of transformed test signals and (b) a step of utilizing the set of transformed test signals to determine the test result.

22. The method of paragraph 20, wherein the other signals include control signals that indicate whether amplification of a control nucleic acid target occurred in individual droplets.

23. A method of sample analysis, comprising: (A) generating droplets, each droplet including a partition of a sample and being capable of amplification of a nucleic acid target, if present, in the partition; (B) detecting signal peaks corresponding to the droplets, each signal peak including a width and providing a value, the value indicating whether amplification of the nucleic acid target occurred in an individual droplet; (C) transforming the value of each signal peak based of the width of such signal peak to create a set of transformed values; (D) comparing the set of transformed values to a signal threshold to a signal threshold to assign individual droplets as positive or negative for amplification of the test nucleic acid target; and (E) estimating a presence, if any, of the nucleic acid target in the sample based on results of the step of comparing.

24. A method of sample analysis, comprising: (A) obtaining droplets, each droplet of at least a subset of the droplets including a partition of a sample and being capable of amplification of a nucleic acid target, if present, in the partition; (B) detecting test signals and reference signals from the droplets, the test signals indicating whether amplification of the target occurred in individual droplets; (C) transforming the test signals based on the reference signals to obtain transformed test signals; (D) comparing the transformed test signals to a signal threshold to assign individual droplets as positive or negative for amplification of the nucleic acid target; and (E) estimating a number of molecules of the nucleic acid target in the sample based on the step of comparing.

25. The method of paragraph 24, wherein the step of obtaining droplets includes a step of obtaining test droplets and reference droplets, wherein the test droplets and the reference droplets represent respective different types of droplets, and wherein the test signals and the reference signals are detected from the test droplets and the reference droplets, respectively.

26. The method of paragraph 25, wherein the test signals and the reference signals are detected optically at a same wavelength or same wavelength range.

27. The method of paragraph 26, wherein the test droplets and the reference droplets contain a same dye, and wherein fluorescence of the same dye is detected as the test signals and the reference signals.

28. The method of paragraph 26, further comprising a step of distinguishing the test signals from the reference signals by intensity.

29. The method of paragraph 28, wherein the step of distinguishing includes a step of interpreting, as test signals, one or more droplet signals within a range of intensities and, as reference signals, one or more droplet signals outside the range of intensities.

30. The method of paragraph 25, wherein the step of detecting is performed in a detection area, and wherein the droplets travel to the detection area in a flow stream.

31. The method of paragraph 30, wherein the test droplets and the reference droplets are intermixed in the flow stream.

32. The method of paragraph 30, wherein the test droplets are spaced from the reference droplets in the flow stream.

33. The method of paragraph 25, further comprising a step of thermally cycling the test droplets before the step of detecting.

34. The method of paragraph 33, wherein the reference droplets are not thermally cycled after the step of obtaining and before the step of detecting.

35. The method of paragraph 24, wherein the test signals and the reference signals are detected from the same droplets.

36. The method of paragraph 26, wherein the step of transforming includes a step of transforming each test signal detected from a droplet based on a corresponding reference signal detected from the same droplet.

37. The method of paragraph 24, wherein the step of obtaining includes a step of generating droplets each including first and second fluorescent dyes.

38. The method of paragraph 37, wherein the step of detecting includes a step of exciting the fluorescent dyes with a same wavelength of excitation light and a step of detecting emission light from the fluorescent dyes at least substantially independently in respective detector channels.

IX. CLINICAL APPLICATIONS FOR DROPLET-BASED ASSAYS

This Section describes exemplary clinical applications for the droplet-based assays disclosed herein. The assays may be used to perform clinical (and/or forensic) tests related to etiology, pathogenesis, diagnosis, surveillance, and/or therapy monitoring of any suitable infection, disorder, physiological condition, and/or genotype, among others, as illustrated below. Pathogen testing may involve pathogen detection, speciation, and/or drug sensitivity applications, among others.

Each clinical (or non-clinical) test listed below may analyze any suitable aspect of a particular nucleic acid target or set of two or more targets (e.g., clinically related targets) using any suitable amplification methodology. For example, the test may be qualitative, to determine whether or not the target (or each target) is present at a detectable, statistically significant level above background in a sample, or the test may be quantitative, to determine a total presence (i.e., a concentration/copy number) of the target (or each target) in the sample. Alternatively, or in addition, the test may determine a sequence characteristic of a target (such as to determine the identity of a single nucleotide polymorphism (SNP) in the target, whether the target is wild-type or a variant, to genotype the target, and/or the like). Any suitable amplification methodology may be used in performing the tests, such as any of those described above in Section I.

The tests may provide diagnosis of a genetic disease by testing for a presence (or absence for diseases characterized by deletions) of a nucleic acid target for the genetic disease. Illustrative genetic diseases that may be diagnosed with suitable disease-specific primers include sickle cell anemia, cystic fibrosis (CF), Prader-Willi syndrome (PWS), beta-thalassemia, prothrombin thrombophilia, Williams syndrome, Angelman syndrome, fragile X syndrome, Factor V Leiden, or the like. Exemplary primers include hemoglobin sequences for sickle cell anemia, cystic fibrosis transmembrane conductance regulator (CFTR) gene sequences for cystic fibrosis, and so on. The diagnosis may include determining the variant for diseases having more than one form (e.g., distinguishing among sickle trait (AS), sickle cell anemia (SS), hemoglobin SC disease, hemoglobin SD disease, and hemoglobin SO disease, among others, for hemoglobin-related diseases). These tests may be performed pre- or postnatally, to screen for a single disease or variant, or for a panel of diseases and/or variants (for example, in prenatal screens, using genetic material obtained from an amniocentesis or maternal peripheral circulation, among others).

The tests may provide detection and/or delineation of native and/or pathogenic gene transcripts. For example, primers may be chosen to amplify one or more targets that signal initiation and/or amplification of any pathophysiological messaging cascade (e.g., TNF-alpha, one or more interleukins, NF-kappaB, one or more inflammatory modulators/mediators), viable infectious agent proliferation, etc.

The tests may be utilized (e.g., forensically) to determine identity, paternity, maternity, sibling relationships, twin typing, genealogy, etc. These tests may be performed by amplifying nucleic acid from the individuals at issue (including self for identity testing) and comparing nucleic acid sequences, nucleic acid restriction patterns, etc. Suitable nucleic acids may include Y-chromosome DNA for paternity testing, mitochondria DNA for maternity testing, genomic DNA for sibling tests, etc.

The tests may provide detection of viruses, their transcripts, their drug sensitivity, and/or pathogenic consequences thereof. For example, the tests may use primers that amplify one or more viral targets (e.g., at least a region of one or more viral genes or transcripts), to diagnose and/or monitor viral infections, measure viral loads, genotype and/or serotype viruses, and/or the like. Exemplary viral targets may include and/or may be provided by, but are not limited to, hepatitis C virus (HCV), hepatitis B virus (HPB), human papilloma virus (HPV), human immunodeficiency virus (HIV), cytomegalovirus (CMV), Epstein-Barr virus (EBV), respiratory syncytial virus (RSV), West Nile virus (WNV), varicella zoster virus (VZV), parvovirus, rubella virus, alphavirus, adenovirus, coxsackievirus, human T-lymphotropic virus 1 (HTLV-1), herpes virus (including for Kaposi's sarcoma), influenza virus, enterovirus, and/or the like. In some embodiments, the tests may provide detection/identification of new viral pathogens.

The tests may provide detection of prokaryotic organisms (i.e., bacteria), their transcripts, their drug sensitivity, and/or pathogenic consequences thereof (e.g., bacterial infections). For example, the tests may use primers that amplify one or more bacterial targets (e.g., at least a region of one or more bacterial genes or transcripts). Suitable bacteria that may be detected include, but are not limited to, gram-positive bacteria, gram-negative bacteria, and/or other fastidious infectious agents. Exemplary bacterial diseases/conditions that may be diagnosed and/or monitored include sexually transmitted diseases (e.g., gonorrhea (GC), *Chlamydia* (CT), syphilis, etc.); healthcare associated infections (HAIs), such as methicillin-resistant *Staphylococcus aureus* (MRSA), *Clostridium difficule* (*C. diff.*), vancomycin resistant entereococci (VRE), etc.; Group B *streptococcus* (GBS); mycobacteria (e.g., causing tuberculosis, leprosy, etc.); and/or the like. Further aspects of tests for HAIs that may be performed by the system disclosed herein are described in the following U.S. provisional patent applications, which are incorporated herein by reference: Ser. No. 61/206,975, filed Feb. 5, 2009; and Ser. No. 61/271,538, filed Jul. 21, 2009.

The tests may provide detection of fungi (single-celled (e.g., yeast) and/or multi-celled), their transcripts, pathogenic consequences thereof (e.g., fungal infections), and/or drug sensitivity. For example, the tests may use primers that amplify one or more fungal targets (e.g., at least a region of one or more viral genes or transcripts). Exemplary types of fungal infections that may be diagnosed and/or monitored may be caused by *Histoplasma* (e.g., causing histoplasmosis), *Blastomyces* (e.g., causing blastomycosis), *Crytococcus* (e.g., causing meningitis), *Coccidia* (e.g., causing diarrhea), *Candida, Sporothrix* genuses of fungi, and/or the like.

The tests may be used for screening, diagnosis, monitoring, and/or designing treatment of diseases such as cancer. For example, tests for cancer may detect one or more cancer mutations (e.g., her2/neu, BRACA-1, etc.), insertion/deletion/fusion genes (bcr-abl, k-ras, EFGR, etc.), amplified genes, epigenetic modifications, etc.; may identify cancer stem cells; may identify, monitor, and/or evaluate residual cancer disease burden, p53 margin assessment, etc.; and/or the like. These tests may use any suitable cancer markers as targets and may be applied to any suitable type of cancer, such as bladder cancer, bone cancer, breast cancer, brain cancer, cervical cancer, colorectal cancer, esophageal cancer, gastric cancer, oropharyngeal cancer, ovarian cancer, prostate cancer, uterine cancer, leukemia, lymphoma, myeloma, melanoma, etc.

The present system may be used to perform any other suitable tests. For example, the system may test, pre- or postnatally for aneuploidy (e.g., Down's Syndrome, Patau Syndrome, Edwards Syndrome, Fragile X Syndrome, etc.), inborn errors of metabolism (e.g., hepatopathies, encephalopathies (e.g., acyl CoA dehydrogenase deficiency)), blood group antigens, a congenital anomalies including but not limited to myelomeningocele (e.g., testing for mutations in methylenetetrahydrofolate reductase (MTHFR), methionine synthase, cystathionine beta-synthase, etc.), and/or the like. Alternatively, or in addition, the system may test for a sign of an auto-immune disorder, such as systemic lupus erythematosus (SLE), psoriasis, etc. Autoimmune testing may include HLA classification, analysis of MHC codon biomarkers, and/or the like. The system may test for signals of neurodegeneration or a predisposition thereto using targets such as parkin, PINK1, tau, alpha synuclein, allele specification and triplet penetration depth in huntingtin gene, etc. Tests may be performed for genotyping enzymes engaged in drug metabolism (e.g., cytochrome P alleles, NAT2 polymorphisms, UGT polymorphisms, etc). Genotyping tests may be performed in determination of susceptibility to any particular disease state. Tests may be performed to determine clonality, such as for immunological applications, oncology applications, etc. Tests may be designed to diagnose and/or monitor acute central nervous system (CNS) infection, such as encephalitis, meningitis, etc., for example, using nucleic acid from one or more viruses and/or bacteria capable of causing these disorders for diagnosis and nucleic acid from the virus or bacterium identified as the cause for subsequent monitoring. Tests also may be configured to diagnose acute ischemic disease. Suitable targets for this diagnosis may include CNS cellular transcripts corresponding to circulating receptor fragments post-stroke (glutamate receptors, NMDA receptors, $2^{nd}$ messenger transcripts, etc.). Other suitable targets may include intracellular cardiomyocyte transcripts released from ischemic cardiac regions. Tests also may be used to assess transcripts (e.g., types, numbers, etc.) in tissue proliferative disorders (e.g., renal failure, cirrhoses, etc.). Exemplary targets for these disorders may include trophic factors and/or extracellular matrix components, among others.

X. MULTIPLEXED ASSAYS

This Section describes exemplary strategies for performing multiplexed detection of nucleic acid targets in the same set of droplets.

Digital PCR assays may be rendered detectable through the use of a 5'-nuclease assay (i.e., a TAQMAN probe) to amplify a target sequence while producing a signal from the probe. The assays disclosed herein may be configured to multiplex the 5'-nuclease assay to permit detection of two or more species of target from individual droplets, which is termed multiplex detection. It is also possible to "query" for multiple target molecules through the presence of the target-specific reagents in each droplet. For example, if one were to have 50 pairs of primers each specific to a different gene sequence in each droplet, then each target molecule present will be counted for analysis. Conversely, any absent target molecules will not be counted. Thus, throughout this Section, the term "query" refers to a digital "yes" or "no" determination for multiple target molecules.

It is possible to distinguish different target molecules in the same volume based on the reporter dyes used in the 5'-nuclease assay. The dyes differ in emission spectra so that they may be distinguished. For example, fluorescein, fluorescein derivatives, and rhodamine dyes may be utilized for multiplexing detection from PCR and the 5'-nuclease assay.

Different dyes could be used to code sets of 5' nuclease reagents. Thus, one dye could signal the presence or absence of one set of 25 targets while a second dye could signal the presence or absence of a different set of 25 targets. For example, one might code one set as targets from chromosome 18 and another set from chromosome 21. One could then query chromosome 18 and 21 to count the number present based on digital results of two sets of assays.

It is also possible to detect different molecules in the same volume based on the melting curve specific to homoduplexes versus heteroduplexes. A detection station may include a controllable heater to produce one or more melting curves for each droplet, to detect multiple target molecules by digital PCR.

Other multiplexed detection strategies may be utilized in the systems disclosed herein. For example, a flap endonuclease assay, commercially known as an INVADER assay, is multiplexed for SNP detection in tube or microplate-based systems. The INVADER assay may be utilized to provide digital information in a multiplex fashion in the systems disclosed herein. The INVADER assay also can be used to query for many target molecules by formulating a set of two or more in every droplet. Coding is also possible.

Molecular beacon probes also may be used for multiplex detection. These probes may use similar dyes to 5-nuclease assay, but the detection method may be different. The structure of the probe when hybridized vs. un-hybridized produces a signal. The hybridized version produces a measurable signal if and only if the target sequence is amplified. It is possible to use different temperatures to multiplex detect while simultaneously using dyes. For example, three sets of probes may be designed to melt away from their target sequences at three different temperatures. The systems disclosed herein may produce multiplex digital results by both temperature and dye. Thus, in this example, the system can multiplex six assays with two dyes and probes that melt at three temperatures. Also, it is possible to couple querying and coding with molecular beacons.

An assay mixture as disclosed herein may utilize various combinations of primers and one or more reporters to perform a multiplexed assay. Exemplary combinations include (1) a single primer pair and no target-specific probe (e.g., use of an intercalating dye or universal probe as reporter for targets), (2) multiple primer pairs to amplify distinct target species and no target-specific probe (e.g., use of an intercalating dye or universal probe), (3) multiple primer pairs to amplify distinct target species and a single color target-specific probe (e.g., a TAQMAN probe), (4) single primer pairs and multiple one color target-specific probes, (5) multiple primer pairs and multiple one-color target specific probes, or (6) multiple primer pairs and multiple color target specific probes, among others.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A device for generating droplets, comprising:
a substantially planar base portion including a bottom surface having a plurality of microfluidic channels formed therein as recessed regions of the bottom surface;
a plurality of protrusions projecting from a top surface of the base portion and each formed integrally with the base portion;
a sample well, a carrier well, and a droplet well, wherein each well has an upper portion created by one of the protrusions; and
a cover layer attached to the bottom surface of the base portion and sealing a bottom side of each microfluidic channel;
wherein the plurality of microfluidic channels includes a first channel, a second channel, and a third channel that meet one another in a droplet-generation region, and
wherein the sample well is configured to supply sample-containing fluid to the droplet-generation region via the first channel, the carrier well is configured to supply carrier fluid to the droplet-generation region via the second channel, and the droplet well is configured to receive sample-containing droplets in carrier fluid from the droplet-generation region via the third channel.

2. The device of claim 1, wherein the cover layer is thinner than the base portion.

3. The device of claim 1, wherein the base portion and the plurality of protrusions are provided by an injection-molded polymer body.

4. The device of claim 3, wherein each well defines a central axis and has a floor and a side wall region, wherein the side wall region surrounds the central axis and extends upwardly from the floor, and wherein the polymer body provides the side wall region of each well.

5. The device of claim 4, wherein the polymer body provides the floor of each well.

6. The device of claim 4, wherein the polymer body defines a plurality of openings each extending completely through the body in a direction orthogonal to the bottom surface of the base portion, and wherein each opening creates the side wall region of one of the wells.

7. The device of claim 6, wherein each opening narrows at a position intermediate a top side of the body and the bottom surface of the base portion.

8. The device of claim 1, where the plurality of microfluidic channels includes a fourth channel that meets the first channel, the second channel, and the third channel in the droplet-generation region.

9. The device of claim 8, wherein the carrier well is configured to supply carrier fluid to the droplet-generation region via the second channel and the fourth channel.

10. The device of claim 1, wherein the device comprises another well that is fluidically connected to the droplet well via the droplet-generation region.

11. A method of generating droplets, the method comprising:
selecting the device of claim 1; and
forming sample-containing droplets in the droplet-generation region.

12. A device for generating droplets, comprising:
an upper member injection molded as a single piece, the upper member defining a plane and a plurality of microfluidic channels arranged parallel to the plane;
a sample well, a carrier well, and a droplet well, each well defining a central axis and including a floor and a side wall region, the side wall region being formed by the upper member, the side wall region extending upwardly from the floor and surrounding the central axis; and
a lower member attached to the upper member and sealing a bottom side of each microfluidic channel;
wherein the plurality of microfluidic channels includes a first channel, a second channel, and a third channel that meet one another in a droplet-generation region, and wherein the sample well is configured to supply sample-containing fluid to the droplet-generation region via the first channel, the carrier well is configured to supply carrier fluid to the droplet-generation region via the second channel, and the droplet well is configured to receive sample-containing droplets in carrier fluid from the droplet-generation region via the third channel.

13. The device of claim 12, wherein the upper member includes a substantially planar base portion having a bottom surface at which the lower member is attached to the upper member, and wherein the lower member is thinner than the base portion.

14. The device of claim 12, wherein the upper member defines a plurality of openings each extending completely through the upper member, wherein the lower member covers a bottom end of each opening, and wherein each opening creates the side wall region of one of the wells.

15. The device of claim 14, wherein each opening narrows at a position intermediate a top side and a bottom surface of the upper member.

16. The device of claim 12, wherein the device comprises another well that is fluidically connected to the droplet well via the droplet-generation region.

17. The device of claim 12, wherein the device includes a plurality of sample wells, a plurality of carrier wells, a plurality of droplet wells, and a plurality of droplet-generation regions, and wherein each droplet-generation region is connected to one of the sample wells, one of the carrier wells, and one of the droplet wells.

18. A method of generating droplets, the method comprising:
selecting the device of claim 12; and
forming sample-containing droplets in the droplet-generation region.

19. A device for generating droplets, comprising:
a body injection molded as a single piece, the body including a base portion and a plurality of annular protrusions projecting from a top surface of the base portion, the base portion defining a plurality of microfluidic channels;
a sample well, a carrier well, and a droplet well, wherein each well has an upper portion created by one of the annular protrusions; and
a cover layer attached to the base portion and sealing a bottom side of each microfluidic channel;
wherein the plurality of microfluidic channels includes a first channel, a second channel, and a third channel that meet one another in a droplet-generation region, and wherein the sample well is configured to supply sample-containing fluid to the droplet-generation region via the first channel, the carrier well is configured to supply carrier fluid to the droplet-generation region via the second channel, and the droplet well is configured to receive sample-containing droplets in carrier fluid from the droplet-generation region via the third channel.

20. The device of claim 19, wherein the cover layer is thinner than the base portion.

21. The device of claim 19, wherein each well defines a central axis and has a floor and a side wall region, wherein the side wall region surrounds the central axis and extends upwardly from the floor, and wherein the body provides the side wall region of each well.

22. The device of claim 19, where the plurality of microfluidic channels includes a fourth channel that meets the first channel, the second channel, and the third channel in the droplet-generation region.

23. The device of claim 19, wherein the carrier well is configured to supply carrier fluid to the droplet-generation region via the second channel and the fourth channel.

24. The device of claim 19, wherein the device includes a plurality of sample wells, a plurality of carrier wells, a plurality of droplet wells, and a plurality of droplet-generation regions, and wherein each droplet-generation region is connected to one of the sample wells, one of the carrier wells, and one of the droplet wells.

25. The device of claim 19, wherein the device comprises another well that is fluidically connected to the droplet well via the droplet-generation region.

26. A method of generating droplets, the method comprising:
selecting the device of claim 19; and
forming sample-containing droplets in the droplet-generation region.

* * * * *